(12) United States Patent
Derowe et al.

(10) Patent No.: US 7,022,131 B1
(45) Date of Patent: Apr. 4, 2006

(54) METHODS AND DEVICES FOR VASCULAR SURGERY

(75) Inventors: Ari Derowe, Hasharon-Hatichon (IL);
Amir Loshakove, Moshav-Bazra (IL)

(73) Assignee: By-Pass Inc., Orangeburg, NY (US)

( * ) Notice: Subject to any disclaimer, the term of this patent is extended or adjusted under 35 U.S.C. 154(b) by 0 days.

(21) Appl. No.: 09/701,531

(22) PCT Filed: May 30, 1999

(86) PCT No.: PCT/IL99/00284

§ 371 (c)(1),
(2), (4) Date: Nov. 28, 2000

(87) PCT Pub. No.: WO99/62415

PCT Pub. Date: Dec. 9, 1999

(30) Foreign Application Priority Data

May 29, 1998 (IL) ........................................ 124694
Mar. 19, 1999 (IL) ........................................ 129067

(51) Int. Cl.
*A61F 2/06* (2006.01)

(52) U.S. Cl. ....................... 623/1.11; 623/898; 606/153
(58) Field of Classification Search ........ 606/151–153; 622/1.11; 623/898
See application file for complete search history.

(56) References Cited

U.S. PATENT DOCUMENTS

| | | |
|---|---|---|
| 1,867,624 A | 7/1932 | Hoffman |
| 2,505,358 A | 4/1950 | Gusberg et al. |
| 2,994,321 A | 8/1961 | Tischler |
| 3,104,666 A | 9/1963 | Hale et al. |
| 3,180,337 A | 4/1965 | Smialowski |
| 3,221,746 A | 12/1965 | Noble |
| 3,519,187 A | 7/1970 | Kapitanov et al. |
| 3,657,744 A | 4/1972 | Ersek |
| 3,776,237 A | 12/1973 | Hill et al. |
| 3,837,345 A | 9/1974 | Matar |
| 3,901,243 A | 8/1975 | Read |
| 3,908,662 A | 9/1975 | Razgulov et al. |
| 3,973,570 A | 8/1976 | Razgulov et al. |
| 4,018,228 A | 4/1977 | Goosen |
| 4,214,586 A | 7/1980 | Mericle |
| 4,214,587 A | 7/1980 | Sakura, Jr. |
| 4,216,776 A | 8/1980 | Downie et al. |
| 4,352,358 A | 10/1982 | Angelchik |

(Continued)

FOREIGN PATENT DOCUMENTS

DE        297 13 335        11/1997

(Continued)

OTHER PUBLICATIONS

Draney, M. et al.; "Coronary Artery Bypass Surgery: Minimally Invasive Techniques"; May 1998; Retrieved from Internet: <http://me210abc.stanford.edu/94-95/projects/Pfizer/Spring/1.html>.

(Continued)

*Primary Examiner*—(Jackie) Tan-Uyen T. Ho
(74) *Attorney, Agent, or Firm*—Feaster & Company

(57) ABSTRACT

An anastomotic connector (60) for attaching two blood vessels, comprising a cylinder-like portion having a lumen, two ends, and an array of cells elements, and a tissue engaging portion (60) comprising at least one set of spikes (64) wherein at least one spike arranged adjacent one of the two ends of said cylinder-like portion. The connector (60) may comprise at least a second set of spikes (66) adjacent the other of the two ends.

19 Claims, 69 Drawing Sheets

U.S. PATENT DOCUMENTS

| | | |
|---|---|---|
| 4,366,819 A | 1/1983 | Kaster |
| 4,368,734 A | 1/1983 | Banko |
| 4,368,736 A | 1/1983 | Kaster |
| 4,523,592 A | 6/1985 | Daniel |
| 4,586,503 A | 5/1986 | Kirsch et al. |
| 4,657,019 A | 4/1987 | Walsh et al. |
| 4,696,300 A | 9/1987 | Anderson |
| 4,696,308 A | 9/1987 | Meller et al. |
| 4,785,809 A | 11/1988 | Weinrib |
| 4,793,349 A | 12/1988 | Weinrib |
| 4,796,627 A | 1/1989 | Tucker |
| 4,846,174 A | 7/1989 | Willard et al. |
| 4,872,874 A | 10/1989 | Taheri |
| 4,917,087 A | 4/1990 | Walsh et al. |
| 4,926,858 A | 5/1990 | Gifford, III et al. |
| 4,930,502 A | 6/1990 | Chen |
| 4,930,674 A | 6/1990 | Barak |
| 4,958,414 A | 9/1990 | Benoit |
| 4,997,439 A | 3/1991 | Chen |
| 5,009,643 A | 4/1991 | Reich et al. |
| 5,035,702 A | 7/1991 | Taheri |
| 5,037,433 A | 8/1991 | Wilk et al. |
| 5,041,082 A | 8/1991 | Shiber |
| 5,053,041 A | 10/1991 | Ansari et al. |
| 5,129,913 A | 7/1992 | Ruppert |
| 5,141,516 A | 8/1992 | Detweiler |
| 5,192,294 A | 3/1993 | Blake, III |
| 5,197,465 A | 3/1993 | Montgomery |
| 5,201,901 A | 4/1993 | Harada et al. |
| 5,234,447 A | 8/1993 | Kaster et al. |
| 5,234,448 A | 8/1993 | Wholey et al. |
| 5,236,437 A | 8/1993 | Wilk et al. |
| 5,250,058 A | 10/1993 | Miller et al. |
| 5,254,127 A | 10/1993 | Wholey et al. |
| 5,275,622 A | 1/1994 | Lazarus et al. |
| 5,284,485 A | 2/1994 | Kammerer et al. |
| 5,292,309 A | 3/1994 | Van Tassel et al. |
| 5,323,765 A | 6/1994 | Brown |
| 5,366,462 A | 11/1994 | Kaster et al. |
| 5,392,979 A | 2/1995 | Green et al. |
| 5,403,333 A | 4/1995 | Kaster et al. |
| 5,403,338 A | 4/1995 | Milo |
| 5,425,739 A | 6/1995 | Jessen |
| 5,441,517 A | 8/1995 | Kensey et al. |
| 5,445,623 A | 8/1995 | Richmond |
| 5,445,632 A | 8/1995 | Blake et al. |
| 5,456,712 A | 10/1995 | Maginot |
| 5,478,353 A | 12/1995 | Yoon |
| 5,484,451 A | 1/1996 | Akopov et al. |
| 5,488,958 A | 2/1996 | Topel et al. |
| D372,310 S | 7/1996 | Hartnett |
| 5,536,251 A | 7/1996 | Evard et al. |
| 5,540,715 A | 7/1996 | Katsaros et al. |
| 5,562,690 A | 10/1996 | Green et al. |
| 5,562,728 A | 10/1996 | Lazarus et al. |
| 5,575,800 A | 11/1996 | Gordon |
| 5,591,178 A | 1/1997 | Green et al. |
| 5,649,946 A | 7/1997 | Bramlet |
| 5,658,282 A | 8/1997 | Daw et al. |
| 5,676,670 A | 10/1997 | Kim |
| 5,676,696 A | 10/1997 | Marcade |
| 5,685,838 A | 11/1997 | Peters et al. |
| 5,690,656 A | 11/1997 | Cope et al. |
| 5,690,662 A | 11/1997 | Chiu et al. |
| 5,695,504 A | 12/1997 | Gifford, III et al. |
| 5,697,943 A | 12/1997 | Sauer et al. |
| 5,702,412 A | 12/1997 | Popov et al. |
| 5,707,380 A | 1/1998 | Hinchliffe et al. |
| 5,709,335 A | 1/1998 | Heck |
| 5,733,308 A | 3/1998 | Daugherty et al. |
| 5,755,778 A | 5/1998 | Kleshinski |
| 5,758,663 A | 6/1998 | Wilk et al. |
| 5,797,920 A | 8/1998 | Kim |
| 5,797,934 A | 8/1998 | Rygaard |
| 5,817,111 A | 10/1998 | Riza |
| 5,817,113 A | 10/1998 | Gifford, III et al. |
| 5,823,971 A | 10/1998 | Robinson et al. |
| 5,824,002 A | 10/1998 | Gentelia et al. |
| 5,824,008 A | 10/1998 | Bolduc et al. |
| 5,827,316 A | 10/1998 | Young et al. |
| 5,830,222 A | 11/1998 | Makower |
| 5,833,698 A | 11/1998 | Hinchliffe et al. |
| 5,868,763 A | 2/1999 | Spence et al. |
| 5,893,369 A | 4/1999 | LeMole |
| 5,910,153 A | 6/1999 | Mayenberger |
| 5,910,155 A | 6/1999 | Ratcliff et al. |
| 5,922,000 A | 7/1999 | Chodorow |
| 5,931,842 A | 8/1999 | Goldsteen et al. |
| 5,951,576 A * | 9/1999 | Wakabayashi ............... 606/151 |
| 5,957,938 A | 9/1999 | Zhu et al. |
| 5,957,973 A | 9/1999 | Quiachon et al. |
| 5,968,069 A | 10/1999 | Dusbabek et al. |
| 5,972,014 A | 10/1999 | Nevins |
| 5,976,159 A | 11/1999 | Bolduc et al. |
| 5,976,178 A | 11/1999 | Goldsteen |
| 5,989,278 A | 11/1999 | Mueller |
| 5,989,287 A * | 11/1999 | Yang et al. ................. 623/1.36 |
| 5,993,468 A | 11/1999 | Rygaard |
| 6,004,330 A | 12/1999 | Middleman et al. |
| 6,004,341 A | 12/1999 | Zhu et al. |
| 6,022,367 A | 2/2000 | Sherts |
| 6,026,814 A | 2/2000 | LaFontaine et al. |
| 6,035,856 A | 3/2000 | LaFontaine et al. |
| 6,036,700 A | 3/2000 | Stefanchik et al. |
| 6,036,702 A | 3/2000 | Bachinski et al. |
| 6,071,292 A | 6/2000 | Makower et al. |
| 6,080,176 A | 6/2000 | Young |
| 6,113,612 A | 9/2000 | Swanson et al. |
| 6,152,937 A | 11/2000 | Peterson et al. |
| 6,171,319 B1 | 1/2001 | Nobles et al. |
| 6,176,867 B1 | 1/2001 | Wright |
| 6,179,848 B1 | 1/2001 | Solem |
| 6,185,792 B1 | 2/2001 | Nelson et al. |
| 6,186,942 B1 | 2/2001 | Sullivan et al. |
| 6,190,353 B1 | 2/2001 | Makower et al. |
| 6,193,734 B1 | 2/2001 | Bolduc et al. |
| 6,206,912 B1 | 3/2001 | Goldsteen et al. |
| 6,248,117 B1 | 6/2001 | Blatter et al. |
| 6,261,315 B1 | 7/2001 | St. Germain et al. |
| 6,302,905 B1 | 10/2001 | Goldsteen et al. |
| 6,309,416 B1 | 10/2001 | Swanson et al. |
| 6,387,108 B1 | 5/2002 | Taylor et al. |
| 6,391,036 B1 | 5/2002 | Berg et al. |
| 6,419,681 B1 | 7/2002 | Vargas et al. |
| 6,428,550 B1 | 8/2002 | Vargas et al. |
| 6,461,320 B1 | 10/2002 | Yencho et al. |
| 6,485,496 B1 | 11/2002 | Suyker et al. |
| 6,497,710 B1 | 12/2002 | Yencho et al. |
| 6,508,252 B1 | 1/2003 | Berg et al. |
| 6,514,196 B1 | 2/2003 | Sullivan et al. |
| 6,514,265 B1 | 2/2003 | Ho et al. |
| 6,517,558 B1 | 2/2003 | Gittings et al. |
| 6,533,812 B1 | 3/2003 | Swanson et al. |
| 6,537,288 B1 | 3/2003 | Vargas et al. |
| 6,588,643 B1 | 7/2003 | Bolduc et al. |
| 6,632,241 B1 | 10/2003 | Hancock et al. |
| 6,652,541 B1 | 11/2003 | Vargas et al. |
| 2001/0004698 A1 | 6/2001 | Blatter et al. |
| 2001/0004699 A1 | 6/2001 | Gittings et al. |
| 2001/0016752 A1 | 8/2001 | Berg et al. |
| 2001/0025643 A1 | 10/2001 | Foley |
| 2001/0047180 A1 | 11/2001 | Grudem et al. |
| 2002/0004663 A1 | 1/2002 | Gittings et al. |
| 2002/0019642 A1 | 2/2002 | Milliman et al. |

| | | | |
|---|---|---|---|
| 2002/0022852 A1 | 2/2002 | Dakov | |
| 2002/0022857 A1 | 2/2002 | Goldsteen et al. | |
| 2002/0087046 A1 | 7/2002 | Sullivan et al. | |
| 2002/0087181 A1 | 7/2002 | Goldsteen et al. | |
| 2002/0099394 A1 | 7/2002 | Houser et al. | |
| 2002/0108621 A1 | 8/2002 | Berg et al. | |
| 2002/0169470 A1 | 11/2002 | Kuhr et al. | |
| 2003/0083541 A1 | 5/2003 | Sullivan et al. | |
| 2003/0083679 A1 | 5/2003 | Grudem et al. | |
| 2003/0093118 A1 | 5/2003 | Ho et al. | |

FOREIGN PATENT DOCUMENTS

| | | | |
|---|---|---|---|
| EP | 0 539 237 | 4/1993 | |
| EP | 0 916 314 | 5/1999 | |
| EP | 1 055 401 | 11/2000 | |
| GB | 2 094 212 | 9/1982 | |
| IT | 1215699 | 2/1990 | |
| WO | WO 89/06515 | 7/1989 | |
| WO | WO 89/08433 | 9/1989 | |
| WO | WO 96/25886 | 8/1996 | |
| WO | WO 96/33673 | 10/1996 | |
| WO | WO 97/13463 | 4/1997 | |
| WO | WO 97/13471 | 4/1997 | |
| WO | WO 97/27898 | 8/1997 | |
| WO | WO 97/28749 | 8/1997 | |
| WO | WO 97/40754 | 11/1997 | |
| WO | WO 98/07399 | 2/1998 | |
| WO | WO 98/16161 | 4/1998 | |
| WO | WO 98/19629 | 5/1998 | |
| WO | WO 98/19634 | 5/1998 | |
| WO | WO 98/19635 | 5/1998 | |
| WO | WO 98/19636 | 5/1998 | |
| WO | WO 98/30152 | 7/1998 | |
| WO | WO 98/32412 | 7/1998 | |
| WO | WO 98/38922 | 9/1998 | |
| WO | WO 98/38939 | 9/1998 | |
| WO | WO 98/38941 | 9/1998 | |
| WO | WO 98/38942 | 9/1998 | |
| WO | WO 98/55027 | 12/1998 | |
| WO | WO 98/57591 | 12/1998 | |
| WO | WO 98/57592 | 12/1998 | |
| WO | WO 99/21491 | 5/1999 | |
| WO | WO 99/37218 | 7/1999 | |
| WO | WO 99/38441 | 8/1999 | |
| WO | WO 99/40851 | 8/1999 | |
| WO | WO 99/40868 | 8/1999 | |
| WO | WO 99/65409 | 12/1999 | |
| WO | WO 00/21436 | 4/2000 | |
| WO | WO 00/27311 | 5/2000 | |
| WO | WO 00/27312 | 5/2000 | |
| WO | WO 00/27313 | 5/2000 | |
| WO | WO 00/45886 | 8/2000 | |
| WO | WO 00/53104 | 9/2000 | |
| WO | WO 00/66007 | 11/2000 | |
| WO | WO 00/66009 | 11/2000 | |
| WO | WO 00/69343 | 11/2000 | |
| WO | WO 00/69346 | 11/2000 | |
| WO | WO 00/69349 | 11/2000 | |
| WO | WO 00/69364 | 11/2000 | |
| WO | WO 00/72764 | 12/2000 | |
| WO | WO 00/74579 | 12/2000 | |

OTHER PUBLICATIONS

Obora, Y. et al.; "Nonsuture Microvascular Anastomosis Using Magnet Rings: Preliminary Report"; Feb. 1978; pp. 117-120; Sur Neurol (United States); vol. 9, No. 2.

Östrup, L. T. et al.; "The UNILINK Instrument System for Fast and Safe Microvascular Anastomosis"; pp. 521-526; Department of Plastic Surgery, Hand Surgery, and Burns; University Hospital, Sweden; presented in part at the First Scandinavian Seminar on Reconstructive Microsurgery, Sweden, Oct. 1979, and at the Symposium on MicroneurovascularSurgery, Denmark, Jan. 1983.

Yachia, D. et al.; "Bio-FragmentableAnastomosisRing in Urological Surgery Involving the Gastrointestinal Tract: Early Experiences and a Historical Review of Mechanical Intestinal Anastomosis"; May 1995; pp. 1426-1428; The Journal of Urology; vol. 153.

Copy of Certified Copy of U.S. Appl. No. 09/187,361, published on May 18, 2000, Galdonik, J. A. et al., "Medical Graft Componentand Methods of Installing Same".

Copy of Certified Copy of U.S. Appl. No. 09/187,364, published on May 18, 2000, Berg, T. A. et al., "Minimally Invasive RevascularizationApparatus and Methods".

US 6,503,260, 01/2003, Schaller et al. (withdrawn)

* cited by examiner

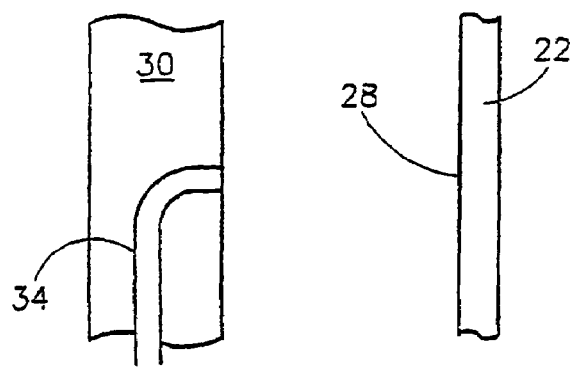
FIG.2A
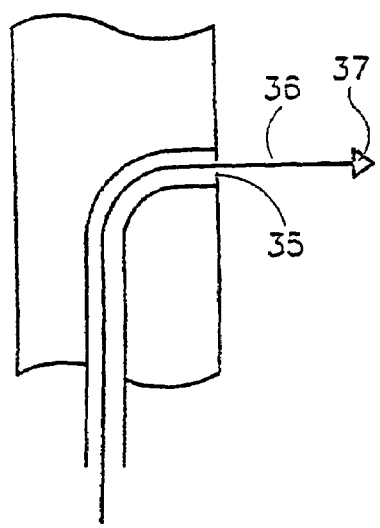
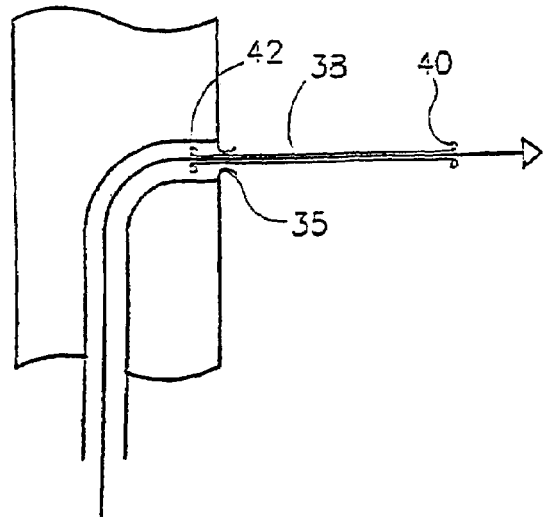
FIG.2B　　　　　FIG.2C

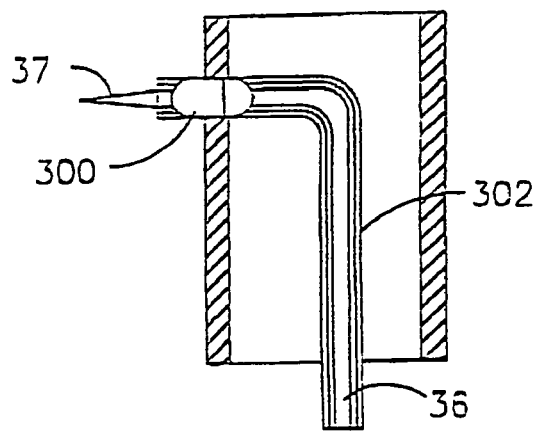 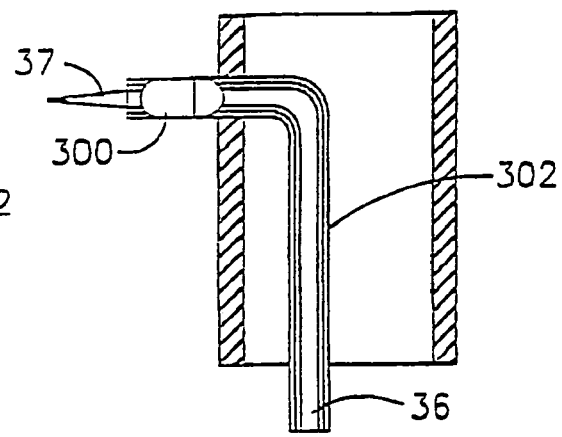
FIG.2J FIG.2K
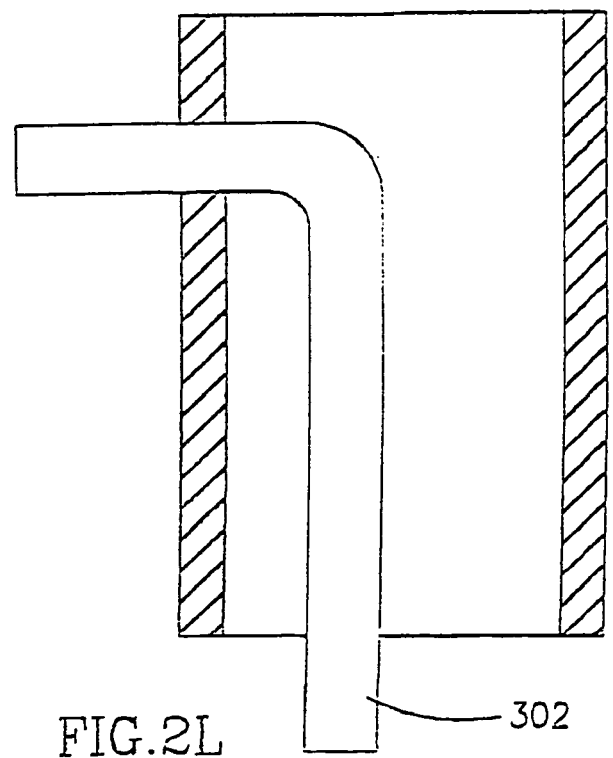
FIG.2L

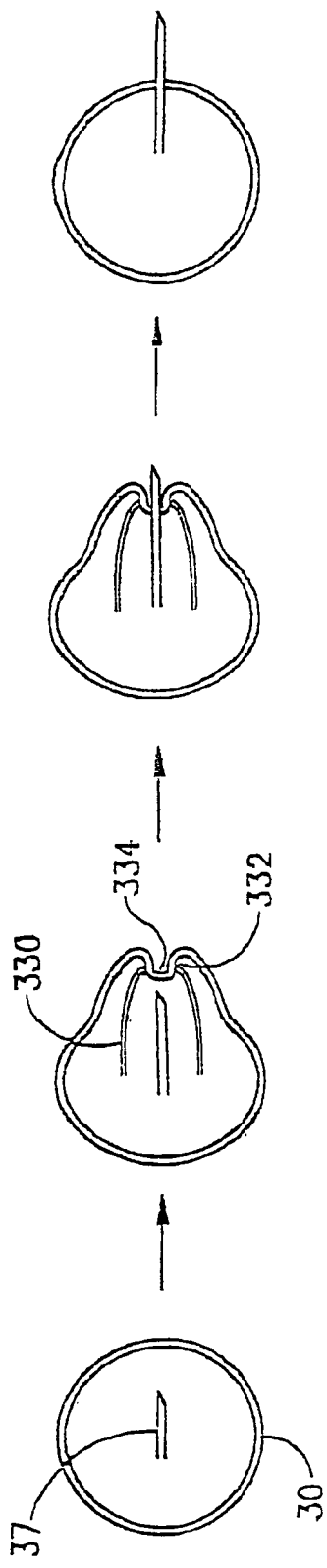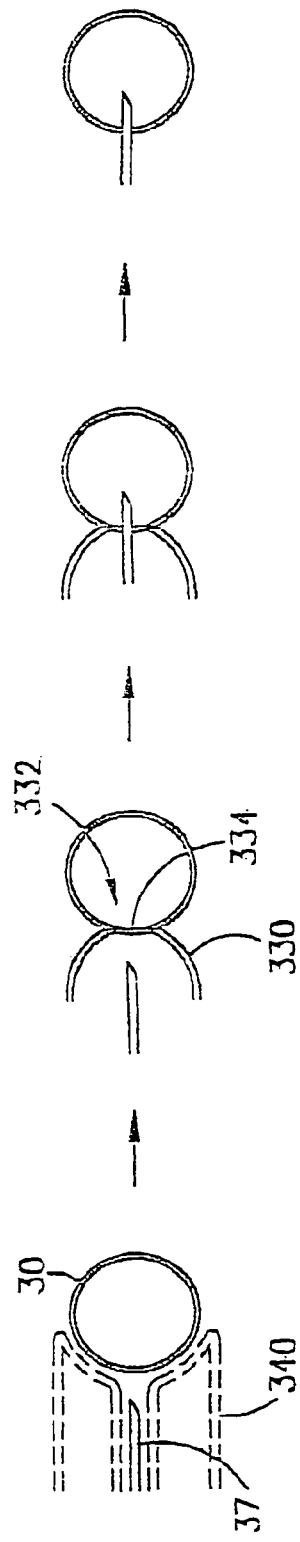

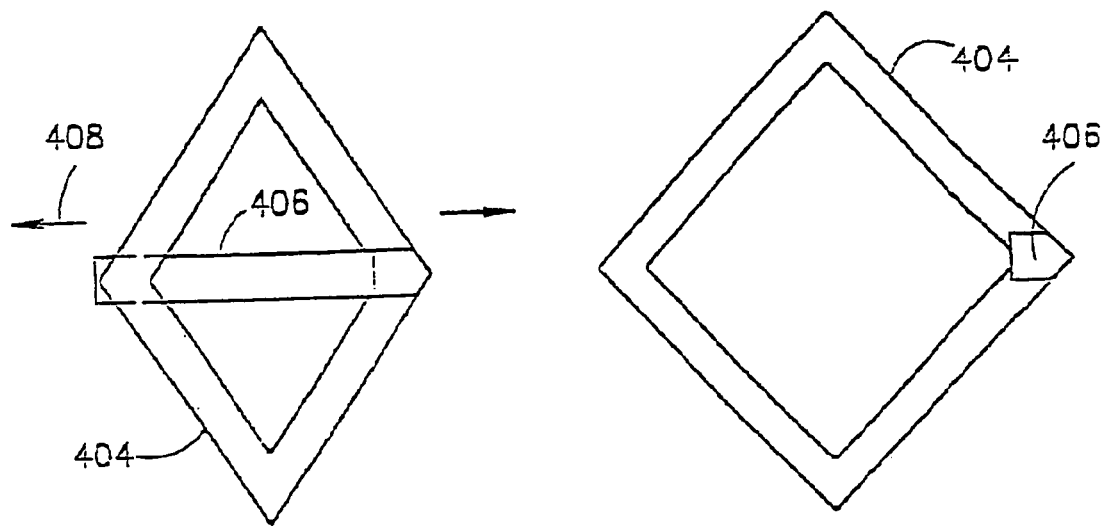
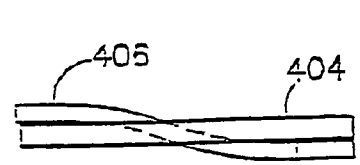
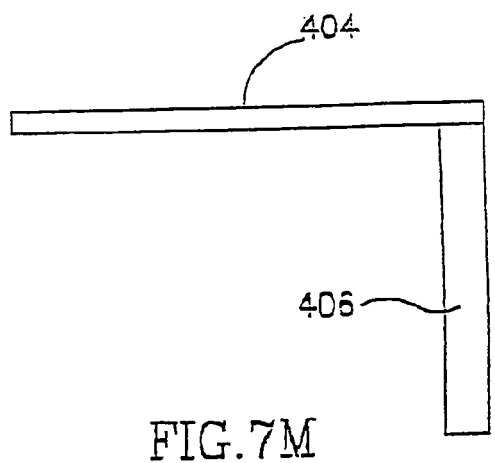
FIG.7L                    FIG.7M

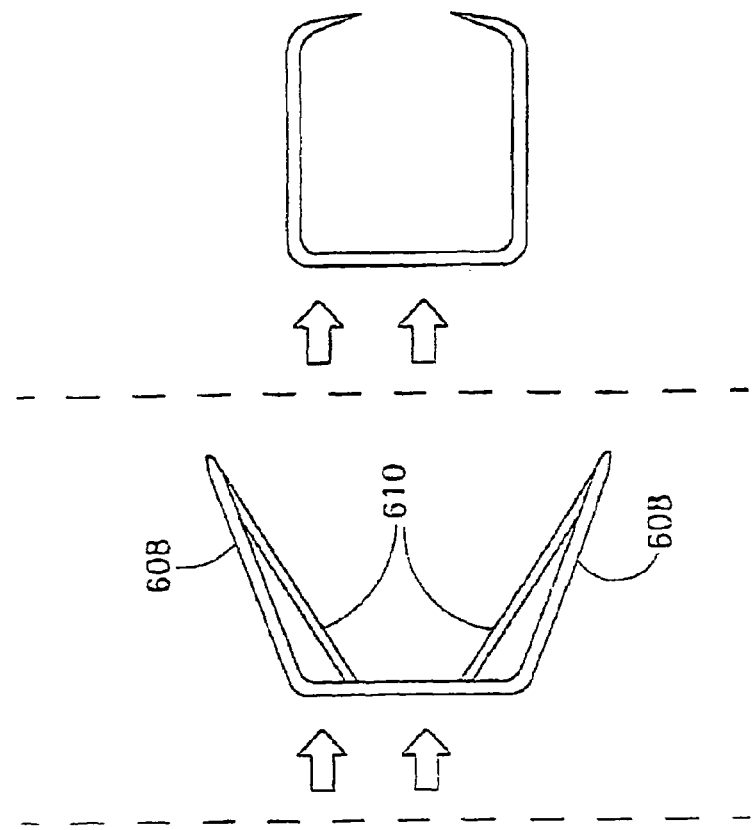
FIG.7R
FIG.7Q
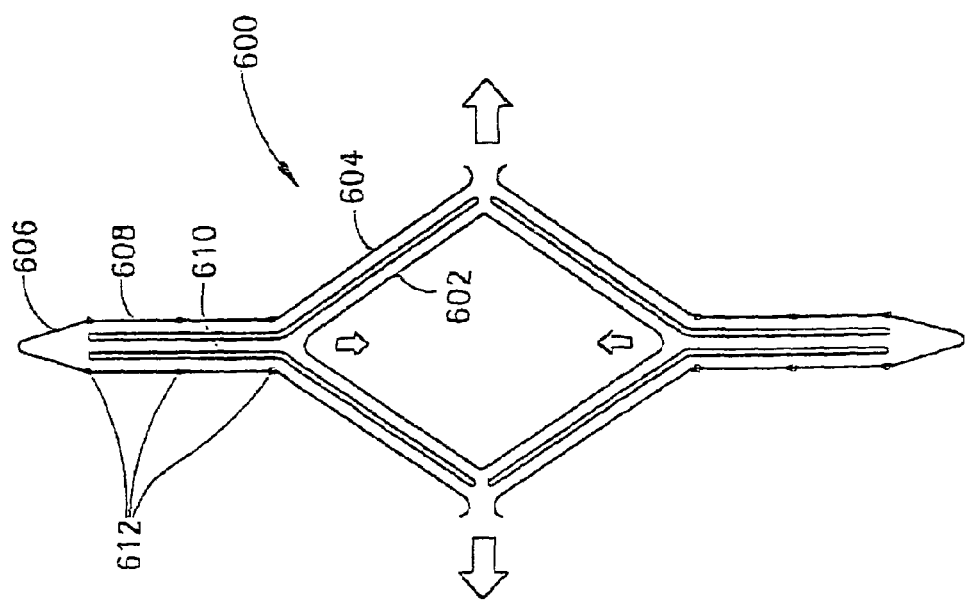
FIG.7P

METHODS AND DEVICES FOR VASCULAR SURGERY

FIELD OF THE INVENTION

The present invention relates to performing an anastomosis and especially to an anastomosis relating to percutaneous bypass surgery.

BACKGROUND OF THE INVENTION

Connecting two blood vessels, anastomosis, is an important surgical technique for reconstructive, therapeutic and cosmetic surgery. The gold standard of anastomosis is manual suturing of the two blood vessels in a side-to-side, end-to-end or end-to-side configuration. Although it is generally desirable to shorten the length of any surgical procedure, this is especially important in coronary bypass surgery, for example minimally invasive procedures in which the heart continues beating and open surgical procedures in which a patient is often attached to a heart-lung machine and his heart is stopped.

In addition to manual suturing of blood vessels, other methods of attaching two blood vessels are known, including method using staples and anastomosis rings. PCT publications WO 97/40754 and WO 97/28749, the disclosures of which are incorporated herein by reference, describe various staplers for coronary bypass surgery, wherein a graft is connected on one of its ends to the aorta and at its other end to an occluded coronary artery, distal to the occlusion. In this type of surgery, the anastomosis is sealed by stapling the graft to the aorta, while pressing both aorta and graft against an anvil. In one publication, the anvil is inserted into the aorta for the stapling and then removed, possibly by taking the anvil apart. In the other publication, the end of the graft is everted over a ring-shaped anvil, so that the anvil is outside of the blood vessel at all times.

Recently, bypass surgery has been performed using minimally invasive (e.g., key-hole and mini-thoractomy) surgery. In this type of surgery, a small hole is made in the chest, instead of cracking open the ribs, and the mammary arteries are used for bypass grafts. The suturing and/or stapling is performed using tools, for example such as those described above.

An even less invasive type of surgery requires no opening of the chest at all. Rather, one or more catheters are introduced into the blood vessels using a percutaneous approach. PCT publications WO 97/27898, WO 97/13471 and WO 97/13463 and their priority documents, namely U.S. application 60/010,614, 60/005,164, Ser. Nos. 08/730,327 and 08/730,496, the disclosures of which are incorporated herein by reference and termed the "Transvascular Applications", describe methods and apparatus for percutaneous treatment of arterial occlusions. Two main methods are taught in these applications. In one method, a tunnel is excavated within tissue (outside the vessel) from one side of the occlusion to the other side of the occlusion, and a stent or a stent/graft is placed within the tunnel. In another method, a conveniently located vein or graft is attached to the occluded vessel and two side-to-side anastomosis are created between the occluded vessel and the vein or graft. The distal and proximal portions of the vein are closed in one of a variety of manners. The connection between the vein and the artery may be made by welding the two blood vessels, or by using one of a variety of connectors that are suggested. One of the disclosed connectors comprises two springs separated by a short segment of a possibly unstented graft. The springs have the form of an inverted funnel, so that the two blood vessels are urged together. Where there is a spacing between the blood vessels, various techniques and/or devices are suggested for stopping the surrounding tissue from compressing the connection between the vein and the artery. One of the purposes of the various types of connectors is to maintain the two blood vessels near each-other, either in contact or compressing tissue between them, presumably so no blood will leak from the connection between the connector and the blood vessels.

In a TIPS procedure, a stent is placed into a passage percutaneously forced, opened or excavated between a portal vein and a hepatic vein. As in some of the embodiments described in the previous paragraph, the relative location of the blood vessels is maintained by the existence of relatively solid tissue surrounding and between the two blood vessels. Thus, there is no requirement that each of the connections between an end of the connector and the respective blood vessel to which it is attached, be, of itself, leak-proof.

In WWW publication "http://me210abc.stanford.edu/94–95/projects/Pfizer/Spring/1.html" (May 1998), the disclosure of which is incorporated herein by reference, a method is described for reducing the complexity of performing a bypass surgery. In this method, a graft is percutaneously brought to the aorta and pushed out of an incision in the aorta near a site of a bypass surgery. A keyhole opening is made in the chest to bring a tool to suture or staple the graft to the aorta and to the coronary which is to be bypassed.

Hinchliffe in U.S. Pat. No. 5,833,698, the disclosure of which is incorporated herein by reference, describes a multi-pin anastomosis connector, with or without a ring interconnecting the pins. Also described is a device, for attaching a graft end to a slit formed in a side blood vessel.

Rygaard in U.S. Pat. No. 5,797,934, the disclosure of which is incorporated herein by reference, describes an end-to side anastomosis device that uses a balloon inside the side artery to evert the lips of an opening in the side artery. The described anastomosis device, which is provided from outside the artery, includes releasable spikes which nail the vessels together.

Popov in U.S. Pat. No. 5,702,412, the disclosure of which is incorporated herein by reference, describes a cork-screw like head which is used to grasp a part of side artery to be punched out. Popov also describes using external clipping devices to apply clips at the circumference of the anastomosis.

Kaster in U.S. Pat. No. 4,366,819, the disclosure of which is incorporated herein by reference, describes a two part anastomotic device for end-to-side anastomosis, using an inner flange and an outer flange. When the flanges are closed an intima-to-intima contact and/or an everted graft can be formed.

PCT publication WO 98/38922, the disclosure of which is incorporated herein by reference, describes an anastomosis device formed of a flexible cord which can be formed into a loop and which has small spikes formed on it to grasp the blood vessels. Spikes can be bent back using an anvil inside the blood vessel. This device is also described as being used for end-to-end anastomosis.

PCT publication WO 98/42262, the disclosure of which is incorporated herein by reference, describes an anastomosis device that uses a plurality of needles preloaded with sutures.

Gillford in U.S. Pat. No. 5,817,113, the disclosure of which is incorporated herein by reference, describes various types of anastomosis devices including devices with bending spikes, with or without a ring (inner or outer). In some of the described devices the spikes are bent twice, each time by about 90 degrees. Another described device uses a ring which is transfixed by a plurality of hooked wires. These wires hook the "side" vessel, while the ring is connected to an "end" of a graft. When the wires are pulled, the anastomosis is closed.

Kaster in U.S. Pat. No. 5,234,447, the disclosure of which is incorporated herein by reference, describes an anastomosis device including a ring with long spikes on either side of the ring.

Snow in U.S. Pat. No. 5,797,933, the disclosure of which is incorporated herein by reference, describes an anastomosis device formed of a thin wire ring with spikes extended to one side of the ring. The ring is somewhat compressed by its having a wave profile. During deployment, the ring is straightened, increasing its radius.

Kim in U.S. Pat. Nos. 5,676,670 and 5,797,920, the disclosures of which are incorporated herein by reference, describe an anastomosis system in which a probe is inserted into a side of a blood vessel. The head of the probe is expanded to allow a mesh shaped anastomosis device to be brought into the vessel. The head is then further expanded to flatten the mesh against the inside of the blood vessel. The anastomosis is completed by applying a glue on the outside of the anastomosis.

WO 98/38941, WO 98/38942 and WO 98/38939, the disclosures of which are incorporated herein by reference, described ideas for performing transvascular bypass procedures. In one application a graft is connected from an aorta to an portion of an artery distal to its occlusion. In another, such a graft is connected from one of the vessels exiting the aorta. In another, a bypass is created by tunneling through the heart tissue.

SUMMARY OF THE INVENTION

One object of some preferred embodiments of the invention is to provide anastomosis connectors, especially suitable for minimally invasive surgery.

An object of some preferred embodiments of the invention is to provide a minimally invasive method of bypassing occluded blood vessels, preferably without sacrificing a nearby artery or vein. Typically, a graft is attached between a first blood vessel and a second blood vessel. In some cases, the graft itself is a blood vessel.

An aspect of some preferred embodiments of the invention relates to anastomotic devices that shrink axially as they expand radially. In a preferred embodiment of the invention, the axial shrinkage and the radial expansion cooperate to perform the anastomosis.

An aspect of some preferred embodiments of the inventions relates to anastomotic devices that extend spikes perpendicularly to a surface of a device and/or bend such spikes, while the device is being deployed. In a preferred embodiment of the invention, the spike extension is timed so that the spikes engage both the participating blood vessels. Alternatively or additionally, at least some of the spikes engage only one of the blood vessels. However the extension is timed so the spikes engage the vessel at a desired portion thereof.

An aspect of some preferred embodiments of the invention relates to anastomotic devices that exhibit step-type behavior in which configuration changes from one configuration to another are sudden, rather than gradual. In a preferred embodiment of the invention, this step-type behavior is used to extend spikes which transfix blood vessels at a desired location relative to the anastomosis location and/or at a desired timing relative to the anastomosis process.

An aspect of some preferred embodiments of the invention relates to an anastomotic connector including a cylindrical body and one or more sets of spikes. In a preferred embodiment of the invention, the cylindrical body defines aperture therein, so that tissue on either side of the anastomotic connector can benefit from a significant amount of contact through the connector. The spikes are bent to engage the two blood vessels. In some cases, one set of spikes is bent outside the body and one set of spikes is bent inside the body. In another embodiment, both sets of spikes are bent or otherwise deformed inside the body. In still other embodiments all the spikes are deformed only outside the body. When the cylinder is expanded, the two blood vessels are brought into contact by the expansion, preferably forcefully, so that a better anastomosis results.

In a preferred embodiment of the invention, the cylinder comprises an array of parallelograms. Alternatively or additionally, the cylinder comprises a solid surface with slits cut therethrough, perpendicular and/or parallel to the axis of the cylinder. In a preferred embodiment of the invention, the coupling between the two axes (radial and axial) is mediated by the shape and/or other parameters of the parallelograms.

In a preferred embodiment of the invention, the coupling between the two axes is dependent on the radius. In one example, when the device is in a radially shrunk configuration, a small radial expansion will produce a large axial shrink. When the device is in a radially expanded configuration, a small additional expansion will only cause a small additional axial shrinkage. Alternatively, other relationships between shrinkage/expansion of the two axes may be used. The type of relationship may be modified by changing the shape and/or aspect ratio of some or all of the parallelograms. In a preferred embodiment of the invention, the relationship and/or elastic properties and/or other properties of the connector are selected for a particular vessel size being connected.

In a preferred embodiment of the invention, an anastomosis that is suspected of leaking may be repaired by radially expanding a connector of the anastomosis by a small amount, thereby causing axial shrinkage and a stronger contact between the two blood vessels.

Alternatively, a T-shaped stent may be attached over the anastomosis connector to repair the leak. Alternatively, in some preferred embodiments of the invention, the radial expansion may be decoupled from the axial shrinkage, at least for some ranges of radial expansion.

In a preferred embodiment of the invention, the anastomosis connector comprises an elastic material. Alternatively or additionally, the connector comprises a plastic material. In one example, in which spikes are plastically bent to engage the blood vessels, the cylinder comprises a super elastic, elastic or shape-memory material having an expanded resting position.

In a preferred embodiment of the invention, the connector comprises steel and/or other non-absorbable materials. Alternatively or additionally, the connector comprises bio-absorbable materials, so that after a period of time, no foreign materials will remain in the body. In one preferred embodiment of the invention, at least the spikes and/or other portions of the connector which are in contact with the blood are formed of a bio-absorbable material. Preferably, the bio-absorbable material is molded and/or crimped on non-bio-absorbable materials. Examples of possible bio-absorbable materials include poly-l-lactid-acid and poly-glycolid-acid, which can both be formed with elastic properties.

In a preferred embodiment of the invention, a connector having a similar type of coupling between radial expansion and axial contraction is used to attach two blood vessels with end-to-end or end-to-side anastomotic connections. Alternatively or additionally, a device with a similar configuration may be used to secure a valve in a blood vessel, such as the aorta or a vein. When the device is inflated, the spikes dig into the blood vessel to hold the valve in place. In these types of connection, axial compression is preferably minimal or non-existent. The device itself may be inserted over an existing valve, whereby the spikes and/or the cylindrical body may be used to compress the old valve against the walls of the blood vessel. Alternatively, the old valve may be cut out, in part or in full using a suitable catheter. In a preferred embodiment of the invention, the valve is inserted while the heart is pumping. The valve is preferably a soft leaflet valve.

In a preferred embodiment of the invention, the anastomosis connector is used for externally performed anastomotic connections, preferably keyhole surgery, instead of for an anastomosis performed from inside the blood vessel. In a preferred embodiment of the invention, two blood vessel ends are inserted into or over an anastomosis device while the device is in a compressed condition. The device is then inflated. Preferably the device comprises an elastic shape-memory or a super-elastic material so that it may be expanded by releasing a constraining ring or holder.

An aspect of some preferred embodiments of the invention relates to simultaneously attaching two blood vessels and increasing the size of a passageway between them. Preferably, such expansion is made possible using an inflatable balloon. Alternatively, a different type of expanding framework may be used, for example, a super-elastic, elastic or shape-memory framework which expands when a constraint is removed or a hinged construction in which pulling a wire causes the construction to increase at least one dimension thereof.

An aspect of some preferred embodiments of the invention relates to a clotting control coatings on an implantable device, for example anastomotic connectors, blood vessel patches, staples, threads and grafts (on their outside). In a preferred embodiment of the invention, the anastomotic device includes one or more of the following three types of portions: (a) a contact portion which is in contact with the blood stream; (b) a layered portion which is sandwiched between the two participating blood vessels; and (c) an outside portion which is outside both the blood vessels. In a preferred embodiment of the invention, a clot retarding material is coated on the contact portion of the anastomosis device. Alternatively or additionally, a clot enhancing material is coated on the layered and/or outside portions of the device. Alternatively or additionally, tissue growth enhancing hormones are coated on the layered and/or outside portions of the device. In some preferred embodiments of the invention, even though the anastomotic device is provided through a blood vessel, once it is deployed, it is in minimal or no contact with the blood flow. Preferably, less than 70%, 80%, 90% or even 98% of the surface of the anastomotic device is out of contact with the blood flow. This selective coating logic of an anastomosis device may also be applied to other implantable devices. Often, in implantable devices, one part of the device is in contact with blood and one is not. the side that is not in contact with blood is preferably treated to coagulate any blood it may come in contact with (for example as a result of a failure of the anastomosis device). Alternatively or additionally, the implant may be coated with a fibrosis inducing coating, for example a graft thus coated will better adhere to adjacent body structures. A surgical staple may have its tines coated with one material and its base with another. A thread may be coated in part with an anti-coagulation coating, for example during insertion into a blood vessel, and in part with a coagulation enhancing coating (for example a coating embedded in the thread or applied when the thread exits the blood vessel. Such coatings can be applied by a needle guiding element which is used in some anastomotic methods of the art.

An aspect of some preferred embodiments of the invention relates to an anastomotic connector which is partly super elastic, elastic and/or shape-memory and partly not. In a preferred embodiment of the invention, the connector is formed of a single material, which is then annealed at portions thereof to make those portions non super-elastic. Alternatively, a device is created from sintered material. The sintered material may have varying concentrations of constituent powered metals in different parts of the mold. In a preferred embodiment of the invention, the mold is for a tube and the tube is then cut, for example using a laser or using a water jet. In a preferred embodiment of the invention, the variations in material composition are radial and/or axial.

An aspect of some preferred embodiments of the invention relates to expandable anastomotic devices. In a preferred embodiment of the invention, the device can be radially and/or axially compressed so that it can be fit inside a blood vessel and/or a small aperture in a blood vessel. In some cases the device is provided through a patent blood vessel. In others, the device is provided from outside the a blood vessel to which it is later connected. In some cases, the graft and/or the connector are provided through the blood vessel, exposed to the blood flow. In a preferred embodiment of the invention, at least one of the anastomosis connectors has a shape which can be changed. This can make it easier to guide such a graft through a catheter and/or endoscope lumen. Preferably, the graft maintains a radially compressed configuration due to the radial compression of anastomotic connectors attached to the graft. Alternatively or additionally, the connectors are maintained radially compressed by an internal guide wire which restrains them from expanding. Alternatively or additionally, the connectors are plastically deformable. Preferably, the shape changing comprises radial shape changing, preferably expansion. Alternatively or additionally, especially where the connector is connected to the graft at a "side" side of the anastomosis, the connector is preferably compressed in a radial direction, so that in its compressed shape at least one radii thereof fits in a desired lumen diameter.

In a preferred embodiment of the invention, a blood vessel graft is brought through the vasculature to a location on a blood vessel and an independent and patent anastomosis between the graft and the blood vessel is formed. By "independent" it is meant that the anastomosis location does not leak, regardless of whether or not the other end is connected. In a preferred embodiment of the invention, the anastomosis is an end-to-side anastomosis, preferably the end being an end of the graft. Alternatively, the anastomosis is an end-to-end, side to side or oblique anastomosis. In a preferred embodiment of the invention, the blood vessel is an Aorta. Alternatively or additionally, the graft is a xenograft or formed of an artificial material.

In a preferred embodiment of the invention, the other end of the graft is also attached, via at least one additional anastomosis to a second blood vessel, preferably other than the first blood vessel. In a preferred embodiment of the invention, the graft is connected to a plurality of blood vessels, preferably using a plurality of side-to side anastomosis connections along its length. Alternatively or additionally, the graft is forked or otherwise has more than two ends each of which is preferably attached to different blood vessels or different positions on the same blood vessel.

Some features of preferred embodiments of the present invention relate to the first anastomosis connection (to the first vessel), while other features relate to the second anastomosis connection (to the second vessel). Many of the features can be applied to either or both of the connections.

An aspect of some preferred embodiments of the invention relates to a graft having attached thereto at least three independent anastomosis connectors. Preferably, at least one of the connectors is attached at an end of the graft. Alternatively or additionally, at least one of the connectors is a side-to-side or side-to-end connector where the graft is a "side" element in the anastomosis.

In a preferred embodiment of the invention, at least one of the anastomotic connectors comprises an everting connector, such that at least one side of the anastomosis, e.g., the graft, is everted over the connector. In some cases, both sides of the anastomosis are at least partially everted with the aid of the anastomotic connector.

In a preferred embodiment of the invention, these second anastomosis connections are performed percutaneously. Alternatively or additionally, these anastomotic connections are performed using key-hole surgery. In one preferred embodiment of the invention, the graft is a patch to be applied to the outside and/or inside of the blood vessel, rather than being a blood carrying vessel of itself. Thus, only one end of the graft is ever connected to a blood vessel.

An aspect of some preferred embodiments of the invention relates to methods and apparatus for creating a vessel aperture in a "side" of a side-to-end or a side-to side anastomosis. In a preferred embodiment of the invention, a small hole is formed and/or punched in the side blood vessel. Then, the hole is expanded so that an anastomotic connector may be inserted into the hole. Thereafter, the hole may be further enlarged, possibly by a radial force exerted by the anastomotic connector or by a device which expands the connector. In a preferred embodiment of the invention, the side vessel is elastically encouraged to reduce the diameter of the hole, thereby providing pressure against the end vessel, so that little or no blood leaks out of the anastomotic joint. In a preferred embodiment of the invention, the anastomosis is thus complete, except for a means for maintaining the end vessel at a minimum radius and inside the hole. Preferably, that means is provided by the anastomotic connector itself. In some preferred embodiments of the invention, the original hole is formed using a vibrating and/or rotating head.

In a preferred embodiment of the invention, the hole is formed in a blood vessel from inside the blood vessel. Preferably, a catheter with a hole forming mechanism at its end is bent 90 degrees, so that the end is perpendicular to the wall of the blood vessel. Possibly, the bend in the catheter rests against the blood vessel wall opposite the hole being formed. Alternatively or additionally, the catheter is provided with an increased stiffness so that less force is applied against the resting point on the blood vessel wall. Alternatively or additionally, the end mechanism grasps the wall of the blood vessel in which the aperture is formed so that little or no contra-force is required. For example, the mechanism can include a clamp and/or a suction tip for maintaining the wall of a blood vessel in a desired position while pushing a sharp guide wire tip through it. Alternatively or additionally to 90 degree connections into and out of blood vessels, at least one of the insertions is performed at an oblique angle to the vessel wall, for example, less than 80, less than 60, less than 40 or even less than 20 degrees. Alternatively or additionally, the final angle of the graft to the vessel is also oblique, for example, at these angles.

When the guide wire is pushed out of the opening made in the first blood vessel the graft is preferably brought out of the blood vessel along the guide wire. Preferably, the anastomotic device remains "stuck" in the opening in the first blood vessel. A balloon is preferably brought along the guide wire into the anastomosis connector and expanded. In some preferred embodiments of the invention, the anastomosis connector is topologically external to the blood vessel, however, due to folding of the vessels, it occupies space inside one or both the blood vessels and the graft. Preferably the anastomosis connector exits the first blood vessel when the anastomosis is completed so that it mostly external to the graft and the blood vessel. In some cases, the connector may have to be pushed out of the blood vessel.

In a preferred embodiment of the invention, the free end of the graft is navigated in the body until it is adjacent to a second blood vessel, at a desired location thereof. Preferably, this navigation is facilitated by an ultrasound imager and/or Doppler sensor, coupled to a guide wire or a catheter on which the graft is carried. Preferably, the sensor is situated outside of the graft, so that it can better sense its surroundings. Possibly, the graft is enclosed in an endoscope. Alternatively, the graft encloses an endoscope. In some cases, the first anastomosis is also performed after such guiding, for example if the graft is brought in to the chest cavity using key-hole surgical techniques.

An aspect of some preferred embodiments of the invention relates to the anastomosis of the graft to a blood vessel, after such navigation. A guide wire, possible the same guide wire as used for a first connection, is inserted into the second blood vessel, to create a hole in the vessel. The insertion may be done by simply pushing the guide wire into the vessel wall. Preferably, the guide wire is inserted into the second vessel for a considerable length. Optionally, the guide wire is bent and/or barbed so that it will not retract from the second vessel. Alternatively, a screw-tip guide wire may be used to screw the guide wire tip into the wall of the second blood vessel. The graft and the second anastomosis connector are brought along the guide wire and inserted into the hole in the second blood vessel, from inside the first blood vessel. Preferably, the attachment is by pushing the end of the graft, preferably with an anastomosis connector attached thereto, into a small hole in the target blood vessel and increasing the diameter of the anastomosis. A balloon is preferably brought along the guide wire to inflate the anastomosis connector and/or widen the opening in the second blood vessel. In a preferred embodiment of the invention, a suction device, for attaching to a moving organ such as the heart, is provide at or near the end of the graft, to steady the graft relative to movements of the heart.

Alternatively to using a balloon to inflate the connector, an anastomosis connector may comprise a super elastic material. In this case, the anastomosis connector is preferably maintained in a compressed position by an enclosing element. Once the connector is in place, the enclosing element is removed and the connector expands to a desired shape. The term "super elastic" is used herein to denote a material which returns to a desired shape when a restraint is removed. In some cases, an elastic material may suffice.

Alternatively or additionally, a shape memory alloy may be used and activated to return to the learned shape.

Alternatively or additionally to using a guide wire to make a pinhole and expanding the hole using an expandable anastomosis connector, a hole puncher (for example as described in the Background of the Invention) may be provided along the guide wire to cut out a portion of one or both the blood vessels. Alternatively or additionally, a slit or an x-shaped cut in the vessel wall may be made by the guide-wire.

In a preferred embodiment of the invention, the graft vessel is reinforced, on its inside and/or on its outside and/or in its body. Preferably, the reinforcing is along its entire length. Alternatively or additionally, only portions of the graft are reinforced, such as its ends or its middle. In a preferred embodiment of the invention, the reinforcing provides radial stiffness. Alternatively or additionally, the reinforcing provides axial stiffness. In a preferred embodiment of the invention, the type and/or degree of stiffness provided varies along the graft. In a preferred embodiment of the invention, the stiffness is symmetrical around the axis of the graft. Alternatively or additionally, the stiffness is asymmetrical, for example, if one side of the graft is to be in contact with the heart, that side may be made stiffer. In a preferred embodiment of the invention, an external spring is attached to the graft so that if the graft is too long, it will spiral gracefully, in a desired manner, rather than kink.

Many types of grafts and/or reinforced grafts are known in the art and they are generally all suitable for use in various embodiments of the present invention.

An aspect of some preferred embodiments of the invention relates to a method of attaching the anastomosis connector to the graft, prior to inserting the graft into the body. In a preferred embodiment of the invention, the anastomosis connector is covered with a flap of graft material and the covered connector is attached to the graft, such that the anastomosis is made via the flap. Preferably, the graft flap is glued to the graft. Alternatively or additionally, the anastomosis connector and/or the graft flap are sutured to the graft or otherwise connected, for example using short spikes. It should be appreciated that the graft flap may comprise a different material from the graft. For example, the flap may be Dacron and the graft may be a human blood vessel. In a preferred embodiment of the invention, the anastomosis connector is provided pre-attached to the flap, which flap is attached to the graft prior to the graft being inserted, either before or after the connector is attached to the flap. Alternatively, the flap is attached to the connector just before the graft is inserted into the body. In a preferred embodiment of the invention, an end of the graft is cut off and used as a flap for the anastomosis connector.

An aspect of some preferred embodiment of the invention relates to an anastomosis connector comprising two portions, which may be connected or separate. When the two portions of the connector are attached to each other to perform the anastomosis there is a reduced requirement to align the portions, at least with respect to their rotation around the graft axis, than with prior art devices. In a preferred embodiment of the invention, the anastomosis connector comprises two rings, one including connection spikes and the other comprising a friction material. When the anastomosis is performed, the spikes are imbedded into the friction material. Preferably, each one of the spikes passes through one or both of the blood vessels. Preferably, one or both of the rings may include eversion spikes, on which to evert the blood vessel. Alternatively or additionally, the connection spikes are used for eversion.

Alternatively or additionally, the two rings both include spikes and friction material. Alternatively or additionally, the two rings comprise a rigid material, such that some of the spikes in one ring match pre-defined holes in the other ring. In a preferred embodiment of the invention, the anastomosis connector is similar to a Nakayama ring anastomosis device, except that the rings are expandable in the present device. Preferably, the rings are expanded prior to their being connected to each other. Alternatively or additionally, the rings are expanded while being connected to each other. Preferably, the rings include a protrusion and/or a depression so that they can both be aligned, for example, using the guide wire or using a balloon with a guiding groove. Alternatively or additionally, the rings have an otherwise non-circular cross-section.

An aspect of some preferred embodiments of the invention relate to a kit, including measuring devices for determining the diameter of a graft, a set of anastomosis connectors having different properties and a delivery system for attaching the graft. Preferably, the kit includes a device for everting the graft over an anastomosis connector.

An aspect of some preferred embodiments of the invention relates to a device for punching holes in a blood vessel, form inside the blood vessel or from outside the blood vessel, where no blood leaks through the punched hole. In a preferred embodiment of the invention, a formed tip is pushed through a wall of the blood vessel and then an outer tube is pushed out over the tip, such that a portion of the vessel wall is captured between the tube and the tip and cut off. Leaking is preferably prevented by the pressure of the wall against the outer tube.

There is thus provided in accordance with a preferred embodiment of the invention, an anastomotic connector for attaching two blood vessels, comprising:
  a cylinder-like portion defining a lumen, having two ends and comprising an array of cells-elements; and
  a tissue engaging portion comprising at least one set of spikes comprising at least one spike arranged adjacent one of the two ends of said cylinder-like portion.
Preferably, said connector comprises at least a second set of spikes adjacent the other of the two ends.

There is also provided in accordance with a preferred embodiment of the invention, an anastomotic connector for attaching two blood vessels, comprising:
  a cylinder-like portion defining a lumen; and
  a plurality of tissue engaging portions for engaging two blood vessels, said plurality comprising at least one spike,
  where radial expansion of said cylinder-like portion causes said at least one spike to engage tissue. Preferably, radial expansion of said cylinder-like portion is de-coupled from axial contraction of said cylinder-like portion.

There is also provided in accordance with a preferred embodiment of the invention, an anastomotic connector for attaching two blood vessels, comprising:
  a cylinder-like portion defining a lumen; and
  a plurality of tissue engaging portions for engaging two blood vessels,
  where radial expansion of said cylinder-like portion is coupled to axial contraction of said cylinder-like portion. Preferably, at a maximum radial expansion, a ratio between axial contraction and radial expansion is more than about 1:10. Alternatively, at a maximum radial expansion, a ratio between axial contraction and radial expansion is between than about 1:10 and 1:5. Alternatively, at a maximum radial expansion, a ratio between axial contraction and radial expansion is between than about 1:5 and 1:2. Alternatively, at a maximum radial expansion, a ratio between axial contraction and radial expansion is between than about 1:2 and 1:1. Alternatively, at a maximum radial expansion, a ratio between axial contraction and radial expansion is between than about 1:1 and 2:1. Alternatively, at a maximum radial expansion, a ratio between axial contraction and radial expansion is between than about 2:1 and 4:1. Alternatively, at a maximum radial expansion, a ratio between axial contraction and radial expansion is less than about 4:1.

In a preferred embodiment of the invention, said radial expansion activates at least one of said tissue engaging portions. Alternatively or additionally, at least one of said tissue engaging portions comprises at least one spike.

In a preferred embodiment of the invention, said cylinder-like portion comprises a plurality of cell elements. Alternatively or additionally, said cylinder-like portion comprises a plurality of cell elements.

In a preferred embodiment of the invention, said at least one spike is arranged to extend out of said lumen when said tissue engaging portions engage tissue in a completed anastomosis. Preferably, said extended spike lies in a plane tangent to said cylinder-like portion. Alternatively or additionally, said extended spike lies in a plane perpendicular to said cylinder-like portion.

In a preferred embodiment of the invention, said at least one spike is arranged to extend into said lumen when said tissue engaging portions engage tissue in a completed anastomosis. Alternatively or additionally, said device is arranged to cantilever said at least one spike into an extended configuration by an expansion of said cylinder-like portion. Alternatively or additionally, said device is arranged to release said at least one spike to assume an extended configuration by an expansion of said cylinder-like portion. Alternatively or additionally, a portion of said cylinder-like portion is arranged to deform into said at least one spike, by an expansion of said cylinder-like portion. Alternatively or additionally, said spike is pre-stressed to lie outside of an axial profile of said cylinder-like portion. Alternatively or additionally, said spike is coupled to a base, and pivotally connected to said cylinder-like portion and where said base extends into said lumen. Alternatively or additionally, said cylinder-like portion includes a plurality of weakenings, such that plastically deforming said cylinder-like portion will extend said spikes to engage said tissue.

Alternatively or additionally, said cylinder-like portion comprises a bi-stable cell, which cell extends said spike in one state and not in the other one of said states. Alternatively or additionally, said cylinder-like portion is arranged to twist, in at least one location thereon, which location is coupled to said at least one spike, whereby said twist causes said spike to extend. Alternatively or additionally, said spike comprises a protrusion to prevent engaged tissue from slipping off said spike. Alternatively or additionally, said spike comprises a protrusion to prevent engaged tissue from slipping along said spike beyond said protrusion. Alternatively or additionally, said spike is arranged to bend at least 90° when it extends. Alternatively or additionally, said spike is arranged to bend at least 150° when it extends. Alternatively or additionally, said spike is arranged to bend at least 180° when it extends. Alternatively or additionally, said spike is arranged to bend at least 210° when it extends. Alternatively or additionally, said spike is arranged to bend at one point thereon when it extends.

Alternatively or additionally, said spike is arranged to bend at at least two points thereon when it extends. Alternatively or additionally, said spike is arranged to bend in a continuous curve when it extends. Alternatively or additionally, said spike is arranged to engages said tissue when it is axially retracted relative to the cylinder-like portion. Preferably, said at least one spike comprises a plurality of spikes and where each of said spikes is independently retractable.

In a preferred embodiment of the invention, said at least one spike comprises at least two spikes and said connector comprises at least a second spike and said second spike is arranged to bend towards said at least one spike and said at least one spike is arranged to bend towards at least a second spike. Preferably, spikes of said at least a second spike are arranged in a radially staggered configuration relative to said at least two spikes.

In a preferred embodiment of the invention, said at least one spike is associated with an individual flat coil spring. Alternatively or additionally, said at least one spike is associated with an axial cell element, which cell element selectively retracts or extends said spike.

In a preferred embodiment of the invention, spikes of said at least a second spike are arranged to be in a same plane as spikes of said at least one spike, when the spikes are in a bent configuration.

In a preferred embodiment of the invention, said lumen has an elliptical cross-section. Alternatively, said lumen has a circular cross-section. Alternatively or additionally, said lumen has a polygonal cross-section. Alternatively or additionally, said lumen has fixed inner diameter.

Alternatively, said lumen has a varying inner diameter. Preferably, said inner diameter has an hourglass profile, being flared at the ends of the lumen. Alternatively, said lumen is flared at one end of the lumen.

In a preferred embodiment of the invention, a cross-section of said lumen varies along said lumen. Alternatively or additionally, said lumen is matched to a coronary vessel. Preferably, said matching includes matching a degree of obliqueness of the lumen cross-section.

In a preferred embodiment of the invention, at least one of said cell elements has parallelogram geometry. Alternatively or additionally, at least one of said cell elements has an elliptical geometry. Alternatively or additionally, at least one of said cell elements comprises a ratchet for maintaining said cell element in a distorted configuration, once such a configuration is achieved. Alternatively or additionally, at least one of said cell elements is arranged to distort out of a plane of said cell, when that cell is expanded along a certain axis thereof. Alternatively or additionally, at least one of said cell elements comprises an outline geometrical shape. Alternatively at least one of said cell elements comprises a substantially full geometrical shape.

In a preferred embodiment of the invention, at least one of said cell elements is planar. Alternatively or additionally, at least one of said cell elements is not planar. Alternatively or additionally, said cells are arranged as bands on at least a portion of said cylinder-like portion, each of said bands comprising substantially a single type of parallelogram. Preferably, said bands are axial bands. Alternatively or additionally, said bands are circumferential bands.

In a preferred embodiment of the invention, substantially all of said cylinder-like portions is composed of cell-elements. Alternatively or additionally, said cell elements meet at junctions and the device comprises at least one substantially rigid strut interconnecting at least two junctions. Alternatively or additionally, said cell elements meet at junctions and the device comprises at least one substantially flexible wire interconnecting at least two junctions. Alternatively or additionally, said cylinder-like portion comprises several cell types and where said cell types are uniformly distributed on said cylinder-like portion.

In a preferred embodiment of the invention, said cylinder-like portion comprises several cell types and said cell types are non-uniformly distributed on said cylinder-like portion. Preferably, said distribution is symmetric. Alternatively, said distribution is asymmetric.

In a preferred embodiment of the invention, the device comprises one or more pressure protrusions on said cylinder-like portion, where said one or more pressure protrusions are arranged to increase a contact pressure between said two blood vessel when said device is deployed.

In a preferred embodiment of the invention, said cylinder-like portion comprises at least one part which is plastically deformable at a force which does not deform other parts of said portion. Preferably, at least one of said other parts reacts elastically at said force. Alternatively or additionally, said part includes weakenings which guide the plastic distortion of said part.

In a preferred embodiment of the invention, said cylinder-like portion comprises at least one part which is super-elastic. Alternatively or additionally, said cylinder-like portion comprises at least one part which comprises a temperature-triggered shape-memory material. Alternatively or additionally, said cylinder-like portion comprises at least one part which comprises a temperature-responsive bi-material composite, which changes its geometry under the effect of small temperature changes. Alternatively or additionally, at least one of tissue engagers comprises at least one part which is plastically deformable at a force which does not deform other parts of said tissue engagers. Preferably, at least one of said other parts reacts elastically at said force. Alternatively or additionally, said part includes weakenings which guide the plastic distortion of said part.

In a preferred embodiment of the invention, said at least one of tissue engagers comprises at least one part which is super-elastic. Alternatively or additionally, said at least one of tissue engagers comprises at least one part which comprises a temperature-triggered shape-memory material.

In a preferred embodiment of the invention, said anastomotic connector is adapted to engage a side of one of said vessels and an end of another of said vessels, to perform a side-to-end anastomosis. Preferably, said anastomosis is sealed by radial pressure exerted by said cylinder-like portion and where said tissue engagers maintain the cylinder-like portion in its position. Alternatively or additionally, said tissue engagers maintain the relative positions of the two blood vessels. Alternatively or additionally, said tissue-engaging portions are arranged on said cylinder-like portion such that when the anastomosis is complete, the cylinder like portion is at a certain angle perpendicular to the "side" vessel. Preferably, said certain angle is between about 70° and about 90°. Alternatively, said certain angle is between about 50° and about 70°. Alternatively, said certain angle is less than about 50°.

In a preferred embodiment of the invention, a cross-section of said lumen is matched to said certain angle.

In a preferred embodiment of the invention, said anastomotic connector is adapted to engage an end of one of said vessels and an end of another of said vessels, to perform an end-to-end anastomosis. Preferably, said connector is adapted to be implanted outside of a vascular system.

In a preferred embodiment of the invention, said anastomotic connector is adapted to engage a side of one of said vessels and a side of another of said vessels, to perform a side-to-side anastomosis. Preferably, said connector is adapted to be implanted outside of a vascular system.

In a preferred embodiment of the invention, said device is composed, at least in part, of a bio-absorbable material. Alternatively or additionally, said cylinder-like portion is composed wholly of a bio-absorbable material. Alternatively or additionally, at least one of said tissue engaging portions is composed wholly of a bio-absorbable material.

In a preferred embodiment of the invention, at least one of said tissue engagers is adapted to engage an everted graft. Alternatively or additionally, at least one of said tissue engagers is adapted to engage a non-everted graft. Alternatively or additionally, at least one of said tissue engagers is adapted to both an everted and a non-everted graft.

In a preferred embodiment of the invention, all of said tissue engagers are adapted to engage said blood vessels inside a body.

In a preferred embodiment of the invention, said cylinder-like portion has an axial dimension of about 0.5 millimeters. Alternatively, said cylinder-like portion has an axial dimension of between about 0.5 millimeters and 2 millimeters. Alternatively, said cylinder-like portion has an axial dimension of between about 2 millimeters and 5 millimeters. Alternatively, said cylinder-like portion has an axial dimension of between about 5 millimeters and 8 millimeters.

In a preferred embodiment of the invention, said cylinder-like portion has a ratio of about 1:1 between its axial dimension and its diameter. alternatively, said cylinder-like portion has a ratio of between about 1:1 and about 1:2 between its axial dimension and its diameter. Alternatively, said cylinder-like portion has a ratio of between about 1:2 about 1:4 between its axial dimension and its diameter. Alternatively, said cylinder-like portion has a ratio of between about 1:4 about 1:8 between its axial dimension and its diameter.

In a preferred embodiment of the invention, said cylinder-like portion is arranged to expand radially by a factor of less than about 1.5. Alternatively, said cylinder-like portion is arranged to expand radially by a factor of between 2 and 4. Alternatively, said cylinder-like portion is arranged to expand radially by a factor of between 4 and 8.

There is also provided in accordance with a preferred embodiment of the invention, an anastomotic connector for attaching two blood vessels, comprising:
  a cylinder-like portion defining a lumen; and
  a plurality of tissue engaging portions for engaging the blood vessels, said plurality comprising at least two spikes,
  where said two spikes extend differently to engage said tissue. Preferably, said spikes bend differently. Alternatively or additionally, said spikes engage the same blood vessel. Alternatively, said spikes engage different blood vessels.

In a preferred embodiment of the invention, said two spikes are arranged to extend simultaneously. Alternatively, said two spikes are arranged to extend sequentially. Alternatively, said two spikes are arranged to extend semi-sequentially, such that there is an overlap between their motion.

In a preferred embodiment of the invention, said two spikes are extended by a same distortion of said cylinder-like portion. Alternatively, the extension of at least one of said spikes is decoupled from distortion of said cylinder-like portion.

In a preferred embodiment of the invention, said two spikes are extended by different degrees of radial expansion of said cylinder-like portion.

In a preferred embodiment of the invention, said extension comprises impaling a portion of a blood vessel. Alternatively or additionally, said extension comprises transfixing a portion of a blood vessel. Alternatively or additionally, said extension comprises pinching a portion of a blood vessel.

There is also provided in accordance with a preferred embodiment of the invention, an anastomotic connector for attaching two blood vessels, comprising:
  a cylinder-like portion defining a lumen; and
  a plurality of tissue engaging portions for engaging the two blood vessels,
  where said connector has at least two configurations, a first configuration in which said tissue engaging portions are at a first extension state and a second configuration where said tissue engaging portions are at a second extension state, where said connector exhibits a bi-modal behavior in changing from said first configuration to said second configuration.

Preferably, said configuration change is effected by expanding said cylinder-like portion. Alternatively or additionally, said configuration change comprises the extension of a plurality spikes. Alternatively or additionally, the connector comprises at least one bi-stable element that controls said configuration change. Alternatively or additionally, the connector comprises at least one restraining element that controls said configuration change.

There is also provided in accordance with a preferred embodiment of the invention, an anastomotic connector for attaching two blood vessel, comprising:
  a cylinder-like portion defining a lumen; and
  a plurality of tissue engaging portions for engaging the two blood vessels,
  where said connector has at least two configurations, a first configuration in which said tissue engaging portions form a vessel piercing tip and a second configuration where said tissue engaging portions are operative to engage tissue.

Preferably, said plurality of tissue engaging portions comprise at least one spike. Alternatively or additionally, said plurality of tissue engaging portions are arranged at one end of said cylinder-like portions and the connector comprises a second plurality of tissue engaging portions adjacent the other end of said cylinder-like portion.

There is also provided in accordance with a preferred embodiment of the invention, an implantable device comprising:
  a first portion designed to come in contact with blood; and
  a second portion designed not to come in contact with blood,
  where said second portion is coated with a coagulation-promoting material.

Preferably, said device is an anastomosis connector. Alternatively or additionally, said device is a vascular device for sealing a hole in a blood vessel.

In a preferred embodiment of the invention, said first portion is coated with a coagulation-retarding material.

There is also provided in accordance with a preferred embodiment of the invention, a graft kit, comprising:
  a sterility-maintaining packaging; and
  a graft having at least two ends and having a side-to-end anastomotic connector attached to at least one of said two ends, where said anastomotic connector includes spikes for engaging a blood vessel.

Preferably, the kit comprises a restrainer for maintaining said spikes in an unengaged configuration.

There is also provided in accordance with a preferred embodiment of the invention, a graft comprising:
  a tubular body having at least one intersection, such that said body has at least three ends; and
  at least two end-to-side anastomotic connectors attached to at least two of said three ends.

There is also provided in accordance with a preferred embodiment of the invention, a hole puncher, adapted for punching a hole in a blood vessel, comprising:
  an outer tube having distal portion, which distal portion has a lip;
  a punch element having a sharp tip and defining a depression distal from the tip, where said depression is of a size adapted to receive a blood vessel,
  where said distal portion of said outer tube has an outer diameter which is substantially the same as an outer diameter of said punch element and where said punch element fits snugly in said distal portion such that said lip can sever blood vessel tissue contained in said depression from tissue outside said depression.

Preferably, said depression is distanced from said tip so that said distance is at least the thickness of the blood vessel. Alternatively or additionally, said puncher is flexible enough to be provided through a blood vessel in which a hole is to be punched.

In a preferred embodiment of the invention, the puncher comprises a handle. preferably, the puncher comprises means for advancing said outer tube relative to said handle and relative to said punch element. Alternatively or additionally, the puncher comprises means for retracting said punch element relative to said handle and relative to said outer tube.

In a preferred embodiment of the invention, the puncher comprises means for advancing a graft into said hole formed by said punch. Alternatively or additionally, the puncher comprises a valve for preventing blood from leaking out of said outer tube once said punch element is removed. Alternatively or additionally, said distal end comprises a stop for preventing entry of said distal end into said hole beyond said stop. Preferably, said stop is at an oblique angle relative to a main axis of said distal end, to guide said hole puncher to form an oblique punch.

In a preferred embodiment of the invention, the puncher comprises a stop for prevention advance of said punch element relative to said distal end, beyond a pre-defined distance. Alternatively or additionally, said punch element is radially expandable from a first, small diameter to a second, working diameter. Alternatively or additionally, said distal end is radially expandable from a first, small diameter to a second, working diameter. Alternatively or additionally, said depression in said punch element is at an oblique angle relative to a main axis of said punch element, whereby an oblique hole is punched thereby. Alternatively or additionally, said lip of said outer tube is at an oblique angle relative to a main axis of said outer tube, whereby an oblique hole is punched thereby. Alternatively or additionally, said hole puncher is arranged to punch an oblong hole.

There is also provided in accordance with a preferred embodiment of the invention, apparatus for everting a vessel over an anastomotic connector, comprising:
  a vessel holder for holding said vessel; and
  an expander, adapted to engage said vessel, at least at an end of said expander, which expander expands from a diameter of less than a diameter of said vessel to a diameter greater than that of said vessel and where in said expanded diameter, said at least said portion can enclose at least a portion of said vessel holder.

Preferably, the apparatus comprises means for selectively moving said expander relative to said vessel, such that said engaged portion overlaps said vessel holder. Alternatively or additionally, the apparatus comprises a holder for an anastomotic connector. Preferably, the apparatus comprises a retainer for maintaining said anastomotic connector in a desired configuration during at least a portion of said eversion.

In a preferred embodiment of the invention, apparatus is separable into two pieces. Alternatively or additionally, the apparatus comprises a guide for maintaining coaxiallity between said vessel holder and said expander. Preferably, said guide comprises an intra-lumen vessel engager for engaging said vessel.

There is also provided in accordance with a preferred embodiment of the invention, a tip mechanism for forming a hole in a blood vessel, from inside the blood vessel, comprising:
    a wire portion;
    a tip coupled to said wire portion; and
    a motor coupled to said tip and adjacent to said tip. Preferably, said wire is at least 10 cm long.

In a preferred embodiment of the invention, said tip is a sharp tip. Alternatively or additionally, said motor is a piezoelectric motor. Alternatively, said motor is a magnetostrictive motor. Alternatively, said motor moves said tip in a rotational motion around a main axis of said wire.

In a preferred embodiment of the invention, said motor moves said tip in an axial motion along a main axis of said wire.

In a preferred embodiment of the invention, said tip is smooth. Alternatively, said tip includes protrusions for engaging soft tissue.

In a preferred embodiment of the invention, said tip has a geometry matched to a geometry of said motor, such that an amplitude of motion of said tip is at least twice the amplitude of said motor.

There is also provided in accordance with a preferred embodiment of the invention, a patch for sealing a hole in a blood vessel, comprising:
    a body which can be selectively collapsed or expanded, such that the patch fits inside an catheter having a diameter suitable for travel in said blood vessel;
    a plurality of tissue engaging elements on said patch; and
    a seal,
    where, when said device is expanded, placed over the hole and the tissue engaging elements engage said vessel, said seal seals said hole.

There is also provided in accordance with a preferred embodiment of the invention, a framework for an endoscopic procedure, comprising:
    a body which can be selectively collapsed or expanded, such that it fits through a tube used to access a surgical area;
    fixation members for attaching said body to tissue at said surgical area; and
    guidance members for guiding one or more tools at said area to perform said endoscopic procedure,
    where said body is operative not to be rigidly coupled to said tube while in a surgical area.

Preferably, said framework has a plurality of stable configurations and where said stable configurations are matched to a particular endoscopic procedure. Preferably, said configurations are achieved by selectively inflating at least one balloon coupled to said framework.

In a preferred embodiment of the invention, the framework comprises a safety line for attaching said framework to a tool which exits said body. Alternatively, is unattached to said tube.

There is also provided in accordance with a preferred embodiment of the invention, a method of performing a bypass, comprising:
    transvascularly providing a graft at a first location in a vascular system;
    forming a hole at said location;
    expelling at least most of said graft out of said hole;
    navigating said graft adjacent a second hole in said vascular system;
    forming a hole at said second location;
    percutaneously performing a first independently patent anastomosis at said first location, which anastomosis does not occlude said vascular system at said first location; and
    percutaneously performing a second independently patent anastomosis at said second location, which anastomosis does not occlude said vascular system at said second location. Preferably, at least one of said first and said second anastomotic connections is performed such that no portion of an anastomotic connector remains in contact with blood in said vascular system. Alternatively or additionally, at least one of said first and said second anastomotic connections is a side-to-side anastomosis. Alternatively or additionally, at least one of said first and said second anastomotic connections is a side-to-end anastomosis. Alternatively or additionally, at least one of said first and said second anastomotic connections is an intima-to-intima anastomosis. Alternatively or additionally, at least one of said first and said second anastomotic connections is an anastomosis between an intima and a inside of a vessel wall.

In a preferred embodiment of the invention, at least most of a graft comprises all of the graft. Alternatively, at least most of a graft comprises all of the graft except for a lip thereof.

In a preferred embodiment of the invention, only an intima of said lip is exposed to blood in said vascular system.

In a preferred embodiment of the invention, expelling at least most of a graft comprises expelling all of the graft out of the lumen of said vessel while maintaining a portion of said graft in a cross-section of sad vessel wall.

There is also provided in accordance with a preferred embodiment of the invention, a method of performing an anastomosis, comprising:
    transvascularly providing a graft at a location in a vascular system;
    forming a hole at said location;
    expelling said graft completely out of said hole; and
    transvascularly performing an independently patent anastomosis at said location, which anastomosis does not occlude said vascular system at said location. Preferably, said anastomosis is a side-to-end anastomosis. Alternatively, said anastomosis is an end-to-end anastomosis.

In a preferred embodiment of the invention, said anastomosis is performed using an anastomotic connector and where said connector is completely outside a blood flow of said vascular system after said anastomosis.

Alternatively or additionally, said anastomosis is performed using an anastomotic connector and where said only spike portions of said connector are in contact with a blood flow of said vascular system after said anastomosis.

Alternatively or additionally, said anastomosis is performed using an anastomotic connector and where said connector forms said hole.

There is also provided in accordance with a preferred embodiment of the invention, a method of anastomosis comprising:

providing an expandable anastomotic device; and inflating said device to simultaneously open an anastomotic passage and perform an anastomotic connection.

There is also provided in accordance with a preferred embodiment of the invention, a method of anastomosis attachment comprising:

inserting an anastomotic device to attach two blood vessels; and inflating a balloon in said device if said attachment leaks.

There is also provided in accordance with a preferred embodiment of the invention, a method of punching a hole in a blood vessel, comprising:

providing a hole puncher to a location in a vascular system, which location has blood flowing therethrough;

transfixing a wall of said vascular system at said location;

removing a portion of said wall using said hole puncher, while said hole-puncher remains transfixing said wall; and transporting a tool across said wall through a lumen of said hole puncher.

Preferably, said removing comprises partially retracting a portion of said hole puncher.

Alternatively or additionally, said removing comprises partially advancing a portion of said hole puncher.

In a preferred embodiment of the invention, the method comprises using said tool to perform an anastomosis connection. Alternatively or additionally, said providing is from inside of said vascular system. Alternatively or additionally, said providing is from outside of said vascular system.

There is also provided in accordance with a preferred embodiment of the invention, a method of everting a graft over an anastomotic connector, comprising:

sliding said anastomotic connector over said vessel, to a point adjacent an end of the vessel;

expanding a portion of said vessel between said point and said end; and everting said expanded portion over of said connector. Preferably, said everting and said expanding use a same tool.

In a preferred embodiment of the invention, the method comprises transfixing said vessel at or about said portion with an anastomotic connector.

There is also provided in accordance with a preferred embodiment of the invention, a method of performing a side to end anastomosis, comprising:

providing a graft to a location on a side of a blood vessel;

forming a hole in said side blood vessel;

engaging one face of said side of the blood vessel, using an anastomosis connector to perform a first portion of the anastomosis; and completing the anastomosis by engaging the second face of said side using the anastomosis connector.

Preferably, said providing is from inside of said blood vessel. Alternatively, said providing is from outside of said blood vessel.

There is also provided in accordance with a preferred embodiment of the invention, a method of performing a bypass procedure, comprising:

transvascularly providing a graft at a first location in a vascular system;

expelling at least most of said graft out of a hole at said first location;

navigating an end of said graft to a second location in said vascular system;

performing an anastomosis at said second location; and thereafter transfixing said graft to said vascular system at said first location, using an anastomotic connector.

There is also provided in accordance with a preferred embodiment of the invention, a method of performing an anastomosis, comprising:

providing a graft at a location in a vascular system;

forming a hole at said location; and simultaneously expanding said hole and completing an anastomotic connection between said graft and said vascular system at said location. Preferably, said forming and said expanding comprises a continuous process. Alternatively, said forming and said expanding comprises a discrete step process.

BRIEF DESCRIPTION OF THE DRAWINGS

The invention will be more clearly understood by reference to the following description of preferred embodiments thereof in conjunction with the figures, wherein identical structures, elements or parts which appear in more than one figure are labeled with the same numeral in all the figures in which they appear, in which:

FIGS. 2A–2I illustrate a bypass technique in accordance with a preferred embodiment of the invention;

FIGS. 2J–2P illustrate a variation of the method of FIGS. 2A–2I, in accordance with a preferred embodiment of the invention;

FIGS. 2Q–2T illustrate hole making mechanisms in accordance with preferred embodiments of the invention;

FIGS. 2TA and 2TB illustrate a method of punching a hole in a blood vessel, in accordance with a preferred embodiment of the invention;

FIGS. 7C–7N illustrate various mechanisms for extending spikes out of a surface of the anastomotic device, in accordance with a preferred embodiment of the invention;

FIG. 7O illustrates a parallelogram portion of a connector, which includes a ratchet mechanism for preventing collapsing of the connector, in accordance with a preferred embodiment of the invention;

FIGS. 7P–7R illustrate a two stage folding of a pair of spikes, in accordance with a preferred embodiment of the invention;

Figure 8A:
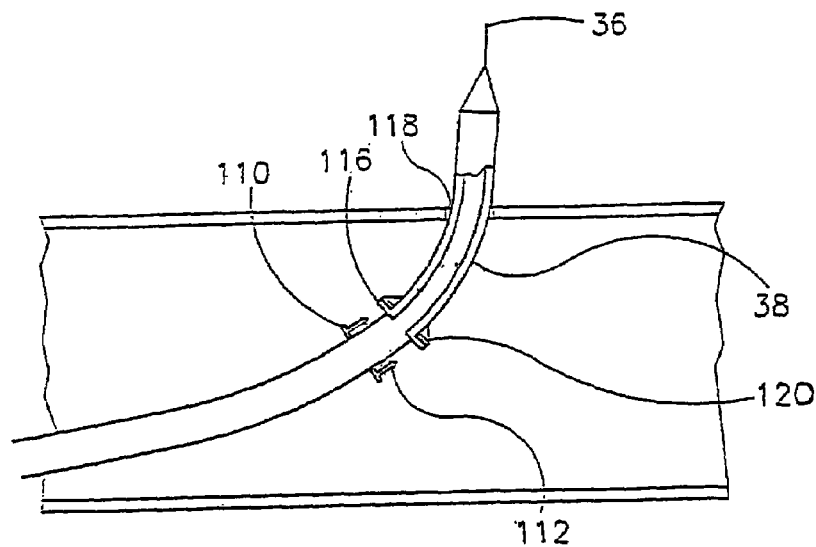
FIGS. 8A–8E illustrate an implantation of an orientation independent two piece anastomosis device and an exemplary device, in accordance with a preferred embodiment of the invention.
Figure 8B:
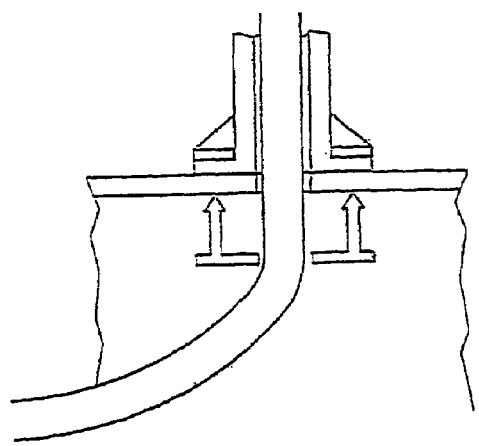
Figures 8C, 8D:
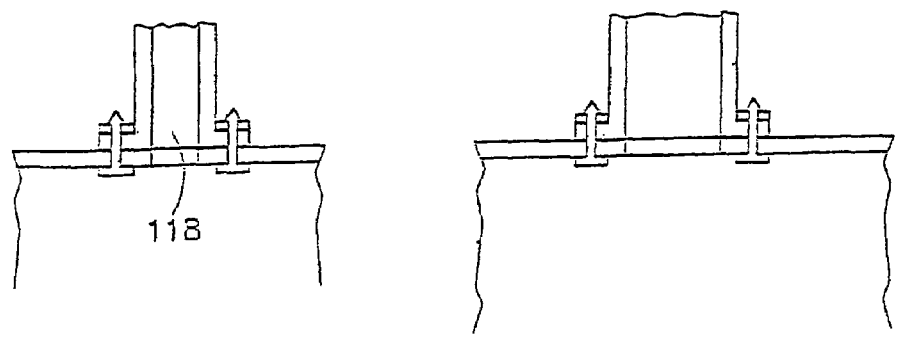
Figure 8E:
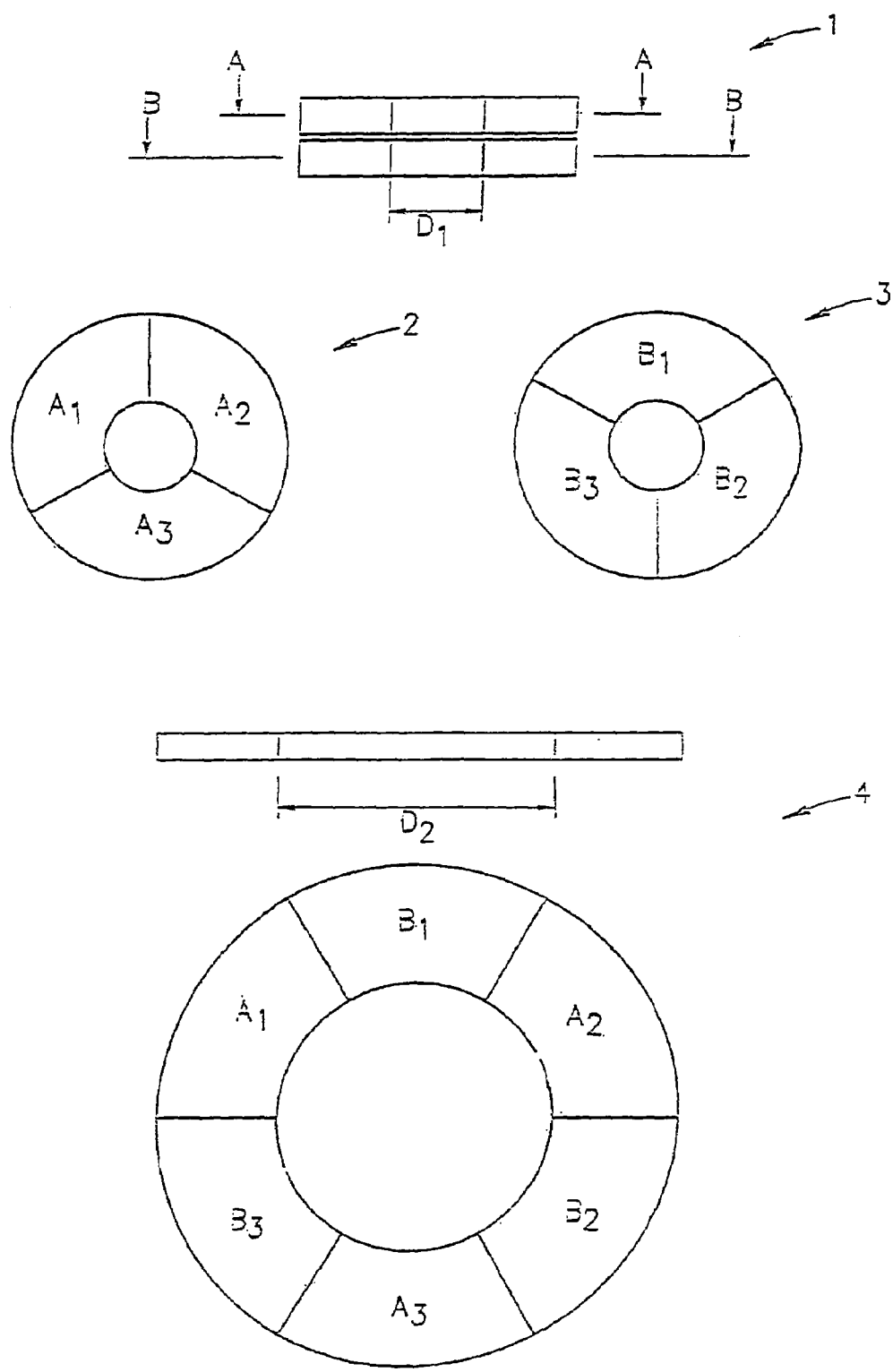
Figure 8F:
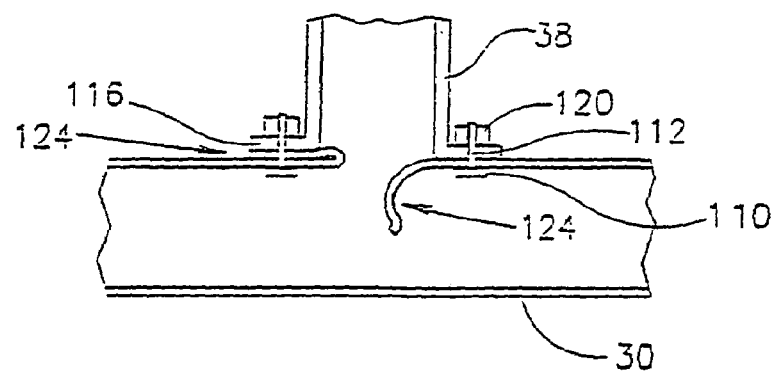
FIGS. 8F–8I illustrate various configurations of anastomotic connections, in accordance with preferred embodiments of the invention.
Figure 8G:
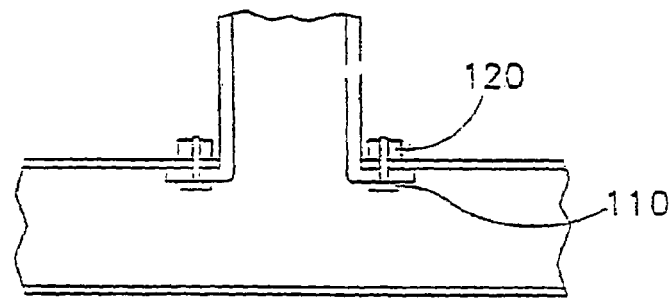
Figure 8H:
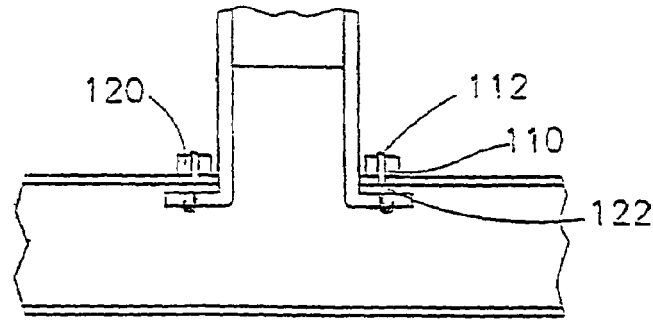
Figure 8I:
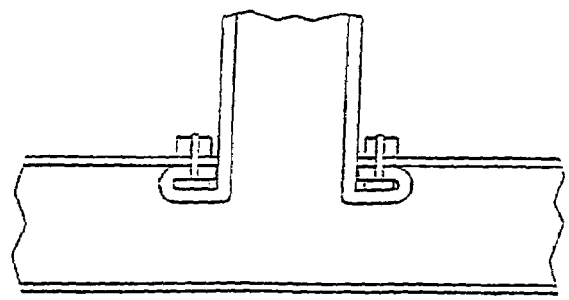
Figure 8J:
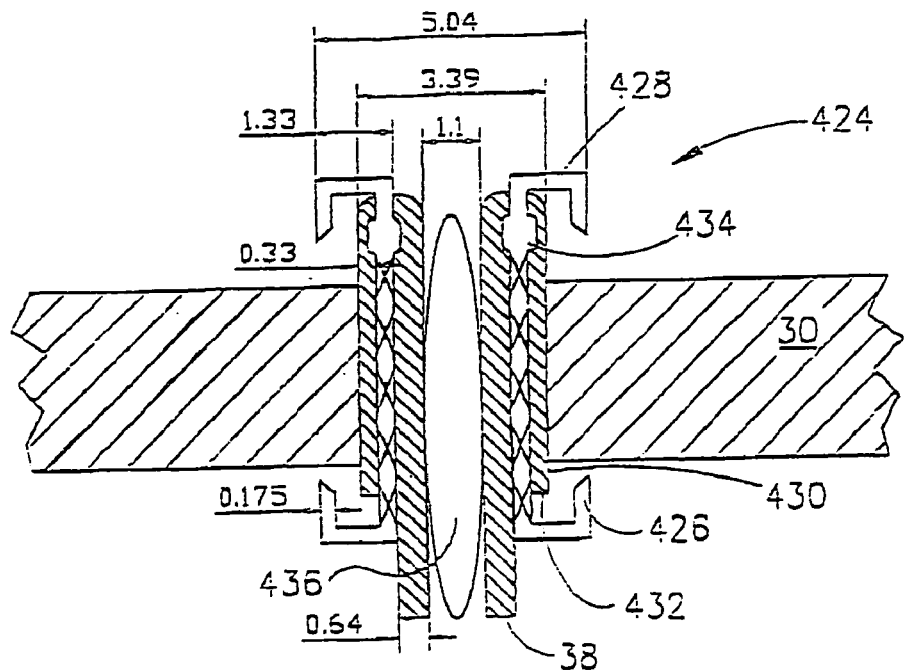
FIGS. 8J–8M and 8O–8P illustrate a family of alternative anastomotic connectors and their deployment, in accordance with preferred embodiments of the invention.
Figure 8K:
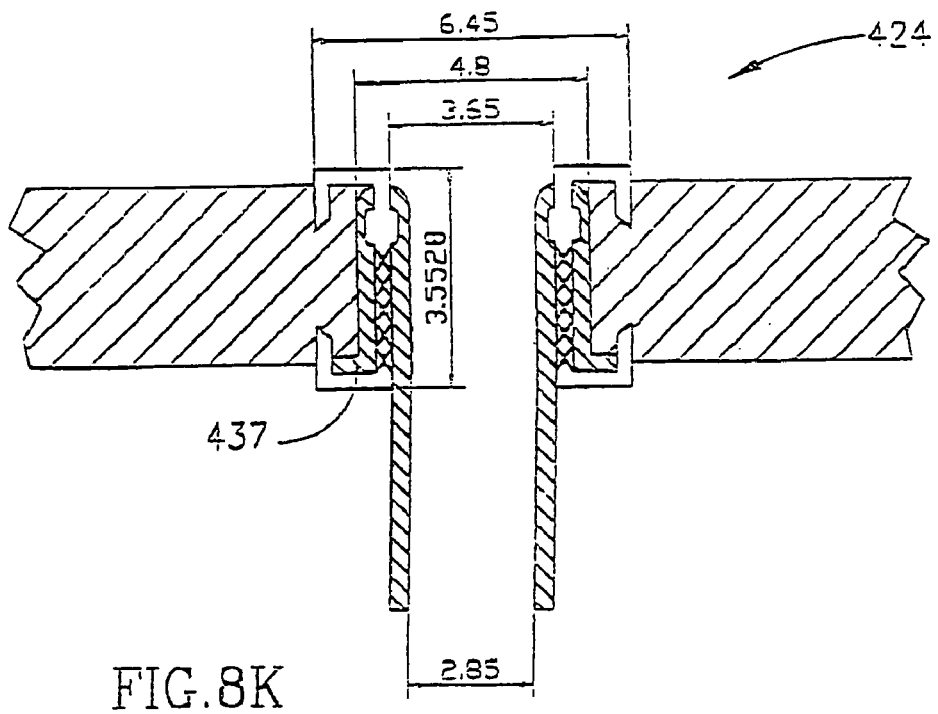
Figure 8L:
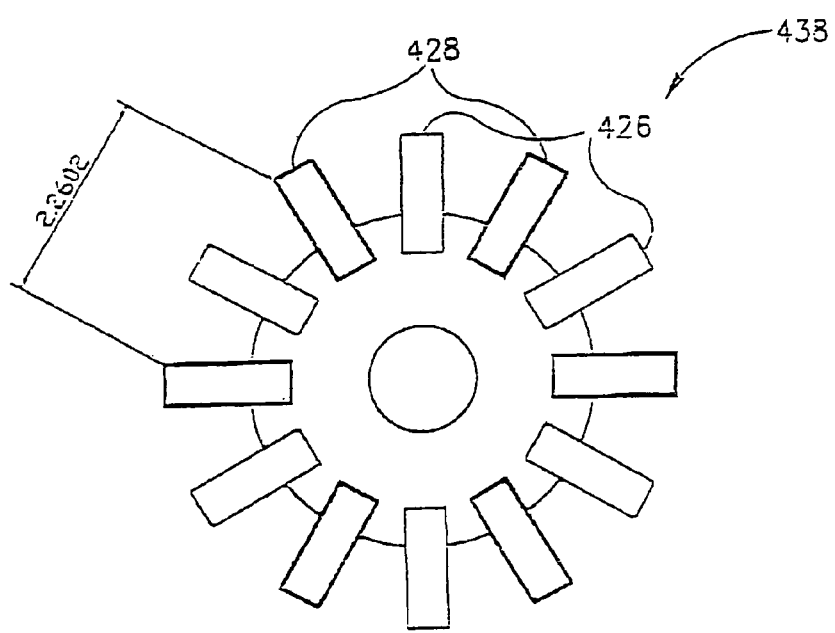
Figure 8M:
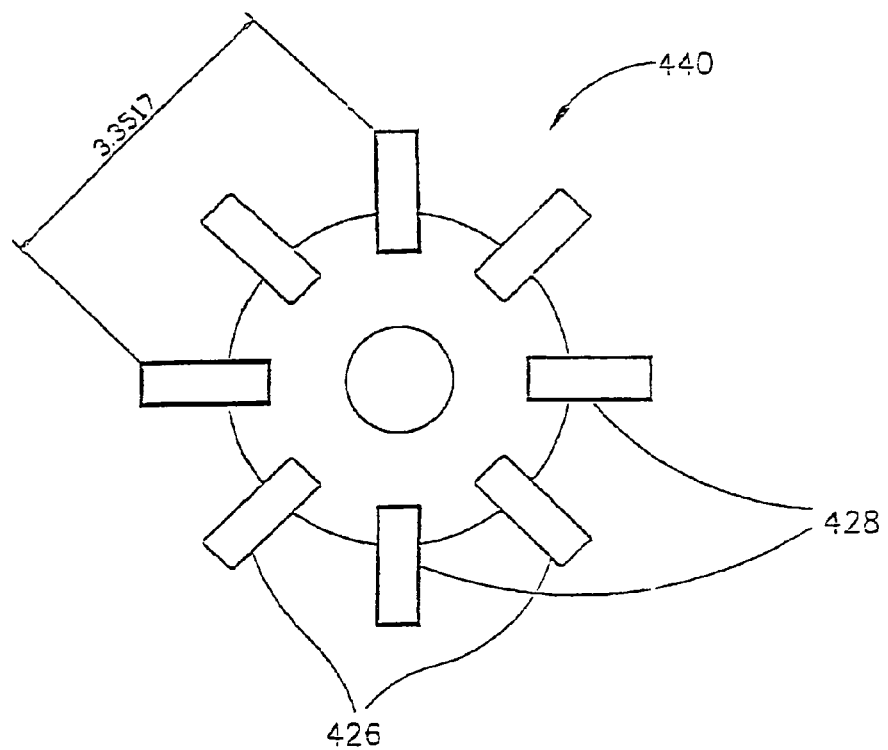
Figure 8O:
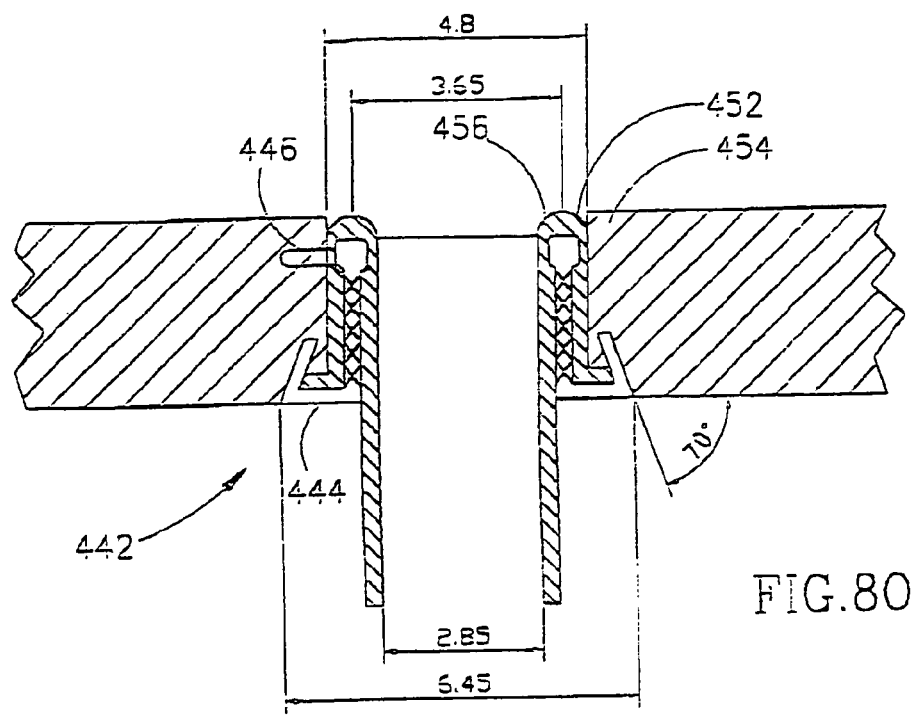
Figure 8P:
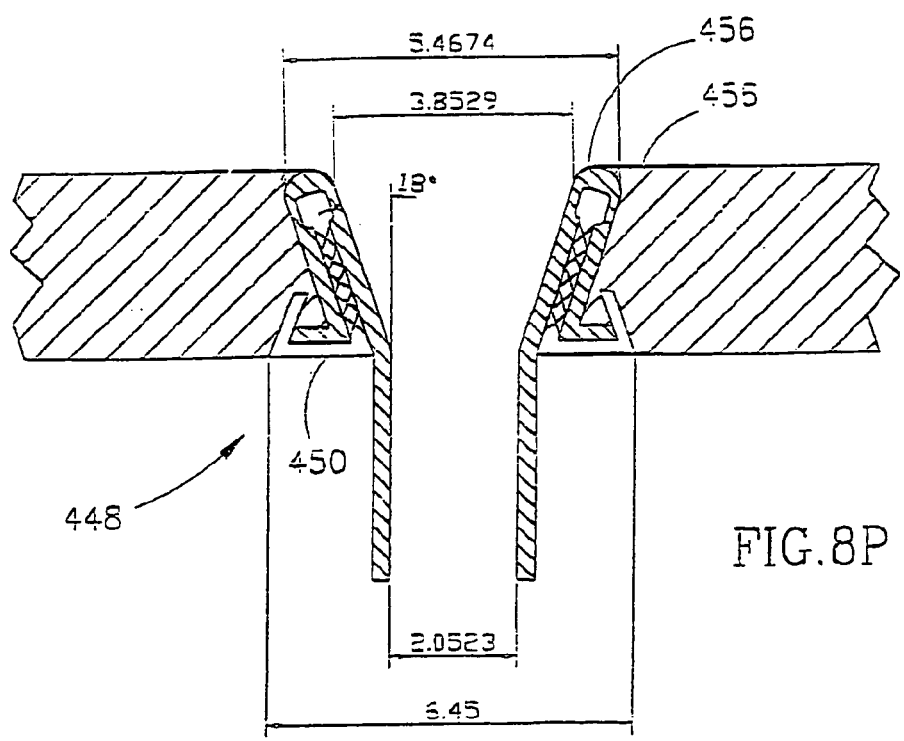
Figure 8Q:
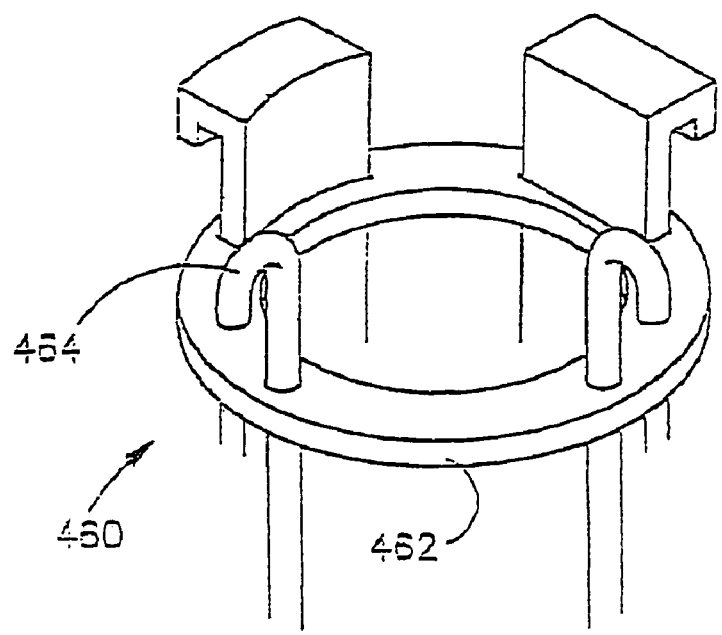
Figure 8R:
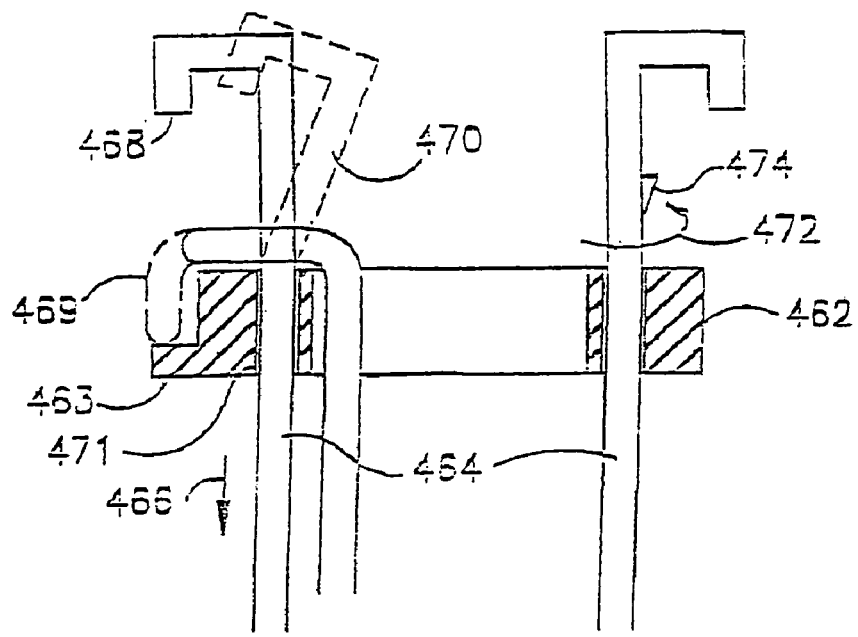
Figures 8S, 8T:
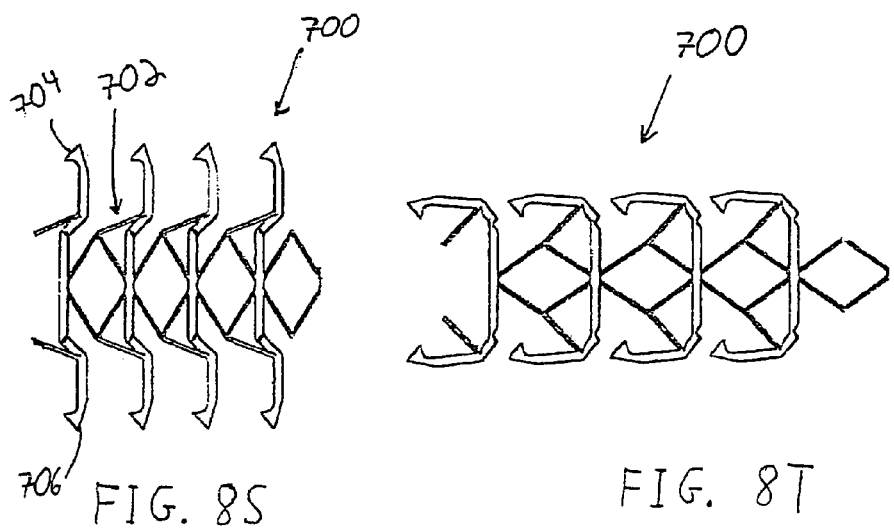
Figure 8U:
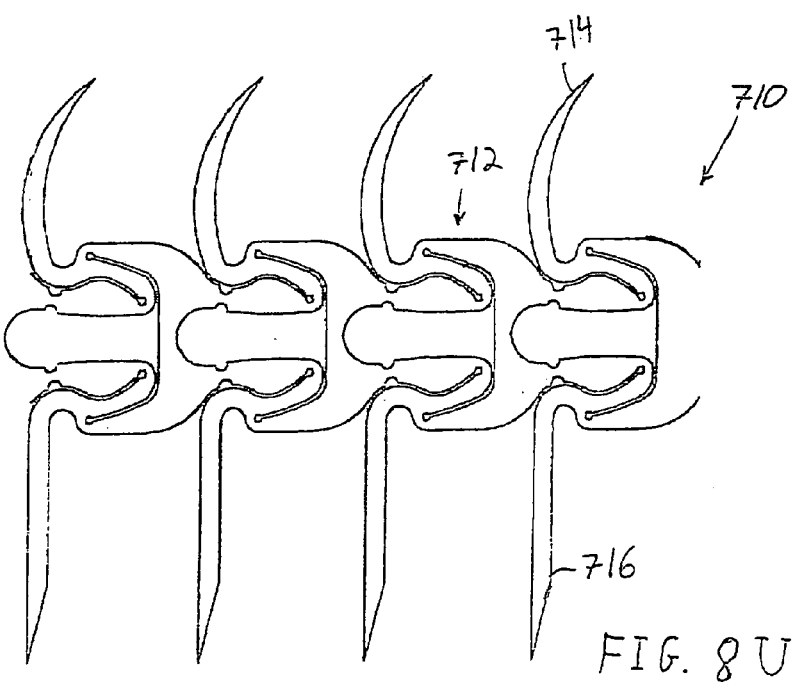
Figure 8X:
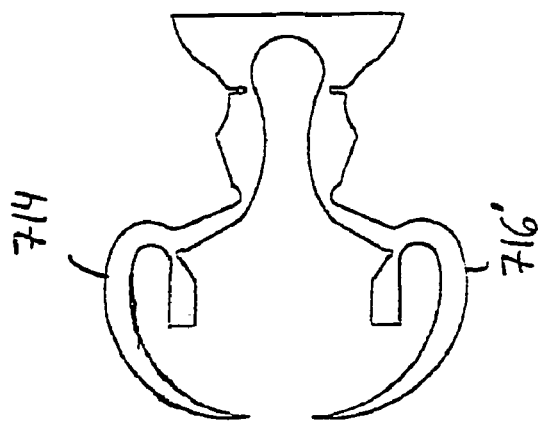
Figure 10A:
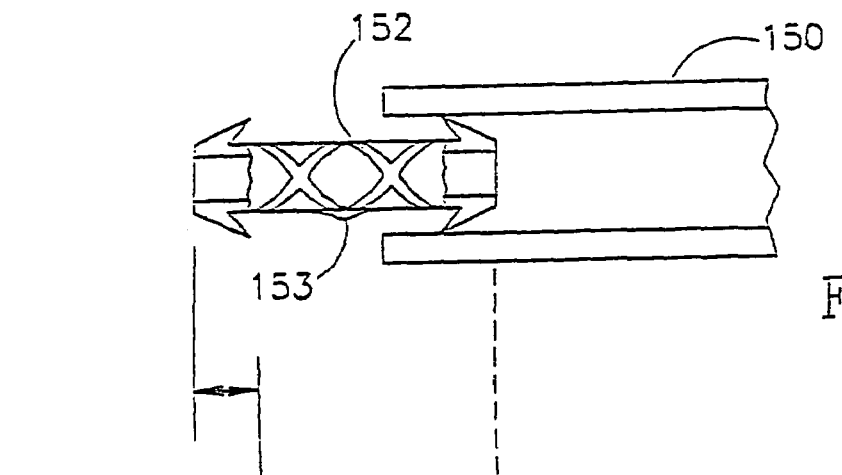
Figure 10B:
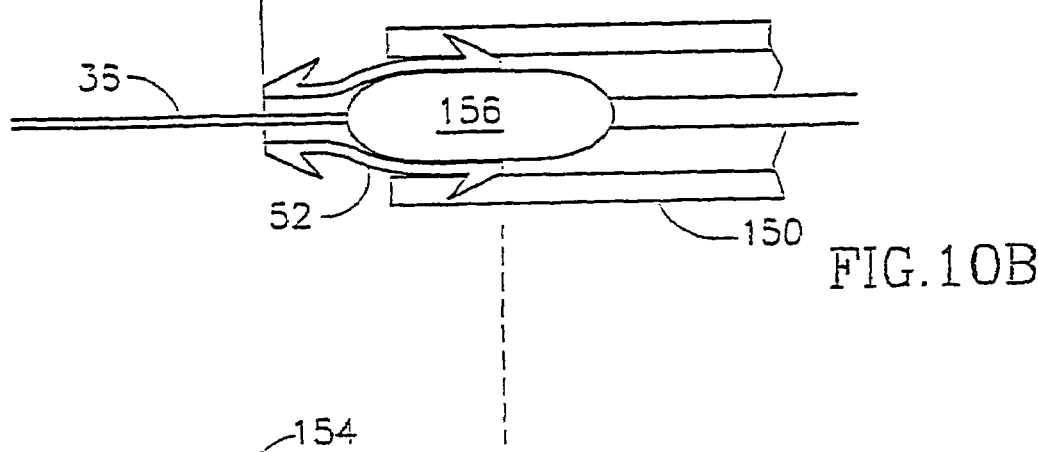
Figure 10C:
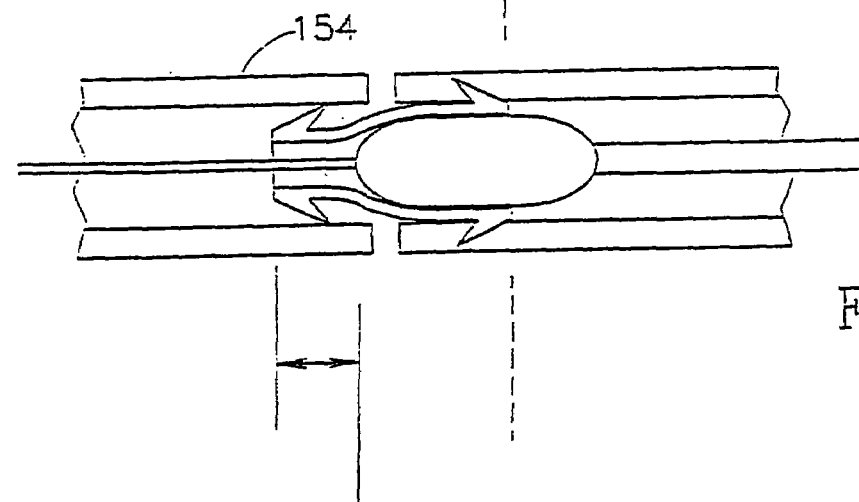
Figure 10D:
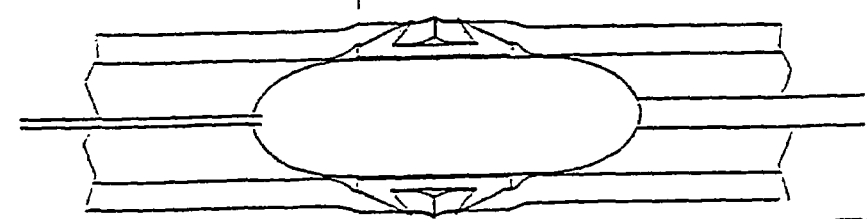
Figure 10E:
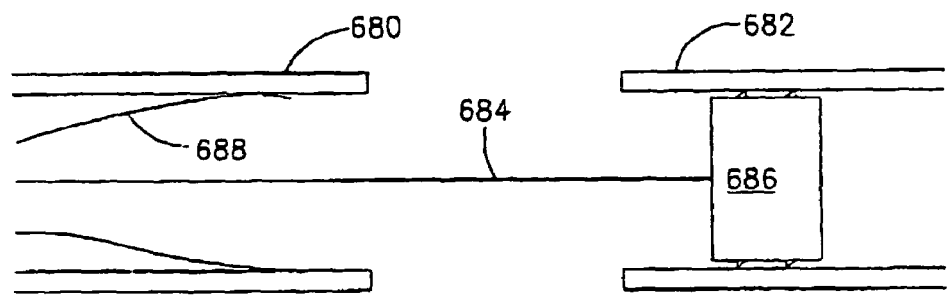
Figure 10F:
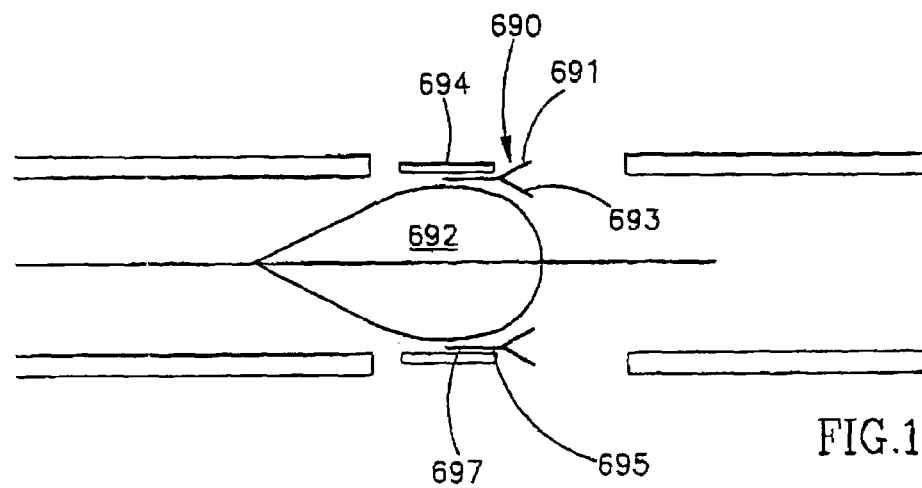
Figure 10G:
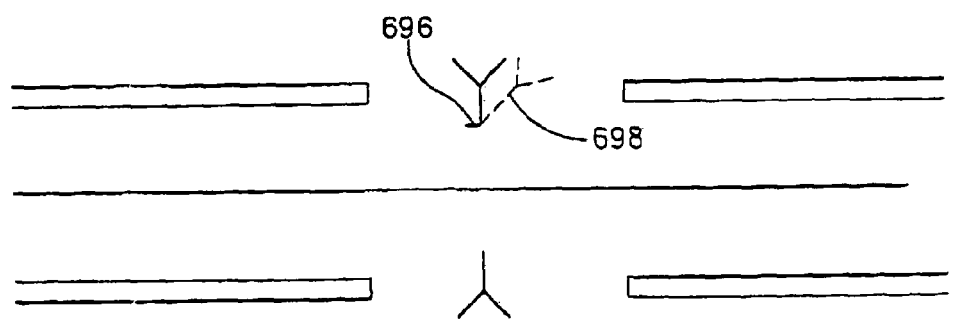
Figure 10H:
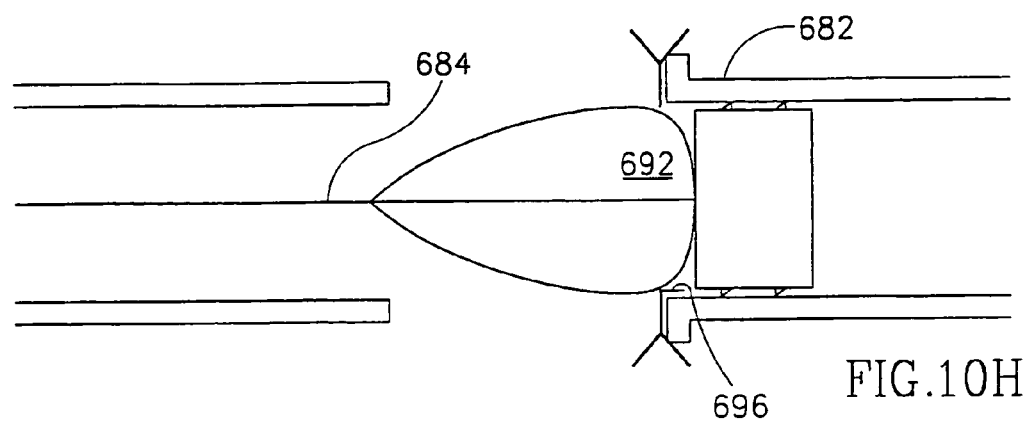
Figure 10I:
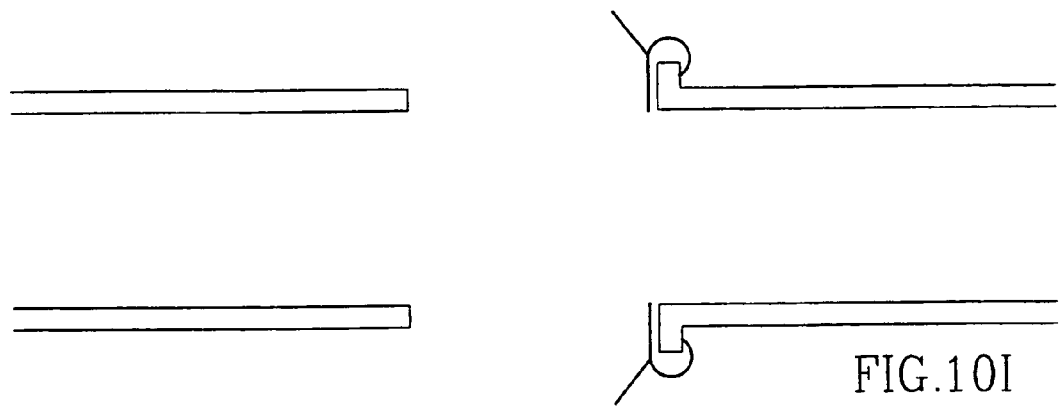
Figure 10J:
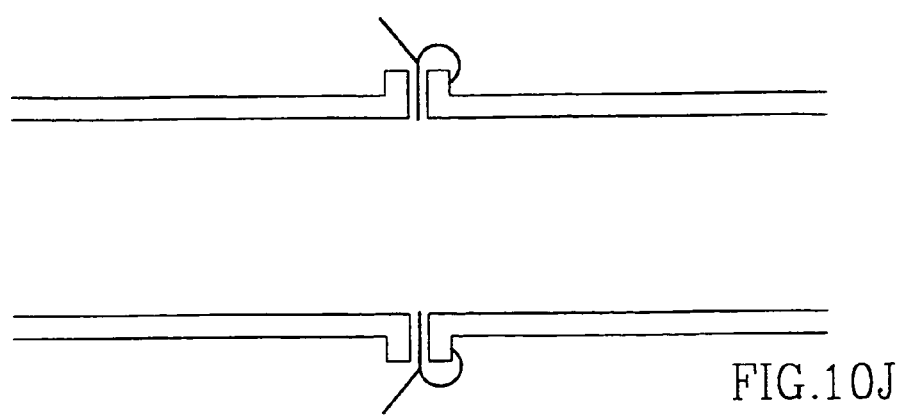
Figure 10K:
Figure 10L:
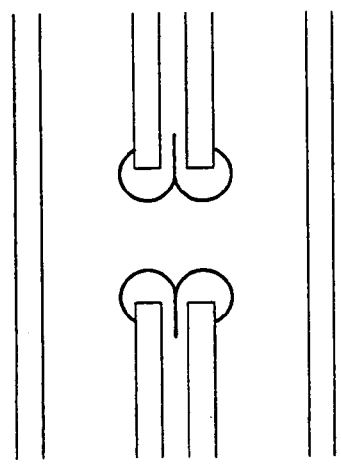
Figure 10M:
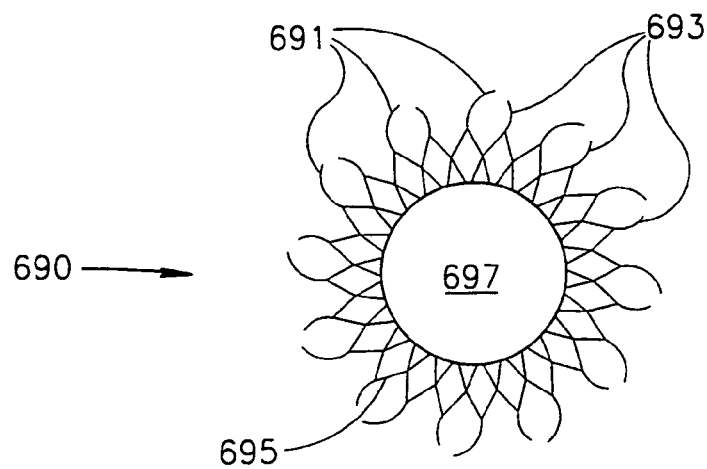
Figure 11:
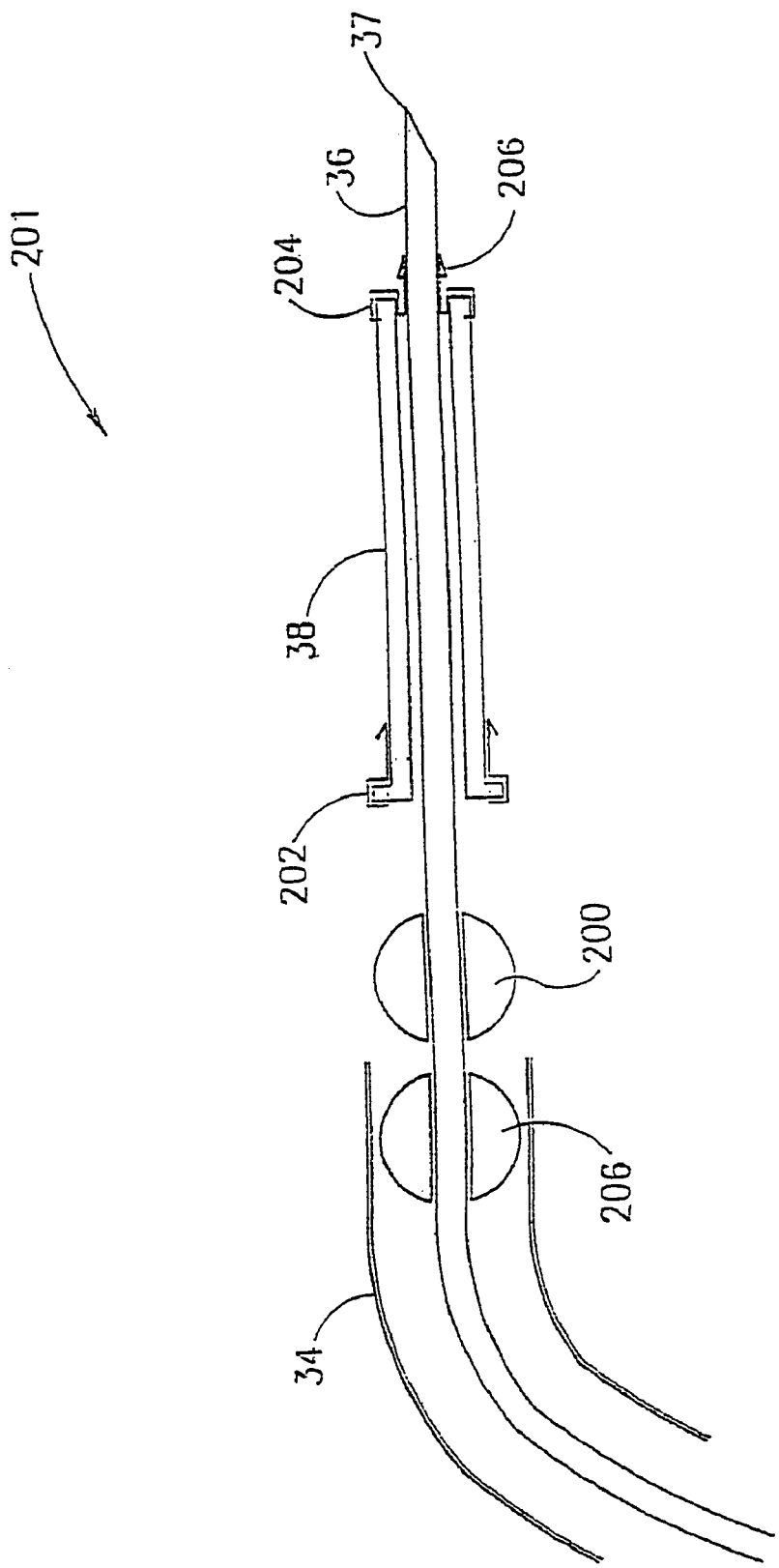
Figures 12A, 12B:
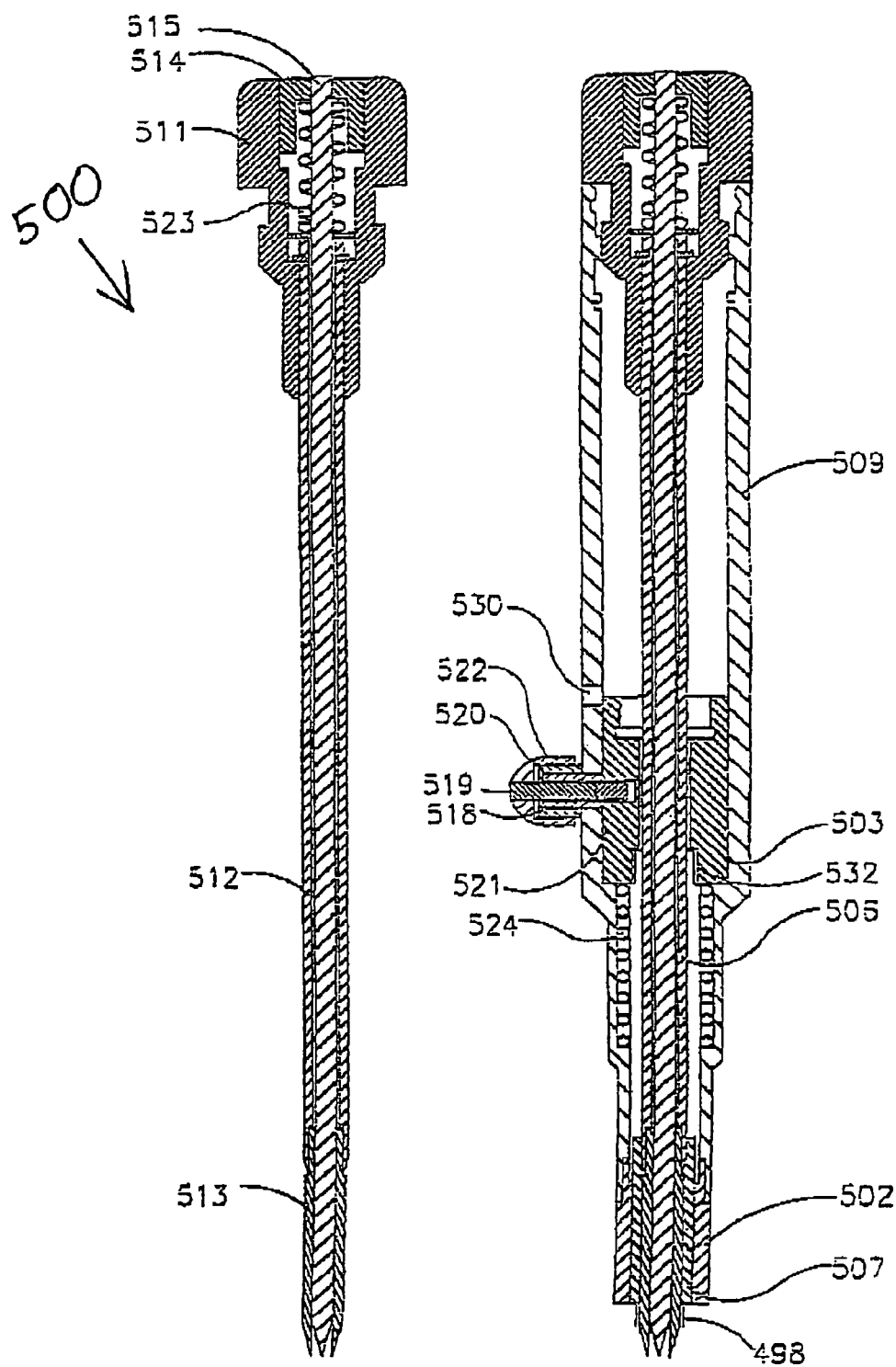
Figure 12C:
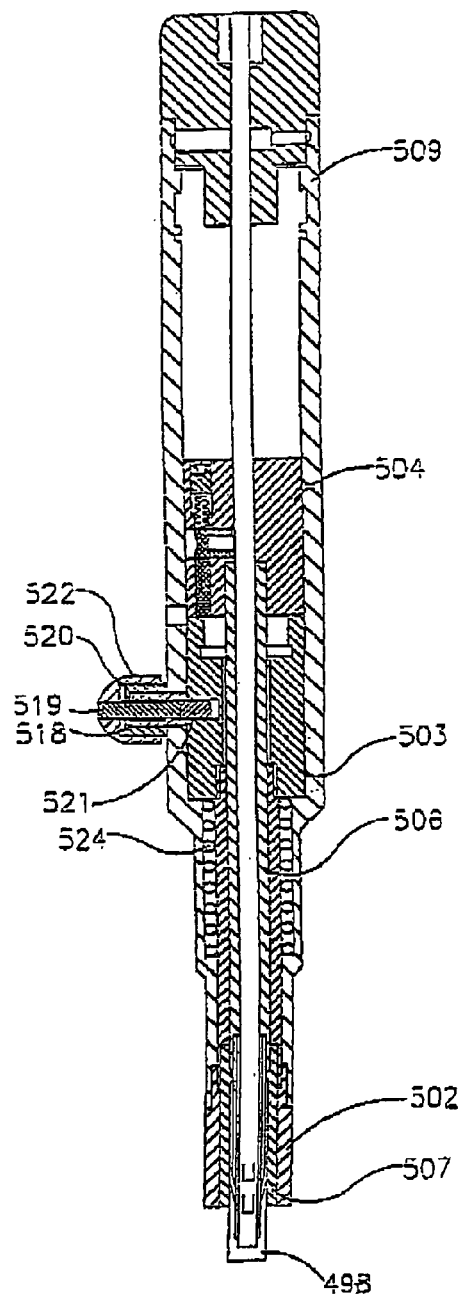
Figure 12D:
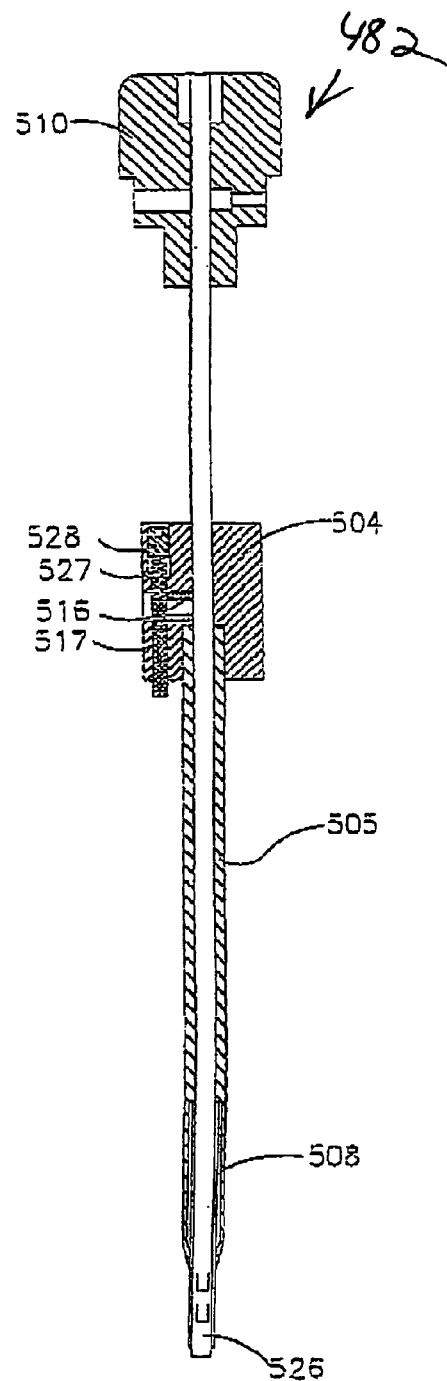
Figure 12E:
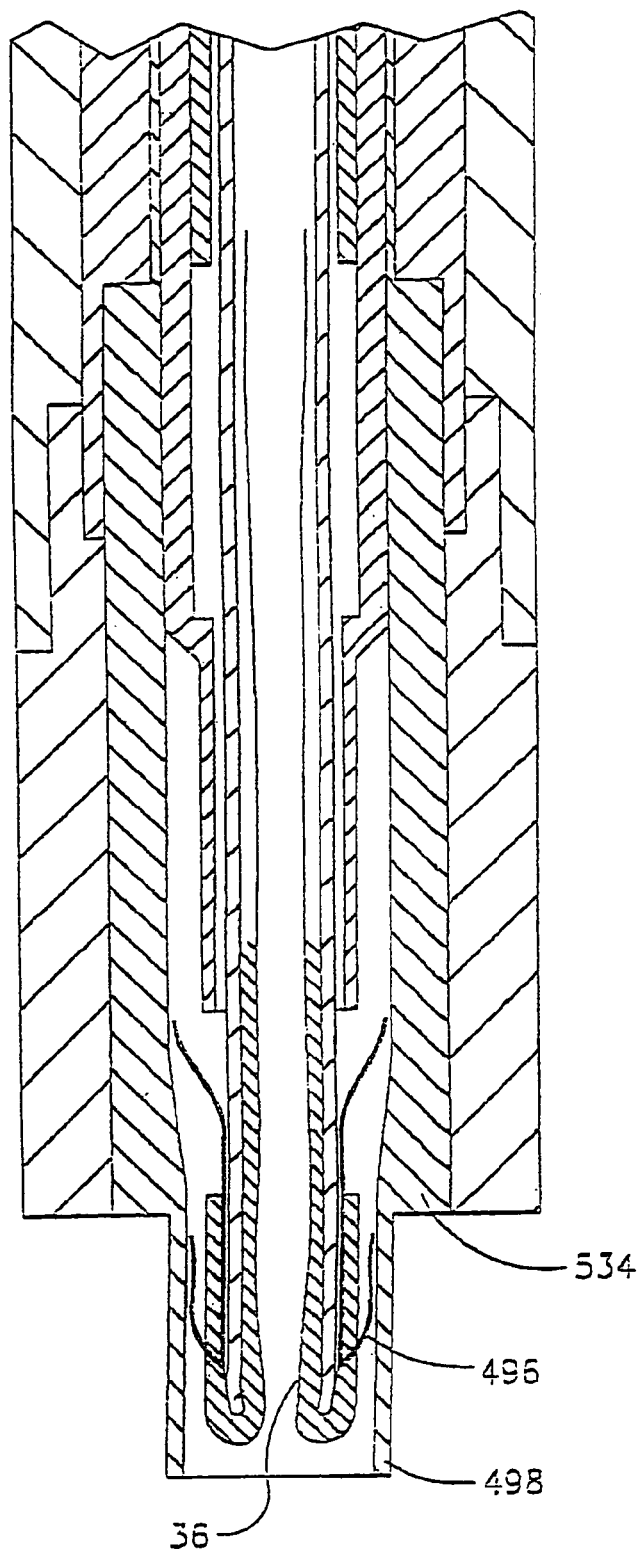
Figure 12F:
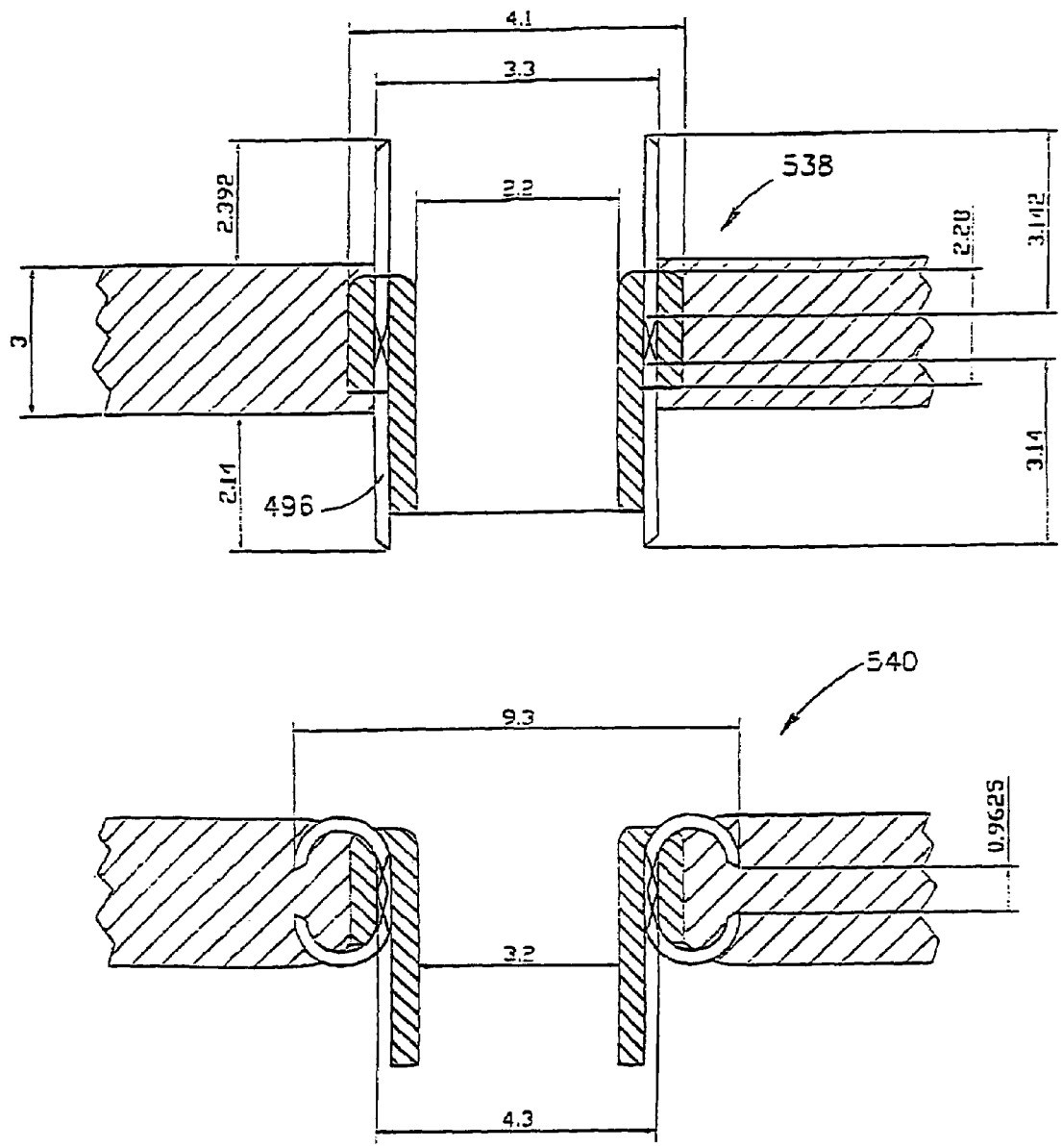
Figure 12G:
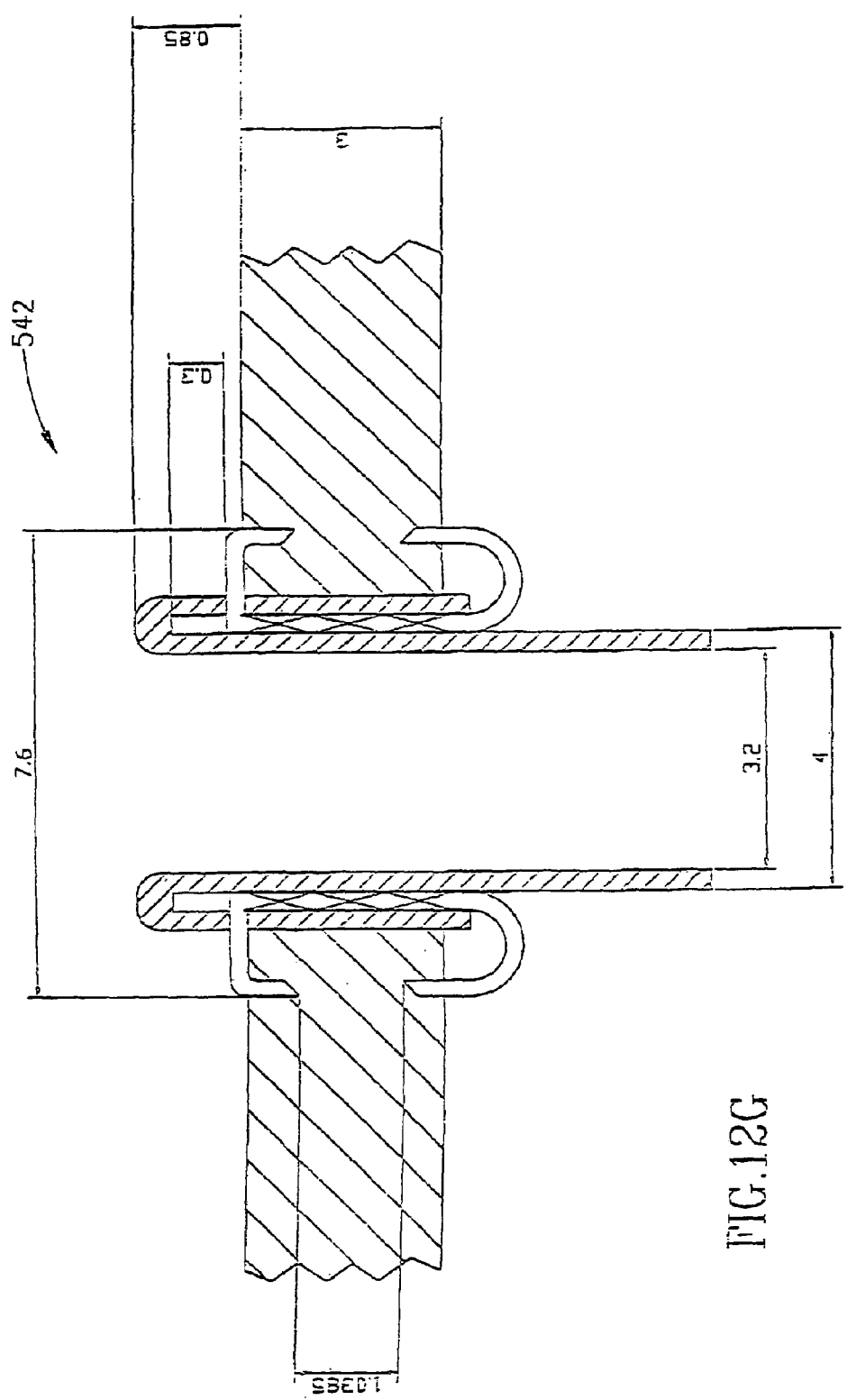
Figure 12H:
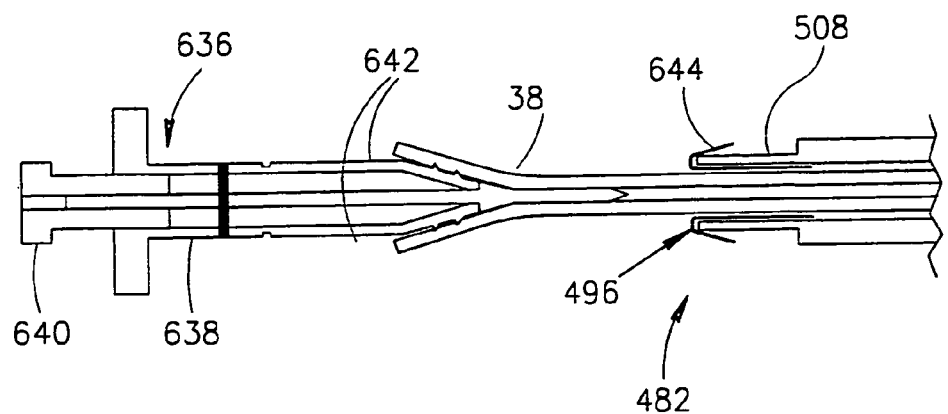
Figure 12I:
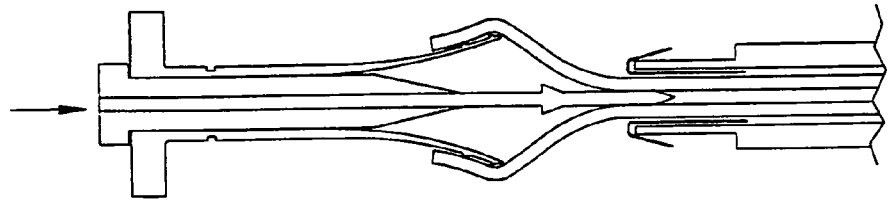
Figure 12J:
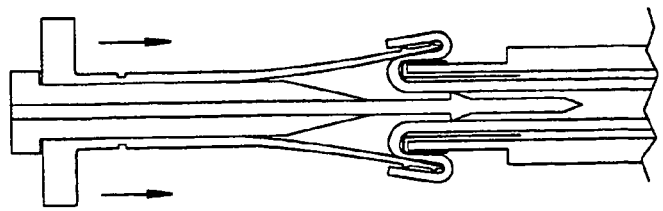
Figure 12K:
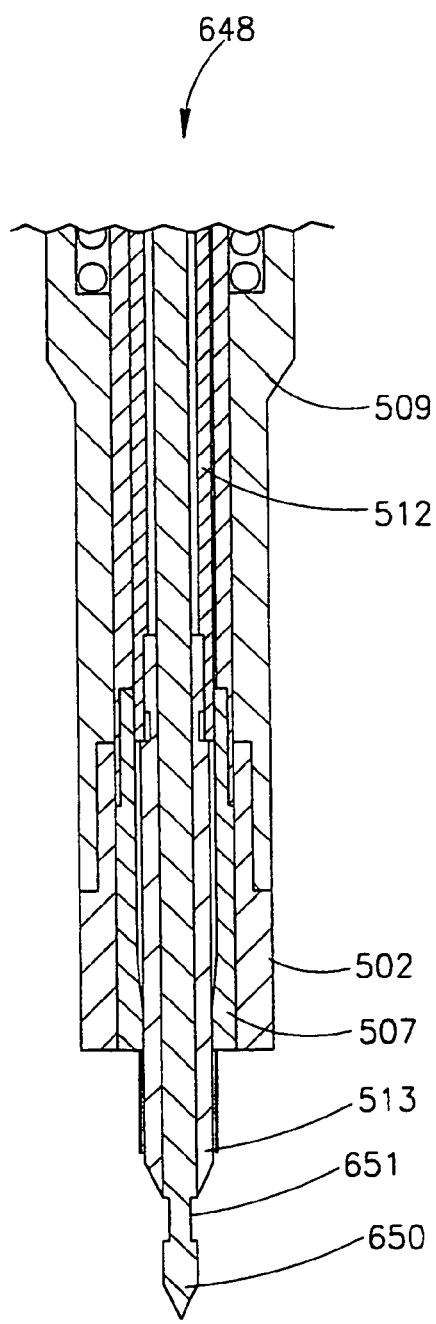
Figure 12L:
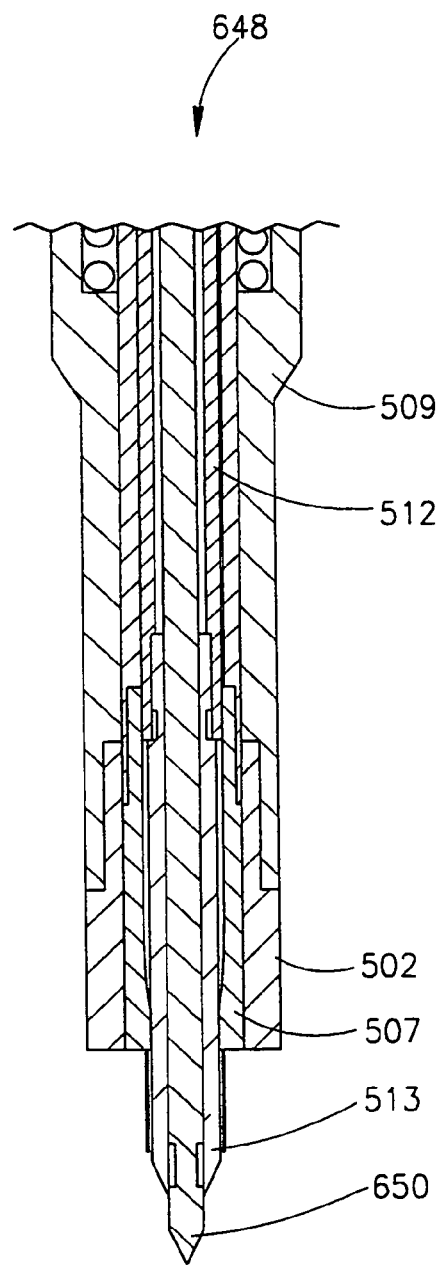
Figure 12M:
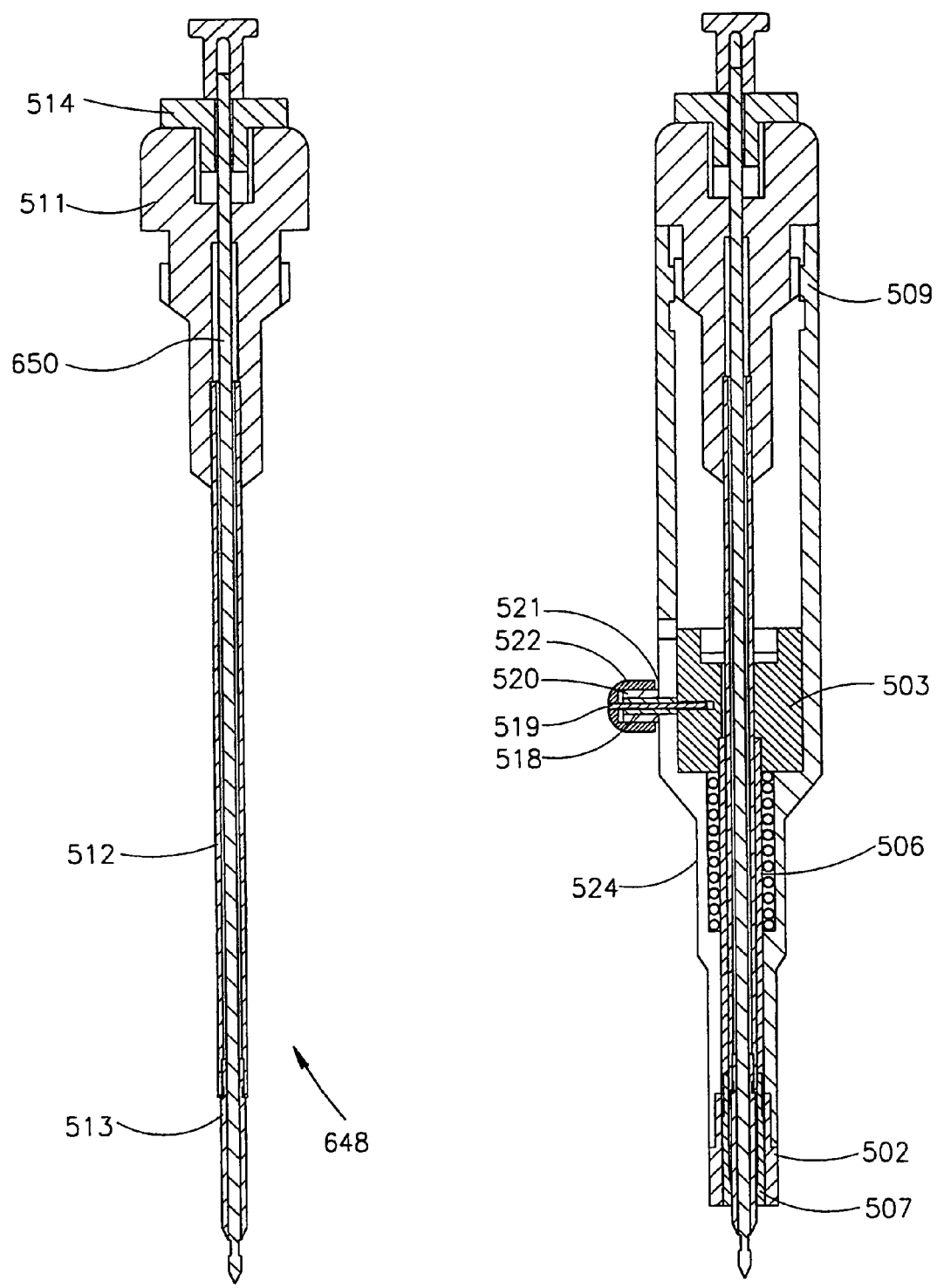
Figure 12N:
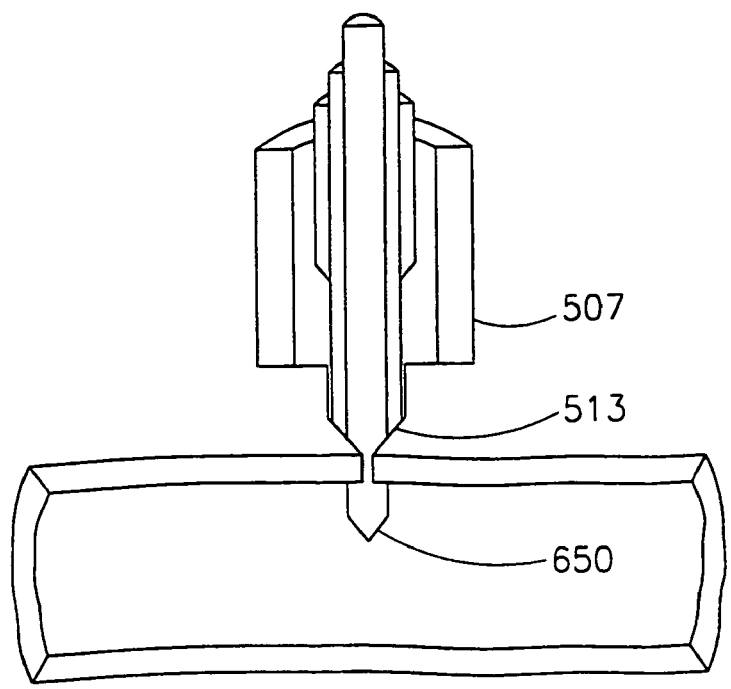
Figure 12O:
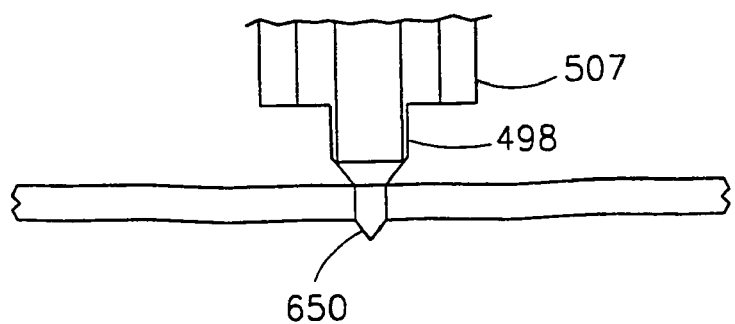
Figure 12P:
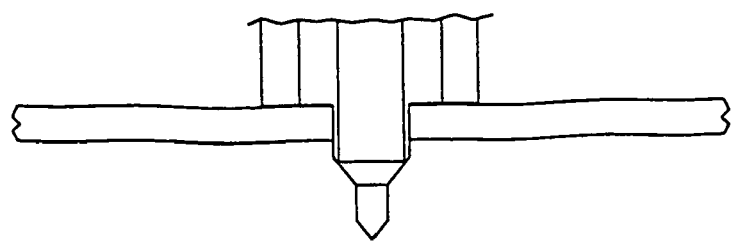
Figure 12Q:
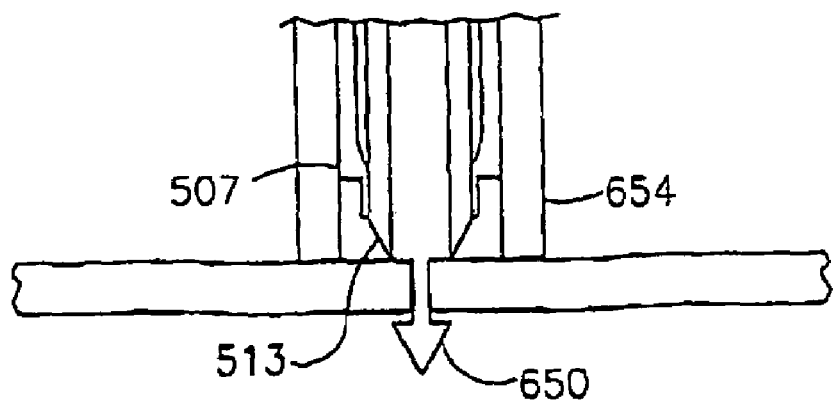
Figure 12R:
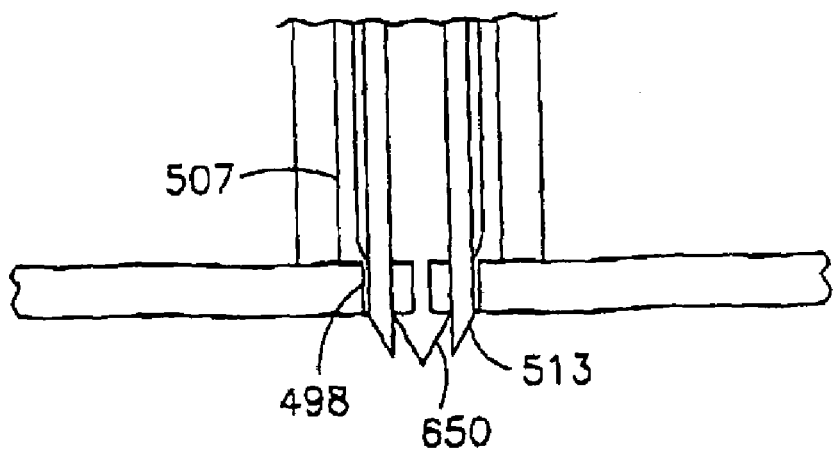
Figure 12S:
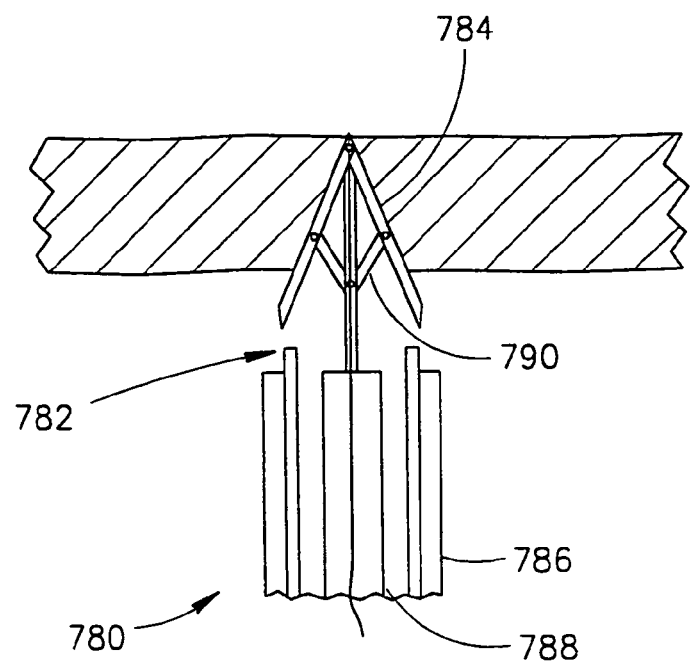
Figure 12T:
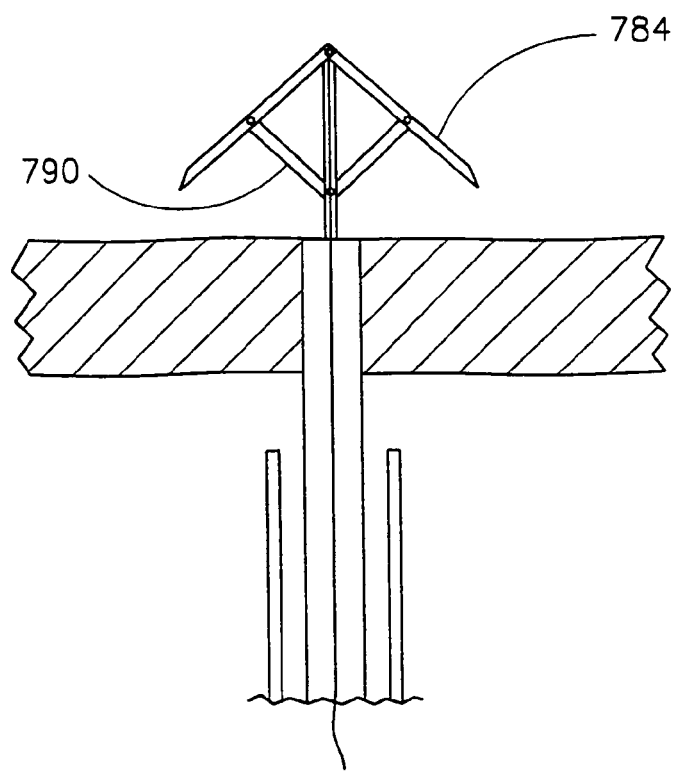

Figure designation 8N has been intentionally skipped;

FIGS. 8Q–8R illustrate a pull-wire anastomotic device, in accordance with a preferred embodiment of the invention;

FIGS. 8S–8X illustrate alternative mechanisms for folding spikes in which a radial expansion is substantially decoupled from axial length changes, in accordance with preferred embodiments of the invention;

FIGS. 8XA–8XH illustrate a family of mechanisms for axial retraction and/or extension of spikes, in accordance with preferred embodiments of the invention;

FIGS. 9A–D illustrate additional devices for attaching graft material to blood vessels, in accordance with preferred embodiments of the invention;

FIGS. 10A–10D illustrate an end-to end anastomosis in accordance with a preferred embodiment of the invention;

FIGS. 10E–10K illustrate an end-to-end anastomosis in accordance with an alternative preferred embodiment of the invention;

FIG. 10L illustrates a side-to-side anastomosis, utilizing a connector similar to that used in the embodiments of FIGS. 10E–10K;

FIG. 10M shows a front view of an anastomosis device suitable for use in FIGS. 10E–10L;

FIG. 11 illustrates a transvascular graft delivery system, in accordance with a preferred embodiment of the invention;

FIGS. 12A–E illustrates a key-hole based graft delivery system, in accordance with a preferred embodiment of the invention;

FIGS. 12F and 12G illustrate anastomotic connectors suitable for the embodiment of FIGS. 12A–E;

FIGS. 12H–12J illustrate a graft everter, in accordance with a preferred embodiment of the invention;

FIGS. 12K–12M illustrate an alternative hole-punching sub-assembly, in accordance with a preferred embodiment of the invention;

FIGS. 12N–12R illustrate two methods of punching a preferably leak-less hole from outside or inside a blood vessel, in accordance with a preferred embodiment of the invention;

FIGS. 12S and 12T illustrate an expanding hole puncher, in accordance with a preferred embodiment of the invention;

FIGS. 13A–D illustrate a method of separately providing an anastomotic connector and a graft, at an anastomosis site, in accordance with a preferred embodiment of the invention; and FIGS. 14A–D illustrate a method of cutting a graft to size, during an anastomosis process in accordance with a preferred embodiment of the invention.

DETAILED DESCRIPTION OF PREFERRED EMBODIMENTS

Figure 1:
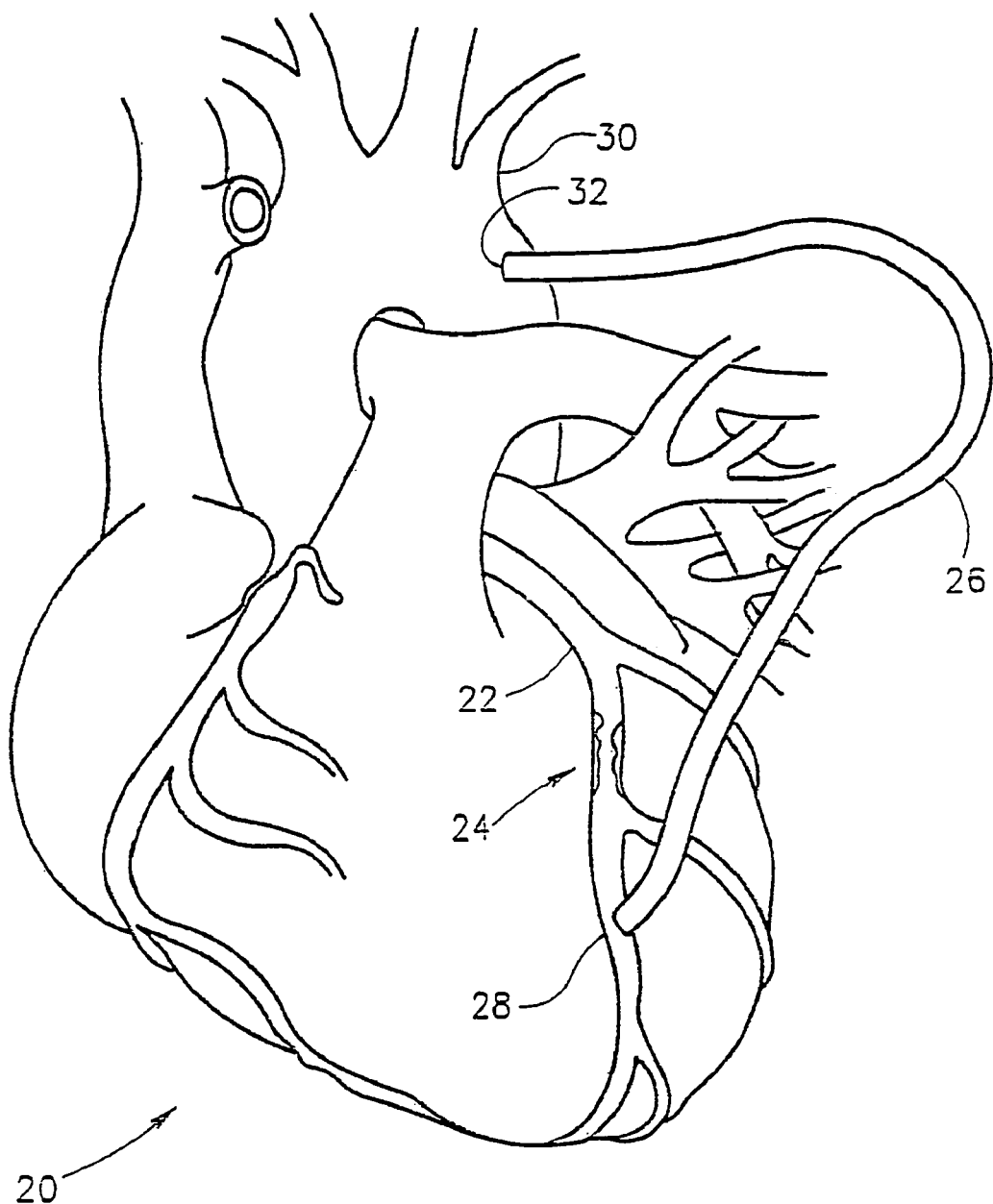
FIG. 1 illustrates a heart with at least one clogged artery and showing a desirable bypass path.

FIG. 1 illustrates a heart 20 having an artery 22 that is clogged, for example, at an occlusion location 24. One medical solution is to provide a graft 26 that connects between an aorta 30 and a point 28 downstream from occlusion 24. Graft 26 is usually connected to aorta using a side-to-end anastomosis 32. The anastomosis at point 28 is usually also a side-to-end anastomosis.

FIGS. 2A–2I illustrate a bypass technique in accordance with a preferred embodiment of the invention, in which most or all of a cardiac bypass procedure may be performed percutaneously, without opening the chest. In a preferred embodiment of the invention, the entire technique can be practiced transvascularly. In a preferred embodiment of the invention, a CABG (Coronary Artery Bypass Graft) procedure is performed. Similar techniques are described in Israel patent application serial number 124,694, filed May 29, 1998, with a like title, the disclosure of which is incorporated herein by reference.

Preferably, the initial step is to harvest a graft from the body of the patient or otherwise provide it. Thereafter, one or more anastomosis connectors are preferably attached to the graft. Alternatively or additionally, the graft comes with ready made anastomosis connectors attached thereto (possibly provided in a kit form or by a technician). The anastomosis connectors are preferably selected to match the blood vessel diameters, conditions and/or other parameters of the anastomosis. In some embodiments of the invention, the anastomosis device is provided separately from the graft to an anastomosis location and the device and the graft are connected near or at the anastomosis connection (see FIG. 13, below).

FIG. 2A illustrates a first step, in which a catheter 34, preferably a J-shaped catheter, is brought into contact with the wall of aorta 30, with the end of the catheter generally directed towards coronary artery 22. The catheter is preferably inserted into the body through the arterial system, for example via the femoral artery.

In a preferred embodiment of the invention, the J-shaped catheter is a bendable catheter that is bent so that the bend area (not shown) rests against the aorta opposite the tip of the catheter, thus, providing a force that maintains the catheter tip in its position. In some preferred embodiments of the invention, the catheter is a bendable catheter, for example by inserting a suitable stylet. Alternatively, the catheter tip may include suction, clamping and/or other mechanism, which attach the catheter tip directly to the aorta wall (described below).

In FIG. 2B, a thin guide-wire 36, having a sharp tip 37 is pushed out through the wall of aorta 30, creating a hole 35. Preferably, catheter 34 is pressed against the wall of aorta 30, so no blood escapes. Alternatively or additionally, and especially if the diameter of wire 36 is small, the elasticity of aorta 30 closes onto the wire and maintains leakage integrity. Although the Fig. shows a barbed guide wire, the guide wire tip may also comprises a smooth taper.

Alternatively, the guide wire tip may be used to punch out a portion of the aorta, when the guide wire is pulled back into the aorta.

In some preferred embodiments of the invention, a protective sleeve (not shown) interposes between the guiding catheter and the guide wire. Possibly, this protective sleeve is used to bend the catheter and/or to maintain the guide wire in a J-shaped configuration.

In a preferred embodiment of the invention, the guiding catheter is an endoscope comprising a plurality of working channels, for example, one for the graft and others for other tools, for example a saline washing fluid provider.

In FIG. 2C a graft 38 is pushed out of hole 35 and into the chest cavity. Preferably, graft 38 is preloaded with at least one anastomosis connector, for example an aortic anastomosis connector 42 and/or a coronary anastomosis connector 40. Alternatively, one or both the connectors may be attached to the graft after it is inserted into the body. It should be noted that in some preferred embodiments of the invention, not all of aortic anastomosis connector 42 exits the aorta. In a preferred embodiment of the invention, the size and/or shape of connector 42 is selected so that the graft is properly aligned with respect to the thickness of the aortic wall. In one example, the connector has an hourglass shape, in which the waist engages the aortic wall. In another example, connector 42 includes lips, which prevent connector 42 from exiting the aorta. Possibly, connector 42 includes a second pair of lips (not shown) which engage the outside of the aorta.

Figure 2D:
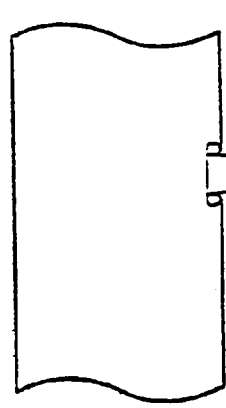

In FIG. 2D, graft 38 is attached to aorta 30, preferably using anastomosis connector 42. Alternatively or additionally, the graft is attached by gluing, welding or suturing. Alternatively or additionally, the graft is sewn, for example using a loaded needle device, such as shown in PCT publication WO 98/42262. Preferably, the device is made smaller and flexible, so as to be suitable for transvascular use, especially for providing the device through the graft to engage a coronary vessel and to attach the graft thereto. In a preferred embodiment of the invention, stapling is performed via a keyhole opened in the chest. Alternatively or additionally, welding is achieved by passing an electric current through the anastomosis connector itself to heat the connector or to provide current through the vessel wall. Alternatively or additionally, the anastomosis is performed by expanding a balloon or another types of expandable device inside anastomosis connector 42 and the expansion causing the connector to perform the anastomosis. Alternatively or additionally, connector 42 is super elastic, elastic or shape-memory and once a restraint is removed, distorts into a configuration suitable for anastomosis. Alternatively or additionally, one or more balloons and/or expandable frameworks are urged against each other with connector 42 held between them, so that connector 42 creates the anastomosis.

It should be noted that, in accordance with some preferred embodiments of the invention, the graft-aorta anastomosis is patent on its own. Preferably, graft 38 is blocked, for example using a balloon along guide wire 36 so that blood does not leak out its distal end.

Figure 2E:
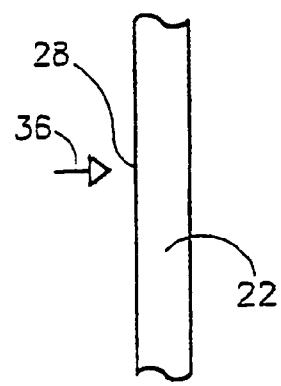
Figure 2F:
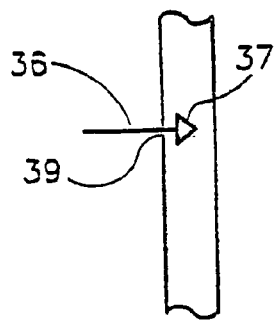

In FIG. 2E, graft 38 and/or guide-wire 36 are navigated so that tip 37 of the guide wire is near coronary artery 22. Such navigation preferably includes two elements, first, actually guiding the guide wire and second, directing the guide wire to a correct location. In some cases, for example if the guide wire is rigid, the navigation step might be performed before the aortic anastomosis step, possibly with some of the graft still inside the aorta. The navigation itself may serve to pull the graft out of the aorta. Typically however, most or all of graft 38 is passed out of the aorta prior to performing the navigation.

The guide-wire may be guided using many methods known in the art, including controllable guide wires and outer sleeves of different shapes. Direction of the guide wire may use a real-time image of the guide wire and/or the surrounding tissue or it may use a pre-determined representation of the body. In a preferred embodiment of the invention, a real-time catheter location system is used to determine the relative locations of tip 37 and point 28 on coronary 22. One such location system is available from Johnson & Johnson Biosense Ltd., of Tirat Hacarmel, Israel. Alternatively or additionally, the navigation is performed using a real-time or near real-time image provided by an imaging system, such as ultrasound, CT, fluoroscopy and MRI. In some navigation systems it may be necessary to mark point 28 (FIG. 1) on coronary 22. Such marking may be achieved by using a contrast material, a radio-opaque marker, a magnetic marker or an intra-body beacon. In some cases, it may be desirable to insert a catheter into artery 22, with such a marker at its tip, to facilitate navigation of catheter tip 37.

If graft 38 is already attached to aorta 30, the graft is preferably uncovered while it snakes around the inside of the body. Alternatively or additionally, an outer sleeve may cover the graft and protect it from contact with internal body tissues. If the aortic anastomosis is already performed, such a covering is preferably flexible and is preferably removed by pulling back it through the "coronary" end of the graft.

An ultrasound imager, especially at or near tip 37 may also be used to determine which obstacles lie ahead of tip 37 and/or to help guide and/or position it. Alternatively or additionally, methods as described in the "Transvascular applications", in the background, may be used. In a preferred embodiment of the invention, graft 38 is attached to body tissue, for example membranes, muscle, and/or blood vessels, along its length. Such attaching may be performed after the anastomosis is finished. Alternatively or additionally, such attaching is performed during the navigation step. The attaching may be achieved by pushing clips out of the lumen of graft 38 and into the tissue. Alternatively or additionally, graft 38 may be preloaded with such clips, which are maintained in a "open" position using a restraint. When the restraint is removed, the clips close and attach to a nearby tissue. Alternatively or additionally, the graft is attached along its length using tissue glue, welding, suturing or other techniques of tissue attachment.

In some preferred embodiments of the invention, the graft may be navigated into the pericardium and along the heart. Alternatively, the graft may enter the pericardium only at a point near the point 28 on vessel 22. Alternatively or additionally, the graft may travel and/or may remain inside the lumen of an organ, such as the lungs or even a blood vessel, such as a vena cava.

Once tip 37 is near coronary vessel 22, the far anastomosis may be made. Preferably, tip 37 is inserted into vessel 22, as shown for example in FIG. 2F, so that graft 38 can be connected to vessel 22. In a preferred embodiment of the invention, a suction, clamping, grasping or another type of attaching device is coupled to guide wire 36 and/or graft 38. This attaching device is used to steady the graft end and/or the guide wire relative to moving tissue, such as a beating heart. The attachment device may attach forward of the advancing wire or to its side. In some embodiments, the guide wire may pass through the attachment device and/or the graft may pass over the attachment device. Possibly, the attachment device is used to remove a portion of the coronary vessel, once the guide wire is properly positioned. In a preferred embodiment of the invention, graft 38 and/or guide wire 36 are enclosed by (or enclose) an endoscope, or are provided side-by-side. An attachment device may be provided through one of the working channels of the endoscope or from inside the graft.

In a preferred embodiment of the invention, prior to insertion of tip 37 into the blood vessel, the entry area is cleaned and a thin coating layer of tissue is removed. In some cases, the tissue layer may comprise heart muscle which overlies the coronary. In other cases, the layer may comprise a coating membrane, for example an adventitia layer. In a preferred embodiment of the invention, this tissue is removed using a knife-like excavating tool which is provided through one of the above working channels or by transverse motion of tip 37 itself.

In a preferred embodiment of the invention, connector 40, in its closed configuration, serves the functions described above for tip 37. In a preferred embodiment of the invention, tip 37 comprises a screw, which is screwed into vessel 22, to create a hole 39 in vessel 22. Alternatively or additionally, a stabilizing tool is guided over guidewire 36, to stabilize vessel 22 relative to tip 37. In a preferred embodiment of the invention, the stabilizing tool is a suction device which attaches itself to vessel 22 or to tissue in a vicinity thereof. Preferably, tip 37 is guided through the suction device. Alternatively or additionally, the stabilizing tool includes a tip having a cross-section shape which matches the cross-section of coronary 22, at a desired approach angle. Alternatively or additionally, the stabilizing device comprises jaws which grab vessel 22. Preferably, the jaws pinch vessel 22, so that a desired entry point for tip 37 is adjacent tip 37. Preferably, vessel 22, in its pinched configuration, presents a narrow aspect to tip 37 and a wide aspect perpendicular thereto, so there is less danger of perforating both sides of vessel 22. Alternatively or additionally, the wide aspect is presented to tip 37, to make aiming easier. Such aiming preferably uses an imager and/or a Doppler sensor (preferably depth gated) to detect the location of flow in vessel 22.

Figure 2G:
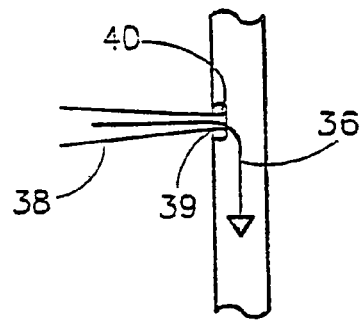

In FIG. 2G, graft 38 is advanced to hole 39 and/or a portion of anastomosis connector 40 is inserted into hole 39. A balloon is preferably guided along guide wire 36 and inflated inside connector 40, so that it expands the anastomosis connection and creates an attachment between vessel 22 and graft 38. Preferably, the balloon is tapered so that it more easily inserted into connector 40. Alternatively or additionally, connector 40 elastically increases in diameter, once it is placed into hole 39 and a restraint removed, to allow enough space for the balloon. Alternatively or additionally, two balloons are used, a narrow one which partially inflates the connector and a wider balloon which completes the inflation of the connector. The leading end of graft 38/connector 40 are preferably tapered, so that they are more easily guided into vessel 22. Alternatively or additionally, guide wire 36 is inserted into vessel 22 for a considerable distance and/or bent, so that there is less chance of guidewire 36 inadvertently leaving vessel 22.

Figure 2H:
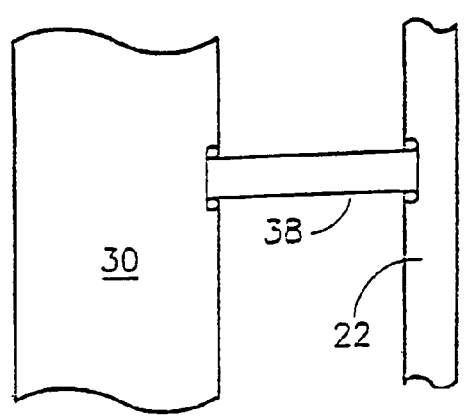

The result, as shown in FIG. 2H is that graft 38 bridges aorta 30 and vessel 22. Typically, the holes in the blood vessels and the anastomosis sites are stabilized and patent even without the continued assistance of the connector, within two weeks. Thus, in some cases, the anastomosis connector may be formed of a bio-degradable substance. In some preferred embodiments of the invention, tissue glue or other blood-blocking materials are applied to one or both of the anastomosis sites, possibly where the two blood vessels contact each other or the anastomotic device. In one example, these substances are applied using keyhole surgery. In another example these substances are applied using a needle which exits through the side of the graft or one of the blood vessels.

In a preferred embodiment of the invention, coagulating materials are applied outside the blood vessels or at the contact area of the blood vessels. Alternatively or additionally, anti-coagulation materials are applied to portions of the anastomosis and/or anastomosis connector which are inside the blood flow. In a preferred embodiment of the invention, the coagulation control materials and/or the tissue gluing materials are applied by coating them onto the anastomotic connector, at certain portions thereof. Alternatively or additionally, coagulation and/or tissue re-growth may be affected by making some of the anastomotic device or a catheter brought to the anastomosis area, radioactive.

In a preferred embodiment of the invention, an anastomotic connector includes a telemetried pressure sensor or a blood velocity meter, so that the patentcy of the connector can be assessed after the connector is implanted. Alternatively or additionally, the connector includes one or more radio-opaque wires or markers so that it is easy to determine (using x-rays) if the connector is maintaining a proper configuration. In a preferred embodiment of the invention, leakage of the device is determined by injecting a radioactive bolus of a chemical not absorbed by the body after the connection is completed. After the bolus is diluted in the blood or removed from the body, checking if the area of the anastomosis exhibits radioactivity, which radioactivity would be indicative of leakage and/or clotting at the connector. Preferably a short-decay radioactive material is used, to minimize radioactive exposure of the patient.

FIGS. 2J–2P describe a variation on the method described above with reference to FIGS. 2B and 2C. Not all the required elements are shown in all the figures, for reasons of clarity and for reducing visual clutter. In a preferred embodiment of the invention, connector 42 is not directly pushed into a hole formed in the aorta by the guide wire. Rather, the hole is first expanded using a balloon or another expandable device and then the connector is inserted into the expanded hole. Alternatively, a guiding sheath is inserted into the hole and the connector is inserted through the sheath. Then, the sheath is removed, leaving the connector in the hole. In some embodiments, the sheath is a working channel of an endoscope. other working channels of the endoscope may be used for tools which assist in one or both of the anastomosis connections and/or with the navigation.

In FIG. 2J, a balloon 300 is advanced over guide wire 36 into the hole made by the guide wire and then inflated. Possibly, balloon 300 is attached to the guide wire and is advanced into the hole by advancing guide wire 36. Balloon 300 is preferably inflated so that it expands the hole made by guide wire 36 (as explain herein by poking a hole or by removing a portion of the vessel wall), until it is wide enough for a guiding catheter 302 to enter the hole.

In FIG. 2K, Balloon 300 is advanced so that it pulls guiding catheter 302 into the expanded hole. Alternatively, catheter 302 is pushed over the balloon. In a preferred embodiment of the invention, catheter 302 has a rigid cross-section, to which size the balloon is expanded. Alternatively, the catheter has a flexible and/or elastic cross-section, which conforms to the shape of the balloon.

In a preferred embodiment of the invention and as indicated in FIG. 2J, part of balloon 300 is inside the catheter and part is out side. In a preferred embodiment of the invention, both parts of the balloon expand to a same radius. Alternatively, the part outside the balloon may expand more, so that guiding catheter 302 more easily slips into the expanded hole. Alternatively or additionally, the outside of catheter 302 may be coated with a material having a low coefficient of friction (with respect to the blood vessel), to assist in the catheter entering the hole. Alternatively or additionally, the end of catheter 302 may extrude a lubricant. Alternatively or additionally, the outside of catheter 302 may include mechanical means to assist insertion, for example, the outside of catheter 302 may be threaded, so that the catheter can be screwed into the hole.

FIG. 2L shows a catheter 302 in position in the hole. Generally, the seal between the aorta wall and the catheter is tight enough so that there is little or no leakage of blood from the hole. Thus it is possible to bring various tools through the catheter to perform activities outside the blood vessel, for example at the coronary anastomosis. As a result, the far anastomosis may be performed and/or corrected, if necessary, prior to performing the near anastomosis. Possibly, the inner radius of catheter 302 is greater than the final inner radius of the graft, to facilitate such remote activities. Possibly, the radius of catheter 302 increases after the it exits hole 35. The above tools may be brought through the graft (once it is inserted into the aorta. Alternatively, the tools may be brought through the catheter at the side of the graft. Possibly, the graft itself is only brought in after some activities are performed at the remote anastomosis, for example locating and/or fixing a guidewire to the anastomosis location. Alternatively, the graft may be passed completely through the hole in the aorta and then one end of the graft possibly brought back to attach to the hole. Alternatively, the one end is attached to a vessel other than the aorta or to the aorta at a position other than the hole. Preferably, the hole is closed using other means, such as a patch, or by attaching a second graft from the hole to another remote anastomosis location.

Figure 2I:
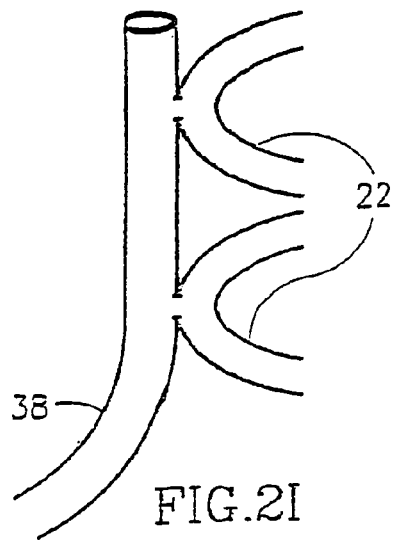
Figure 2M:
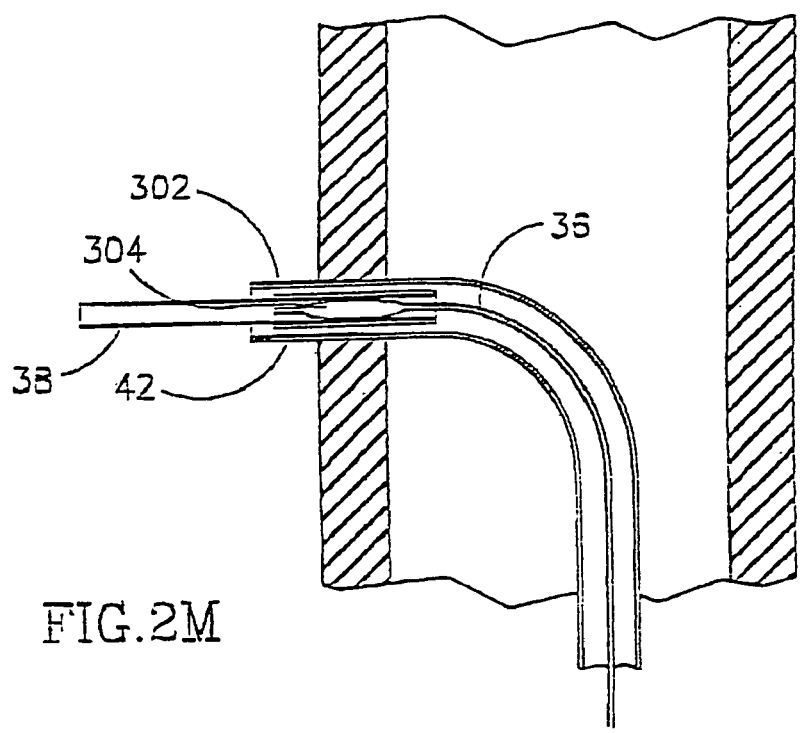

In FIG. 2M, graft 38 is positioned so that an anastomotic connector 42 is in hole 35. In a preferred embodiment of the invention, as shown for example in FIG. 2C for connector 40, connector 42 comprises lips which prevent the connector from advancing beyond hole 35. Alternatively or additionally, connector 42 has an hourglass profile so it self-centers in hole 35. In a preferred embodiment of the invention, catheter 302 has a flexible exterior, so that connector 42 can engage hole 35 through the intervening catheter. Alternatively, catheter 302 has an inflexible exterior geometry which, itself, engages the hole. Preferably, catheter 302 also has a suitable interior geometry, so that when graft 38 and connector 42 are inserted, they are properly aligned with hole 35. In FIG. 2M, an endoscope 306 is shown, in accordance with preferred embodiments of the invention. This endoscope may be used to provide balloons, grafts, connectors and/or for navigation of the graft to the remote anastomosis location.

Figure 2N:
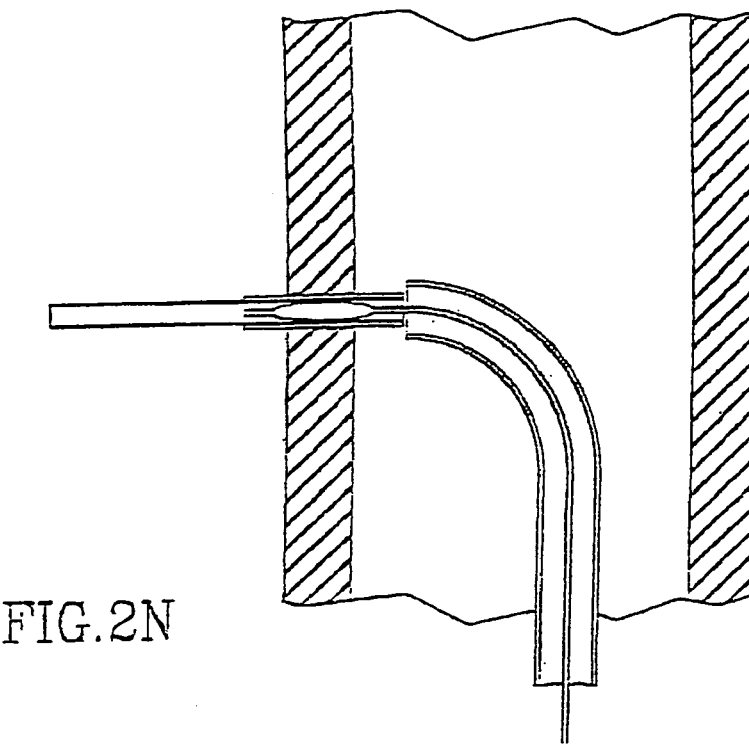

Thereafter, guiding catheter 302 may be retracted, for example as shown in FIG. 2N, to allow connector 42 to engage hole 35 in aorta 30. Generally, hole 35 will shrink and engage connector 42 so that there is no leakage. Alternatively, catheter 302 may remain abutting against the wall of aorta 30, to prevent bleeding. Preferably, the far end of graft 38 is sealed to prevent blood from leaking out through the graft (unless the far end is already attached to a blood vessel).

Figure 2O:
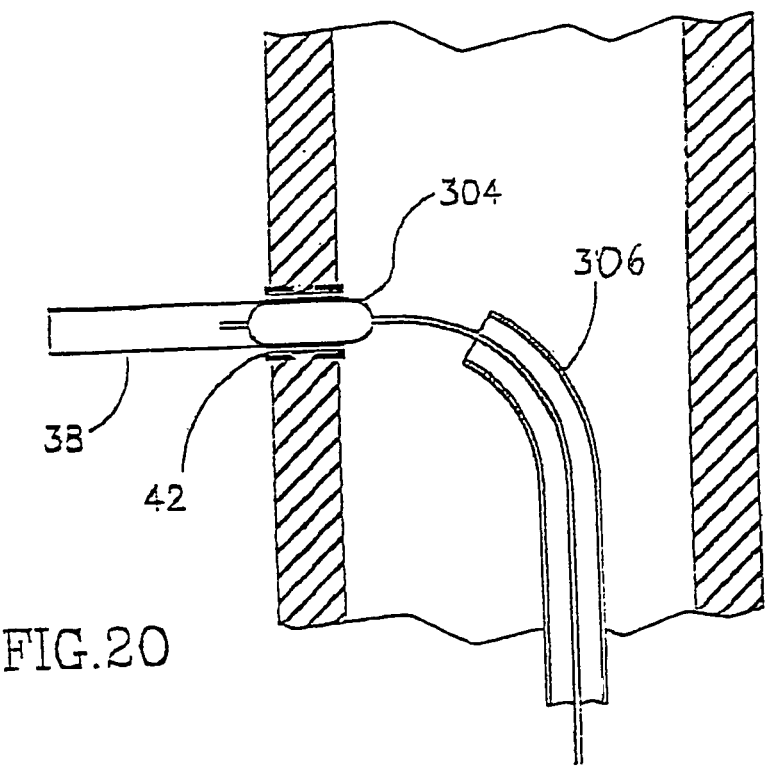

In FIG. 2O, a balloon 304 is expanded inside connector 42. Possibly, balloon 304 is provided into the connector prior to the removal of catheter 302. Alternatively, it is provided, after the removal, preferably being guided over guide wire 36. Alternatively to using a balloon, connector 42 may comprise a super-elastic, elastic and/or shape-memory material which expands when an constraint (e.g., catheter 302 or guide wire 36) is removed.

In a preferred embodiment of the invention, the expanded geometry of balloon 304 is matched to the desired shape of the expanded anastomosis device. In one example, Balloon 304 comprises fingers which extend to bend spike-portions of the connector (described below). In another example, Balloon 304 expands to an hour-glass shape, to better position and/or shape connector 42. Alternatively or additionally, balloon 304 axially shortens when it radially expands, to assist in the correct shaping of connector 42. Alternatively or additionally, balloon 304 comprises a multi-step balloon which expands in a step-wise manner to sequentially provide a plurality of different geometry's. The selection between the geometry's may depend on the inflation pressure, for example by providing thicker and thinner portions in the balloon, where the thicker ones require a greater pressure to stretch, or on a position and/or rotation of a guide wire which is enclosed by the balloon. In one example, A first inflation pressure causes the balloon to expand to a first step, where spikes on the connector are extended perpendicular to the surface of the connector. A second inflation pressure causes the spikes to bend another 90 degrees and a third inflation pressure causes the connector to expand and/or axially shrink.

Figure 2P:
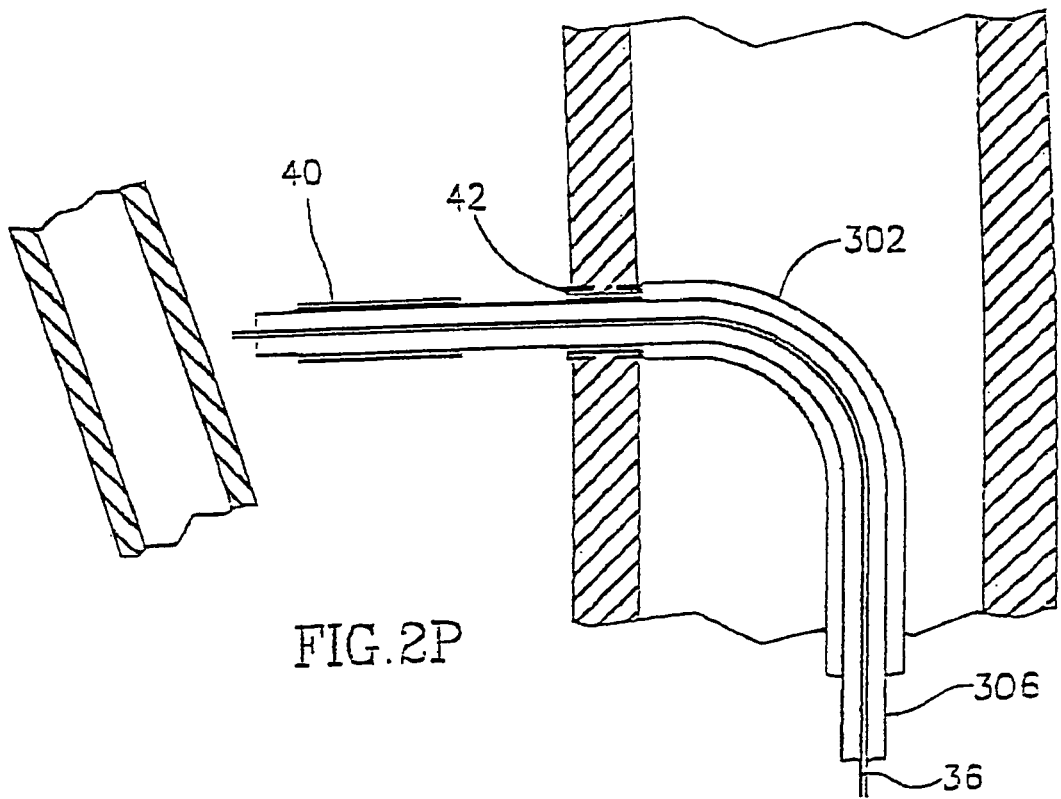

In FIG. 2P, the aortic anastomosis is complete and the coronary anastomosis is ready to be performed (if not already performed).

It should be noted that although a plurality (possibly even four) of balloons may be used for expansion of the various hole sand anastomotic connectors, possibly a smaller number of balloons or even a single balloon may suffice. In one example, a single balloon comprises a multi-step balloon whose final geometry is step-wise dependent on the inflation pressure. In an extreme example, no balloon is used, for example, if the connectors are self-expanding and/or by using a non-balloon expandable structure. One example of a non-balloon expandable structure comprises of two base-to base tetrahedrons, in which the non-base sides are rigid and in which the two opposing vertexes are attached by a wire which may be shortened (e.g., by pulling the wire).

Alternatively or additionally to end-to-side anastomosis connections at the coronary end illustrated in FIG. 2H, side-to-side anastomosis connections may be used, as described for example in the "Transvascular applications". FIG. 2I shows an example of such connections, where a single graft 38 is attached to two, possibly different coronary arteries 22. The end of graft 38 is preferably blocked and or is used for an end-to side or an end-to-end anastomosis. Alternatively or additionally, graft 38 is prepared so that it does not have a distal opening. When side to side anastomosis connections are made, graft 38 may have pre-formed holes in its side or holes may be made during the connection process. In a preferred embodiment of the invention, each side of the side-to side anastomosis is individually patent, without requiring compression of intervening tissue, as in some known methods.

FIGS. 2Q–2T illustrate methods and apparatus of forming a puncture in a blood vessel (aorta or coronary, i.e., from inside or from outside), in accordance with preferred embodiments of the invention. In some of the described embodiments, it is an object to avoid contact with portions of the blood vessel to be pierced, other than at or near the piecing area, to avoid damage to the blood vessel. One solution, is to provide a piercing tip which does not require a base to rest against.

Figure 2Q:
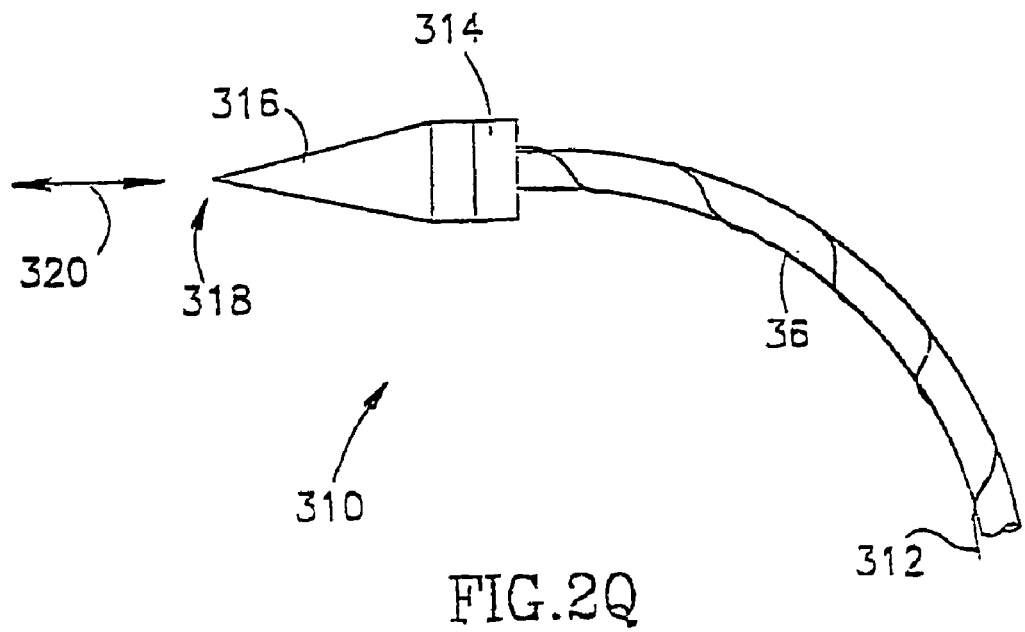

FIG. 2Q illustrates a vibrating tip 310, for a guide wire 36, which may be used for piercing a blood vessel in accordance with a preferred embodiment of the invention. Additionally, this tip may be used for penetrating through a different type of layer, for example of soft tissue, or even a hard tissue, such as a calcified aorta. In a preferred embodiment of the invention, tip 310 is made to vibrate rapidly in along an axis indicated by an arrow 320 (and/or at another angle, such as perpendicular to the arrow), thereby piercing a blood vessel against which it is placed. In a preferred embodiment of the invention, tip 310 comprises a vibrating potion 314, a mechanical amplifier 316 and a vibrating end 318. In a preferred embodiment of the invention, mechanical amplifier 316 has the shape of a horn (a cone) so that the amplitude of axial motion at the narrow end is about four or more times greater than at the wide end. In one exemplary embodiment, vibrating portion 314 comprises one or more layers of piezoelectric material, electrified by a wire 312. Amplifier 316 is formed of Titanium or Aluminum and may have a base diameter of 3 mm. The surface of amplifier 316 may be smooth. Alternatively, the surface may be rough, for example to engage tissue against which it vibrates and into which it is inserted. Alternatively or additionally, the surface may have formed thereon one-way barbs, so that tip 310 can easily enter by less easily exit tissue.

Alternatively to piezoelectric vibration, other ways of generating vibration may be provided, for example, resonant vibration responsive to externally applied acoustic waves, transmitted through the tissue or along the guide wire. Alternatively, magneto-strictive vibration may be achieved by forming vibrating portion 314 out of a suitable material and applying an AC magnetic filed in the vicinity of portion 314. Alternatively, other vibrating methods may be used, for example using a solenoid. In a preferred embodiment of the invention, the frequencies are between 5 and 50 Hz and the amplitudes are between 0.1 and 1 mm. Alternatively higher frequencies, for example between 50 Hz and 1000 Hz, higher amplitudes, for example between 1 and 3 mm, lower frequencies, such as between 1Hz and 5Hz, and/or lower amplitudes, such as between 0.01 and 0.1 mm, may be used.

Figure 2R:
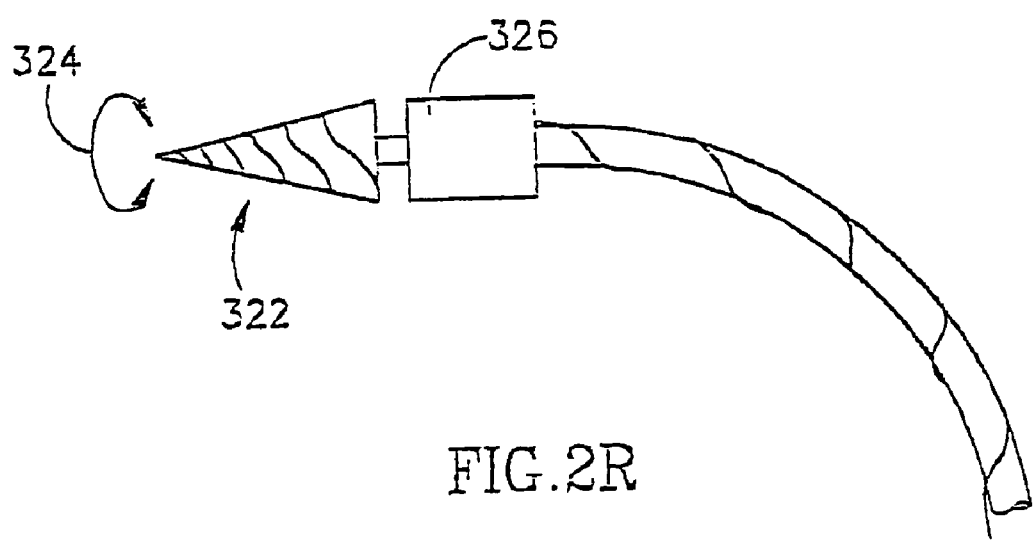

FIG. 2R illustrates a tip 322 which rotates as indicated by an arrow 324. The rotation may be continuous in one direction, pulsed and/or reversing. Tip 322 is preferably threaded to engage the tissue into which it is inserted. The rotation is preferably provided by a motor 326, which may be, for example, a magnetic motor or a piezoelectric motor. Possibly, the motor is rotated using an externally applied AC magnetic field, for example one caused by a rotating magnet. The rotation may be in addition to or instead of axial motion. Rotational motion may be achieved by making vibrating portion 314 not perpendicular to guide wire 36. U.S. Pat. No. 4,846,174 and PCT/US89/00261, the disclosures of which are incorporated herein by reference, describe mechanism which are useful for such rotating and vibrating tips.

Alternatively or additionally, to vibrating or rotating tips, a tip 37 of a guide wire may be shot through the blood vessel, like a harpoon. In one example, the tip is shot using a pneumatic or hydraulic pressure build-up in the guiding catheter. In another example, the tip is shot using a suddenly applied magnetic filed which acts on a magnetic tip. Preferably, the motion of the tip is axially restrained, for example by a wire connected thereto, to avoid undesirable penetration of the tip into non-local tissue.

FIG. 2S illustrates a process of clamping and piecing, in accordance with a preferred embodiment of the invention. In an axial view of blood vessel 30, a tip 37 is to penetrate the wall of vessel 30. One or more clamping devices 330, for example a pair of pincers, pinch the wall of vessel 30, so that a portion 332 is pinched inwards. A location 334, which it is desired to penetrate with tip 37, is preferably presented to tip 37. Preferably, the orientation and/or position of clamping device 330 is selected so that particular location is pierced. Alternatively, once clamped, the clamping may be removed, if the location is deemed unsuitable. In a preferred embodiment of the invention, tip 37 and devices 330 are coupled, so that advancing tip 37 causes it to pierce location 334. Once such piecing is confirmed, clamping device 330 may be removed and the piercing process is completed. In some embodiments of the invention, tip 37 punches a hole (removing material) in vessel 30, rather than just piercing it.

Figure 2T:
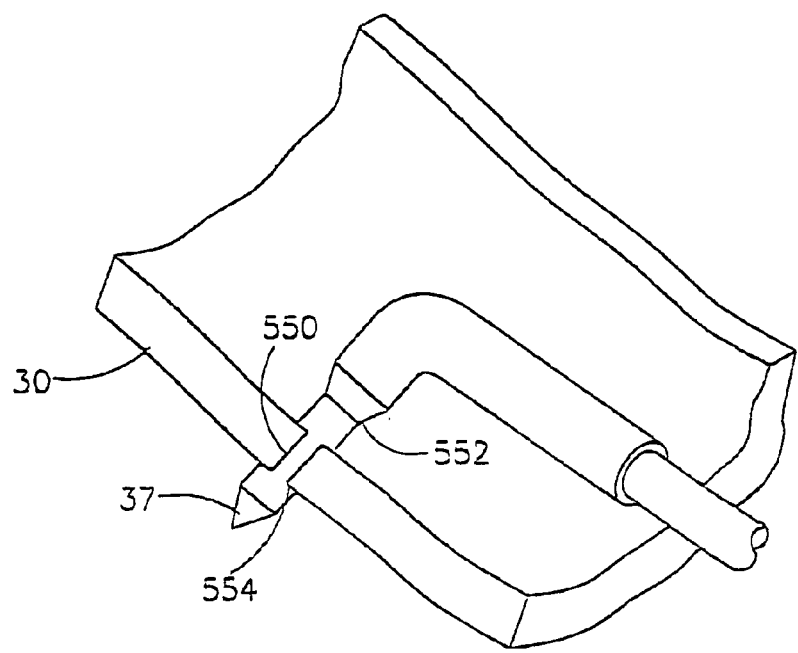
Figure 2T:
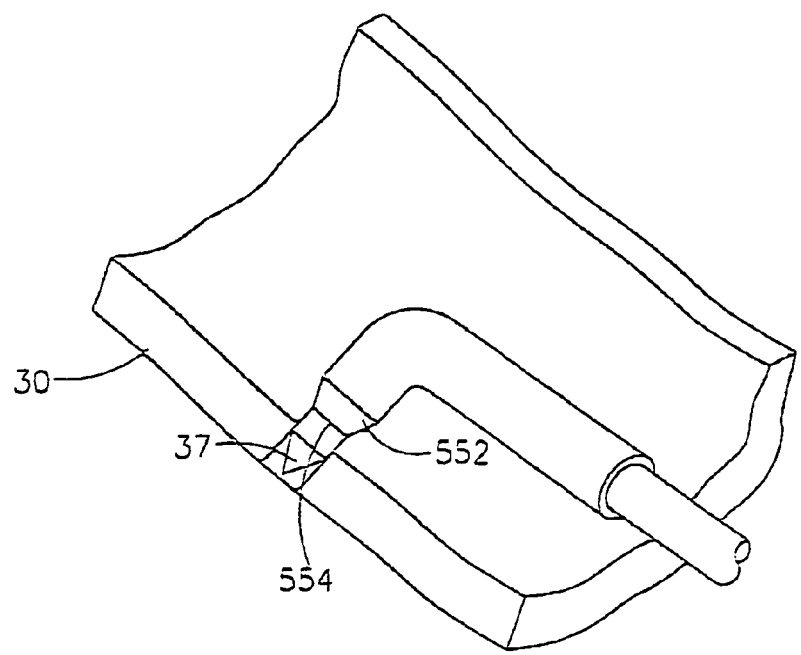

FIG. 2T illustrates a process similar to that of FIG. 2S, in which the piercing is performed from outside the blood vessel. Optionally, a tool 340 aligns tip 37 against the blood vessel to guarantee that tip 37 enters at a desired angle and/or orientation (angle from the plane of the figure). Alternatively, such guaranteeing is performed by clamping devices 330.

FIGS. 2TA and 2TB illustrate a method of punching a hole in a blood vessel, in accordance with a preferred embodiment of the invention. In FIG. 2TA, a tip 37 penetrates a wall of a vessel 30, such that a portion of the wall is grasped by an inner reduced diameter portion 550. When tip 37 is retracted (relative to the rest of the catheter), as shown in FIG. 2TB, the wall is pinched and cut between an inner lip 554 of portion 550 and a cutting base 552 of the guiding catheter. In a preferred embodiment of the invention, the hole into which tip 37 is inserted is formed by tip 37 itself. Alternatively, the hole may be formed by a special cutting guide wire, which can be retracted prior to the advance of tip 37 or along which tip 37 rides.

In a preferred embodiment of the invention, the punched hole has a cylindrical volume. Alternatively or additionally, the volume comprises an oblique cylinder, with an elliptical cross-section at the vessel wall. Alternatively or additionally, the volume is conical. Alternatively, the volume is hourglass shaped. Alternatively, the volume comprises two base-to-base truncated cones.

In a preferred embodiment of the invention, one or more of a plurality of measurements may be performed at the hole in the blood vessel. In one example, the thickness of the vessel is measured, for example using an ultrasonic imager or distance or thickness sensor. Such a sensor (or other sensors described herein) may be provided at tip 37 or from a working channel of an endoscope which assists in the anastomosis. In another example, the elasticity of the vessel is measured, for example, by applying a known force and/or a known displacement to the vessel wall using a pressure transducer, and measuring the response (motion and/or pressure) at the transducer. In another example, the hardness of the vessel wall and/or reflections from it, are used to determine if there is a calcification on the inside (or outside of the vessel. These measurements may be applied either or both from inside and from outside a blood vessel. Alternatively or additionally, if a piezoelectric vibrating tip is used, such a tip may also be used to perform the sensing.

In a preferred embodiment of the invention, the sending is used to determine a desired hole size to be punched. Desirably, the hole is large enough so that the vessel is not unduly strained by the expansion of the hole and the hole is small enough so that the vessel walls will exert a pressure which aids in leak suppression and/or in holding the anastomotic connector in place. Possibly, a first, small hole is punched, to assess the radial force applied by the wall, and if the force is greater than desired (indicating undue strain on the vessel), a larger hole is punched.

In a preferred embodiment of the invention, the area of the punched hole is treated, for example, to prevent dissection of the vessel wall. In one example, the circumference of the hole is coagulated, for example using an electric field or a laser beam. Possibly, the coagulation is applied at spots on the circumference. Alternatively, a continuous coagulation is applied, for example by tip 37 itself being one electrode of an RF coagulation circuit. Alternatively or additionally, the punched hole is coated with tissue glue.

In a preferred embodiment of the invention, a drug may be applied to the punched area, for example to assist in healing, to prevent dissection and/or to assist in the hole punching process. In one example, the drug may induce the dilation of corollary blood flow. In another example, the drug may induce relaxation or expansion of the blood vessel, for example to stabilize the state of the blood vessel dilation or to assist in performing the punch. Possibly, similar effects may be achieved by applying low voltage electric currents to the blood vessel, to stimulate local relaxation or contraction.

In a preferred embodiment of the invention, an anastomotic connector is hollow. For example, the connector may be formed of two concentric tubes, with glue or a drug disposed between the tubes. When the connector is radially expanded, the glue or drug can be forced out of openings in the surface or between the layers. Preferably, the openings are at points whose final position relative to the anastomosis can be relatively guaranteed.

Alternatively or additionally, at least portions of the anastomotic device act as an RF antenna or as an eddy current generator, such that when an RF field or an AC magnetic file dare applied (respectively), at least the portions of the device heat and weld the anastomosis shut.

Alternatively to punching a hole in the blood vessel, a hole may be cut in the vessel by forming a circular cut-out. In one example, such a circular cut-out is formed by cutting along the circumference of the hole with a laser, a knife, a rotary cutter or an ultrasonic scalpel. Alternatively, the hole may be ablated, for example using RF ablation, micro-wave ablation or chemical ablation. Alternatively, a cutting tool may be placed inside a hole and used to cut sideways into the vessel wall.

Alternatively or additionally to using percutaneous techniques, the navigation, the final alignment with the artery (or vein) and/or the anastomosis to the artery (e.g., suturing) may be performed using a key-hole surgery technique. It should however be appreciated that key-hole surgery is aided by using the above described technique to bring, to a location adjacent a coronary vessel, a graft, one end of which is already attached to the aorta. Thus, only a key-hole procedure at the anastomosis location (coronary and/or aorta) is required.

In a preferred embodiment of the invention, after the bypass is performed, the graft is tested for leakage. Preferably, a contrast media is injected and a fluoroscopic image is acquired after a short wait to determine if any of the contrast material has leaked from the vascular system. In case of such leaks, the anastomosis may be strengthened, in some preferred embodiments of the invention, by inflating a balloon inside a leaking anastomosis connector to increase its contact with the wall of the vessel to which it is connected. Alternatively or additionally, a stent and/or a graft may be inserted within the leaky connector so that it is situated between the connector and the blood flow. Alternatively or additionally, the leaking anastomosis may be repeated, by disconnecting the graft from the vessel, providing a suitable anastomosis connector and activating the provided connector, to create the anastomosis.

Alternatively or additionally, key-hole surgery is performed only at the leaking anastomosis, for example, to suture it.

Many variations on the technique described above may be performed, within the scope of preferred embodiments of the invention. In the above description, tip 37 punches a pinhole (which is later enlarged) in aorta 30 and vessel 22. Alternatively, tip 37 may be used to punch a hole of a desired size and/or cross-section, in aorta 30 and/or in vessel 22. In a preferred embodiment of the invention, the hole is smaller than the final anastomosis cross-section. Alternatively, the hole is of approximately the final diameter.

The above technique may also be used to connect other blood vessels, for example, for femoral bypass or for a venous-arterial shunt. In addition, other body lumens may be connected, for example, in the intestines, in the urinary tract, in the bile system, and/or in the respiratory system.

It should be appreciated that guide wire 36, even after it perforates the aorta, does not necessarily allow blood to leak from the aorta. Thus, in some preferred embodiments of the invention, the above technique may be practiced, even if catheter 34 does not isolate hole 35 and/or without stopping the heart and/or without reducing the systemic and/or local blood pressure. Alternatively or additionally, it may be desirable to reduce the risk level so one of the above described techniques of reducing leakage from hole 35 and/or reducing the availability of blood at hole 35, may be practiced.

The description of FIG. 2A suggests the desirability of using a "J" shaped catheter and/or pointing the guide wire in the direction of target point 28. However, it should be appreciated that graft 38 is navigated in the body, possibly around obstacles (such as the heart itself). Thus, the initial direction of the guide wire exiting the aorta may be decided by other considerations, such as the location of the graft along the aorta, the ease of repairing the anastomosis, interaction of the anastomosis size, location and angle with blood flow in the aorta and in the graft, and/or plaque location and arteriosclerosis of the aorta. Once the vessel is outside the aorta, it can be guided to point 28.

In a preferred embodiment of the invention, a desired layout of graft 38 is determined before starting the procedure. Such a layout depends not only on the desirability of the end points, but also on the available maximum length of graft 38, the desire to minimize its length, available locations to attach the graft to anatomical structures, a desire to minimize the possibility of kinks and/or sharp bends in the graft, a desire to minimize the possibility of the graft getting pinched between two anatomical structures and a desire to minimize the probability of the graft being pulled out of one of the blood vessels to which it is attached.

In a preferred embodiment of the invention, as shown in FIG. 21, graft 38 may be used for a plurality of bypasses, for example, to bypass the entire left anterior descending coronary artery, especially if it has multiple occlusions. In a preferred embodiment of the invention, this is achieved using a plurality of side-to-side connections. Alternatively or additionally, graft 38 may be forked or contain other types of intersections allowing various legs of the graft to be attached at different places. Alternatively or additionally, a second graft 38' may be pushed out of graft 38, after graft 38 is in place, possibly using the techniques described herein. Alternatively or additionally, a side-to end anastomosis may be performed between the two grafts either before or after the first graft is inserted into the body. Alternatively or additionally, a side-to-side anastomosis is performed. When the second artery is at the "side" side of the anastomosis, the two ends of the second graft are preferably pushed out of the first graft together, until an anastomosis connector attached to the graft reaches the hole through which the graft was pushed out. Then, the anastomosis is preferably performed. It should however be appreciated that the procedures described herein may be applied to substantially any coronary artery.

As described herein, graft 38 is preferably provided through a blood vessel. In an alternate preferred embodiment of the invention, graft 38 is provided using other body organs as passageways, for example, using the lungs, intestines or other hollow organs. Alternatively or additionally, the graft is provided via the body cavity itself, for example, it is pushed into the body from the outside, via hole in the skin. In these embodiments, both of the anastomosis connections are preferably performed from the graft into a target blood vessel. The guide wire is preferably brought into the graft from a hole near its center and selectively guided to an end, depending on the end to be grafted. The hole may be patched, for examples, using methods described herein or known in the art. Alternatively, the two end anastomosis connections are performed using an endoscope which encloses or is parallel to the graft, without requiring a guide wire to pass through the graft at all. In one embodiment, the tip of the endoscope is used for piercing the blood vessel. The graft is inserted along the endoscope or possibly in a groove therein and then the endoscope is removed, leaving the graft in the blood vessel. Possibly, the endoscope has a deformable cross-section, to assist in removal of the endoscope without shifting the graft from inside the blood vessel.

Alternatively or additionally, the anastomosis connections are performed by attaching two grafts, one to each target vessel, for example using a side-to-end anastomosis, and then performing an end-to-end anastomosis on the free ends of the two grafts. Such an anastomosis may be performed percutaneously, for example by providing a catheter through one of the target vessels. Alternatively or additionally, the end-to-end anastomosis may be performed using key-hole approach. It should however be appreciated that a percutaneous approach is usually preferable to key-hole surgery, since it causes even less trauma to the body. However, in some cases, a key-hole surgical procedure is required anyway, so that it may be aided by a percutaneous procedure. Alternatively or additionally, to a key-hole procedure, a transvascular procedure may interact with an endoscopic procedure, whereby a flexible endoscope is guided to a desired location in the body, adjacent where a transvascular procedure is being performed.

Figure 2U:
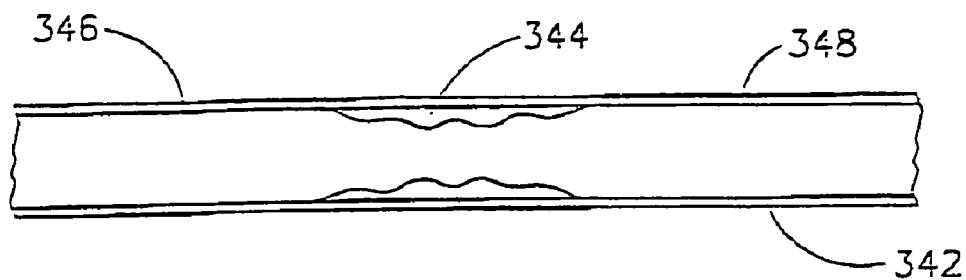
FIGS. 2U–2W illustrate end-to-end anastomosis connections in accordance with preferred embodiments of the invention.
Figure 2V:
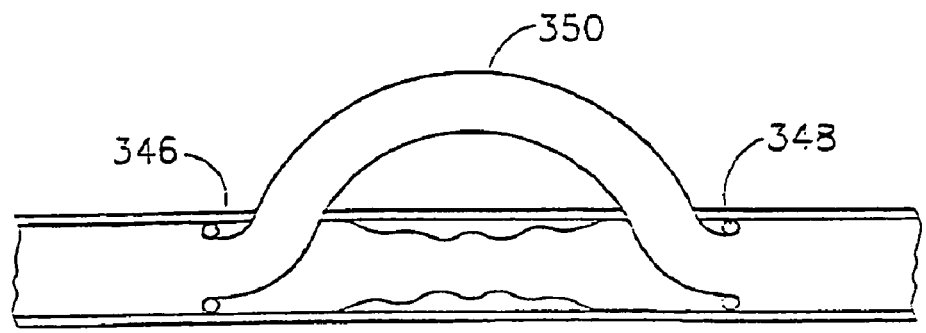
Figure 2W:
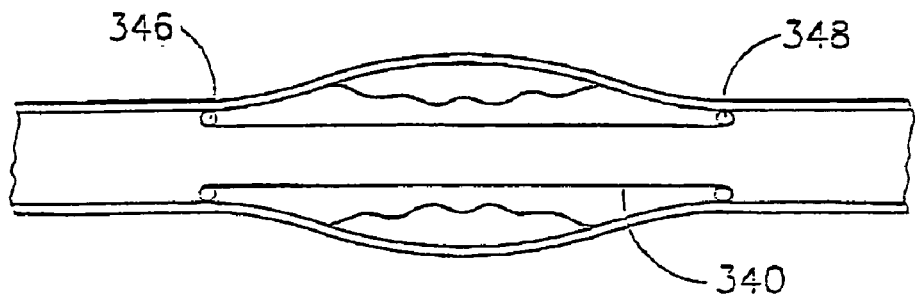

FIGS. 2U–2W illustrate end-to-end anastomosis connections in accordance with preferred embodiments of the invention. FIG. 2U shows a blood vessel 342, possibly a coronary vein or artery having an occlusion 344. In accordance with some preferred embodiments of the invention, a bypass may be performed between a pair of points 346 and 348 which are on either side of occlusion 344. The bypass may comprise a graft which attaches using a side-to end anastomosis at point 346 and an end-to-side anastomosis at point 348, for example using the methods and apparatus as described herein. Alternatively, an end-to-end inside anastomosis, as shown in the Fig., may be performed at one or both of 346 and 348. Alternatively, as shown for example in FIG. 2V, a graft 350 may be connected to point 346 using an end-to-end anastomosis. The connection at point 348 may be end-to-side (possibly oblique), end-to-end or an enclosed connection, in which graft 350 is inserted through the side of vessel 342 and is bent so that it is coaxial with vessel 342. In a preferred embodiment of the invention, the end-to-end anastomosis at point 346 is achieved by expanding a guiding catheter (not shown, similar to catheter 302) to block the entire lumen of vessel 342 at point 346. Such an expandable catheter may for example include an outer balloon layer which can be radially expanded against vessel 342. A cutting tool is then extended through the lumen of the guiding catheter to sever (partially or completely) vessel 342. Then, graft 350 may be navigated out of the catheter to point 348, at which an anastomosis may be formed. Similar navigation techniques as described herein may be used. Additionally, a guide-wire (not shown) may be provided to pass occlusion 344, for example between the guide catheter and the wall of vessel 344, prior to the severing, to mark location 348.

FIG. 2W illustrates a different type of end-to-end anastomosis which is somewhat similar to stent grafting. In this method, graft 350 does not exit vessel 342. Rather, a guidewire is passed through occlusion 344 and the occlusion is expanded enough so that a graft can be passed therethrough. In some cases the occlusion is so complete that it is necessary to drill a hole through occlusion 344, for example using laser or a rotary ablator. In a preferred embodiment of the invention, vessel 344 is sealed at or before point 346, so that if the seal of vessel 342 is compromised by the expansion, no blood will leak out. Such sealing may use balloons or an expandable catheter. Expanding anastomotic connectors are then expanded at the two ends of graft 350, to complete the procedure. Alternatively, in FIGS. 2U and 2V, the seal at point 346 may be formed by an end-to-end anastomosis between graft 350 and vessel 342. After this graft is completed, the rest of the graft is advanced either through the occlusion or around the occlusion. Typically, graft 350 is folded or otherwise contracted so that it fits between point 346 and occlusion 344. Alternatively, a first anastomosis is performed at point 348. Alternatively, graft 350 is inverted prior to insertion and is then un-inverted after the seal (or anastomosis) is made at point 346.

Several distinctions should be noted between a stent and a connector in accordance with some preferred embodiments of the invention:

(a) An anastomosis connector, in some preferred embodiments of the invention, requires less contact with the blood than a stent, since it is mostly, if not totally, outside the blood vessel. For example, the embodiment of FIG. 8U would may be considered undesirable for use in a stent, due to the large amount of surface area it has.

(b) The total area of contact between the connector and the blood vessels is generally smaller, since the connector is not usually required to structurally support a significant portion of the blood vessel.

(c) An anastomosis connector usually comprise less metal (per volume and/or surface unit) than a stent, since the connector usually needs to provides less support.

(d) An anastomosis device, in some embodiments described herein, is in contact mostly with the outside of the blood vessel, while a stent is mostly (or wholly) in contact with the intima. One reason for this is that the blood vessel is everted for anastomosis, in some preferred embodiments of the invention.

(e) In preferred embodiments of the invention, an anastomotic device grasps a blood vessel from one or two sides, in a way that may prevent dissection of the blood vessel. A stent usually only pushes against the blood vessel and does not engage the interior of the vessel wall, from one or two sides.

Referring especially to FIGS. 2A–2G, in a preferred embodiment of the invention, guide wire 36 has a tip diameter of, for example, 0.018 inches and tapers slightly. When inserting the guidewire into vessel 22, preferably one, two or three centimeters are inserted into the vessel. The anastomosis connector has, for example, an outer diameter of about 0.8 mm, in its closed configuration and is made of stainless steel with a thickness of between 0.1 and 0.2 mm.

The above description is generally applicable with respect to the various types of anastomosis devices used, in accordance with preferred embodiments of the invention, to connect graft 38 with vessel 22 and/or aorta 30. There are several considerations in selecting a configuration for an anastomosis device, some of which are listed below. It should be appreciated that some of the considerations are have a greater effect on some of the preferred embodiments, than other considerations.

(a) Bringing the two vessel together. In some preferred embodiments of the invention, the anastomosis device brings the two vessels closer together.

(b) Non-desirability of leaks. In some preferred embodiments of the invention, the anastomosis device provide a large area of contact between the two blood vessels, preferably completely surrounding the anastomosis connection. The probability of leaks occurring in this embodiment is reduced. Alternatively or additionally, the connection may be strengthened after the anastomosis connector is in place, in accordance with some preferred embodiments of the invention.

(c) Non-desirability of vessel flaps remaining in the blood flow. In some preferred embodiments of the invention, such flaps are trapped by the anastomosis connection. Alternatively or additionally, the flaps are pushed out of the blood flow. Alternatively or additionally, such flaps never come into existence, since the anastomotic connections are made by stretching a pin-hole, not by cutting a cross. A cross shaped slit or a straight-line slit may be cut using a guide wire with a suitably shaped tip. Alternatively or additionally, a sharp tip of the guide wire may be used to cut any desired shape by moving it along the surface of the blood vessel.

(d) A requirement to maintain a minimum cross-section of the anastomosis connection. In a preferred embodiment of the invention, the anastomotic connector comprises a ring portion, which maintains the connection cross-section to be at least the inner diameter of the ring. Alternatively or additionally, the connection between the two blood vessels is such that the configuration is not under tension or is under a minimal amount of tension when the anastomosis is open. For example, if the lips of the (expanded) pinhole are folded back the tension is much greater on the lips than if they are not folded back. Alternatively or additionally, the blood pressure maintains the anastomosis open. The fact that the anastomosis is on a major blood vessel, in accordance with some preferred embodiments of the invention, aids in keeping it open. Alternatively or additionally, a portion of the "side" vessel is cut out, so that there is an opening therein which is covered by the "end" vessel.

(e) Desirability for a minimum amount of contact of non-endothelial surfaces with the blood. This consideration includes both a desire to minimize the contact between foreign objects and the blood flow, and a desire that after the anastomosis is complete only endothelial surfaces of the blood vessels are in contact with the flow. Various connectors in accordance with preferred embodiments of the invention, as described herein, meet one or both considerations.

(f) Probability of the connection remaining leak proof for a long time. In a preferred embodiment of the invention, the anastomosis connector provides a tissue-to-tissue contact area, in which there is little or no tissue necrosis. Thus, after a short while, a bridge is formed between the tissues of the two vessels.

(g) Requirement to perform eversion of vessel tips, especially if vessels are hardened or otherwise sensitive. Some types of anastomosis require a 90 degree or a 180 degree eversion of the vessels. Although this usually results in a best connection, it may not be possible in some cases, for example if the vessels are hardened or prone to cracking. Some of the anastomosis connectors described herein require little or no eversion. An additional benefit of not requiring eversion is a reduction in the difficulty in preparing the vessels for anastomosis. Preferably, only the graft vessel is prepared before the procedure. The intra-body vessels cannot usually be prepared for anastomosis using percutaneous tools and in some preferred embodiments of the present invention, need not be prepared.

(h) The number of pieces inserted into the body. There is usually a desire to minimize the number of object inserted into the body and/or the blood stream, to minimize the danger of one of the pieces getting lost or stuck. In some preferred embodiments of the invention, the anastomosis connector comprises a single piece, which is pre-attached to the graft. Other embodiments utilize two or more pieces.

(i) The simplicity and speed of performing the anastomosis. In a preferred embodiment of the invention, the speed and simplicity of the anastomosis procedure are improved over those used in the prior art.

(j) The type of connection between the blood vessels. Various types of connections are provided in accordance with preferred embodiments of the invention, as described above and as described below with reference to FIGS. 3A–3O. In particular, in some preferred embodiments of the invention the anastomosis connection is an intima-to-intima connection.

(k) The type of force holding the vessel together. Various attachment means are provided in accordance with preferred embodiments of the invention, including, mechanically pushing the two contact surfaces together, for example utilizing pins piercing both surfaces, glue, welding and/or plastic flowable material provided at and/or around the anastomosis connection.

(l) The strain on the blood vessel. The strains are mainly a result of a blood vessel being maintained in an unnatural configuration because of the anastomosis. In a preferred embodiment of the invention, the type of strain may be traded off with the type and/or quality of the connection. For example, strain may be a result of eversion. In a preferred embodiment of the invention, for a given procedure, no eversion is required, or eversion may be limited only to a blood vessel which can take the strain. In some embodiments, strain may be the result of stretching a pinhole in a "side" connected vessel. In a preferred embodiment of the invention, a larger hole may be made in this vessel to reduce the strain. In addition, strain may be a result of bending or everting a blood vessel. Various types of eversions are provided for in some of FIGS. 3A–3O. In a preferred embodiment of the invention, some of the strain is carried by the anastomosis connector itself. Preferably, the connector is attached to the vessels at many points, so that the strain may be divided over all the connections. In addition, if one connection fails, this does not necessarily mean the anastomosis will leak. Another type of strain is the result of the contact area being substantially non-planar, as for example in a diagonal connection or in an end-to-side connection between two vessels of similar diameters. Preferably, the connector achieves a non-planar shape to conform to the shape of the contact area, thereby minimizing the tension on the vessels. Alternatively or additionally, the graft is precut to have a non-flat end, so as to reduce the strain on it.

In some cases, the long term strain is minimized. Alternatively or additionally, the strain applied during the anastomosis is minimized. Alternatively or additionally, a tradeoff is achieved by which an acceptable strain is present. Preferably, the type of anastomosis performed takes into account a maximum desired strain threshold.

(m) The requirement to provide the anastomosis connector through a narrow-diameter catheter lumen. In a preferred embodiment of the invention, the connector is expandable and/or distortable, so that it may be conveyed in a configuration which fits a desired lumen size. Alternatively or additionally, the connector comprises a plurality of staples or other local connectors and the connection is made using an expandable anvil or framework which is brought through the lumen and expanded to have a diameter larger than the cross-section of the anastomosis. Alternatively or additionally, the minimum diameter of the graft with the connector attached may also be controlled and is different for different types of connectors and/or connection configurations. For example, configuration 82 in FIG. 4B can have a smaller diameter than configuration 80.

(n) Turbulence. The connection between the two blood vessels may cause turbulence, stagnation and/or clotting. In a preferred embodiment of the invention, the angle and/or size of the anastomosis is selected to minimize turbulence. Alternatively or additionally, a connector type and/or an anastomosis type is selected to minimize turbulence, for example, by providing a low profile anastomosis connection.

(o) Blockage of the graft or the end-vessels. In a preferred embodiment of the invention, most or all of the anastomosis connection is outside the blood vessels, so that the flow of blood in the anastomosis area is minimally impeded. Alternatively or additionally, in large blood vessels, a small portion of the cross-section may be sacrificed to achieve a better, faster and/or lower cost anastomosis.

Figure 3A:
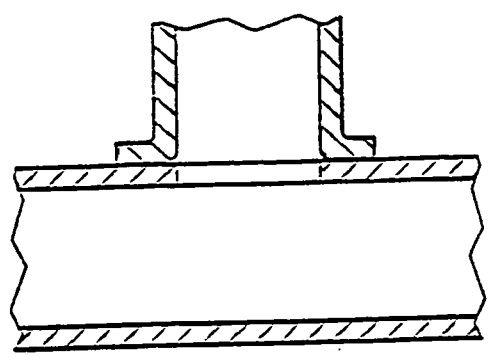
FIGS. 3A–3H, 3HA and 3I–3O illustrate different types of side-to-end and end-to-end joints, achievable in accordance with preferred embodiments of the invention.
Figure 3B:
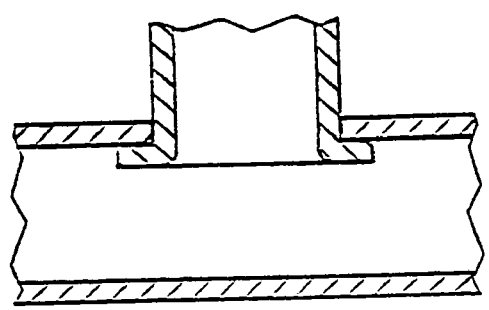
Figure 3C:
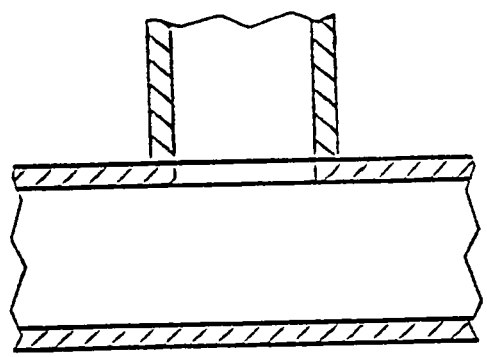
Figure 3D:
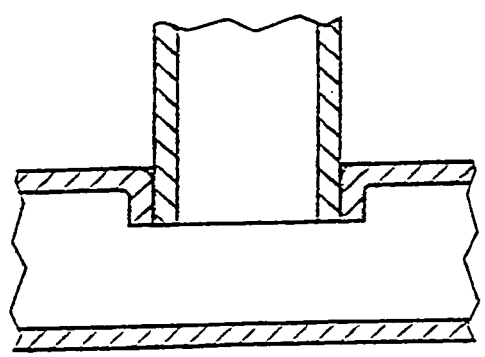
Figure 3E:
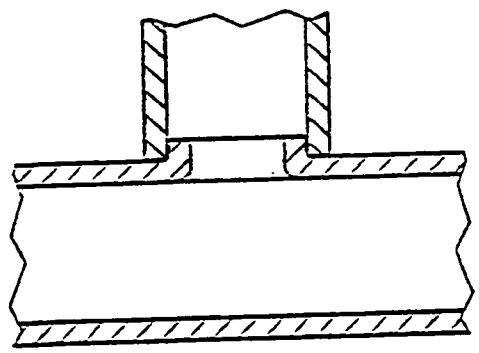
Figure 3F:
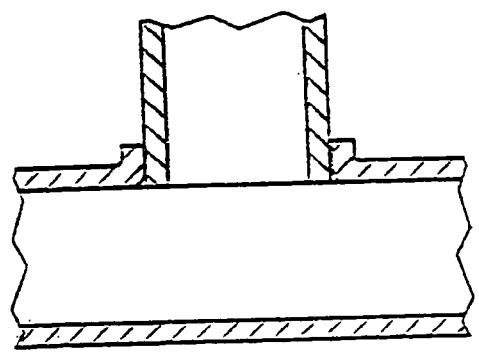
Figure 3G:
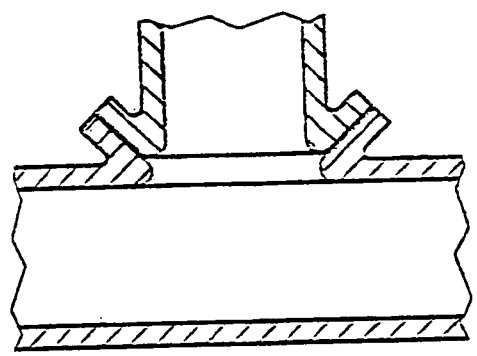
Figure 3H:
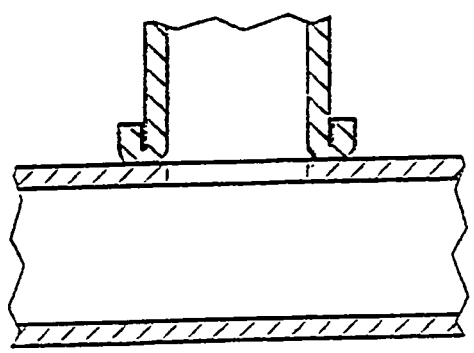
Figure 3H:
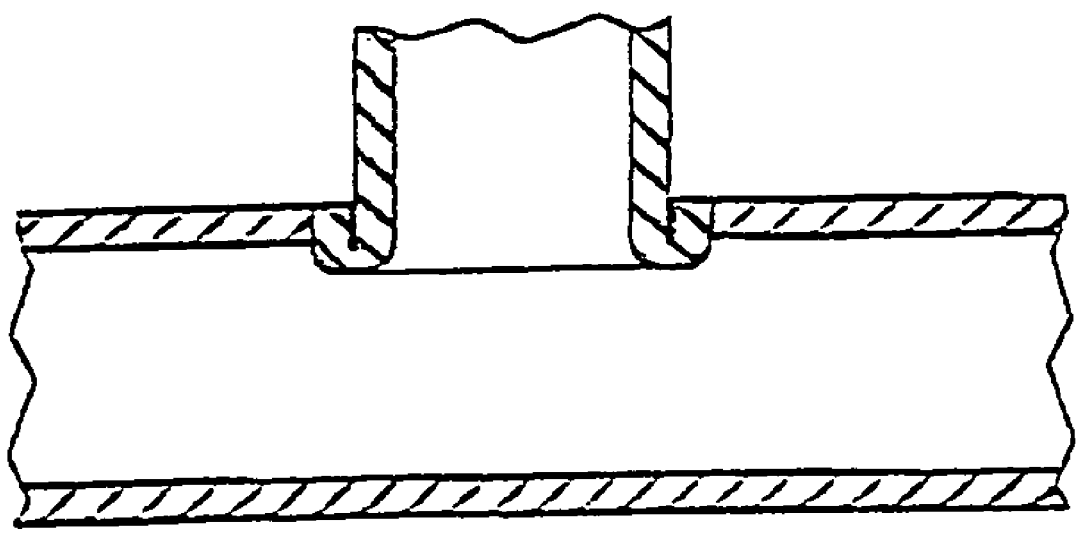
Figure 3I:
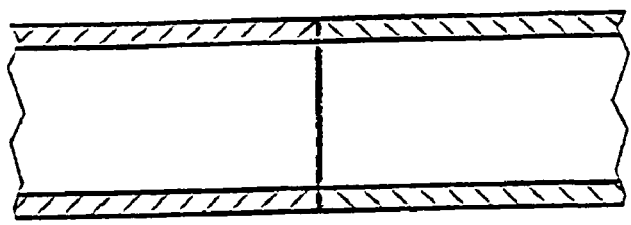
FIG. 3P illustrates a side-to-side anastomosis, in accordance with a preferred embodiment of the invention.
Figure 3J:
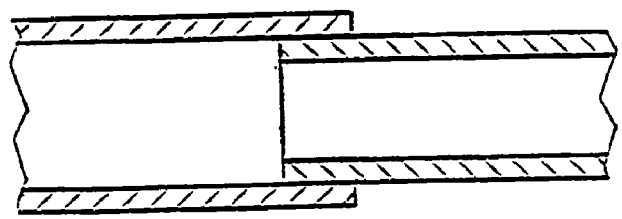
Figure 3K:
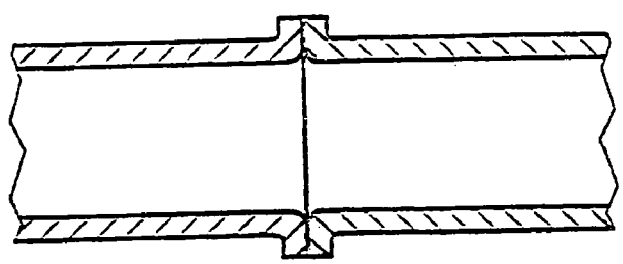
Figure 3L:
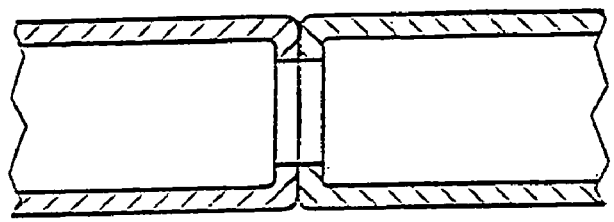
Figure 3M:
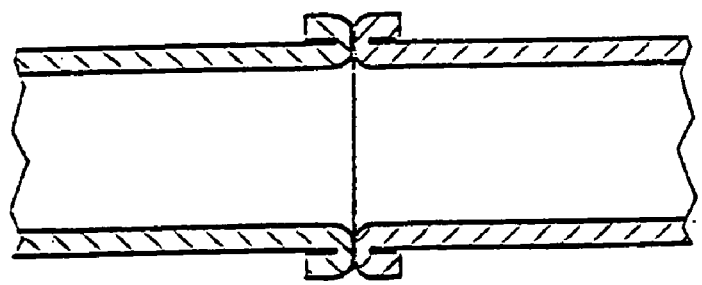
Figure 3N:
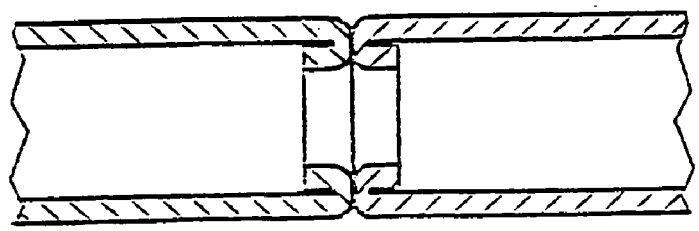
Figure 3O:
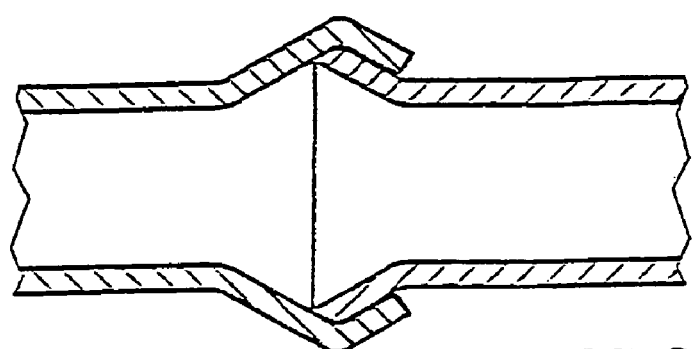
Figure 3P:
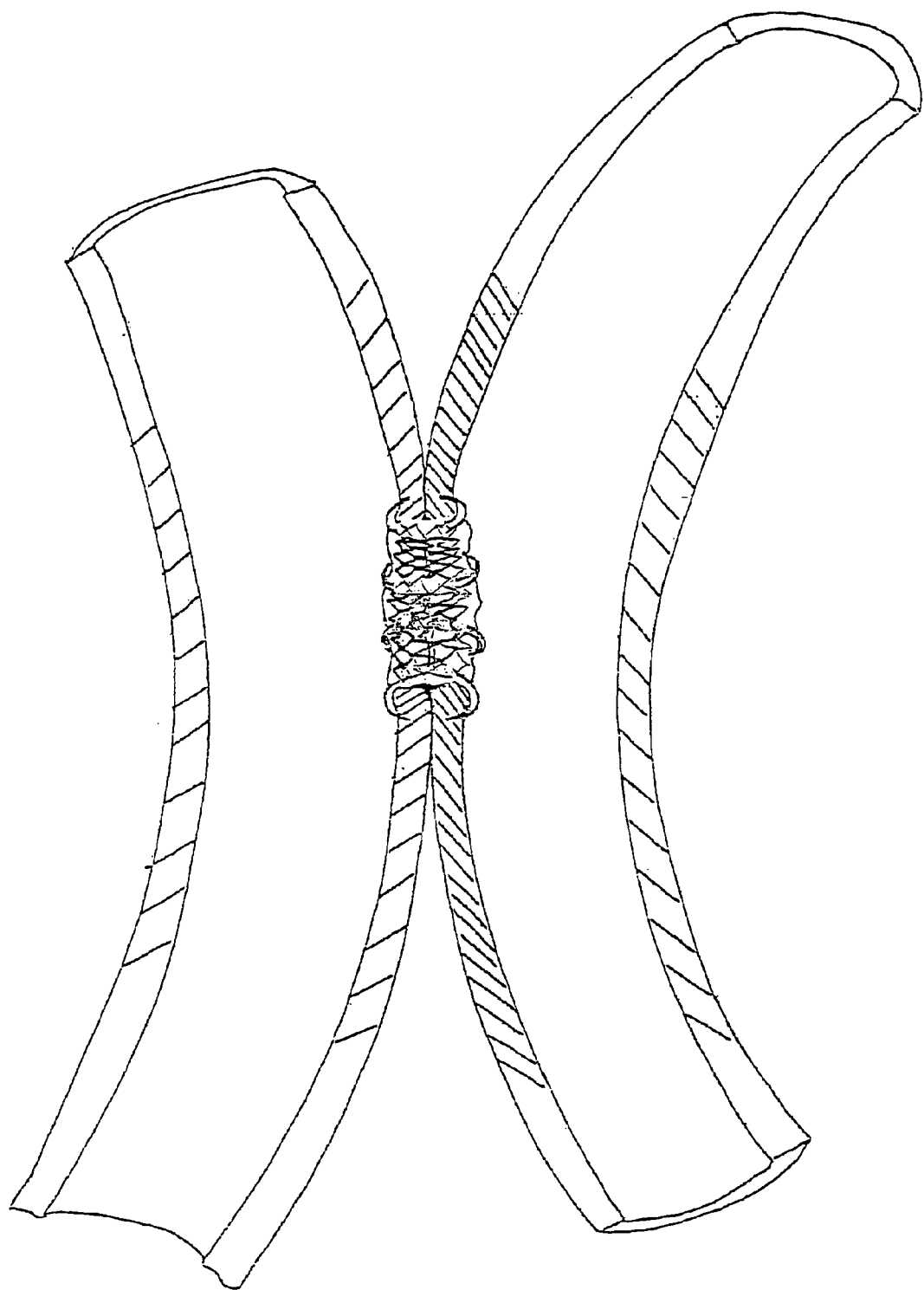
Figure 4A:
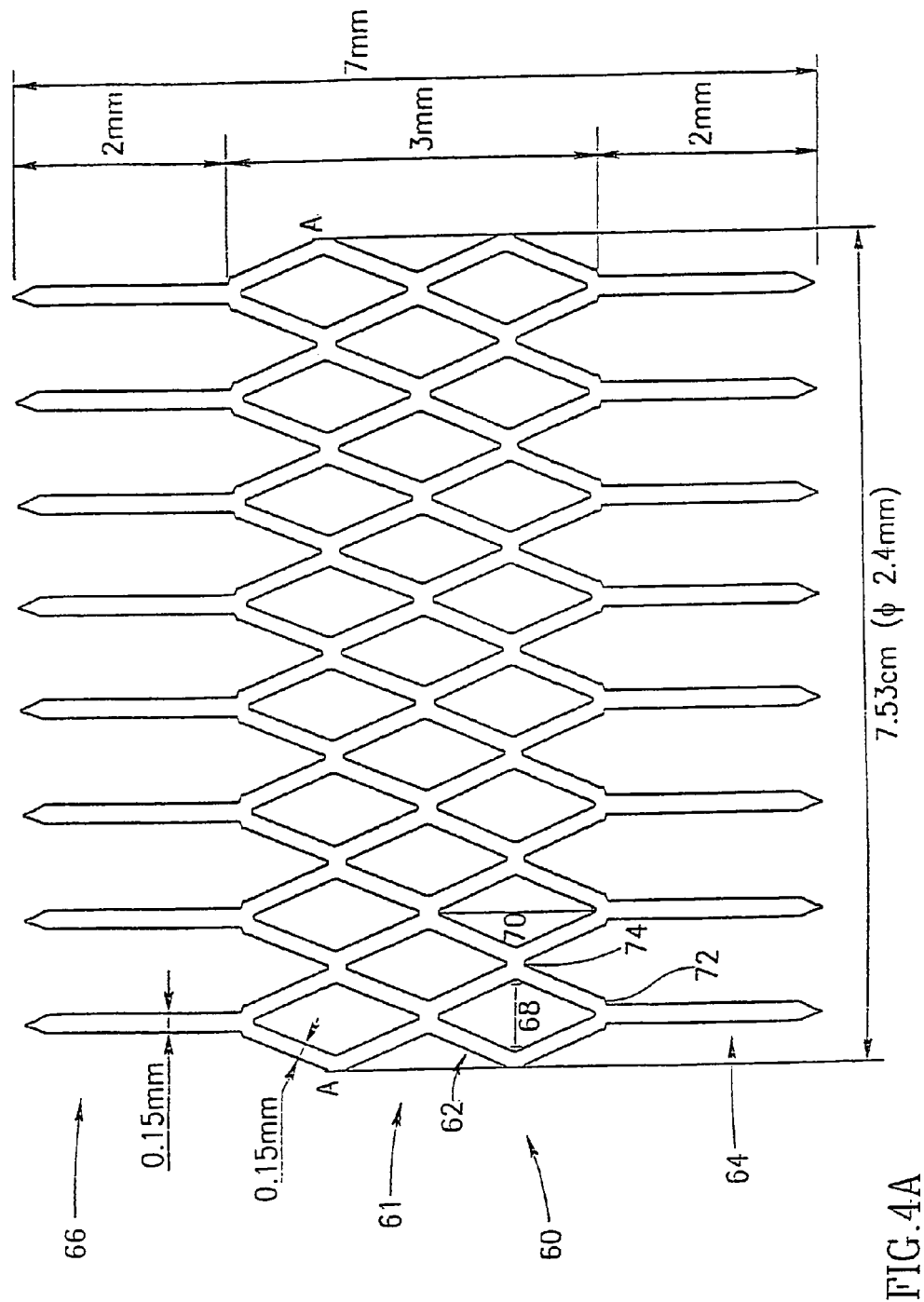
FIGS. 4A–4D illustrate a one piece anastomosis connector, in a plan view and in various stages of deployment, in accordance with preferred embodiments of the invention.

FIGS. 3A–3O illustrate different types of side-to-end and end-to end anastomosis connections (with no connector shown), achievable in accordance with preferred embodiments of the invention. FIGS. 3A–3HA illustrate end-to-side anastomosis connections. FIGS. 3I–3O illustrate end-to-end anastomosis connections. Typically, an anastomosis connector, as described below, either will pierce the blood vessels on both sides of the contact area or will follow the contour of the contact area. Alternatively, the connector may be completely outside the blood vessels. FIG. 3P illustrates a side-to-side anastomosis, in cross-sectional view, in accordance with a preferred embodiment of the invention. In a preferred embodiment of the invention, an anastomotic connector, for example similar to the connector shown in FIG. 4A is provided, for example using a system as described with reference to FIG. 8. Alternatively, the tip of the connector is threaded and the connector is rotated to engage and hole the side of the enclosing vessel.

FIG. 4A illustrates a one piece anastomosis connector 60, in plan view, in accordance with a preferred embodiment of the invention. Connector 60 preferably includes a first spike section 64, a central section 61 and a second spike section 66. Preferably, the central section comprises a plurality of parallelograms 62. When installed, central section 61 is preferably closed, for example, by overlapping at the two lines marked "A". This closing may be by manual welding, supplying a connector or by connector 60 being formed as a cylinder. Alternatively or additionally, connector 60 is formed to naturally assumes a cylindrical shape. Alternatively or additionally, connector 60 is simply rolled into a cylindrical shape, without the two sides being connected. Although two spike sections, one at each side of the device have been described, in other preferred embodiments of the invention, a fewer or a greater number of spike sections may be provided, for example, one, three, four or five. Alternatively or additionally, the spikes in a spike section may be arranged in bands around the circumference, in axial bands, in groups and/or in other arrangements. Alternatively or additionally, the spike sections may be formed in the center of the connector or in central section 61.

In a preferred embodiment of the invention, all the parallelograms 62 are of equal size. Alternatively or additionally, they are not all the same size and/or shape, for example to better control the final geometry of the connector or the deployment of the spikes. In a preferred embodiment of the invention, section 61 comprises a plurality of bands, each of which has a different parallelogram size and/or shape, for example for providing an hour-glass or a tapered profile. The bands may be radial. Alternatively or additionally, the bands are axial, for example, to control particular spikes provided along or at an end of the band. Alternatively or additionally, a different spatial distribution of parallelograms is used. The spikes may be connected at outer vertexes 72 of section 61. Alternatively or additionally, some or all the spikes of at least one of the sides are connected to inner vertexes 74. The ratio between an axial radius 70 and a radial axis 68 of the parallelogram is preferably a controllable property of the device.

Connector 60 may be formed to have elastic tensions in portions thereof so that it has a resting shape other than that of a cylinder. Preferably, connector 60 comprises a super-elastic, elastic and/or shape-memory material. While being deployed, connector 60 is preferably maintained in a desired geometry using mechanical restraints. Alternatively or additionally, connector 60 is formed of a shape-memory alloy, which is activated when the connector is deployed. Alternatively or additionally, at least portions of connector 60 are formed of a plastic material, which is plastically distorted, for example by a balloon, into a desired configuration. These different elastic characteristics may be combined in a single device. For example, the spikes may have a super elastic, elastic or shape-memory tendency to fold out and grab tissue and the cylinder may be super elastic, elastic or shape-memory, so that when relived of constraints, it expands radially slightly, thus providing room for a balloon to be inserted therein. The rest of the deformation is preferably provided by plastic deformation. Alternatively or additionally, some portions of connector 60 may be specifically made weaker so that any plastic deformation tends to concentrate at those locations. Thus, it is possible to predetermine where connector 60 will bend, when inflated by a balloon, for example.

In a preferred embodiment of the invention, connector 60 is formed of a stainless-steel central section 61 welded to super-elastic or shape-memory spikes (e.g., NiTi). Possibly, the spikes are formed with a ring, possibly containing whole or partial parallelograms, which ring is welded to section 61. Possibly, the connector is cut, preferably using a laser, after it is welded. Alternatively or additionally, the connector is first welded then cut. Alternatively, the connector is all formed of a super-elastic, elastic and/or shape-memory material, which material is annealed at portions thereof, for example at central section 61, to not have an innate tension. Alternatively or additionally, the material is annealed to make is a more plastic material.

In some preferred embodiments of the invention, connector 60 is, at least to some extent a passive device, whose final geometry is determined by external considerations, such as by a balloon which expands the connector or by additional shaping elements which may be provided at the connector during deployment thereof. Alternatively or additionally, connector 60 is, at least to some extent, an active device, for example being composed of shape-memory material. In an active device, the forces that determine the devices shape arise from the device itself Typically however, some control over the device's final configuration, can be exerted by providing suitable restraining elements while the device is being deployed.

In a preferred embodiment of the invention, connector 60 is an assistive device, whose passive responses to external forces and/or activity as a result of internal forces are directed towards assisting the anastomosis process as a whole and/or particular steps thereof. An assistive anastomosis device preferably aids the anastomosis process in one or more of the following ways:

(a) Grasping tissue so it does not move during critical steps of the anastomosis.

(b) Everting and/or guiding the eversion of one or both vessel so that a desired type of intima contact is achieved.

(c) Exerting pressure between tissue portions, especially to stop blood leakage.

(d) Aligning of the connector and/or the blood vessels. One particular type of alignment is self-centering of the connector in the aorta.

(e) Tightening. One type of tightening assistance is tightening limitations, to avoid over-tightening of the device during deployment. Another type of tightening assistance is self tightening, so that the device does not become loose during the time after it is implanted and.

(f) Deployment of the connector in steps, rather than as a continuum. In some preferred embodiments of the invention, the deployment of the device is in clearly defined steps. Thus, the results of each step can be checked for suitability. Also, a single step can be undone and or adjusted, if necessary. Further, the treating physician can work at a slower pace, if necessary. Alternatively or additionally, the tissue has time to achieve a steady state between steps, allowing better control over the deployment. One example of a step-by-step deployments is if first the front spikes extend, the extension (when completed) releasing a restraint which allows the connector to expand, thereby causing axial shortening. The restraint may be released, for example, by a base of the spike moving or twisting.

(g) Piercing and expanding holes in blood vessels. In a preferred embodiment of the invention, the end of connector 60 (when un-expanded) can serve as a tip for piercing a blood vessel. Alternatively the end of connector 60 can serve as a device (possibly a punch or a portion thereof, such as the outer tube) for cutting out a portion of the vessel wall. Alternatively or additionally, connector 60 may expand inside the hole thereby increasing its radius.

In a preferred embodiment of the invention, the maximum radial expansion in the center of the connector is smaller than at it upper or lower (axial) ends. Thus, when inflated it will assume an hour-glass form, so that it holds better. Such a form may also assist in everting the tips of the graft and/or the aorta. Also, such a form may assist in self-centering of connector 60 in the hole made in the side of aorta 30. Alternatively or additionally, the connector is made stiffer at its center, so that when inflated by an elastic balloon, the connector will tend to expand more at its ends that at its center. In a preferred embodiment of the invention, different levels of stiffness may be achieved by varying the shape of the parallelograms and/or the thickness of the sides and/or by surface treating portions of the connector and/or by heat-treatment of portions of the connector and/or by using special coatings on portions of the connector.

In a preferred embodiment of the invention, the connector is not symmetrical in its final configuration, around its axial axis and/or around a radial line. In one example, the lower portion has a maximal radial expansion higher than the upper portion. In a preferred embodiment of the invention, this asymmetry matches characteristics of the connection type and/or the relative sizes of the blood vessels. In a preferred embodiment of the invention, the parallelogram's sizes and stiffness' are varied so that the connector everts over itself, possibly 90 or 180 degrees and/or assumes the shape of a top-hat, with a "T" cross-section. This type of connector may be used as a "T" shaped patch to patch a failed side-to-end anastomosis. Alternatively or additionally, this type of configuration is used for everting a "side" interface of an anastomotic connection.

In a preferred embodiment of the invention, element shapes other than parallelograms are used; for example, other four-sided shapes, pentagons, hexagons, circles and/or arbitrary shapes formed of straight lines and/or curved lines. In a preferred embodiment of the invention where a triangular shaped element is used, preferably one of the sides of the triangle is pre-formed so that when it is distorted it folds out to engage tissue and does not fold out into the blood stream.

In a preferred embodiment of the invention, connector 60 is radioactive, preferably, to retard intimal growth. Preferably, the level of radioactivity is not constant along the length of the connector. Preferably, portions of the connector which are at or near the contact between the two blood vessels are not radioactive. Alternatively or additionally, only portions of the connector which are in contact with the blood are radioactive. Alternatively or additionally, the spikes are not radioactive, at least in portions thereof which engage the vessel walls.

Alternatively or additionally, the resting form of connector 60 is not a simple cylinder. In a preferred embodiment of the invention, the connector naturally assumes a form shown by one of the cross-sections in FIG. 4B, below. Alternatively, such a shape may be dictated by a suitably shaped anvil-balloon, against which the connector is expanded.

One characteristic of some preferred embodiments of the connector shown in FIG. 4A, is a coupling between radial expansion and axial contraction. In a preferred embodiment of the invention, when connector 60 is expanded in a radial direction, it contracts in an axial direction. An example of this relationship is illustrated in FIGS. 4B–4D that show different amounts of radial expansion.

Figure 4B:
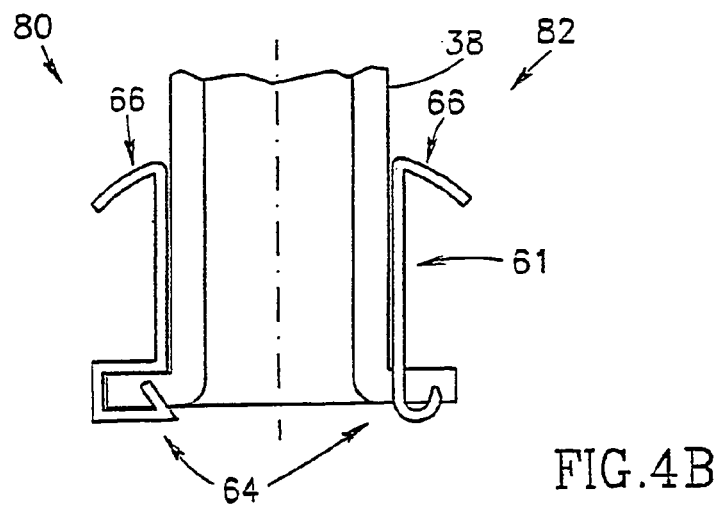

FIG. 4B shows in cross-section two possible starting configurations, 80 and 82, for mounting a connector 60 on a graft 38. In both configurations, spikes 66 are bent and spikes 64 are bent to engage the graft. However, in configuration 80, spikes 64 conform to the outside of the eversion of the graft, while in configuration 82, spikes 64 pierce through the everted portion of the graft. Typically only one of configurations 80 or 82 will be used in any particular connection. In some cases however, both configurations may be used in a single connector.

Figure 4C:
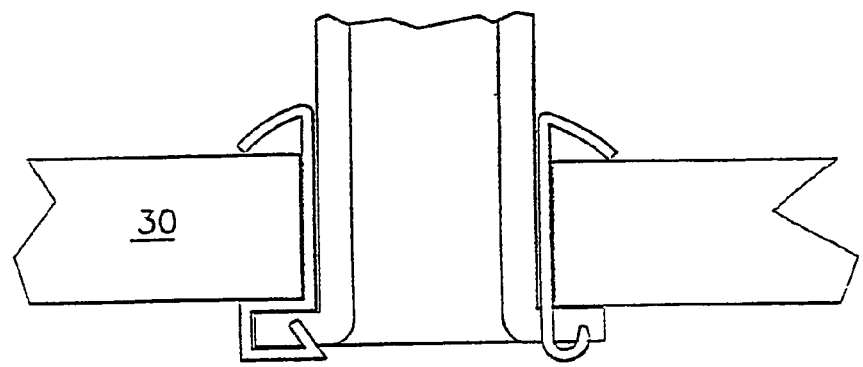
Figure 4D:
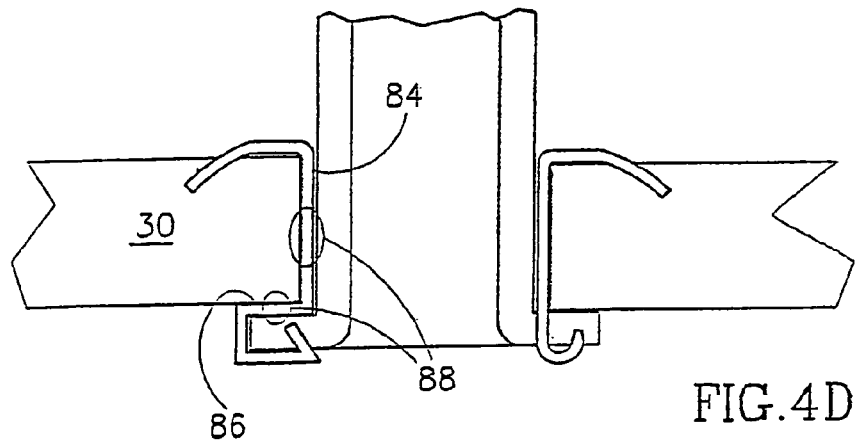

In FIG. 4C a wall of aorta 30 is shown in cross-section, where it is not yet engaged by spikes 66. This configuration is preferably achieved by pushing the configuration of FIG.

4B out of the aorta, along a guide wire, until the everted part of graft 38 comes into contact with the aorta, as shown in FIG. 4C.

FIG. 4D shows the result of expanding a balloon inside graft 38. As a result, the inner radius of connector 60 increases. Simultaneously, the hole in aorta 30 may also be expanded. Also simultaneously, connector 60 experiences an axial contraction, which urges spikes 66 into the aorta and which forces together the everted portion of graft 38 and aorta 30. In this anastomosis two surfaces which are forced into contact are indicated in FIG. 4D as 84 and 86 respectively, namely (i) the aorta and the side of the graft and (ii) the inside of the aorta and the everted portion of the graft. Although connector 60 runs along one (configuration 82) or both(configuration 80) of these surfaces, there is a large amount of tissue-to-tissue-contact, since the connector is preferably not a solid surface.

As can be seen in FIGS. 4B–4D, various types of spikes and spike deformations may be practiced in accordance with preferred embodiments of the invention. The spikes may extend at an angle to the surface of, for example, 45°, 90°, 135° 180° (parallel with an offset) or 270°. Typically, the spikes are extended at one angle (possibly 0°) before deployment and the deployment changes the angle. The deployment of the connector may deform the spikes in several ways: the spikes may bend an additional amount, for example 45 or 90 degrees; and/or the spikes may extend in a same direction, for example as spike 66 does in FIG. 4D. In addition, the axial shortening of the connector may also affect the position of the spikes, effectively shortening or lengthening them. As can be appreciated, a single connector may utilize a plurality of spike angles and deployment methods, possibly in a non-symmetric manner. The direction of the spike deformation can be axial, perpendicular to the connector surface, parallel to the connector surface or a combination thereof. Some ways of achieving perpendicular deployment are described with reference to FIGS. 7C–7N.

In a preferred embodiment of the invention, connector 60 has a non-constant thickness. In a preferred embodiment of the invention, the non-constant thickness is used to provide varying amounts of elasticity and plasticity to different parts of the connector. Alternatively or additionally, increases in thickness, for example as shown at locations 88 in FIG. 4D, possibly comprising a ring around the connector, are used to provide a better seal against blood escaping the anastomosis.

Figure 4E:
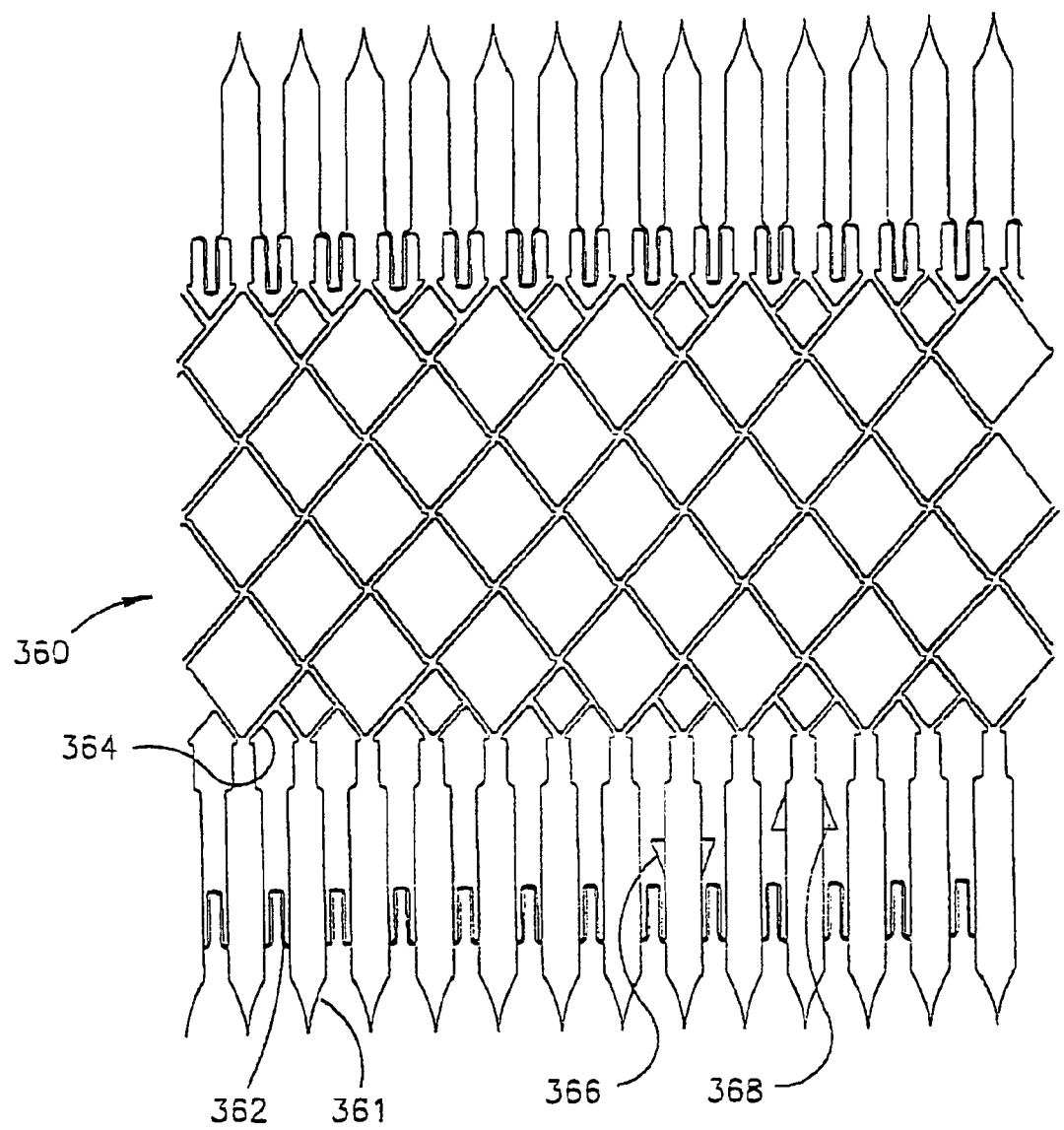
FIG. 4E illustrates a one piece anastomosis connector, in accordance with another preferred embodiment of the invention.

FIG. 4E is a plan view of an anastomotic connector 360, in accordance with a preferred embodiment of the invention. Several features are illustrated in connector 360, not all of which are required in a single connector. A first feature is wires 362 which interconnect spikes 361 of the connector. These wires limit the maximum expansion achievable by the spike portion of the connector. Alternatively or additionally, these wires stop spikes 361 from digging too deeply into the blood vessels. If the spikes dig in deeply enough, the blood vessel will contact the parallelograms, which being "V" shaped at the point where they contact the spikes, could mangle the blood vessel. In some preferred embodiments of the invention, the "V" shaped expansion at the base of spikes may be used to slice through a graft which is transfixed on the spikes, by expanding the radius of the connector such that the graft is forced to expand over the base of the spikes and be cut.

A second feature is struts 364 that form smaller parallelograms at the base of the spikes. These struts can serve the purpose of allowing a larger number of spikes than parallelograms in a circumference. Another purpose they can serve is limiting the radial expansion of the spike area, thereby limiting the expansion of the anastomosis opening, for example so avoid ripping the graft by over expansion, while allowing the rest of the connector to expand to a radius greater than that of the graft, if necessary. Another purpose they can serve is as a stop to stop the vessel from destroying itself on the parallelograms. The terms "wires" and "struts" as used herein are used to differentiate between the functions of two structural elements: wires apply tension, while struts can withstand compression and torque, to some extent. Both struts and wires may be connected between spikes, parallelogram sides, and/or parallelograms vertices. Additionally, struts and wires may be connected parallel, perpendicular or at a different angle to the connector axis.

A third feature is a tissue block 366, which can serve to prevent the blood vessel from slipping off the spikes. A fourth feature is a tissue block 368, which limits the advance of the blood vessel along the spike. The two types of blocks (and/or any of the above features) can be used in conjunction, to define an area of the spike within which the vessel will come to a rest.

FIGS. 4F–4I illustrate anastomosis connectors which require a minimum amount of physician intervention, during deployment, in accordance with a preferred embodiment of the invention.

Figure 4F:
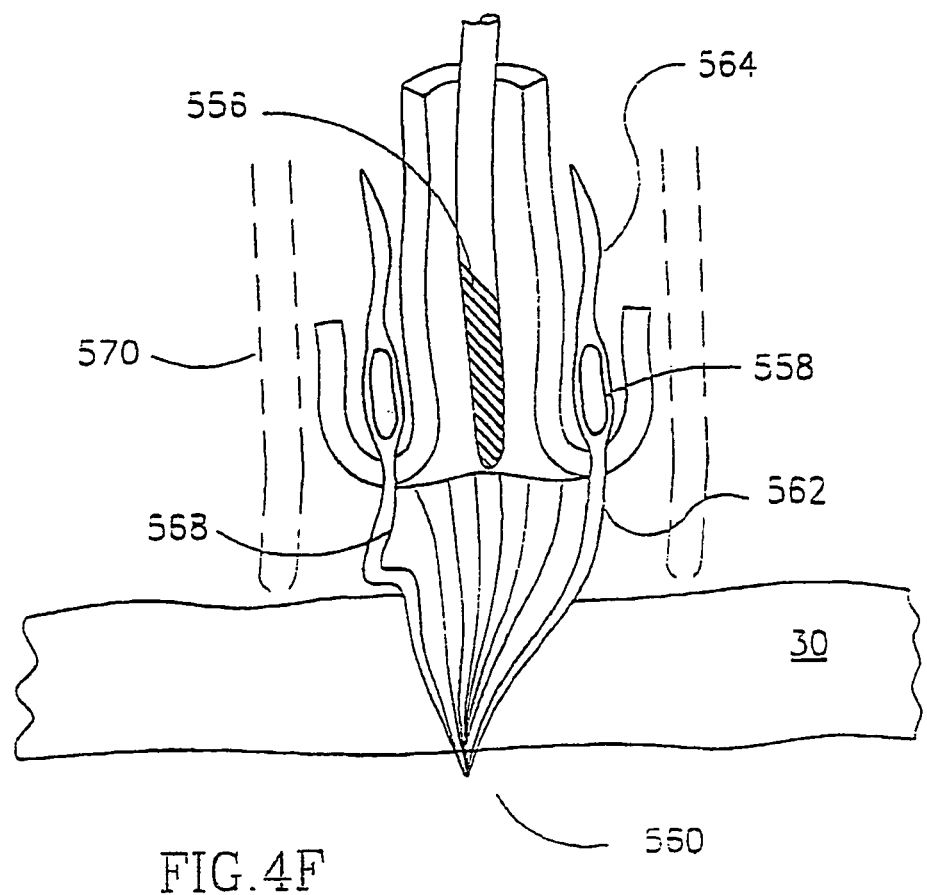
FIGS. 4F–4I illustrate anastomosis connectors which require a minimum amount of user intervention, in accordance with a preferred embodiment of the invention.
Figure 4G:
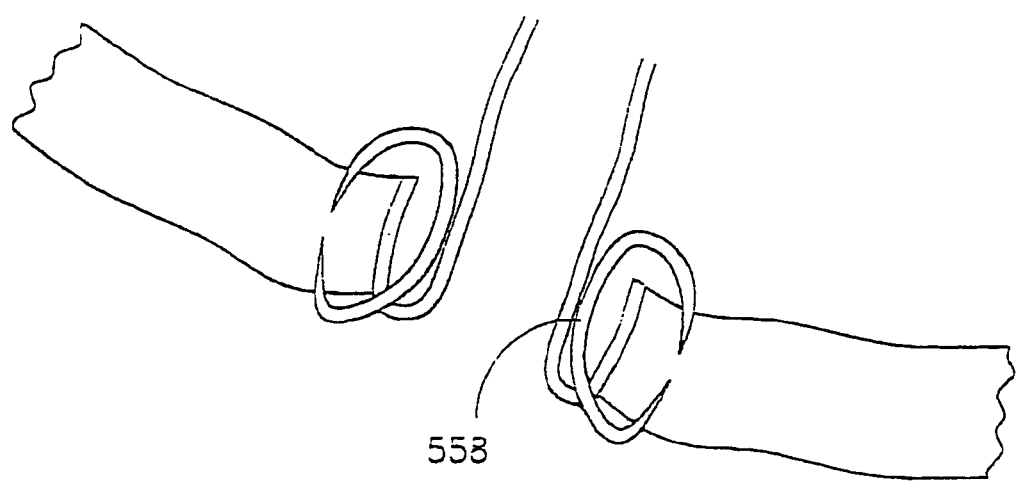

FIGS. 4F and 4G illustrate a connector 558, in which one set of spikes 562 is formed into a tip 560, which tip is used to penetrate vessel 30. In FIG. 4F, connector 558 is shown before expansion and in FIG. 4G, connector 558 is shown after expansion and the completion of the anastomosis.

In a preferred embodiment of the invention, connector 558 is plastically expanded using a balloon 566. Alternatively, connector 558 is formed of a super-elastic, elastic or shape-memory material which distorts by itself into the form shown in FIG. 4F. In a preferred embodiment of the invention, tip 560 is maintained by a guide wire (not shown) which engages rings or hooks (not shown) on the inside of spikes 562. When this guide-wire is retracted, the spikes can bend, for example into the geometry shown in FIG. 4G. Alternatively, spikes 562 are in a bi-stable state (as described below), in which the spikes can either be in the form of a tip 560 or in the form of individually deployed spikes. In a preferred embodiment of the invention, spikes 562 are moved from a stable state by the force applied by vessel 30 against tip 560 or against the base of the spikes. Alternatively, the stable state may be unbalanced by a partial inflation of a balloon inside tip 560, by allowing expansion of connector 558 or by applying force against tip 560 from inside the connector.

In a preferred embodiment of the invention, tip 560 has a step profile, as indicated by reference 568, which limits the advance of tip 560 to a desired penetration depth, at which the expansion of the connect preferably has the desired effects. Force against this step may also dislodge the restraining wire and/or upset the stable state in a bi-stable spike configuration. Alternatively, the profile is a continuous profile. Preferably, tip 560 is smooth. Alternatively or additionally, tip 560 comprises barbs (to prevent retraction) and/or is at least partially threaded.

In some preferred embodiments of the invention, device 558 is used for an oblique anastomosis. In a preferred embodiment of the invention, step profile 558 is oblique, to support an oblique hole mailing. Alternatively or additionally, the cross-section of tip 560 has a non-circular which is not centered on its axis, for example the tip having the geometry of an off-center cone, so that a non-oblique insertion angle presents less resistance than a perpendicular one.

Alternatively or additionally, an external restraining sleeve 570 is provided. In a preferred embodiment of the invention, sleeve 570 includes one or more protrusions which are forced back by contact with vessel 30. When these protrusions move back, the restraint of sleeve 570 is lessened or removed, allowing the connector and especially tip 560, to expand.

Figure 4H:
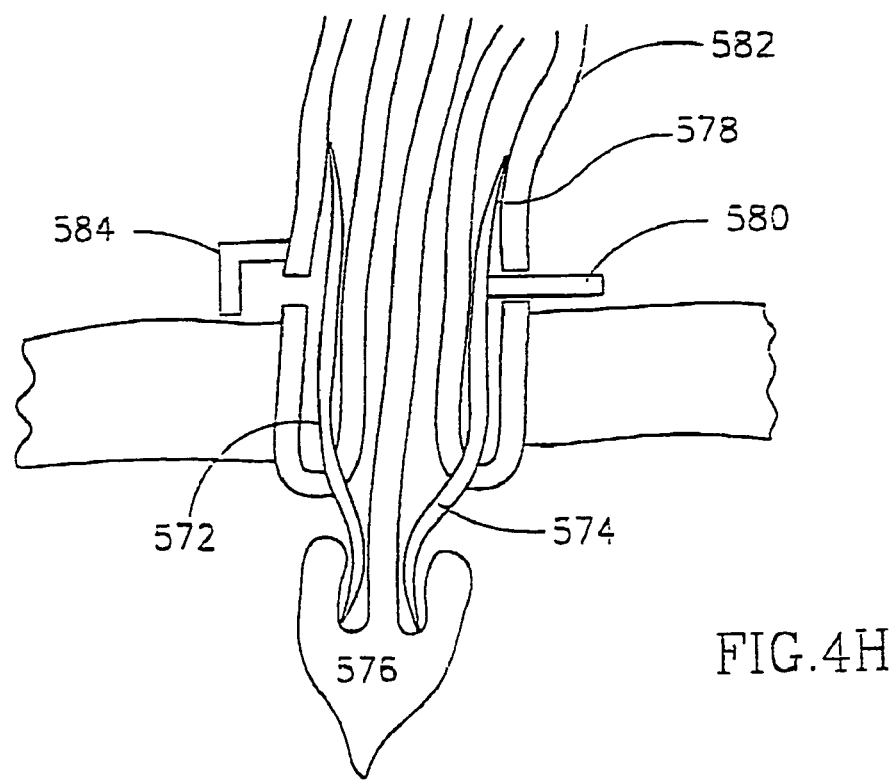
Figure 4I:
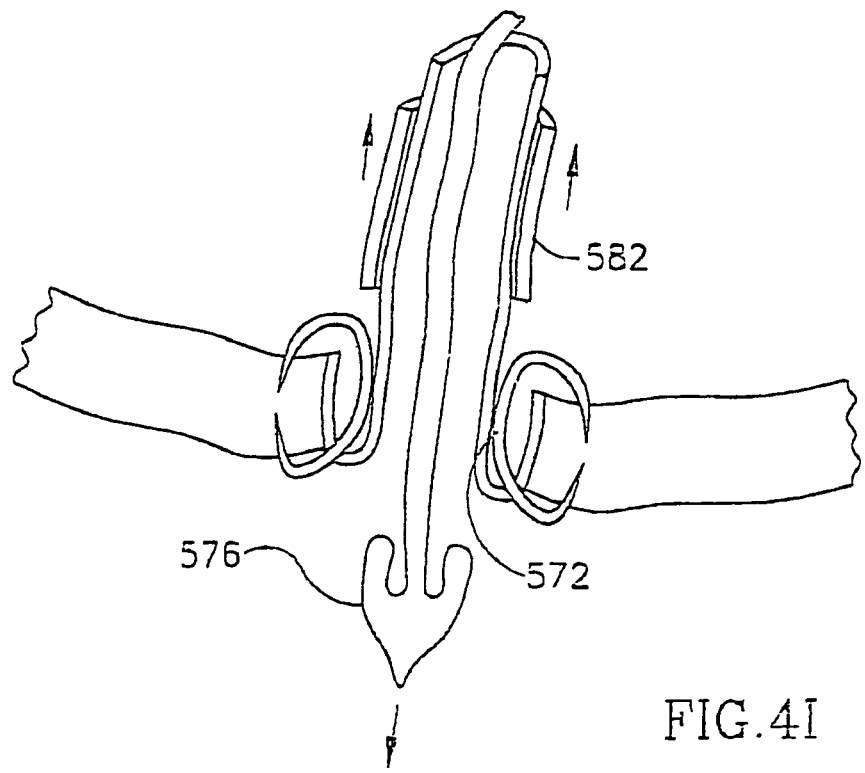

FIGS. 4H and 4I illustrate a connector 572, in a restrained configuration and in an expanded configuration, respectively. Forward spikes 574 of connector 572 are preferably restrained by a hollow tip 576, which can also be used for penetrating the wall of vessel 30. Back spikes 578 are preferably restrained by a sleeve 582. In FIG. 4H connector 572 is shown after insertion into vessel 30. In a preferred embodiment of the invention, the advance of connector 572 is limited by one or more arms 580 (or a ring) which protrudes from connector 572 (shown only in this Fig.). Alternatively or additionally, the advance is limited by a protrusion 584 from the restraining sleeve, through which sleeve the advancing force is applied (shown only in this Fig.). Alternatively or additionally, the advance is limited by connector 572 having an hour-glass shape or by a widening of the back of the connector (not shown).

In FIG. 4I, tip 576 has been advanced, releasing forward spikes 574 to engage the vessel. Sleeve 582 has been retracted to release back spikes 578, to also engage the vessel.

In a preferred embodiment of the invention, if the deployment of the device is not satisfactory, the device may be expanded using a balloon. Preferably, the device has a temperature transition for losing its elastic properties at about body temperature. Thus, a few seconds after the connector is inserted, it behaves, at least in part, as a plastic material.

As can be appreciated, some of the devices described herein may be applied in a one- or two-step process, in which a physician has only to advance the connect/graft against a blood vessel to perform an anastomosis. It should be noted that the device of FIG. 4F (in some embodiments thereof, for example super-elastic embodiments) may also be applied without an object in the lumen of the graft, thus being suitable for both sides of an anastomosis, for example in key-hole surgery. Additionally, the anastomosis process is preferably fast enough so that it may be performed even with a beating heart, even on an aorta, with a low a risk of hemorrhage.

Figure 5:
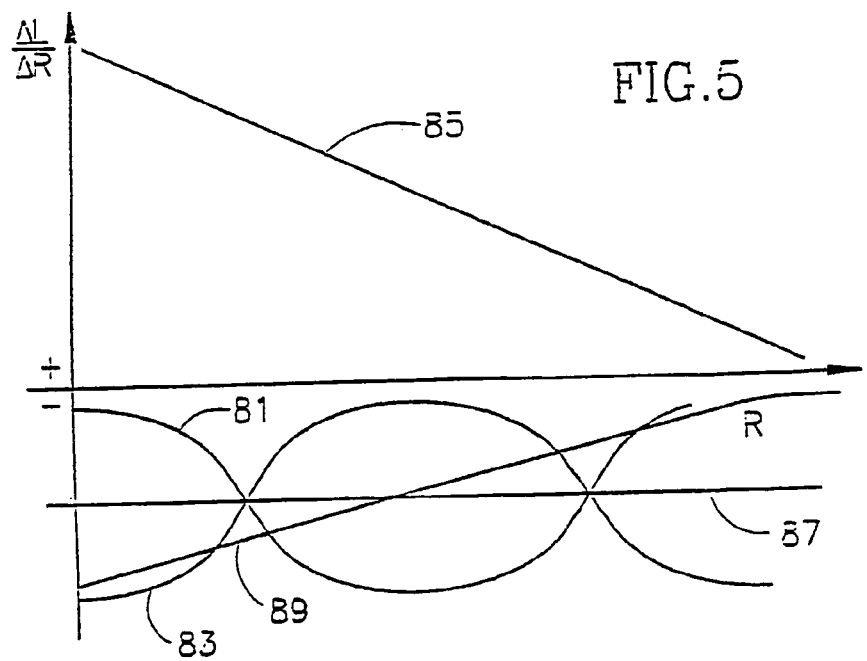
FIG. 5 is a graph illustrating various possible couplings between radial expansion and axial contraction in an anastomosis connector as shown in FIG. 4A.

FIG. 5 is a graph illustrating various possible relationships between radial expansion and axial contraction in anastomosis connector 60, achievable using different angles for the parallelograms and/or various struts, wires and/or ratchet mechanisms, described below. As shown in FIG. 5, both positive and negative couplings are possible. In addition, the coupling may be dependent on the instant radius of the connector. Thus, in a fully inflated configuration, additional inflation will not provide much additional axial contraction. A reference number 85 indicates a positive, decreasing coupling, where increasing the diameter increases the axial dimension, however, to a lessor degree as the radius increases. A reference number 87 indicates a negative, constant relationship, whereby increase in radius always decreases the axial dimension. A reference number 89 indicates the coupling described above, whereby a large axial shortening is achieved when the radius is small and a small axial shortening is achieved when the radius is large. References 81 and 83 indicate non-monotonic coupling, where the decrease in axial dimension is relatively constant over a "working range" of the device.

In a preferred embodiment of the invention, the spikes are not straight (as shown in FIG. 4A). In a preferred embodiment of the invention, the spikes are tapered over a considerable portion of their length. Alternatively or additionally, the spikes are jagged. Alternatively or additionally, the spikes have an inverse taper or are barbed, so that they form a more stable connection. Alternatively or additionally, instead of spikes, the "spike" portion is a relatively continues surface, such as a band, which surface can evert in a manner similar to a rivet, and thereby engage the blood vessel.

In a preferred embodiment of the invention, the lumen of the anastomotic connection is circular. However, in some preferred embodiments of the invention, a non-circular connector lumen may be preferred, for example an oval lumen, a polygonal lumen or a figure "8" lumen. Alternatively or additionally, the diameter and/or geometry of the lumen may vary along the lumen. The outside form of the connector is generally the same as the lumen. However, in some embodiments, the outside of the connector may include protrusions or may have a different geometry (and thus varying thickness) than the lumen. In some embodiments of the invention, the center of the lumen lies along a curved or piece-wise line. Such an embodiment may be useful for inducing certain desired flow patterns in the flow at the anastomosis connection. Alternatively or additionally, the inner surface of the lumen includes protrusions for forming such a desirable flow pattern.

In some case, it may be desirable for the anastomosis connection to be oblique, for example to provide betted blood flow dynamics. An oblique connection may be additional or alternative to the use of a non-circular lumen cross-section (cross-section measured perpendicular to the end vessel main axis).

Figure 4J:
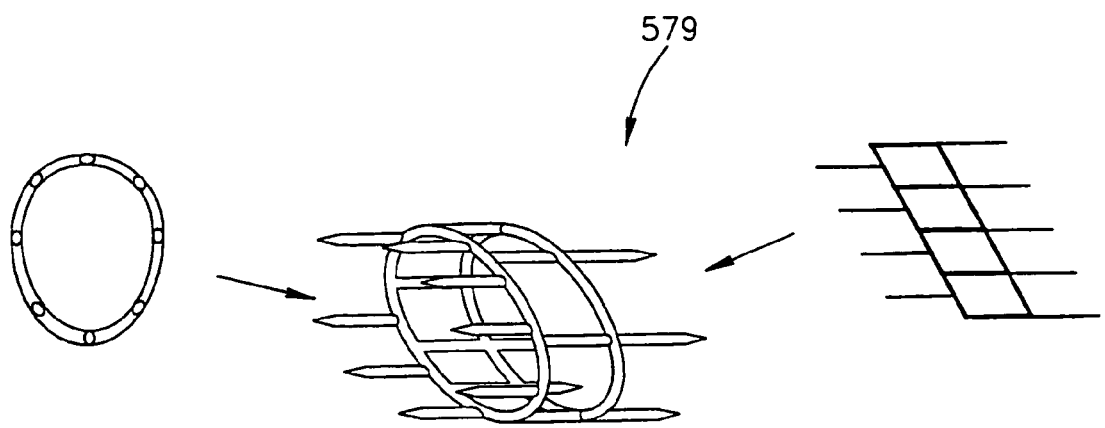
FIG. 4J illustrates an oblique anastomotic connector in top, isometric and side views thereof.
Figure 4K:
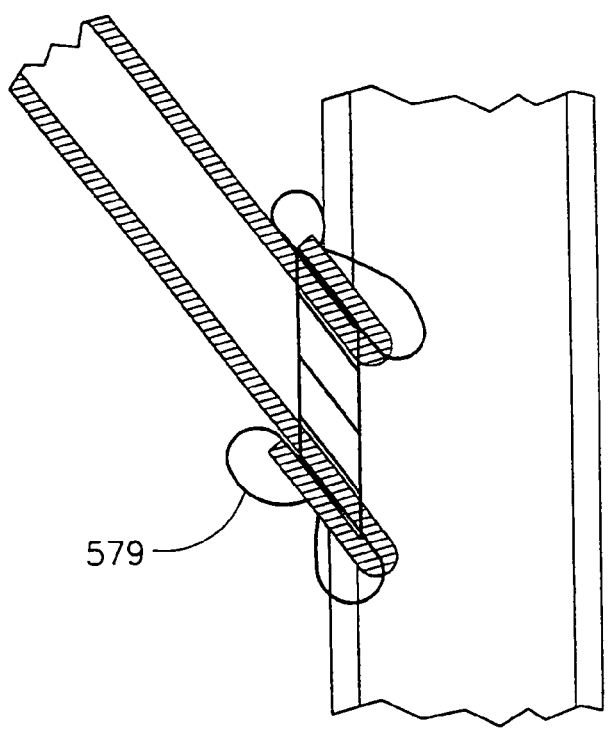
FIG. 4K illustrates the connector of FIG. 4J, as deployed in a completed oblique anastomosis.

FIG. 4J illustrates an exemplary oblique anastomotic connector 579 in top, isometric and side views thereof. FIG. 4K illustrates connector 579, as deployed in a completed oblique anastomosis. It should be appreciated that many of the connectors described herein may be made oblique by varying their structure. In some cases, it may be desirable to match the spike lengths and/or extension to the oblique angle of the device, to prevent damage to the blood vessels.

Figure 6A:
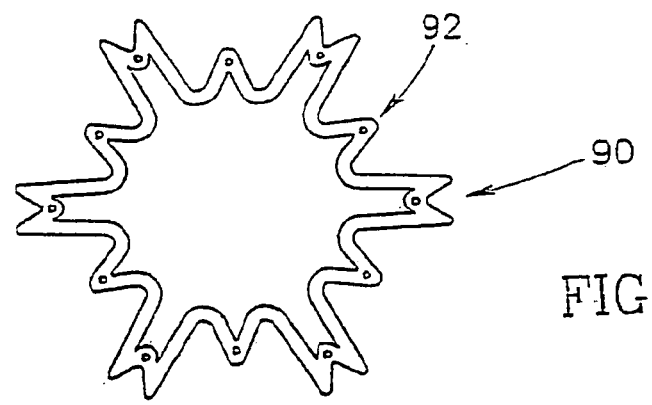
FIGS. 6A–6E illustrate an additional one piece anastomosis connector and its deployment, in accordance with a preferred embodiment of the invention.
Figure 6B:
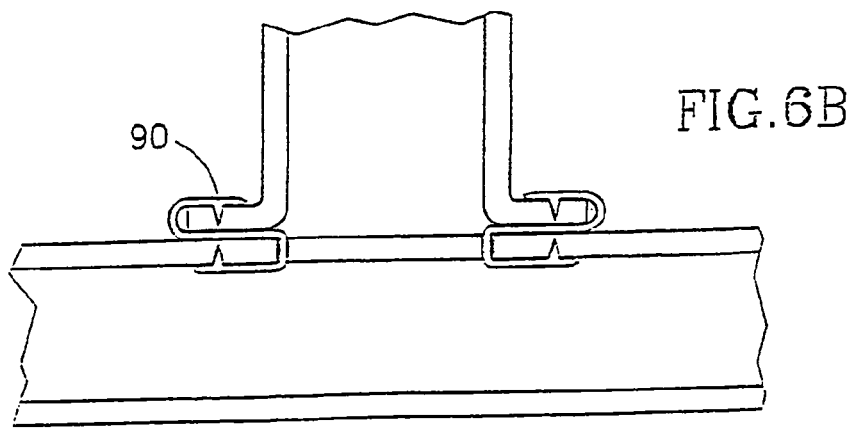

FIGS. 6A and 6B illustrate an alternative one piece anastomosis connector 90, in accordance with a preferred embodiments of the invention. In FIG. 6A the connector is shown in plan view, in a compressed configuration. Dots 92 indicate short spikes which are preferably used to engage the blood vessels. In a preferred embodiment of the invention, however, the connector will be attached to graft 38, as shown in FIG. 6C, prior to inserting the graft into the body.

When inflated and/or allowed to return to a resting condition, some of the spikes and the band to which they are attached fold up and some fold down, resulting in the configuration of FIG. 6B, which illustrates connector 90 in its final configuration. FIGS. 6C–6E illustrate steps in achieving this configuration.

Figure 6C:
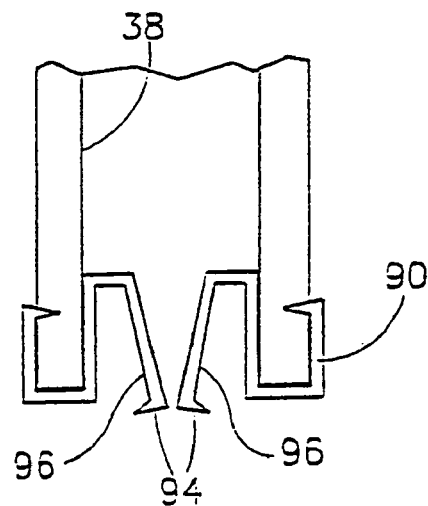
Figure 6D:
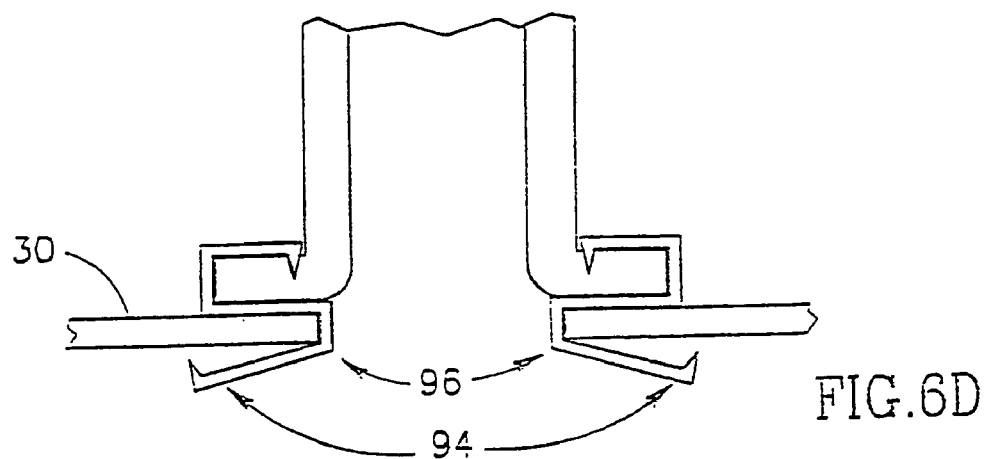
Figure 6E:
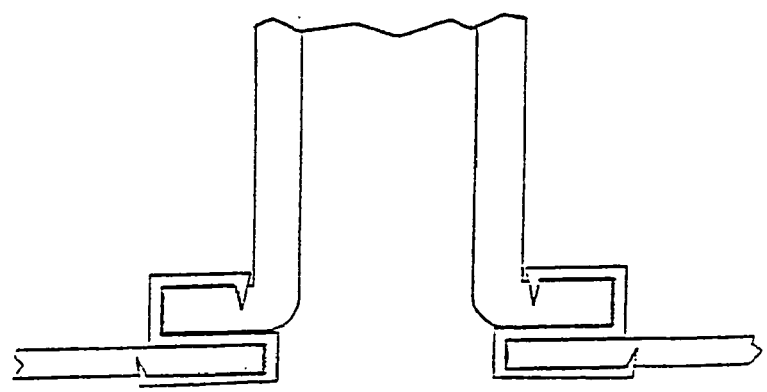

In FIG. 6C, connector 90 is mounted on a graft 38. A plurality of inner arms 96 are inside the graft, a plurality of spikes 94 on the arms do not engage tissue and the graft itself is not everted. The arms may comprise substantially rectangular pieces. However, In a preferred embodiment of the invention, the arms comprise a Gaussian-like (or half-sine-wave) portion of metal which has a spike at its tip. Thus, connector 90 preferably has a smooth outline. In FIG. 6D, the graft is expanded, for example using balloon or relaxing a constraint on a super-elastic, elastic or shape-memory connector 90, so that arms 96 bend out and the graft becomes everted. In FIG. 6E, either the expansion is continued or connector 90 is squeezed against a balloon, so that spikes 94 engage the aorta. Connector 90 may be squeezed for example, by providing one balloon on each side of the connector and inflating the balloons. Alternatively or additionally, the body of a catheter (not shown) may provide an anvil against which connector 90 is compressed.

In the example of FIGS. 6A–6E, the connector supports a multi-step connection process, in which each additional inflation further modifies the shape and/or configuration of the connector and advances a step of the connection, i.e., engaging the graft, everting the graft and finally engaging the aorta. Each one of these steps may be mediated and/or assisted by a different part of the connector.

In a preferred embodiment of the invention, a different type of connector is provided, formed of a soft material, for example silicone. This connector comprises a tubular portion, which engages either the inside or the outside of the graft and one or more leaves which fold out against the inside of the aorta. In a preferred embodiment of the invention, these leaves include barbs which engage the aorta. Alternatively or additionally, the tubular portion includes a depression which engages the cross-section of hole 35 (FIG. 2A). Alternatively or additionally, the tubular section includes a ring, embedded in the soft material, which maintains the cross section of the hole 35 and/or in which the depression is formed, so the connection does not slip. In some embodiments, no leaves are required.

In a preferred embodiment of the invention, the soft material comprises a graft material, preferably a biological graft material, inside of which an expandable ring is embedded. Alternatively or additionally, the graft is everted 180 degrees over such a ring. The everted portion of the graft is inserted into the hole in aorta 30 in a compressed form and when it is expanded it opens the hole and the graft-covered ring engages the walls of aorta 30, in a groove along the outer rim of the ring.

Figure 7A:
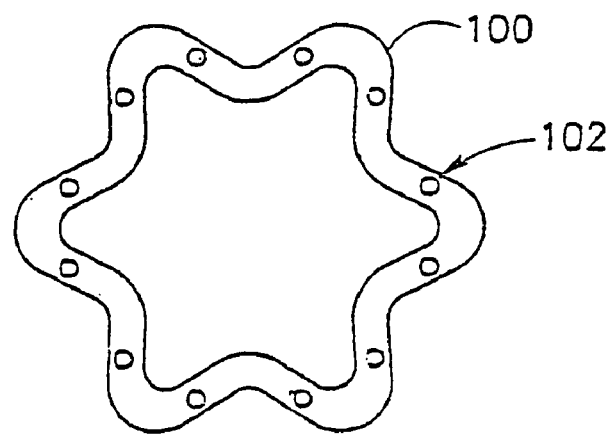
FIGS. 7A and 7B illustrate a pin based anastomosis device, in accordance with a preferred embodiment of the invention.
Figure 7B:
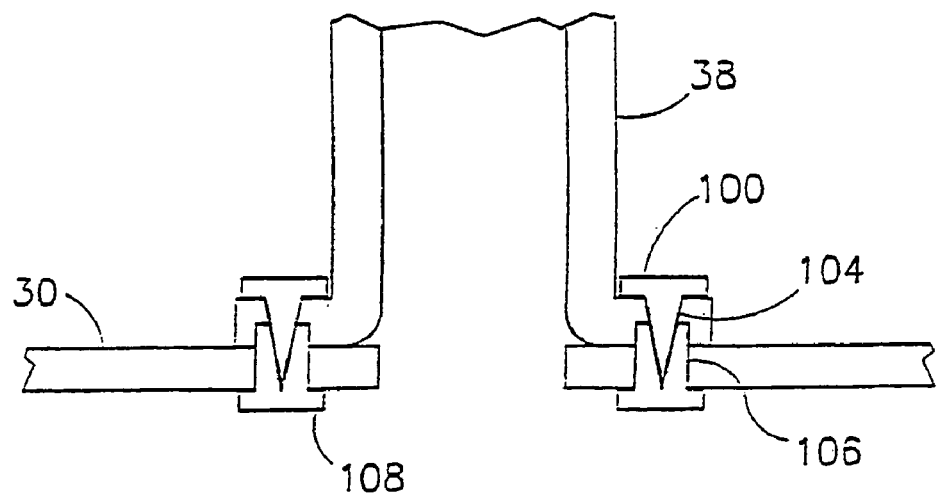

FIGS. 7A–7B illustrate a pin based ring anastomosis connector 100, in accordance with a preferred embodiment of the invention. FIG. 7A shows connector 100 in a radially compressed configuration. Dots 102 indicate spikes. Connector 100 may be used by itself to affect anastomosis. Alternatively or additionally, connector 100 may be used with a second, possibly similar ring. FIG. 7B shows connector 100 after it is deployed, in conjunction with a second ring 108. Spikes 104 of ring 100 engage pre-formed holes 106 in ring 108. Alternatively or additionally, spikes 104 may be longer than shown and fold back after piercing graft 38 and aorta 30. Thus, a second ring may not be required, although one may be provided as a base for the folded back spikes. Preferably, the rings are folded back against an anvil, for example an inflatable balloon or a collapsible ring structure which is urged against the spikes for bending them and then removed from the body.

In a preferred embodiment of the invention, both rings 100 and 108 include spikes and pre-formed holes. Alternatively or additionally, at least one of the rings has only spikes or only holes. Alternatively or additionally, to holes 106, ring 108 may have formed therein a groove or a plurality of closely-set holes which spikes 104 may engage without aligning the two rings. Alternatively or additionally, spikes 104 engage a piercible friction material, such as silicone, which holds the spikes, for example by friction, instead of or in addition to holes 106. The entire ring or portions thereof may be formed of the friction holding material Alternatively or additionally, the friction holding material may comprised in a layer on top or below a non-piercible portion of the ring.

In a preferred embodiment of the invention, spikes 104 are jagged, to better engage the friction material.

FIGS. 7C–7N illustrate various mechanisms for extending spikes out of a surface of the anastomotic device, in accordance with a preferred embodiment of the invention. Alternatively or additionally, these mechanisms may be used to control other aspects of the connectors' final or intermediate geometry, for example internal radius, shape and/or local variations in the geometry, such as the provision of ratchet mechanisms and/or other mechanisms which lock the spikes and/or the final connector geometry.

Figure 7C:
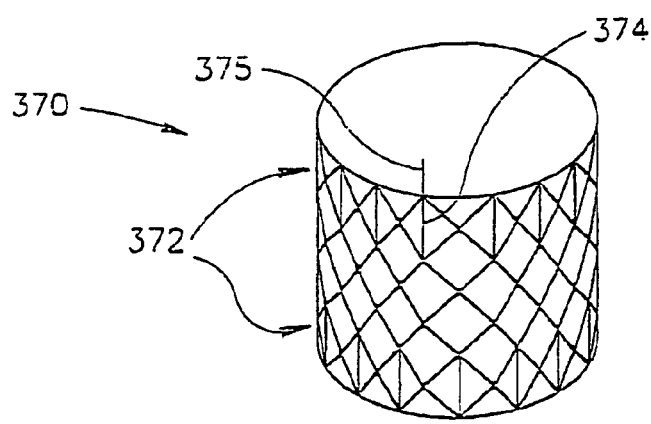
Figure 7D:
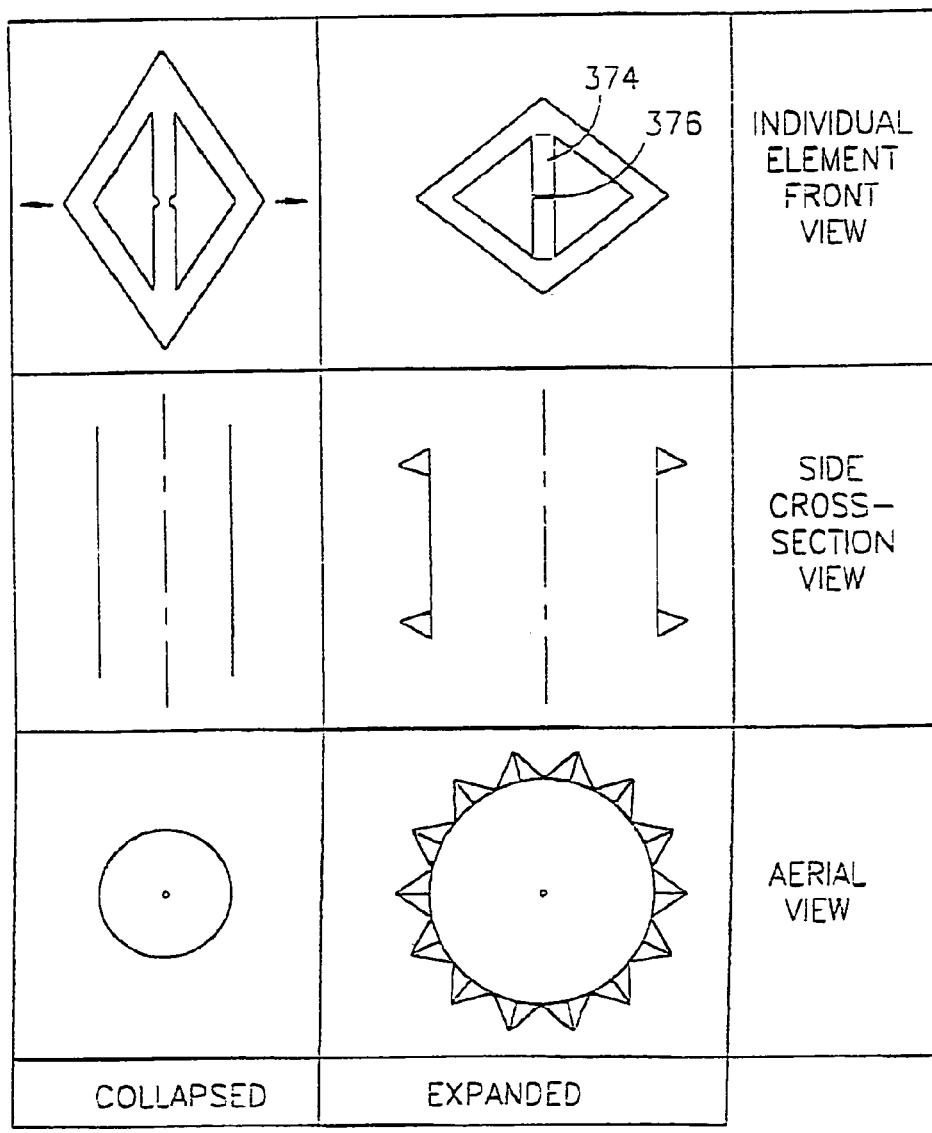

FIGS. 7C and 7D illustrate a strut based system in which a strut limits the distortion of a parallelogram. However, when the parallelogram is distorted, so that its width (perpendicular to the connector axis) increases, its length, or at least the distance between the top and bottom vertices, must decrease. As the strut is non-compressible, but bendable at a designated portion thereof, when the parallelogram width is increased by the expansion of the connector, the parallelogram bends out of the plane of the connector so that the two vertices which are connect to the strut come together. FIG. 7C illustrates a connector 370 having two bands 372 in which some or all of the parallelograms include axially-disposed struts 374 which limit the axial extension and/or shortening of the parallelogram. A smaller or larger number of such bands may be provided. Additionally, bands, or individual strut-including parallelograms may be provided at other parts of the device, for example for spikes which are in the middle of the device or to cause the device to have bumps. In a preferred embodiment of the invention, the parallelograms themselves serve as the spikes. Alternatively or additionally, extensions of the parallelograms, for example a spike 375 may be provided.

FIG. 7D is a table illustrating front, side and top views of a single parallelograms, a cross-sectional view and a complete connector 370, respectively, in a state before deployment and in a state after deployment. A weakening 376 is shown in a middle (or other desired point) of strut 374, to promote bending of strut 374 at that particular point. In addition, a weakening may be selectively applied to the outside of the inside of connector 370, to promote inward or outward folding. Alternatively, the direction of folding is determined by a balloon which is inside the connector when it expands.

Figure 7E:
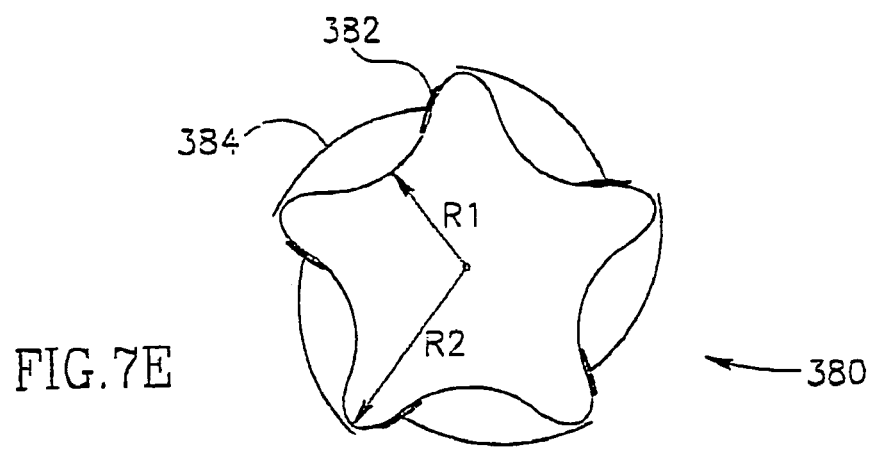
Figure 7F:
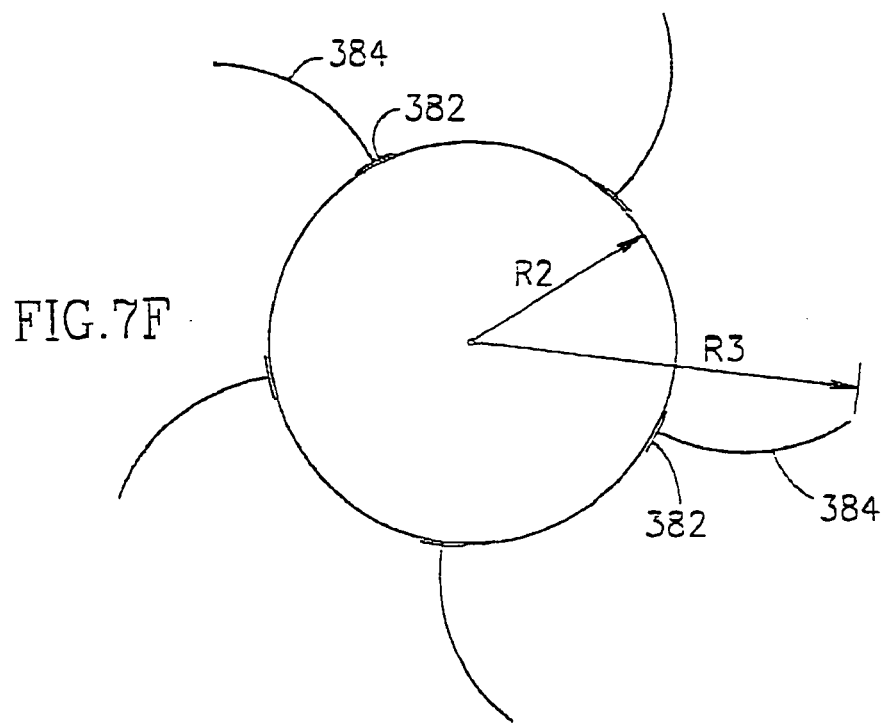

FIGS. 7E and 7F illustrate a connector 380 in which spikes are extended by a change in surface geometry of the connector. As shown in FIG. 7E, the connector has a radius R2 and a smaller radius R1, where the smaller radius is at portions of the connector which are distorted inwards. A plurality of spikes 384 are each connected to a base plate 382. In the embodiment shown, the spikes are generally perpendicular to the base plates and the base plates are parallel to the connector surface. However, due to the distortion of the connector, the surface, at least in the area of the base plates is substantially perpendicular to the a circle enclosing the connector, so the spikes do not extend from the surface. Once the connector is expanded, as shown in FIG. 7F, the surface of the connector (at least in the areas of base plates 382) is parallel to the enclosing circle and the spikes extend.

Figure 7G:
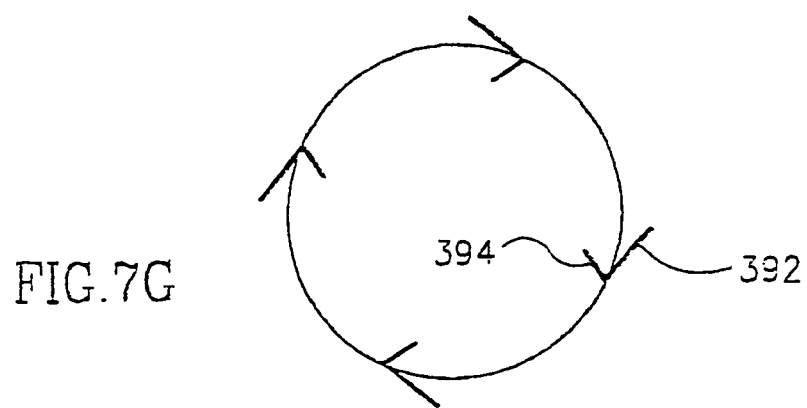

FIG. 7G illustrates a connector 390 similar to connector 380 of FIGS. 7E and 7F. However, instead of the surface of the connector being non-circular, as in FIGS. 7E and 7F, a plurality of base plates 394 are not parallel to the surface of the connector. Instead, base-plates 394 protrude into connector 390. A plurality of spikes 392 are attached to the base plates at an angle, preferably being perpendicular, but in some cases, a smaller angle, such as less than 70°, less than 60° or less than 40°, may be desired. When a balloon is expanded inside connector 390, the base-plates are urged against the sides of connector 390, so that they are substantially parallel to the surface. Thus, spikes 392 are extended.

In some preferred embodiments of the invention, at least some of the spikes are extended super-elastically, or elastically, for example by the spikes being made of a suitable material (e.g., super elastic) or by the spikes being connected to a base formed of a suitable material (e.g., super-elastic). The super-elastic or elastic portion is "trained" to a configuration where the spikes are extended and then the spikes are collapsed and restrained. When the connector is deployed, the restraints are relaxed and/or removed and the spikes return to their previous position. Alternatively to super-elastic materials, the spikes or their base may be formed of a shape-memory material. During deployment, the spikes are preferably heated to above the transition temperature and they extend. Possibly, the transition temperature is below the body temperature. Alternatively, the connector is heated, for example using a heated balloon or by radiating radiation, such as RF or ultrasound, at the connector.

Figure 7H:
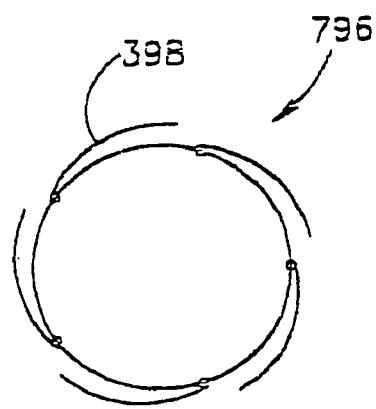
Figure 7I:
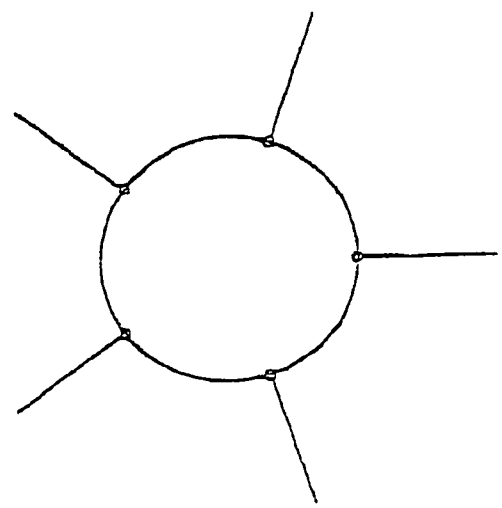

FIG. 7H shows a super-elastic, elastic or shape-memory connector 396 in a collapsed configuration, in which a plurality of spikes 392 are radially collapsed. FIG. 7I shows the same connector after the spikes extend radially.

Figure 7J:
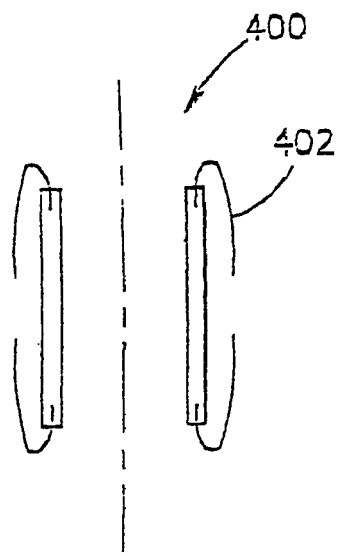
Figure 7K:
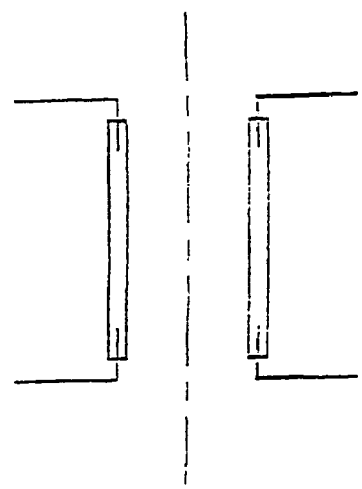

FIG. 7J shows a super-elastic, elastic or shape-memory connector 400 in a collapsed configuration, in which a plurality of spikes 402 are axially collapsed. FIG. 7K shows the same connector after the spikes extend axially.

FIGS. 7L and 7M illustrate a geometry in which the connector itself forms a restraint to prevent the extension of the spikes. When the connector is distorted, for example as a result of expansion the restraint is released and the spikes extend.

In FIG. 7L, a parallelogram 404 is shown in a front and a side view. The extension of a spike 406 is restrained by the body of the parallelogram. When parallelogram 404 is distorted in the direction of an arrow 408, the restraint is released, (because the spike is shorter than the new diagonal of the parallelogram) and the spike can extend, as shown for example in FIG. 7M.

FIGS. 7P–7R illustrate a two stage folding of a pair of spikes, in accordance with a preferred embodiment of the invention.

FIG. 7P illustrates a schematic connector 600, having a single parallelogram band with a spike at each end. Each parallelogram is formed of at least a first, outside parallelogram 604 and at least one inner parallelogram 602. For simplicity, two spikes are shown extending from the parallelogram, each spike being formed by an inner extension 610 and an outer extension 608 which combine at a tip 606 of the spike. In addition, a plurality of weakenings 612 are preferably provided along the spike. As can be noted from the figure, the angles of inner parallelogram 602 are different than from outer parallelogram 604. Thus, when the parallelogram is radially expanded, inner parallelogram 602 is distorted more. As a result, extension 610 shortens more than extension 608, causing the spikes to fold (shown in FIG. 7Q, possibly in a manner similar to a human finger). As the radial expansion continues, outer parallelogram 604 is also distorted, causing the spike to bend some more (shown in FIG. 7R). Alternatively to two parallelograms, three or more concentric parallelograms can be provided. In some preferred embodiments of the invention, asymmetric geometric shapes are used instead of the parallelograms, which shapes may be different for the inner and outer elements and/or be oriented differently, so that other bending effects can be achieved.

Figure 7N:
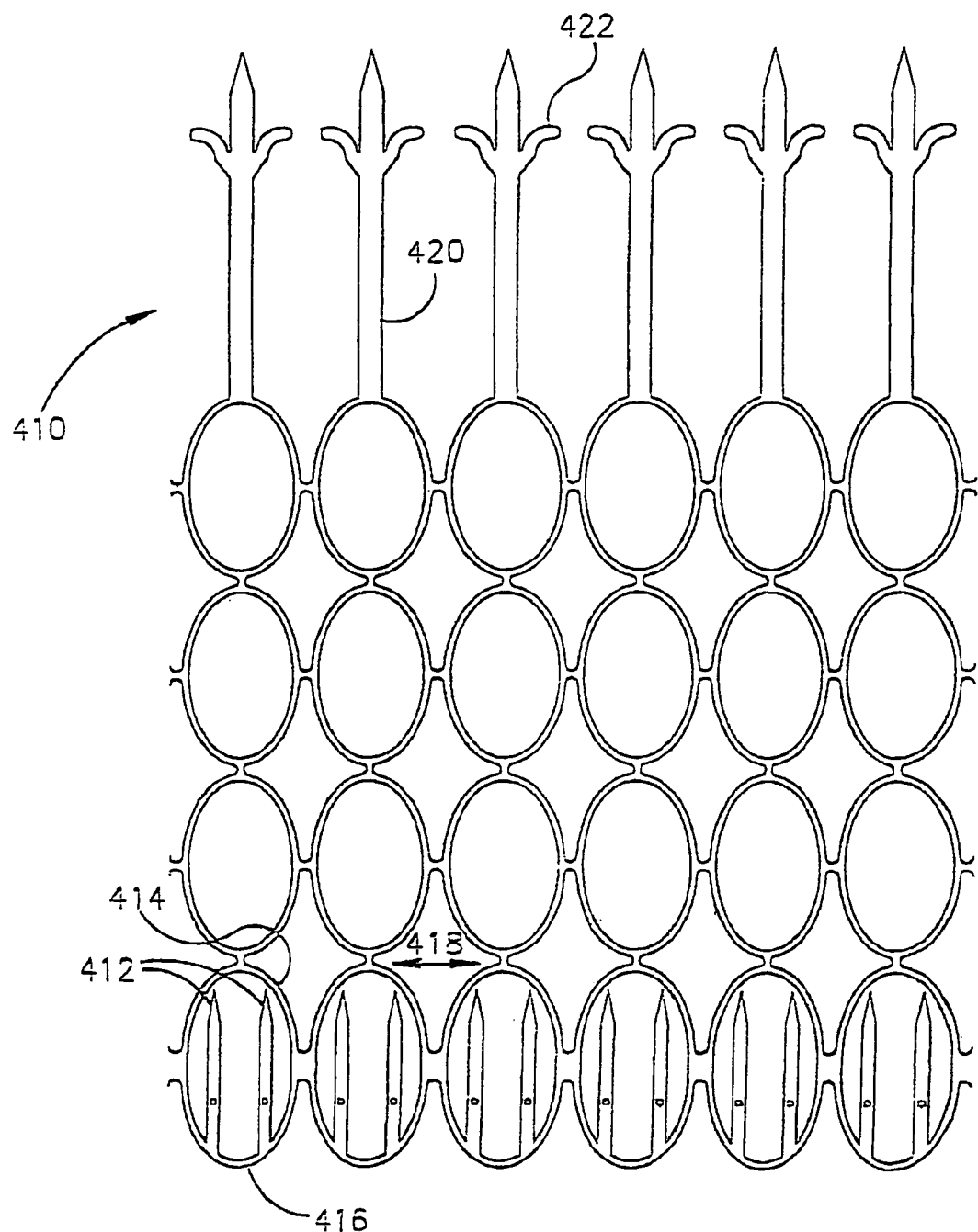
Figure 70:
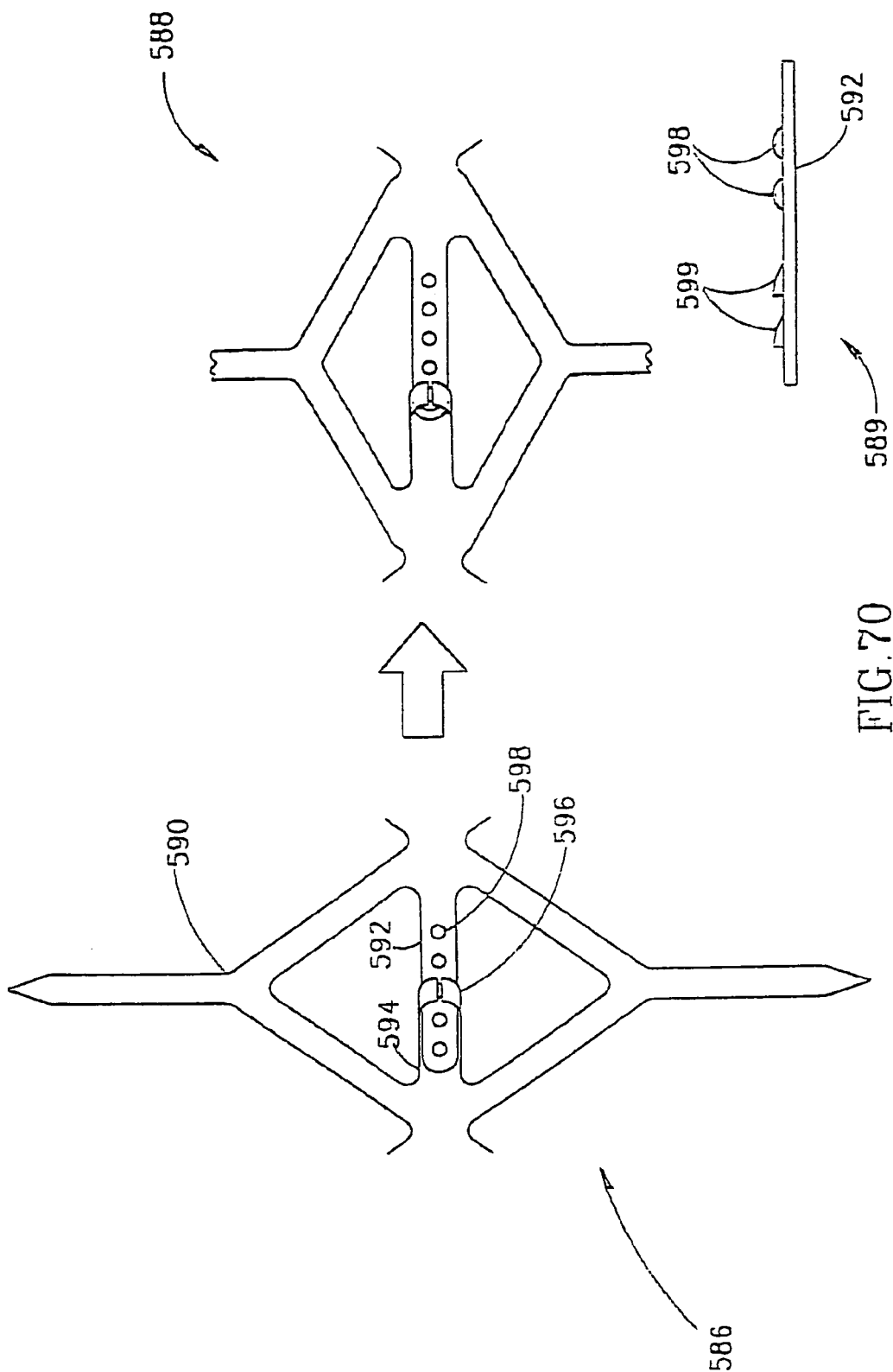
Figure 7S:
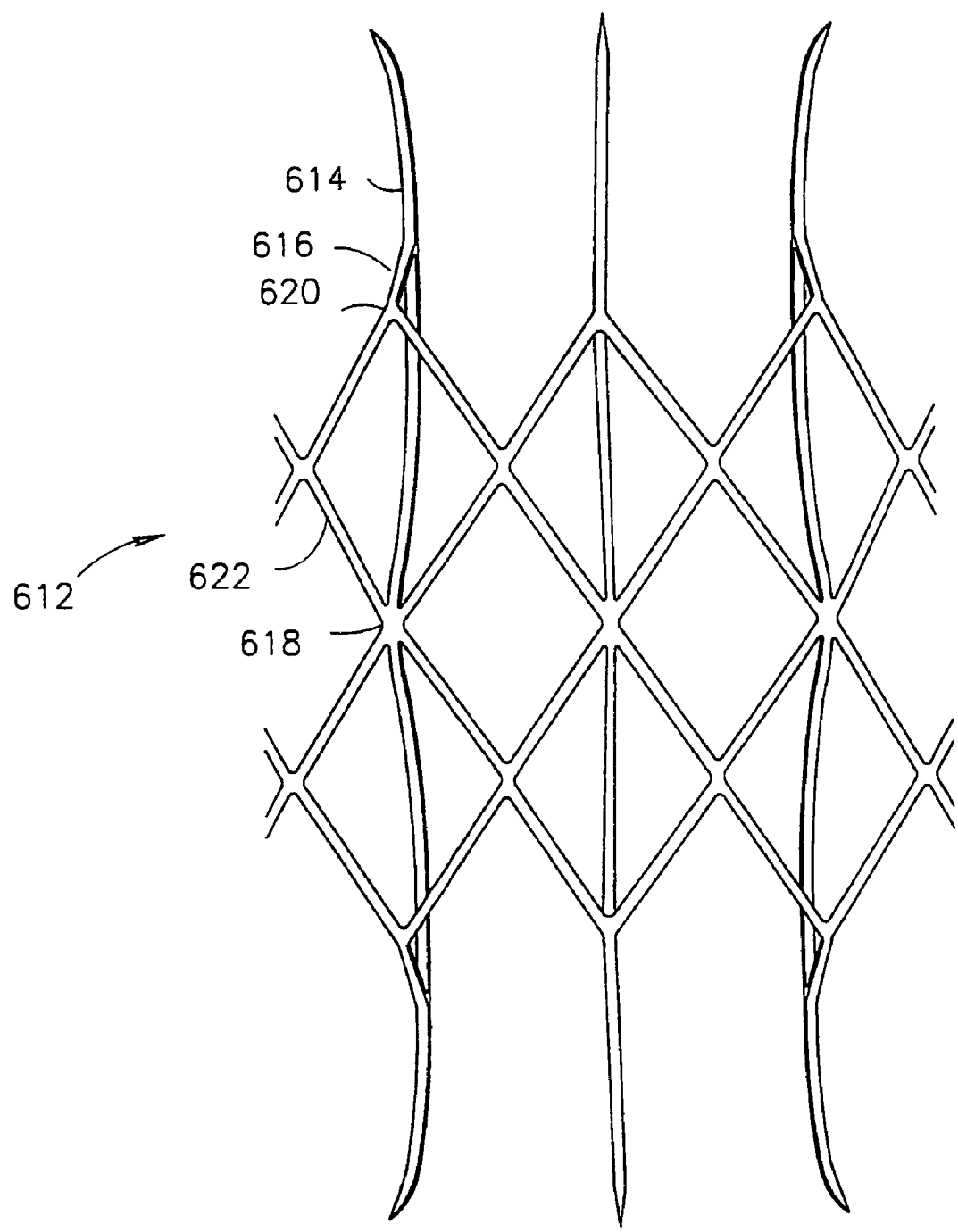
FIGS. 7S–7T illustrate a connector with cantilevered spikes, in accordance with a preferred embodiment of the invention.
Figure 7T:
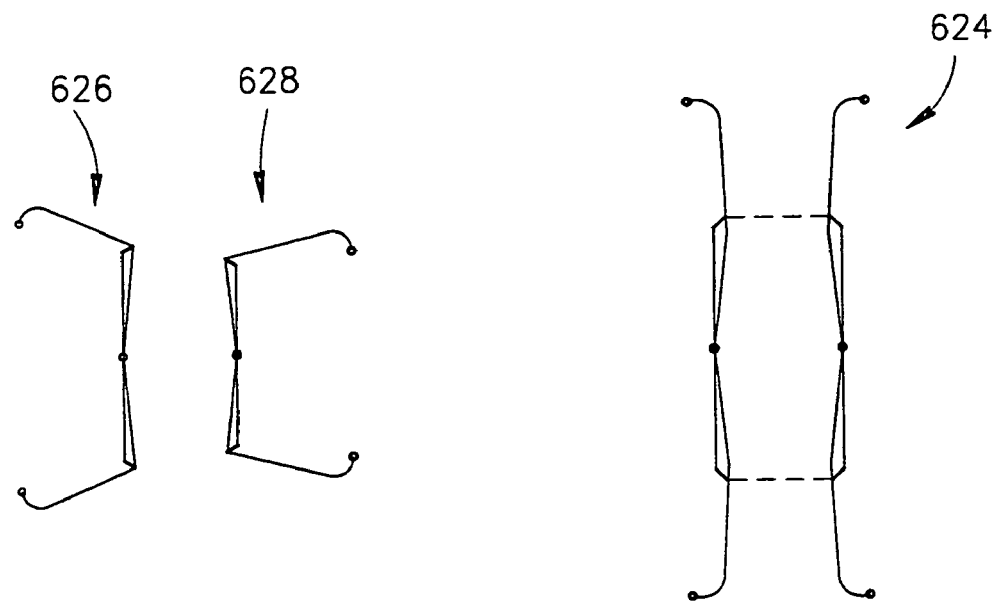

FIGS. 7S–7T illustrate a connector 612 with cantilevered spikes 614, in accordance with a preferred embodiment of the invention. For an individual parallelogram 622, a spike 614 is attached at one end to an inner vertex 618 and somewhere along its length to a lever 616, which is attached to an outer vertex 620 of the parallelogram. When the parallelogram is radially expanded, it axially shortens, until the spike is bent by lever 616 to be perpendicular to connector 620. By providing a plurality of levers 616 at different points along spike 614 (possibly each lever attached to a different size and/or shaped parallelogram), other bending effects can be achieved. The end of spike 614 is preferably pre-bent to a certain angle. FIG. 7T shows side-cross-sectional views of connector 612, during deployment. A reference 624 shows connector 612 prior to radial expansion, a reference 626 shows an intermediate state and a reference 628 shows a final deployment state.

In a preferred embodiment of the invention, a spike may exhibit two or more extension steps by each extension step utilizing a different mechanism and/or a different triggering. In one example, a first extension step is by super-elastic restoration (triggered by releasing of a restraint) and a second extension step is by twisting of the spike base by radial expansion of the connector (triggered by expansion of the connector).

Alternatively or additionally to super elastic and shape memory materials, the spikes or their base may be formed of a bi-metal which distorts as a result of body heat. Alternatively to using two dissimilar metals, one of the "metals" may be formed of a non-metallic bio-compatible material, such as a ceramic material or a plastic material.

In an alternative embodiment of the invention, a spike may be extended by protrusions on the balloon that expands the connector. Preferably, the balloon is aligned with the connector so that the protrusions can apply force to the correct portions of the connector.

Figures 7U, 7V:
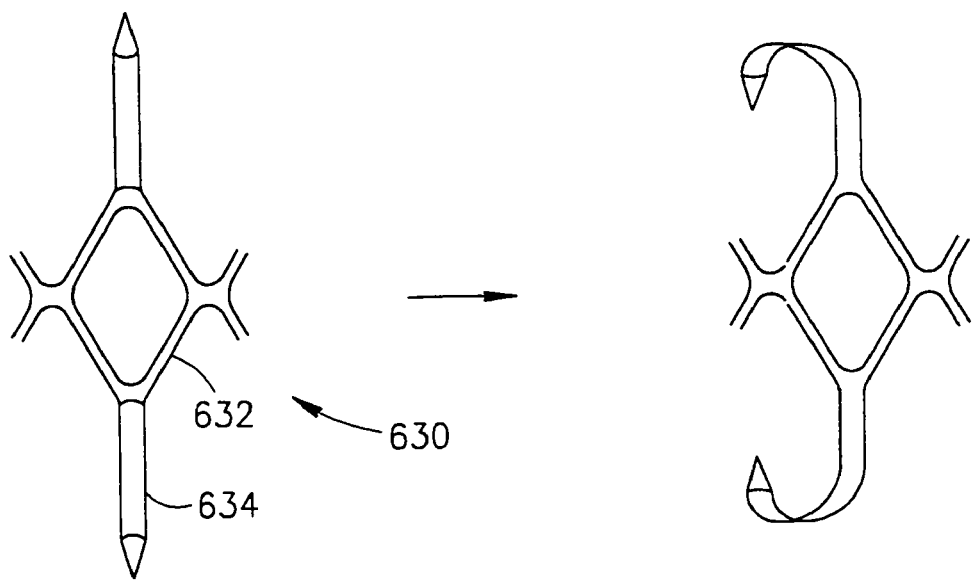
FIGS. 7U–7V illustrate a bi-stable spike configuration, in accordance with a preferred embodiment of the invention.

FIGS. 7U–7V illustrate a bi-stable spike configuration 630, in accordance with a preferred embodiment of the invention. Configuration 630 comprises a parallelogram 632 and a spike 634. In a preferred embodiment of the invention, spike 634 has a non-flat profile, for example an arc-segment, seen more clearly in FIG. 7V. In a preferred embodiment of the invention, spike 634 has two stable states, a first one shown in FIG. 7U, in which the profile of the spike keeps it straight and a second one shown in FIG. 7V, in which the spike bends at a desired location. In a preferred embodiment of the invention, when parallelogram 632 is distorted (by expansion or by being pressed against by a balloon), the profile of the spike is flattened, allowing it to bend as shown in FIG. 7V. In a preferred embodiment of the invention, the spike is elastic, super-elastic or shape-memory, and trained to a certain bend. However, the spike is prevented from bending by its profile. Alternatively or additionally, the spike is bent plastically, using a balloon or using other methods, for example as described herein. Alternatively or additionally, to a bi-stable configuration, a multi-stable configuration, having three or more stable configurations may be used. Additional bi-stable constructions and especially cells for the cylindrical portion of the connector, which constructions may be useful for anastomotic connectors in accordance with some preferred embodiments of the invention, are described in PCT publication WO 98/32412, the disclosure of which is incorporated herein by reference.

FIG. 7N is a plan view of a connector 410 in which a plurality of spikes 412 are extended out of the connector plane when the connector is radially expanded (as indicated by an arrow 418. In connector 410, the parallelograms of previous embodiments of connectors are replaced by ellipses 414. Spikes 412 are connected to a lower side of an ellipse. When the ellipse is expanded, the lower side twists and the spikes are extended out of the connector plane. Alternatively, the spikes are super-elastic, elastic of shape-memory and twist when a restraint is released.

An additional feature shown in FIG. 7N is a tissue block 422 on a spike 420. This tissue block stops tissue from advancing too far onto connector 420. Alternatively or additionally, the tissue block causes the spike set on the opposite side of the connector to do the advancing when the connector shrinks axially.

Alternatively or additionally, to parallelograms and ellipses, other geometrical shapes may be used for the distorting elements of the anastomotic connector, for example hexagons, squares, trapezoids, asymmetric four-sided shapes and circles. Additionally, a plurality of different geometrical shapes may be combined in a single connector.

FIG. 7O illustrates a parallelogram portion 590 of a connector, which portion includes a ratchet mechanism for preventing collapsing of the connector, in accordance with a preferred embodiment of the invention. Different types of ratchet mechanisms may be suitable. In the example of FIG. 7O, the ratchet mechanism includes a belt 592 having a plurality of bumps 598 formed thereon. These bumps are engaged by an engager 596 formed on a mating strip 594. Reference 586 indicates parallelogram 590 in an un-expanded condition and reference 588 indicates parallelogram 590 in an expanded position. As the parallelogram expands (radially) belt 592 slips through engager 596. As shown by a reference 589, a side view of belt 592, the bumps may be formed symmetrically (598) or asymmetrically (599). In a preferred embodiment of the invention, the asymmetric bumps preferentially restrict backwards movement. Alternatively, the bumps restrict any type of movement, and assuming the forces at deployment are larger than during the life-time of the device, the connector does not collapse. In a preferred embodiment of the invention, such a ratchet mechanism provides a self-tightening capability to the device. Although a belt with bumps has been described, other ratchet mechanisms may be used, for example, a belt with holes an a single bump on the engager. In this embodiment, the engager may be formed at a vertex of the parallelogram, possibly eliminating a need for a separate mating strip 594.

In a preferred embodiment of the invention, the ratchet mechanism may be utilized in association with a flexibility of the connector, to restrict the final connector geometry. In one example, the ratchet is connected axially, rather than radially. Thus, the radial expansion will set the axial shortening, however, even if the device radially shrinks, for example elastically, to a "trained" radius, the axial shortening will remain. Thus, it is possible to axially shorten the connector without changing the designed radius. In an opposite example, the axial shortening may be limited using flexible struts arranged axially in the parallelograms. When the connector is radially expanded, it will shorten axially, distorting the struts. When the expansion force is removed (e.g., a balloon), the radial expansion will remain, due to a trans-axial ratchet mechanism, but the axial shortening will be at least partly undone by forces exerted by the flexible struts. Thus, independent control of axial and radial expansions/contraction may be achieved using suitable axial and trans-axial ratchet mechanisms.

FIGS. 8A–8D illustrate a method of performing an anastomosis in accordance with a preferred embodiment of the invention. In FIG. 8A, a graft 38 is guided along a guide wire 36 through a hole 118 and out of the aorta. A friction ring 120 is attached to a preferably everted portion 116 of the graft. Preferably, a tapering 114 is provided to ease the exit of the graft from the aorta. A ring 110 with pins 112 is shown positioned further proximally along guidewire 36. Alternatively, the ring with the pins may be on the graft and friction ring 120 be further along guide wire 36. Alternatively or additionally, no friction ring is provided and pins 112 will engage only graft 38 and preferably fold back. In FIGS. 8A–8C, the graft and the anastomosis connectors are preferably in a compressed configuration. Alternatively or additionally, the connectors are expanded before inserting attaching ring 110 to ring 120.

In FIG. 8B, graft 38 is outside aorta 30 and is preferably pulled back against the aorta, for example by pulling back guide wire 36. Ring 110 is pushed forward so that pins 112 pierce aorta 30, graft 38 and friction ring 120. In a preferred embodiment of the invention, ring 120 is pushed by inflating a balloon on guide wire 36, just proximal to ring 110, so that the inflation of the balloon pushes the ring forward. Alternatively or additionally, a second balloon may be inflated on the other side of ring 120, to urge ring 120 towards ring 110. Alternatively or additionally, one or both of these pushing forces are applied by pulling wires coupled to graft 38 and rings 110 or 120.

In FIG. 8C, the anastomosis is nearly complete, however, an opening 118 is not yet expanded. In FIG. 4D, the opening is expanded and the anastomosis is complete. Opening 118 may be created by making one or both of rings 110 and 120 of a super elastic, elastic or shape-memory material and by reliving a constraint which maintains them in a compressed configuration. Alternatively or additionally, a balloon may be inflated in opening 118 to plastically deform the anastomosis connection. Alternatively or additionally, the same balloon used for urging the rings together may be further inflated, to expand the opening. In a preferred embodiment of the invention, the balloon has two inflation levels, a first inflation level at which the balloon urges the rings towards each other and a second inflation level at which a more distal portion of the balloon expands radially. Alternatively or additionally, the balloon is deflated after urging the rings together, advanced into opening 118 and re-inflated to expand the opening.

It should be appreciated that similar methods may be used in conjunction with a ring connector which does not use a second ring and in which the spikes are folded back by pushing them against an anvil. A balloon would then preferably perform the function of an anvil. Alternatively or additionally, the balloon expands an anvil which then collapses when the balloon is deflated.

FIG. 8E illustrates a friction ring in accordance with an alternate preferred embodiment of the invention. Views 1–3 show the ring in a side view and in cross-sectional views, when the ring is collapsed. In view 4, the ring is unfolded and has a larger diameter. Portions "A" and "B" interleave to form a single ring which is folded such that a top layer comprises of portions "A" and a bottom layer comprises of portions "B". In a preferred embodiment of the invention, the spikes of ring 110 are inserted into portions B of the ring, in FIG. 8B above.

In a preferred embodiment of the invention, the friction ring may include a plastic or a super-elastic, elastic or shape-memory stiffener, so a stiff ring is required only on one side of the anastomosis. Alternatively or additionally, neither side comprises a stiffener, rather, both are relatively flexible.

FIGS. 8F–8I illustrate different relative placements of the ring(s), aorta 30 and graft 38, in accordance with preferred embodiments of the invention. In FIG. 8F, ring 110 is in the aortic blood flow. In addition, an aortic flap 124 may be left dangling as a result of creating the hole in the aorta. In a preferred embodiment of the invention, such an aortic flap is pushed put with graft 38 and is then trapped by spikes 112 and/or by the pressure between rings 110 and 120 (shown as flap 124'). In a preferred embodiment of the invention, ring 120 is wider than everted portion 116 of graft 38. Thus, ring 120 may form an external seal against aorta 30. Preferably, ring 120 includes a depression to accommodate everted portion 116, so that the outer portion of ring 120 is flush against the aorta. In a preferred embodiment of the invention, ring 120 includes short spikes to which everted portion 116 is attached. Alternatively or additionally, ring 120 includes a ridge facing ring 110.

In FIG. 8G, everted portion 116 of the graft is inside the aorta. In a preferred embodiment of the invention, silicon ring 120 is not preloaded on everted portion 116, rather ring 110 is so preloaded. To perform the anastomosis, ring 120 is preferably pulled back (or pushed back) onto spikes 114, preferably using a balloon on the outside of graft 38. Alternatively or additionally, the balloon is inflated inside graft 38, to hold ring 120 from inside the graft.

In FIG. 8H, everted portion 116 is also inside the aorta. However, ring 110 is now between the aorta and everted portion 116. In a preferred embodiment of the invention, ring 110 includes short spikes 122 which engage everted portion 110. Alternatively or additionally, ring 110 is glued or otherwise attached to everted portion 116. In a preferred embodiment of the invention, ring 110 includes a sealant material which seals the gap between everted portion 116 and aorta 30. Alternatively or additionally, ring 110 includes a coating which induces blood clotting and/or tissue bonding at the connection. In a preferred embodiment of the invention, no ring 120 is used. Rather, spikes 114 bend back upon themselves after they pierce aorta 30, in a manner indicated above.

In a preferred embodiment of the invention, preferably where no ring 120 is used, spikes 114 are preferably superelastic, elastic or shape-memory and have a resting state whereby the spikes are bent at or near their base. In a preferred embodiment of the invention, spikes 114 are maintained at a straight configuration using a thin framework which fits between everted portion 116 and aorta 30. Once the pins pass through the aorta, the framework is removed, allowing the pins to fold back and/or to bring together everted portion 116 and aorta 30.

In FIG. 8I everted portion 116 is everted by 180 degrees, so there is no non-endothelial contact between the anastomosis connector and the blood. In addition, only smooth surfaces are presented to the blood (no ragged edge of graft 38), so there is less chance of turbulence. In a preferred embodiment of the invention, after the anastomosis is completed, the connector is pushed out of the aorta, preferably using a balloon, so that the entire connector is outside both blood vessels, for example as in FIG. 3G, with the connector outside the protrusion of the anastomosis.

In a preferred embodiment of the invention, the connection between the rings is provided by magnetic force, for example as described in "Non-suture micro-vascular anastomosis using Magnet rings: Preliminary report", by Obora Y., Tamaki N. and Matsumoto S., in Sur Neurol (UNITED STATES) February 1978, 9 (2) p 117–120, ISSN 0090-3019, the disclosure of which is incorporated herein by reference. In a preferred embodiment of the invention, the rings comprises a magnetic material. Alternatively or additionally, only rigid parts of the rings are magnetic and are situated or held within or between non-magnetic, more elastic parts. Alternatively or additionally, only one of the rings is magnetic, with the other ring preferably being ferromagnetic. Preferably, the magnetic portion is extra aortic, so that it does not impede flow. Alternatively or additionally, a magnetic force may be used to bring the two rings together, even if the maintenance of the connection is mechanical. In one example, indicated above, one ring is magnetic and the other is ferromagnetic. In another example, a magnetic force is applied from outside the body, for example using a large electromagnet. Alternatively or additionally, the two rings are magnetized so that they automatically align in a desired relative orientation, for example, so that spikes and holes line up.

In some of the above described embodiments, the ring performs two functions, namely aligning the spikes with the tissue to be pierced and maintaining the anastomosis opening. In addition, the ring exerts pressure along its entire circumference, not only where there are through spikes. In some anastomosis connections, some of these functions are not required and/or may be performed without a ring. In one example, if a round opening is cut in the aorta, there is no need to maintain the opening size. In another example, if the spikes are close enough together and/or in other situations, there will be no leakage, even if the ring does not apply pressure along the entire circumference of the anastomosis. In a preferred embodiment of the invention, the alignment function is performed by a framework which is removed after the anastomosis is completed. Thus, the completed anastomosis comprises a plurality of spike connectors without a stiffening ring. In a preferred embodiment of the invention, the spikes remain interconnected by a flexible connector, such as a silicone ring. Alternatively or additionally, the spikes are not interconnected. In a preferred embodiment of the invention, such a framework comprises an anvil against which the spikes are bent. Alternatively or additionally, the framework comprises a ring which is removed from the spikes after the spikes are inserted.

FIGS. 8J–8P illustrate several embodiments of the invention, in which the anastomosis device urges the graft radially against the lips of the hole in the aorta.

FIG. 8J is a side cross-sectional view of an anastomotic connector 424 which is positioned in a hole in a wall of aorta 30, but is un-expanded. Connector 424 comprises a central section 430, a plurality of upper spikes 428 and a plurality of lower spikes 426. Lips 430 of a graft 38 are everted 180° over connector 424. Also shown is an un-inflated balloon 436 which is positioned inside the connector, for expanding it.

FIG. 8K shows connector 424 after balloon 436 is expanded. As explained above, the radial expansion causes axial shortening, which shortening causes spikes 426 and spikes 428 to engage aorta 30. Preferably, the seal against blood leakage is by the inward pressure of the aorta, which pressure acts against the expanded (and preferably relatively rigid) central section 430. Thus, the spikes are only required in order to maintain the relative positions of the graft and the aorta, not for holding the anastomosis together. In FIG. 8K, a portion 437 of lip 432 is shown to be everted by spikes 426, possibly forming an additional sealing location in the anastomosis. Alternatively, lip 432 is made shorter so that there is no portion 437 to be everted.

In a preferred embodiment of the invention, the pressure-seal between the aorta and the graft is enhanced, using a bead 434. In a preferred embodiment of the invention, the bead comprises a thickening of the connector material. Alternatively or additionally, the bead comprises a portion of the connector that rotates out of the connector plane. Alternatively or additionally, the bead comprises an element that folds out, as described above concerning spikes. In a preferred embodiment of the invention, the bead is not continuous, rather, a plurality of individual beads are formed around the circumference of the connector. Possibly, a plurality of bands of beads is provided on the connector. Alternatively or additionally, The bead comprises a substantially continuous bead (possibly excepting weakened locations at parallelogram vertices) that circles the connector.

FIGS. 8L and 8M illustrate a connector 438 and a connector 440 which illustrate different arrangements of spikes. In both of the illustrated connectors spikes 426 and spike 428 are staggered, possibly reducing the trauma to the aorta. In connector 438 (FIG. 8L) six spikes 428 and six spikes 426 are provided. In connector 440 (FIG. 8M) four spikes 428 and four spikes 426 are provided. In alternative embodiments, different numbers of spikes may be provided, possibly different numbers of spikes 426 and of spikes 428. Additionally, staggering schemes other than 1/1 may be used. One advantage of staggering is that relatively longer spikes may be used. Possibly, an advantage of longer spikes is that they can pin together the various layers of the aorta and prevent dissection of the aorta.

Figure designation 8N is intentionally skipped.

FIGS. 8O and 8P illustrate connectors 442 and 448 in which only lower pins (corresponding to pins 426) are used. Thus, the anastomosis connection does not require any part of the connector to be in contact with the blood. In FIG. 8O, lower spikes 444 are preferably folded in, to better grasp the aorta. Alternatively or additionally, a plurality of hidden spikes 446 may be provided to engage the aorta and prevent axial movement of the graft. Possibly, spikes 446 also prevent dissection of the aorta, especially if they are curved, barbed or not parallel to the aorta wall.

A particular feature of this type of anastomosis is that there is created a pocket 452 for blood to enter between the graft and the aorta. This pocket is formed between a topmost end 456 of the graft (which has a rounded profile) and an edge 454 of the hole in the aorta (which has a square profile). Blood may enter that pocket and cause dissection of the aorta. Also possibly, the blood will pool and promote clot formation. In a preferred embodiment of the invention, spikes 446 are provided to urge end 456 against edge 454, so no blood can enter. Alternatively or additionally, bead 434 serves this purpose.

In FIG. 8P, connector 448 forms a flared anastomosis, in which the extent of the pocket is reduced and/or the pocket is eliminated, because end 456 is urged against edge 454 by the form of the anastomosis connection.

FIGS. 8Q and 8R illustrate a pull-wire anastomotic device 460, in accordance with a preferred embodiment of the invention. FIG. 8Q is a perspective schematic view of connector 460 showing a base ring 462 and a plurality of spikes 464 that pass through the ring. The cross-section of the spikes may be circular. Alternatively, the cross-section may be rectangular, may be an arc-portion or have other geometry's. Alternatively or additionally, the cross-section of the spike may vary along the length of the spike.

FIG. 8R is a side cross-sectional view of connector 460. When performing the anastomosis, the spikes 464 (all together or possibly temporally staggered) are pulled in the direction indicated by an arrow 466, relative to base ring 462. A barb 468 at the end of the spike engages the aorta. Graft 38 is preferably everted over the spike, so that when the base-ring is brought towards the aorta, the everted portion of the graft abuts the aorta. Possibly, the eversion is a 90° eversion. Alternatively, the eversion is a 180°, as indicated for example by a reference number 469. In some embodiments, ring 462 remains outside the aorta. In other embodiments, part or all of ring 462 is brought into the hole in the aorta. Possibly, ring 462 includes a rim 463, which limits the advance of the ring into the aorta.

In a preferred embodiment of the invention, barbs 468 do not extend beyond base-ring 462, during the insertion of the anastomosis device. In one embodiment of the invention, a spike 464 is bent inwards, as indicated by a dashed profile 470, so that barb 468 is within the maximum radius of ring 462. In a preferred embodiment of the invention, spike 464 is pre-bent. However, a rigid tunnel 471 in base-ring 462 forces the spike portion which passes through the base-ring to be perpendicular (or at any other desired angle) to the base ring. Thus, when the bent portion 470 of the spike is brought into tunnel 471, barb 468 is extended outwards. Alternatively, the spike may comprise elastic, shape memory or super-elastic materials, as described above. In another embodiment of the invention, spike 464 is rotated 90°, during deployment, as indicated by an arrow 472, so that the barb moves from the plane of the connector to extend outside the connector.

Alternatively or additionally to barbs 468 moving out of the connector plane during the deployment of connector 460, base-ring 462 comprises an expandable base ring, which has a smaller radius while it is being inserted.

In a preferred embodiment of the invention, connector 460 includes a one-way block 474 which prevents the removal of base-ring 462, after the anastomosis is performed. Alternatively, the removal is prevented by a kink in the spike, for example one caused by bend 470. Alternatively or additionally, the removal is prevented by a bending or flattening of the spikes. In a preferred embodiment of the invention, the spikes are formed of a single material having same mechanical properties along their entire length. Alternatively, especially for the embodiment using bend 470, a spike may comprises a first, flexible, portion and a second, more rigid, portion. Possibly, the flexible portion comprises a thread. In a preferred embodiment of the invention, an extending (waste) part of the spike is cut-off by an insertion device, possibly while flattening the spike to prevent the cut end from retracting through hole 471.

Alternatively or additionally, the spikes are self-shortening. In one embodiment of the invention a self-shortening spike is formed by a two-layer material in which one is elastic, super elastic or shape memory and is stretched (or shrunk) by a certain amount. When a restraint is removed (or the or shape-memory is activated), the spike twists in a spiral, shortening by a much more than the certain amount. Possibly, a plurality of weakenings are provided along the spike to assure spiral collapsing. Such an axially shortening may also be for other parts of the connector, for example, for causing axial shortening of the connector. Possibly, the spikes twist over substantially their entire length, thereby being screwed into the blood vessel tissue.

FIGS. 8S–8X illustrate a mechanism for folding spikes in which a radial expansion is substantially decoupled from axial length changes, in accordance with a preferred embodiment of the invention. FIGS. 8S and 8T illustrate part of a ring segment of an anastomotic device 700. In a complete device, the right end of the part shown is attached to the left end, forming a ring which is perpendicular to the plane of the paper. Device 700 is formed of a plurality of cells 702, having a spike 704 extending perpendicular to the segment and/or a spike 706 extending in the opposite direction. Thus, device 700 has a similar form as device 60 of FIG. 4A. As shown in FIG. 8T, when the device is radially expanded (shown here as a lengthening of the segment) spikes 704 and spikes 706 are folded towards the ring segment. Preferably, the movement of the spikes is on a plane which is tangent to the surface of the device 700. However, by a suitable weakening of a joint 710 which connects spike 704 to cell 702, motion in other planes can be achieved. It should be noted that also motion in the tangent plane enables the spikes to engage tissue that is outside the anastomotic connector.

Although only a single ring with spikes on two sides thereof is shown, a device having a plurality of segments may also be constructed in accordance with a preferred embodiment of the invention. It should be noted that a characteristic of some embodiments of device 700 is that there is substantially no axial shortening coupled with the radial expansion. Thus, in a device with several types of ring segments, various types of relationships between axial and radial expansion, such as shown in FIG. 5, can be achieved.

Figure 8W:
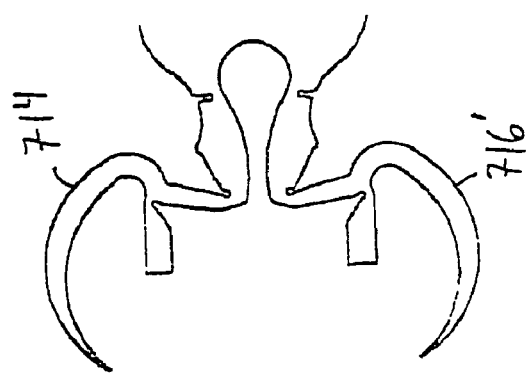
Figure 8V:
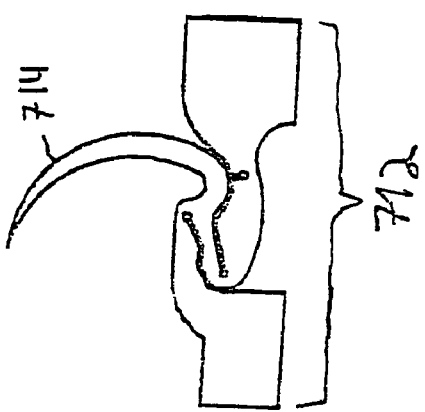
Figure 8X:
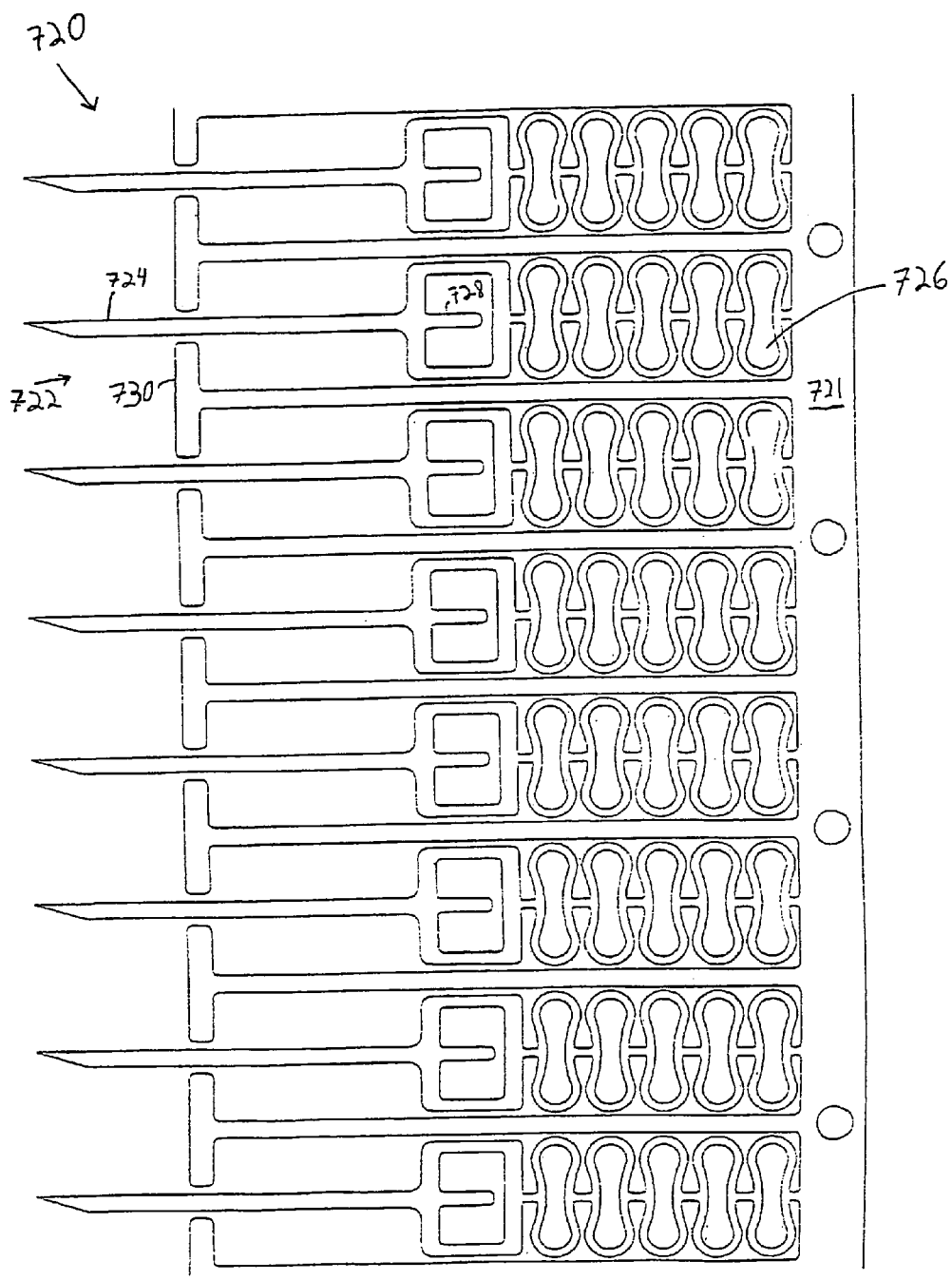
Figure 8X:
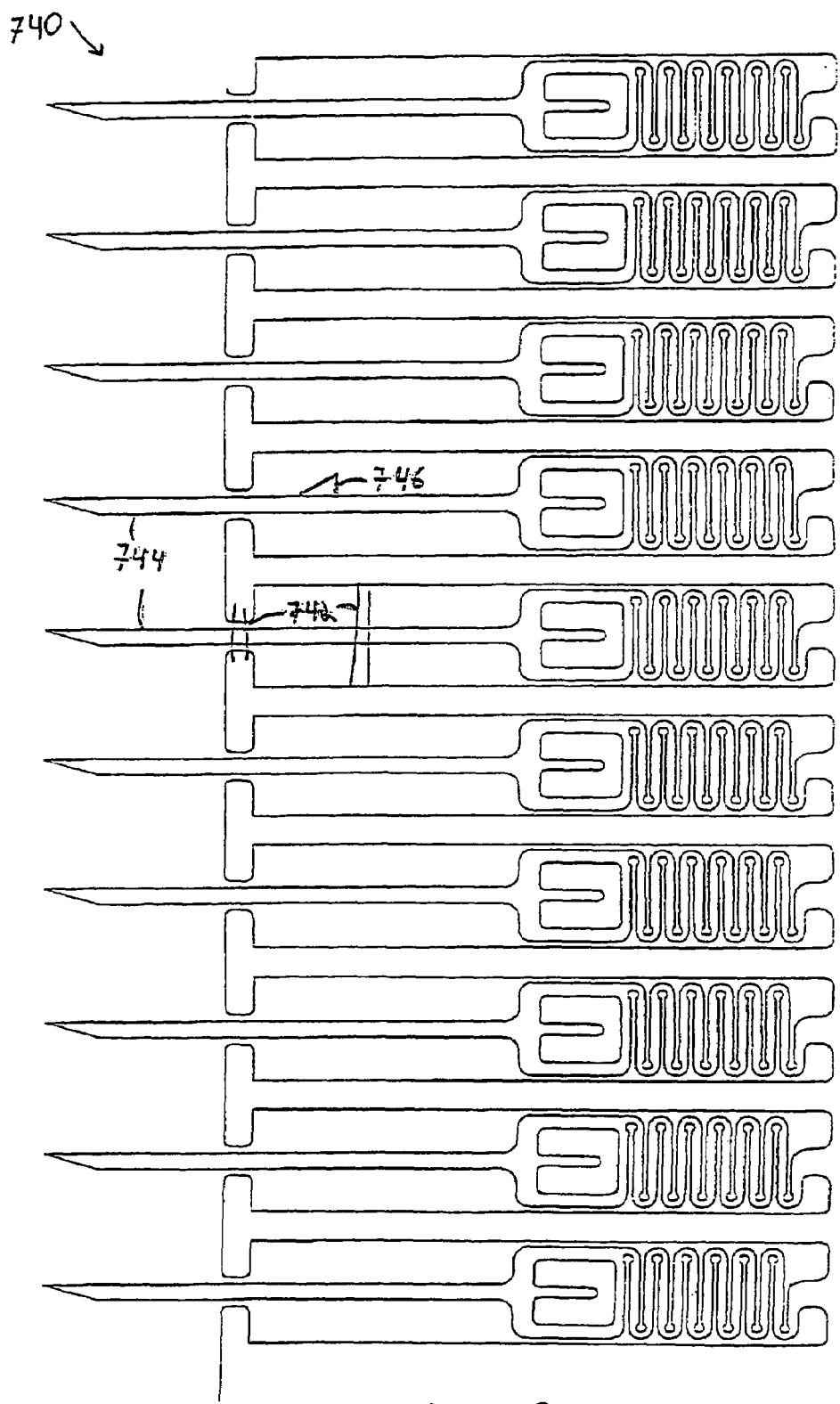
Figure 8X:
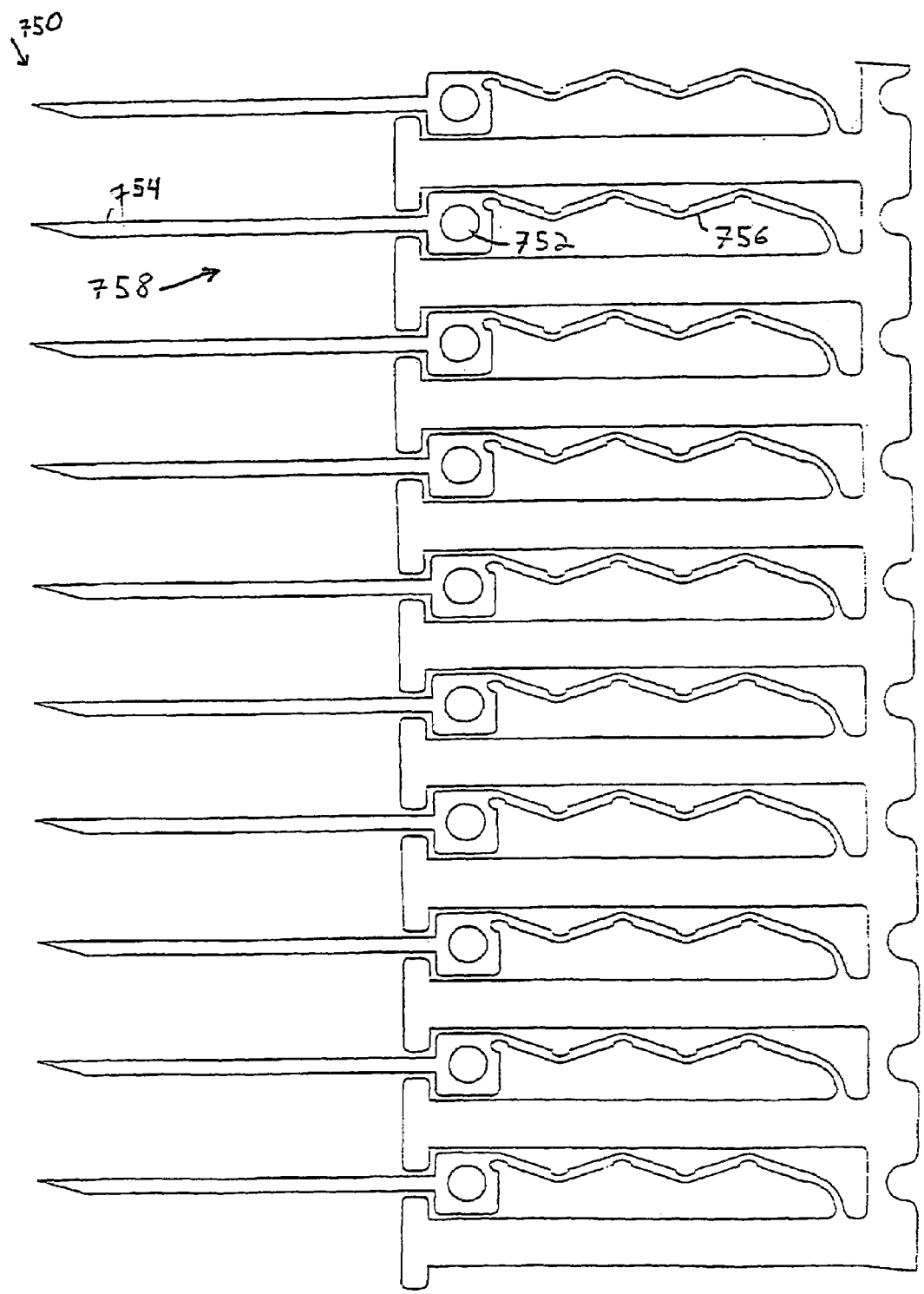
Figure 8X:
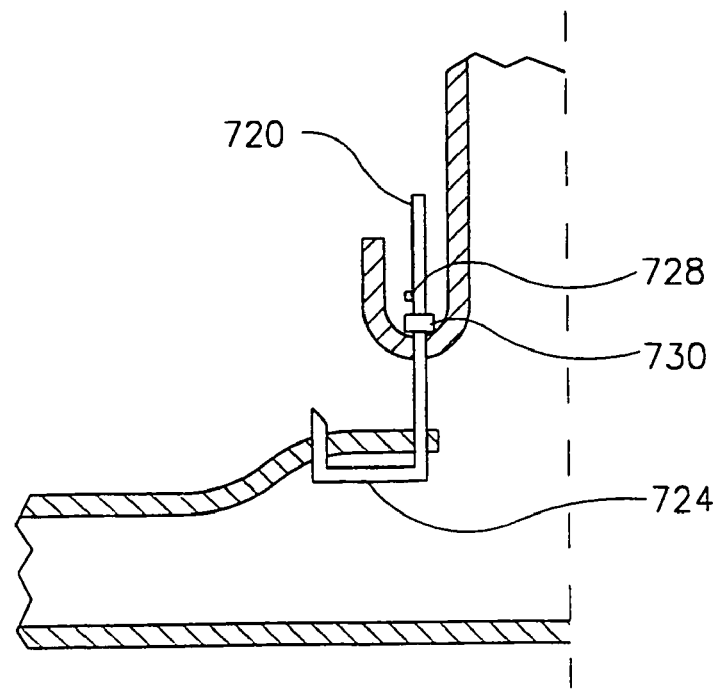
Figure 8X:
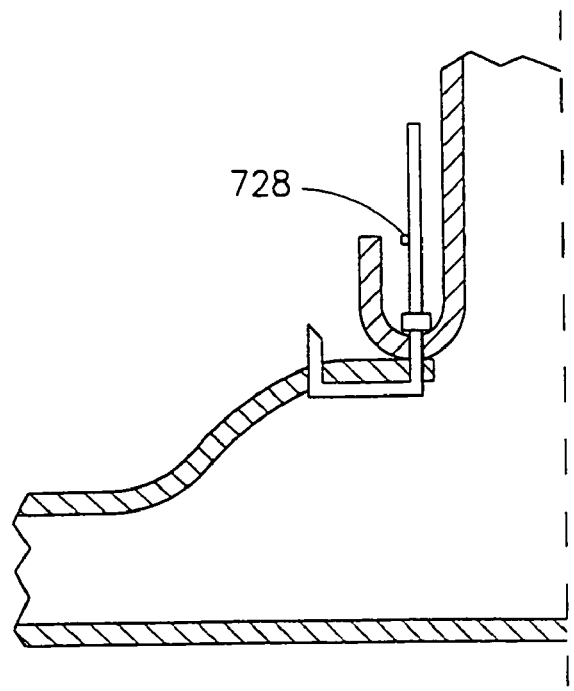
Figure 8X:
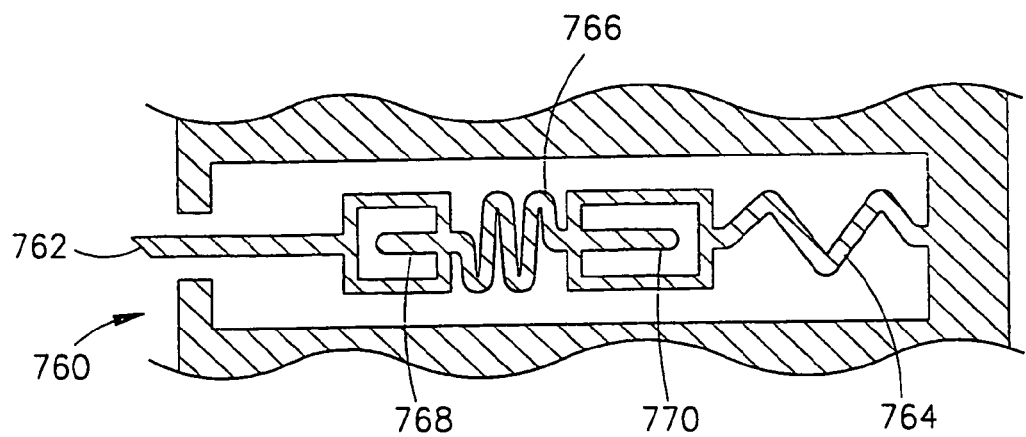
Figure 8X:
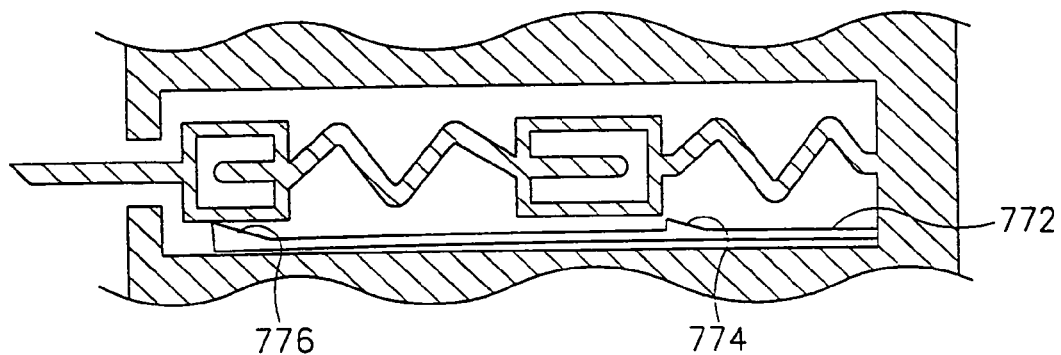
Figure 8X:
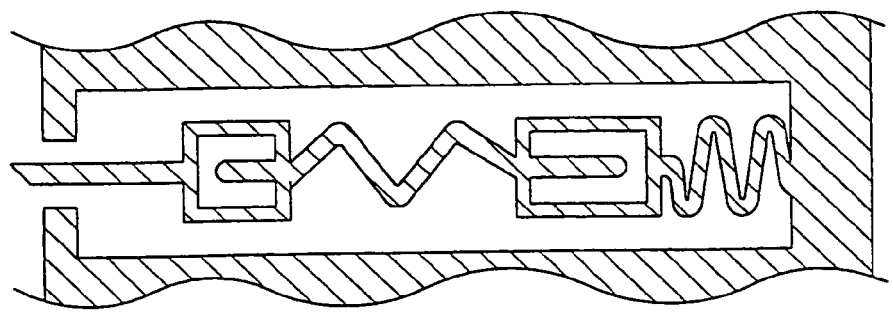

FIG. 8U shows a device 710 having features similar to those of device 700. A cell 712 replaces cell 702. In addition, two types of spikes are shown, a straight spike 716 and a round spike 714. FIGS. 8V, 8W and 8X show the effect of radial expansion on a spike 714. In FIGS. 8W and 8X two spikes are shown, to show the relative positions of two opposing spikes, as may be used in some embodiments of the invention. As the radial expansion proceeds, spike 714 advances in a scythe like motion, hooking and then engaging the tissue into which the spike enters. It should be noted that an anastomosis device 700 or 710 can be made very narrow, for example substantially the same as a thickness of the "side" vessel", so that there is a minimal protrusion.

FIGS. 8XA–8XH illustrate a mechanism for axial retraction and/or extension of spikes, in accordance with a preferred embodiment of the invention.

FIG. 8XA illustrates an anastomotic device 720, in a plan view. A plurality of spike cells 722 are attached to a body 721. Each spike cell preferably comprises one or more spikes 724, one or more rings 726 and/or one or more anchors 728. Springs 726, as shown, are in a relaxed state. In alternative embodiments, the springs are "normally extended", rather than "normally retract" as shown.

In a typical use, a graft is everted or otherwise transfixed by spikes 724. A plurality of tissue stops 730 are preferably provided to limit the advance of the graft on the spikes. Spikes 724 are then advanced, preferably by applying an advancing force onto anchors 728. This advancing step can be performed inside the body or outside of it. In some embodiments, advancing the spikes causes them to pierce and/or transfix a vessel to which the graft is to be connected. In other embodiments, shown below, the advancing causes the spikes to advance into a hole in said vessel. When the anchor is released, spikes 724 retract. In some embodiments, the retraction engages the "side" vessel. Alternatively or additionally, the retraction seals the anastomosis. In a preferred embodiment of the invention, each spikes retracts an individual amount, thereby matching irregularities in the anastomosis or in the two blood vessels.

FIG. 8XB illustrates a variant device 740 in which a spike 744 is restricted from movement perpendicular to the device surface by one or more bands 742. This restriction is useful, for example, if spikes 744 are pre-bent. However, as long as a spike 744 is retracted, bands 742 will maintain in the plane of its spike cell. In use, the spike's tip is pressed against the side vessel and then the spike is advanced, piercing and/or transfixing the side vessel before the spikes bend.

Generally, the retraction of the spikes is not complete, for example due to the transfixed tissue opposing the retraction of spring 726. Alternatively or additionally, the relaxed states of the spring does not fully retract the spikes. Alternatively or additionally, the spikes include a protrusion 746 wheich resists the complete retraction thereof. Alternatively or additionally, once the spikes are bent, they resist a complete retraction.

In a preferred embodiment of the invention, the anastomosis connector can be removed by completely retracting the spikes so that they disengage from the tissue. Preferably, bands 742 straighten the spikes 744 so that they do not damage the blood vessels during the removal.

FIG. 8XC shows a variant device 750 having a plurality of spike cells 758, in which the extension of a spike 754 has a plastic deforming effect on a spring-like element 756. An anchor 752 (shown here as a hole which can be engaged by a suitable protrusion on a deployment device) can be engaged and pulled along the tracks defined by cell 758, to retract the spike.

FIG. 8XD shows device 720 in a side cross-sectional viewed while being deployed in a side-to end anastomosis. As shown, spikes 724 are extended and bent. In a preferred embodiment of the invention, spikes 724 are inserted into the body bent. Alternatively or additionally, the spikes are manufactured or treated to be bent and are maintained in a straight configuration using a restrainer or using bands 742 (not shown). When advanced or when the restrainer is retracted, the spikes bend elastically or super-elastically. Alternatively or additionally, the spikes may be formed of a temperature-triggered shape-memory alloy. Alternatively or additionally, bands 742 are arranged to bend spikes 724 and/or point them at an angle to the axis of the device, as they are extended. Alternatively or additionally, the spikes are bent by an inner mandrel (not shown), for example an inflatable balloon.

In FIG. 8XE, anchor 728 is released (or retracted), so that the spikes are shortened. Retracting the anchor or releasing it preferably use an outer or an inner tube-tool (not shown) which engage the anchor. The exact form of the tube-tool depends on the anchor used. In the example of protrusions 728, which extend out of the surface of device 720, a simple tube which fits over the connector can be used.

It should be noted that each spike is independent. Thus, in a preferred embodiment of the invention, the retraction and/or release of the anchors may be for individual anchors or for sub-groups of the entire set of anchors.

Alternatively or additionally, to retraction and advancement using an external tool, the motion of a spike may be controlled by the device itself. In one example, anchor 728 is coupled, for example by a wire, to a vertex of a parallelogram which forms a part of the body of device 720. When the device expands radially, the vertex retreats from the edges of the device, pulling the spike back with it (preferably along the tracks defined by cell 722). In another example, as a parallelogram vertex retracts, it twists out of the surface of device 720, releasing anchor 728.

FIGS. 8XF–8XH illustrate a dual action mechanism 760 for a single spike 762, in which a single spike moves both advances and retracts. In an elastic example, spike 762 is connected in series to a normally expanded spring 766 and to a normally retracted spring 764. When an anchor 768 associated with spring 766 is released, spike 762 advances, as shown in FIG. 8XG. When an anchor 770 associated with spring 764 is released, spring 764 retracts, retracting spike 762, as shown in FIG. 8XH. The starting and ending retraction length need not be the same. Alternatively or additionally, one or both of the "springs" can be plastic deformations element deformed by moving the suitable anchors. Alternatively or additionally, the springs can be in other orders than shown and/or can have different lengths.

In a preferred embodiment of the invention, the release of the anchors is by a suitable deployment tool. Alternatively or additionally, the anchors are self-triggered. FIG. 8XG illustrates an optional self-trigger 772, which maintains spring 764 in an extended state, using a protrusion 774 on the spring. When anchor 768 advances far enough it pushes against a protrusion 776 of the self-trigger, causing the self-trigger to bend and release spring 764. The release causes spring 764 to constrict and retract the spike. Self trigger 772 may be in the same plane as cell 760 or above or below it. In some devices, the self-trigger may be plastically deformed or cut but the motion of spike 762. In a preferred embodiment of the invention, the two springs are in two layers, so that when spring 764 retracts is causes a deformation (preferably a bending) of spike 762.

It should be noted that such axial motion and/or double action motion may also be utilized for anastomotic devices which form their own holes in the blood vessel. Preferably, the spikes are bi-stable or are restrained in the shape of a tip, so that once they advance, the restraint/bi-stable shape is released and when the tips are retracted the bend outwards to engage the blood vessel and complete the anastomosis.

In some preferred embodiments of the invention, the devices of FIGS. 8XA–8XH include radial expansion capabilities, which may or may not be coupled to the extension of the spikes, as described. In other embodiments, no radial expansion is provided.

Each of cells 722 may be axially rigid. Alternatively or additionally, especially if the cells are interconnected at both ends, a radial expansion of the device may cause an axial shortening of the cells. For example, if each cell wall comprises a flattened parallelogram, instead of a single piece and/or by providing suitable weakenings thereon.

As described above, the cells are used for extension and retraction of the spikes. Alternatively or additionally, such cells may be used for controlling the axial length of the device. In one such example, the device comprises two rings, which rings are interconnected by self lengthening and/or self-shortening cells. In another such example, releasable springs are used to cause axial shortening of the device, rather than by releasing a restraint around the entire device. In some embodiments, the force of a single released spring can be used to trigger the release of other springs in addition to or instead of directly deforming the anastomotic connector.

Alternatively or additionally, to the cells being axially arranged, the cells may be arranged in a trans-axial and/or a diagonal direction (relative to the main axis). Thus, the spike scan be extended and/or retracted in various directions. Also, both the axial length and the circumference may be controlled using suitably arranged cells.

It should be appreciated, that as in other embodiments of the invention, there is a wire range of control techniques which may be practiced. In particular, various allocations of control mechanisms between the device and the deployment tool can be achieved.

Figure 9A:
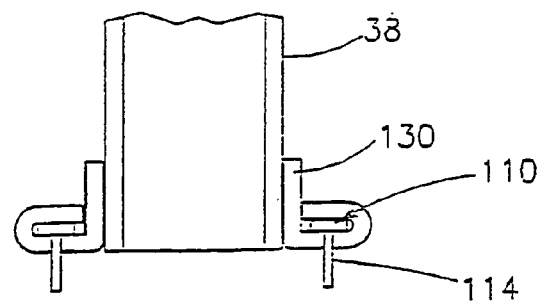

FIG. 9A illustrates a sleeve attachment 130 for a graft 38, in accordance with yet another preferred embodiment of the invention. In many cases, everting graft 38 may damage the graft. In a preferred embodiment of the invention, a sleeve attachment 130 is everted over a ring 110 and then attached to graft 38. Alternatively or additionally, the sleeve is first attached to the graft and then everted over the connector. In a preferred embodiment of the invention, sleeve 130 comprises a blood vessel segment that has a larger inner-diameter than graft 38. In a preferred embodiment of the invention, sleeve attachment 130 is glued to graft 38. Alternatively or additionally, the attachment is sutured to graft 38. Alternatively or additionally, it is welded and/or attached using a plastic flowable material.

Figure 9B:
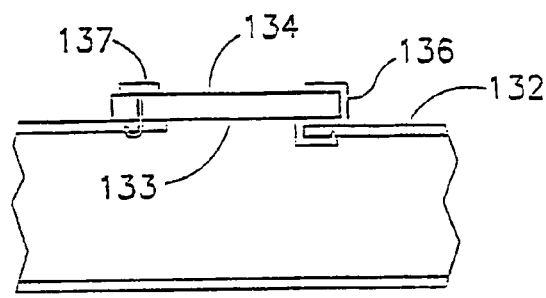

FIG. 9B illustrates attaching a patch 134 to the outside of a blood vessel 132, using devices and/or techniques as described herein. Although a flat patch 134 is shown, patch 134 may comprises a graft with an end tied off. Preferably, the patch is pushed out of vessel 132, through a hole 133. A connector 136 pulls the patch against vessel 132. Alternatively or additionally, a spike type connector 137 may be used to maintain the patch in contact with the vessel. A connector such as a connector 137 does not maintain hole 133 in an open configuration, so there is usually less strain on vessel 132. In many cases, there will be no leakage through hole 133, even if the patch is not hermetically sealed, due to the elasticity of the walls of vessel 132.

Patching a blood vessel may be desirable if the vessel wall is damaged at that point, to relive strain, for example caused by an anastomosis and/or to support an electrode or a different wire or tube which exits the blood vessel. In a preferred embodiment of the invention, such a patch is applied for a side-to-side anastomosis, either on the outside of vessel 132 or on its inside. Preferably, a single connector is used both for the anastomosis and for the patching.

Figure 9C:
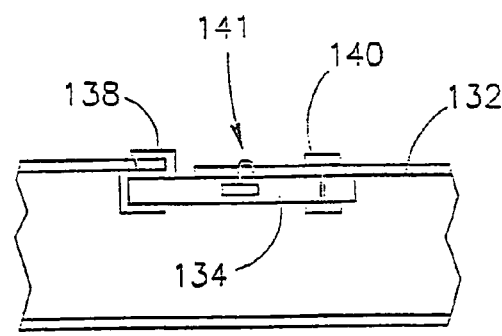

FIG. 9C illustrates configurations in which patch 134 is inside the blood vessel. In a configuration 138, the connector is situated along the edge of the patch, possibly covering any ragged edges and engages vessel 132. Preferably, the engagement is by pins which pass through the vessel. Alternatively or additionally, connector 138 passes through a hole in vessel 132, as shown for example in FIG. 9B. In configuration 140, a spike pierces both patch 134 and vessel 132. The spike may bend back. Alternatively or additionally, a friction material, such as a ring is provided on the other side of vessel 132, preferably after being pushed out through a hole in vessel 132. In configuration 141, a spike is embedded in- or otherwise attached to-patch 134, so that there is no contact between the connector and the blood flow.

A PCT application titled "Vascular Port Device", filed in the Israel receiving office on even date as the instant application, with same applicants, the disclosure of which is incorporated herein by reference, describes various types of seals for holes in blood vessels. In particular, some of these seals may be applied over an existing catheter to seal an existing hole.

Alternatively or additionally, some of these seals are actually anastomotic devices, which, when they fail, can self-seal. One type of sealing mechanism described is that spikes, which engage the blood vessel around the rim of the hole in the blood vessel, move towards each other, thereby causing the rim portions to abut and seal the hole. The present application describes various mechanisms that can be used to control the expansion and/or collapsing of an anastomotic connector, such that the spikes move towards each other and seal the hole of the anastomosis.

Figure 9D:
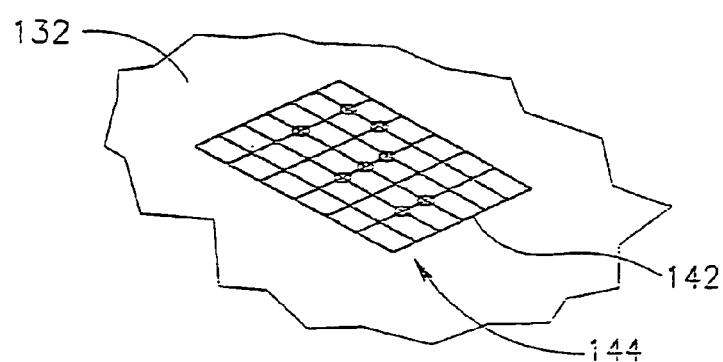

FIG. 9D illustrates a strain reliving device 142, attached to vessel 132, either on its inside or on its outside. In a preferred embodiment of the invention, device 142, shown as a grid, is covered with a graft material. Dots 144 indicate pins that engage vessel 132 itself. In a preferred embodiment of the invention, the pins are super-elastic, elastic or shape-memory and are maintained in a configuration where they are pointing away from the vessel wall. When device 142 is positioned in a desired location, a restraint is released and the pins bend to engage the vessel wall. The pins may be distributed evenly over device 142. Alternatively or additionally, the distribution is uneven, preferably to match a strain pattern.

In a preferred embodiment of the invention, device 142 is used to relive strain on a wall of vessel 132. The distribution of pins 144 will usually affect the amount and directionality of the strain in vessel 132. Although device 142 is shown as being substantially planar, in a preferred embodiment of the invention, device 142 may be curved or even cylindrical, to match the shape of the vessel.

In a preferred embodiment of the invention, device 142 provides a framework for an endoscopic procedure or for a catheter based procedure, and as such, it may be inserted outside of the blood stream. In a preferred embodiment of the invention, device 142 is attached to a heart or to an aorta, preferably for aid in performing a bypass procedure. Preferably, the framework is provided through an endoscope. Preferably the framework remains loosely coupled to the endoscope, for example via a cable for providing power (such as air pressure) or via a safety line.

Device 142 may include rails or other guidance mechanisms for guiding the procedure,
such that tools and/or endoscopes or other tubes may travel along the guide rails. Such rails preferably follow the surface of device 142. In a preferred embodiment of the invention, the rails include junction points or otherwise identifiable points where a guided tool may fix its position relative to the device.

In a preferred embodiment of the invention, device 142 may be controlled to be at a selected one of two or more configurations, for example, by inflating a balloon therein.

Preferably, when the device changes configuration, it changes the relative positioning of body tissues and/or tools which are attached to different parts of the device. When the procedure is completed, the device may be removed by folding it. Preferably, the device is removed using the same endoscope/catheter used to insert it. Alternatively or additionally, it may be removed via a keyhole or other surgical wound or using a different catheter. Preferably, all the pins are bent in such a direction that folding the device retracts them from the tissue. In a preferred embodiment of the invention, the device is folded by engaging it with one or more arms comprising a super-elastic, elastic or shape-memory material and relieving a restraint on the arms so that they fold, folding the device with them. Alternatively or additionally, the holding strength of the pins may be reduced if they comprise a shape-memory material that is cooled below its critical point. Alternatively or additionally, the framework is maintained in an expanded configuration using an inflatable device, such as a balloon. When the balloon is deflated, the device preferably collapses as a result of its own elasticity.

Many variations on the above-described devices may be practice within the scope of some preferred embodiments of the present invention. In a preferred embodiment of the invention, the connector is smooth, at least in portions thereof that are in contact with blood flow, to enhance bio-compatibility. Alternatively or additionally, the connector is rough or has grooves defined therein, at least in portions thereof which are in contact with blood vessel tissue, to enhance attachment to the blood vessel.

In a preferred embodiment of the invention, the spikes are sharp to better pierce the blood vessels. Alternatively or additionally, the spikes are blunt, for example to promote tearing rather than cutting. In a preferred embodiment of the invention, the spikes have a flat rectangular cross-section, for example for ease of manufacturing. Alternatively or additionally, the spikes have a triangular or a circular cross-section, for example, for better mechanical stability. In a preferred embodiment of the invention, not all the spikes have the same cross section and/or sharpness and/or tip shape, for example to provide a range of mechanical and/or adhesion characteristics.

In a preferred embodiment of the invention, spikes are placed close together, so that they can support the anastomosis. Alternatively or additionally, the spikes are relatively few and/or far apart and the anastomosis is supported by rings to which the spikes are connected and which exert pressure on the anastomosis. In a preferred embodiment of the invention, the spikes and/or the rings are arranged in two or more concentric layers and/or have different bending locations, for example, so that a double seal/anastomosis is formed.

It should be appreciated that a single anastomosis connector may include features from different ones of the connectors described above, for example, a connector may include both spikes which hold together the vessel and the graft and a structure which urges the vessel and the graft together.

Much of the above description has centered on the anastomosis connection at the aortic side of a bypass, however, these anastomosis connections may also be applied to the coronary side of the bypass. It should be noted that once the end of graft 38 and the connector attached thereto are inserted into coronary vessel 22, the situation is the same as when graft 38 is inside the aorta, i.e., the graft may be pulled out. However, it should be noted that vessel 22 has a smaller diameter, so a lower profile connector may be desirable. In addition, it may not be desirable to push a large connector out of the aorta to vessel 22. Thus, a smaller connector is preferably used for the arterial end of the graft. Alternatively or additionally, the connector used for vessel 22 may combine the functions of tip 37 and of at least part of the anastomosis process.

In a preferred embodiment of the invention, a failed anastomosis may be removed, either during the attachment process or after it is completed. In one example, if the anastomosis at vessel 22 fails, the tip of graft 38 may be cut off and a new anastomosis connector provided along guide wire 36, for connecting at a new point. In some cases, the hole in vessel 22 will not leak without any further treatment. Alternatively or additionally, the hole is patched, either as described above or using techniques known in the art, for example, coating it with a flowable material. Alternatively or additionally, when the graft is cut, the end of the graft near vessel 22 is sealed off.

FIGS. 10A–10D illustrate an end-to end anastomosis in accordance with a preferred embodiment of the invention. When provided, an anastomosis connector 152 has a diameter smaller than that of a vessel 150. A balloon 156 is inflated under one end of connector 152, so that it expands radially and spikes thereon engage the walls of vessel 150. A second vessel 154 is then brought to a position where it overlaps the second end of connector 152. When the second end of connector 152 is inflated, it expands radially and preferably also contracts axial.

Thus, a better contact is formed between the two blood vessels.

In a preferred embodiment of the invention, connector 152 includes a ridge 153, preferably around most or all the circumference of connector 152. Thus, when the two blood vessels are brought together, the ridge guides an automatic eversion of the two blood vessels.

In a preferred embodiment of the invention, the ridge is not continuous and contains holes and/or gaps, so that the two blood vessel surfaces can be in contact through the ridge.

In a preferred embodiment of the invention, connector 152 is used for an externally meditated anastomosis. Preferably, connector 152 is formed of a super elastic, elastic or shape-memory material and is constrained to be radially compressed by a device which circles connector 152 at ridge 153. After the two blood vessels are placed on the connector, the restraint is removed and the two blood vessels are automatically engaged by connector 152, advanced towards each other and attached to each other. Possibly, they are also everted over ridge 153.

In a preferred embodiment of the invention, when a graft is implanted and found to be too long, it may be sectioned and the sectioned portions be attached using an end-to-end anastomosis, as described above. Alternatively or additionally, the graft is attached to supporting tissue so that it does not move around.

FIGS. 10E–10K illustrate an end-to-end anastomosis between a first vessel 680 and a second vessel 682, in accordance with an alternative preferred embodiment of the invention.

As a preliminary step, shown in FIG. 10E, second vessel 682 is preferably threaded using a guide wire 684 and then a roughened balloon 686 is inflated in its lumen to grasp vessel 682. Blood flow from vessel 688 may be blocked by a blocking catheter 688, through which the following process may be performed. Alternatively or additionally, the catheter may be used to sever the ends of one or both vessels and to locate or assist in locating the ends in the body.

In FIG. 10F, a connector 690 is provided. In a cross-sectional view, connector 690 may have a "Y" profile. Preferably, connector 690 includes a first set of spikes 691 for engaging vessel 680 and a second set of spikes 693 for engaging vessel 682. The two sets of spikes are preferably connected to a body 695 that has a base 697. If connector 690 is deployed using plastic techniques, a balloon 692 may be provided. Alternatively or additionally, if connector 690 is deployed using elastic, super-elastic or shape-memory techniques, a restraining element 694 may be provided.

In FIG. 10G, connector 690 is flattened, so that its profile is perpendicular to the two blood vessels. Possibly, a portion 696 of the connector remains axial. Several methods as described herein may be used to flatten connector 690. In one embodiment, connector 690 is elastically striving to resume a flattened configuration, once restraining element 694 is removed. In another embodiment, the base of connector 690 is restrained from expanding by its geometry. Thus, when a balloon 692 is inflated inside of it, the rest of the connector follow the counter of the balloon. Possibly, an orientation as indicated by reference 698 is achieved, rather than a perpendicular orientation. Possibly, the rotation and/or further rotation of connector 690 is performed after the two vessel are brought against the connector and/or after the two vessel are engaged by the spikes.

In FIG. 10H, vessel 682 is brought towards connector 690, for example by retracting guide wire 684. The severed end of vessel 682 is thus partially everted over connector 690. Possibly, folding into the lumen of vessel 682 is prevented by balloon 682, balloon 692 and/or an axial portion 696.

In FIG. 10I, spikes 693 bend and engage vessel 682. Several methods may be used to bend these spikes. In one example, expansion of connector 690 will cause the spikes to bend, possibly, without appreciable bending of the other spikes, by each set of spikes being connected to differently shaped parallelograms, which respond differently to different amounts of radial expansion. In another example, the spikes are elastic, super-elastic or shape-memory and bend when a restraint is released, again, possibly by the expansion of connector 690. Alternatively or additionally, spikes 693 and spikes 691 bend together, at a later time, for example as a result of further expansion of connector 690.

In FIG. 10J, vessel 680 is advanced and everted. In FIG. 10K, spikes 691 are bent, completing the anastomosis. Preferably, expanding connector 690 radially enhances the grasping of spikes 691 and 693. Preferably a plurality of tissue blocks are formed on these spikes, so that when the spikes bend more, they urge the vessels against each other.

FIG. 10L illustrates a side-to-side anastomosis, utilizing a connector similar to that used in the embodiments of FIGS. 10E–10K. In this type of connection, the connector is first rotated to be perpendicular to the flow between the vessel (opposite the rotation in FIG. 10G and then the vessels are urged together. Possibly, the connector is advanced end first and then rotated.

In this embodiment, however, the spikes are inside the blood flow, so they can also be bent using suitable balloons.

FIG. 10M shows a front view of an anastomosis device 690 suitable for use in FIGS. 10E–10L. In the embodiment shown, connector 690 comprises a base-ring 697, which may, for example be plastically deformable. The figure shows the resting state of the device, i.e., when a restraint is removed, the device will achieve the shape shown. However, when the ring is expanded, for example using a balloon, spikes 691 and 693 will be bent, preferably suing one of the many mechanism described herein.

In a variation of a standard anastomotic procedure, two severed parts of a blood vessel may be reattached by first attaching a "half" anastomotic connector to each severed end and then attaching the two "halves" connectors, for example using a graft which bridges the two connectors or by mechanically attaching the two device halves. A half connector may be, for example half of the connector shown in FIG. 10A. A use of such a procedure is trauma surgery, such as for connecting severed limbs or when implanting certain organs, where many end-to-end anastomosis connections are to be performed. Preferably, each pair of "half" connectors is marked to allow easy identification of the matching ends. Alternatively or additionally, each pair of "halves" is connected by a wire. Thus, the task of identifying the severed vessels and determining whether the remaining vessel lengths are sufficient can be separated from the actual anastomosis connection activity and without previously performed connections interfering with the work.

FIG. 11 illustrates a graft delivery system 201, in accordance with a preferred embodiment of the invention. Referring back to FIGS. 2A–L, a "J" shaped catheter 34 includes a lumen through which a guide wire 36 may be provided. The lumen may also be used to perform suction, for collecting debris, to provide other tools, to inject contrast media, drip anti-clotting drugs, to provide saline solution and/or to seal off the work area from the blood flow. Guide wire 36 has a sharp tip 37 which is preferably tapered and which may be used to pierce both aorta 30 and vessel 22. Alternatively or additionally, the guide wires are switched so that different guide wires are used for the different vessels.

A graft 38 is preferably preloaded with anastomosis connectors 202 (aortic) and 204 (coronary), prior to being inserted into the body. Connector 204 preferably includes a tapering surface 206 to ease its insertion into the holes created by tip 37. Alternatively or additionally, a tapering surface 206 may be independently provided over guidewire 36 and retracted when not needed. Preferably, tapering surface 206 is an inflatable tapering and/or otherwise expandable surface.

In FIG. 11, a narrower connector profile is used for connector 204 than for connector 202. However, this is not a requirement of all the preferred embodiments of the present invention. A balloon 200 is preferably provided over guide wire 36 to expand the connectors. A second balloon 206 may also be provided. The second balloon may have a narrower cross-section than balloon 206. Alternatively or additionally, balloon 206 may be used in conjunction with balloon 200, to squeeze an anastomosis connector.

In a preferred embodiment of the invention, catheter 34 is not used and graft 38 is exposed to the blood. Some or all of the elements shown in FIG. 11 are preferably disposable. Alternatively or additionally, at least some of the elements are sterilizable, for example, guide-wire 36.

FIGS. 12A–12E illustrate an applicator kit 480 (not marked on the figures) for an anastomosis connector, in accordance with a preferred embodiment of the invention useful for key-hole surgery. In a preferred embodiment of the invention, kit 480 comprises a holder 509 (FIG. 12B, 12C), which can selectably hold an aortic puncture sub-assembly 500 (FIG. 12A) or a graft insertion sub-assembly 482 (FIG. 12D). A close up of the tip of the holder, including the graft insertion sub-assembly and an inserted graft, is shown in FIG. 12E.

Referring to FIG. 12A, puncture sub-assembly 500 is preferably designed to reduce the danger of puncturing both sides of the aorta. In a preferred embodiment of the invention, a hole-making pin 515 is protected by a protective sleeve 513. When the tip of hole-making pin 515 is pushed into the side of an aorta, protective sleeve 513 retracts (against a spring 523) and exposes the sharp tip of hole-making pin 515, which tip penetrates the aorta. Once the aorta is penetrated, protective sleeve 513 can slide back forward and protect the other side of the aorta from hole-making pin 515. Spring 523, protective sleeve 513 and hole-making pin 515 are preferably coupled through a cap which comprises elements 514 (body) and 511 (top seal).

Referring to FIG. 12B, aortic punch sub-assembly 500 is shown inserted in holder 509. Attention is directed to an extension 498 of an inner sleeve 507 of holder 509. When the hole is punched in the aorta, this extension also enters the aorta. However, further advance of the holder is blocked by a step-type increase in radius of holder 509.

Once the aorta is pierced, aortic punch sub-assembly 500 can be removed. In a preferred embodiment of the invention, holder 509 includes a seal 532, for example a silicon gasket or a tri-leaflet valve made of a flexible and resilient material. Thus, when sub-assembly 500 is removed blood is stopped from exiting the aorta, by the seal. In some cases, some blood will pass by the seal and fill holder 509, above the seal. In a preferred embodiment of the invention, a pressure relief exit (or valve) 530 is provided, for blood to exit the holder when new tools are inserted into the holder.

Referring to FIG. 12D, graft insertion sub-assembly 482, comprises a plunger 526 on which a graft (not shown) is mounted. In a preferred embodiment of the invention, a connector graft is mounted on the graft in the following manner. A connector is held inside a restraining element 508, so that one set of spikes is extended. A graft is loaded either on or inside plunger 526 and plunger 526 is inserted through a body 505 and restraining element 508 which is attached at the end of the body. Then, the graft is everted, possibly manually, over the extended spikes.

Preferably, plunger 526 is held by a pin 516 so it does not move relative to a block 504, which is fixed to body 505. When plunger 526 and body 505 are inserted into holder 509, pin 516 is released using a mechanism including a pin 517, when pin 517 contacts a holder block 503 of the holder. The release of the pin allows plunger 526 to advance (relative to restraining element 508) until the anastomotic connector is properly positioned relative to the holder tip (and thus the aorta). It should be noted that the device does not expand at this point, since it is constrained by inner-sleeve 507.

Referring to FIG. 12E, an everted graft 36 is shown with a mounted anastomotic connector 496. When plunger 526 is advanced, the extended spikes of connector 496 are preferably folded back by a tapering 534 formed in inner sleeve 507.

Referring back to FIG. 12C, a pin-type mechanism (518, 519, 520, 521 and 522) preferably maintains holder block 503 fixed relative to holder 509. Inner sleeve 507 is preferably coupled to holder block 503. When the pin-mechanism is released, a spring 524 preferably retracts holder block 503, thereby retracting inner sleeve 507 and extension 498. As extension 498 is the only thing retaining connector 496 from expanding, the connector expands and performs the anastomosis.

FIG. 12F illustrates an exemplary anastomotic connector 496, in a collapsed configuration 538 and in an expanded configuration 540. This connector is similar to the connector of FIG. 8J, except that the spikes are bent in arcs, rather than in straight angles. Such a modification may also be applied to other connector embodiments described herein. In addition, depending on the location where the spike exits the graft, a portion of the graft may protrude into the aorta. In some cases, this protrusion may aid in sealing pocket 454 (FIG. 8O). Additionally or alternatively, the engagement of the aorta by the spikes may cause a radial compression of the wall of the aorta.

It should be noted that in the embodiments of FIG. 12G, as well as in other embodiments, such as those of FIGS. 8O and 8P, it is not necessary for the graft to be everted 180°. Rather, an eversion of 90° may be sufficient. Further, since the graft is pressed against the "side" vessel, the eversion may be completely dispensed with. However, small spikes (or other protrusions) are preferably provided inside the anastomosis connector to engage the graft and prevent it from slipping off the anastomotic connector, during the deployment process.

FIG. 12G illustrates an alternative connector, similar to connector 496 of FIG. 12F, but in which one set of spikes is curved and one is bent at substantially right angles.

FIGS. 12H–12J illustrate a graft everter 636, in accordance with a preferred embodiment of the invention. Everter 636 preferably comprises an outer body 638, an inner body 640 and expandable arms 642. A graft 38 is preferably extended from a graft delivery sub-assembly 482, with a connector 496 already loaded in restraining element 508. Graft 38 is preferably engaged by roughened (possibly by sand-blasting) or barbed ends of arms 642. Thus, when plunger 640 is advanced, the arms extended radially, expanding the graft radius (FIG. 12I). The entire everter 636 is then advanced towards sub-assembly 482, so that the graft everts and is engaged by extended spikes 644 of connector 496. The spikes may extend radially or may extend axially, in either case they preferably transfix the graft in the everted configuration. Thereafter, arms 642 are released, for example by axial rotation, to present a smooth side to the graft, and the graft finishes the eversion over the connector. In some embodiments of the invention, everter 636 is coupled to the vessel holed. In other embodiments, the tool tools are separate.

In some cases, an oblique connection is desired. In these cases, the eversion may be oblique as well. In a preferred embodiment of the invention, an oblique eversion is achieved using an oblique anastomotic connector. Alternatively or additionally, the oblique eversion is achieved by the tip of the vessel holder being non-perpendicular to the main axis of the vessel holder. Alternatively or additionally, the everter provides asymmetric expansion and/or asymmetric advancing.

FIGS. 12K–12M illustrate an alternative hole-punching sub-assembly 648, in accordance with a preferred embodiment of the invention. Unlike sub-assembly 500, sub-assembly 648 punches a hole, removing a portion of the aorta in the process, rather than just forming a hole.

In a preferred embodiment of the invention, the difference between sub-assembly 648 and sub-assembly 500 is in the provision of an indent 651 in a hole-punching element 650 of sub-assembly 648. FIG. 12K shows a tip of assembly 648, with punching element 650 extended and FIG. 12L shows the tip with element 650 retracted. FIG. 12M, corresponds generally to FIGS. 12A and 12B and illustrates sub-assembly 648 as a whole and as inserted in holder 509.

FIGS. 12N–12R illustrate two methods of punching a preferably leak-less hole from outside or inside a blood vessel, in accordance with a preferred embodiment of the invention. Although the reference numbers are copied from FIGS. 12A–12M, the methods of both sets of figures may also be practiced in a transvascular approach, especially with regard to punching a hole in the coronary vessel in an aorta-coronary bypass procedure.

In FIGS. 12N–12P, a hole punching element 650 is forced into aorta 30 (FIG. 12N).

Then, element 650 is retracted against protective sleeve 513, cutting off a piece of the aorta within indent 651 (FIG. 12O). Protective sleeve 513 and extension 498 are then advanced into the punched hole, until protective sleeve 507 abuts against aorta 30 (FIG. 12P).

In FIGS. 12Q–12R, an outer sleeve 654 is advanced such that only punching element 650 is forward of it, then the holder 509 is pushed against aorta 30, causing element 650 to enter it (FIG. 12Q). In FIG. 12R, protective sleeve 513 is advanced over punching element 650 to remove a part of the aorta. Simultaneously, or afterwards, element 650 may be retracted. In an alternative embodiment, sleeve 507 is fused with protective sleeve 513 and extension 498 to form a single element.

FIGS. 12S and 12T illustrate an expanding hole puncher 780, in accordance with a preferred embodiment of the invention. FIG. 12S shown puncher 780 in a compressed configuration and FIG. 12T shows puncher 780 in an expanded configuration. In a preferred embodiment of the invention, hole puncher 780 comprises an expanding tip 784 and an expanding anvil 782. In a particular embodiment of the invention, tip 784 is super-elastic, elastic or shape memory and is restrained from expanding by a tube 788. Once tube 788 is retracted, tip 784 expands, for example using an umbrella mechanism 790. Alternatively or additionally, tip 784 is expanded using a balloon (not shown). Tip 784 is preferably expanded after it pierces the blood vessel, however, it may be expanded before too.

Anvil 782 preferably comprises a tube 782, which is maintained at a compressed diameter by an enclosing restraining tube 786. When tube 786 is retracted, tube 782 expands, so that can be used as an anvil (or a knife edge or a scissors part) against the base of tip 784.

In a preferred embodiment of the invention, the hole puncher is removed by returning tube 788 and tube 786 to their original positions, thereby collapsing tip 784 and anvil 782. Alternatively or additionally, the tip and anvil may have a normally collapsed configuration, with the expansion achieved, for example, by a balloon inserted in each of tip 784 and anvil 782. When the balloons are deflated, the tip and anvil collapse. Alternatively or additionally, other expansion/collapsing mechanisms may be used.

It should be appreciated that any of the above embodiments of hole punchers may be constructed to be expandable.

As indicated above, in some cases it is desirable to punch an oblique-profile hole and/or punch a hole for an oblique anastomosis. In a preferred embodiment of the invention, the hole punching element and/or the depressions thereon are made oblique. Alternatively or additionally, the lips against which the element cuts are made oblique. Alternatively or additionally, the tissue stop for controlling the advance of the hole puncher into the blood vessel is made oblique.

The hole formed by the hole puncher (or by other means) is preferably smooth, for example being circular or elliptical. Alternatively, a different convex shaped hole, such as a triangle or higher-order polygon may be cut. Alternatively, a concave hole may be cut, for example, a circular hole with a sine-wave variation on its circumference. Alternatively or additionally, a partial amount of vessel tissue may be removed surrounding the hole, for example, so that the hole has a sloping rim at least along some of its circumference. Alternatively or additionally, such selective tissue removal is used to weaken the blood vessel and/or to prevent tearing and/or to guide stress formed by the anastomosis.

The above description of a graft application kit is only exemplary and many variations will occur to a man of the art, for example, the use of other restraining mechanisms or other releasable fixing mechanisms to replace the pin-mechanisms suggested.

In a preferred embodiment of the invention, the graft application kit is made flexible, for use through an endoscope and/or a catheter or made elongated, for use through in key-hole surgery. Preferably, the releasing mechanisms are remotely operated, for example using pull wires. Alternatively or additionally, the springs are replaced by wires which are connected to springs outside the body.

Figure 13A:
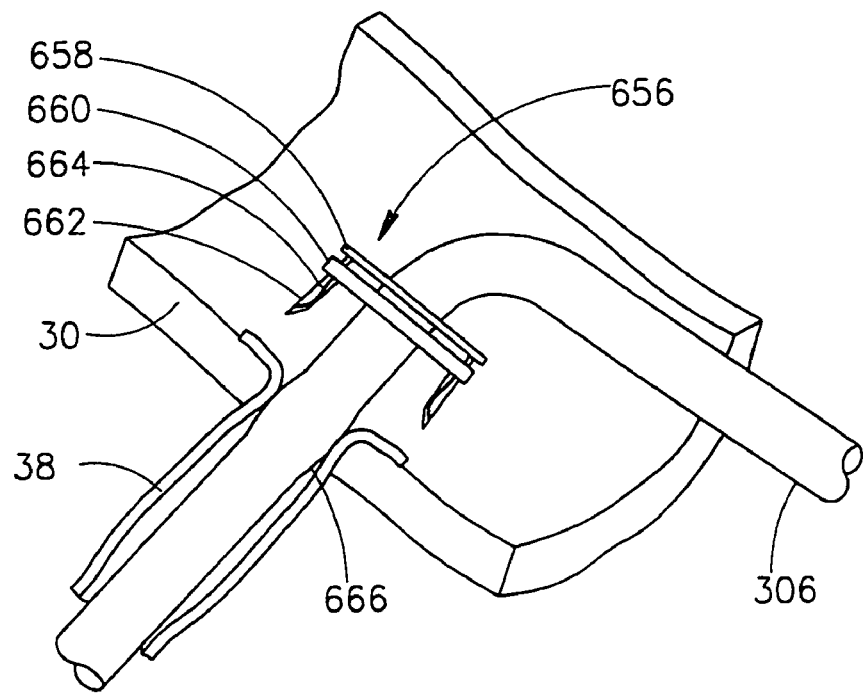

FIGS. 13A–D illustrate a method of separately providing an anastomotic connector 664 and a graft 38, at an anastomosis site, in accordance with a preferred embodiment of the invention. In FIG. 13A, a graft 38 is shown, which is urged against lips of a hole in aorta 30, by endoscope 306, possibly, by an expanded portion 666 thereon. Thereafter, a connector provision assembly 656 is advanced along endoscope 306. In a preferred embodiment of the invention, assembly 656 comprises an impaler base 660 on which a plurality of impaler tubes 662 are mounted. In each tube, a spike of connector 664 is provided. Alternatively, each tube holds an individual staple. Alternatively, the tubes 662 are replaced by a hollow cylinder, inside which connector 664 is maintained in a flattened condition. The staples are coupled to an advancer 658.

Figure 13B:
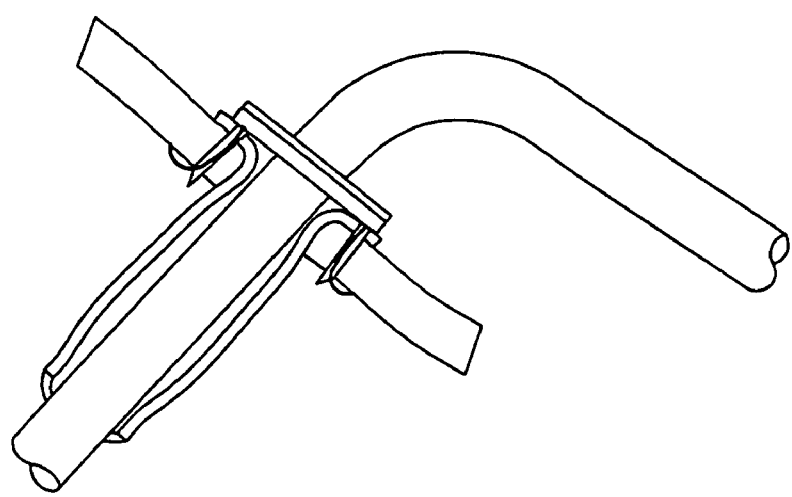

In FIG. 13B, the ends of graft 38 are impaled by impaler tubes 662 and advancer 658 is advanced relative to impaler base 660, so that the tips of the staple extend, and bend to engage the walls of aorta 30. Preferably, the staples are elastic, super-elastic or shape-memory.

Figure 13C:
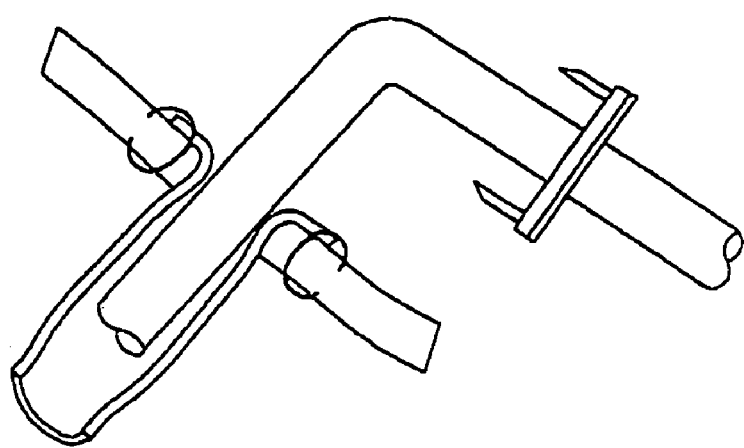

In FIG. 13C, both base 660 and advancer 558 are retracted, so that the other side of the staples are decoupled from advancer 558 and also bend, to engage graft 38 and/or aorta 30.

Figure 13D:
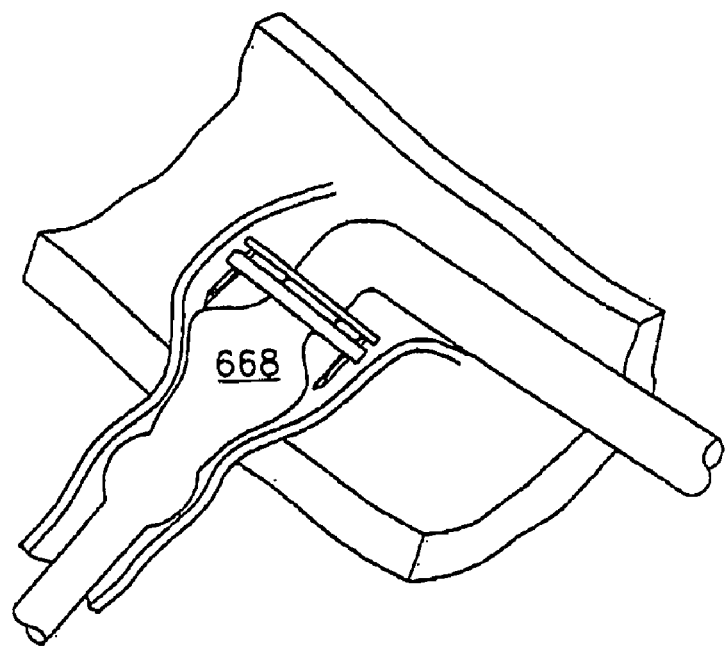

In an alternative embodiment shown in FIG. 13D, graft 38 is not cut to size prior to insertion of the anastomosis device. Preferably, a larger expanded portion 668 is formed in endoscope 302, such that tubes 662 are guided by portion 668 to engage graft 68 substantially perpendicular thereto. Additionally, graft 38 is at least partially everted by portion 668. Once graft 38 is engaged by tubes 662, the rest of graft 38 may be cut off, for example using a cutter (not shown). Alternatively or additionally, expanded portion 668 is deflated and tubes 662 and graft 38 are advanced into the aorta, as shown in FIG. 13B. Alternatively to an expanded portion, 668, a balloon or a different framework may be used.

Figure 14A:
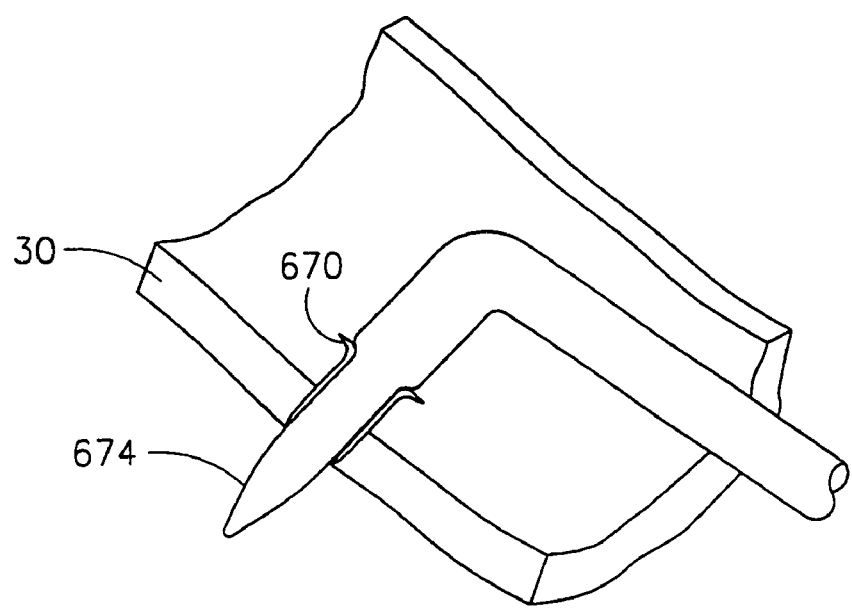
Figure 14B:
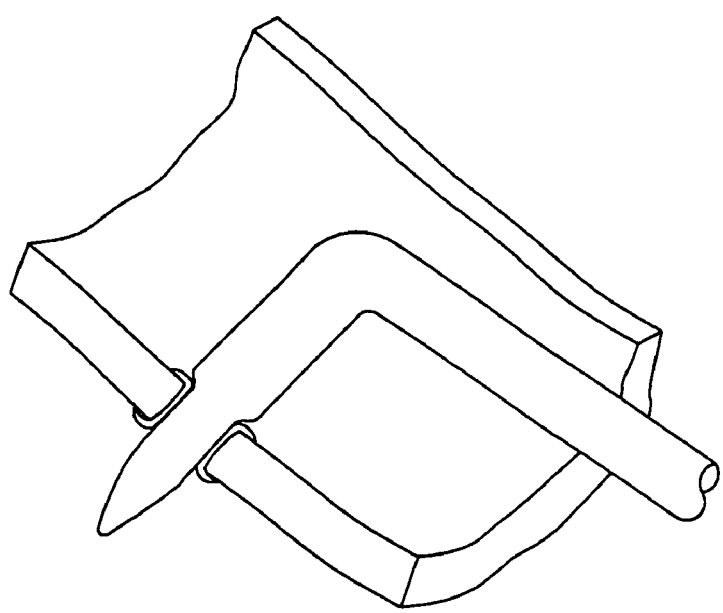
Figure 14C:
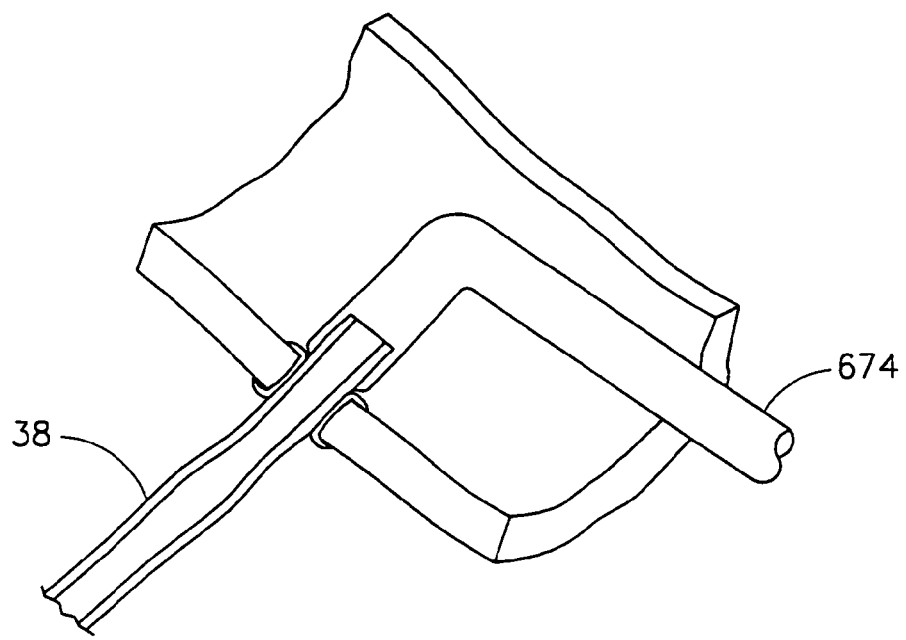
Figure 14D:
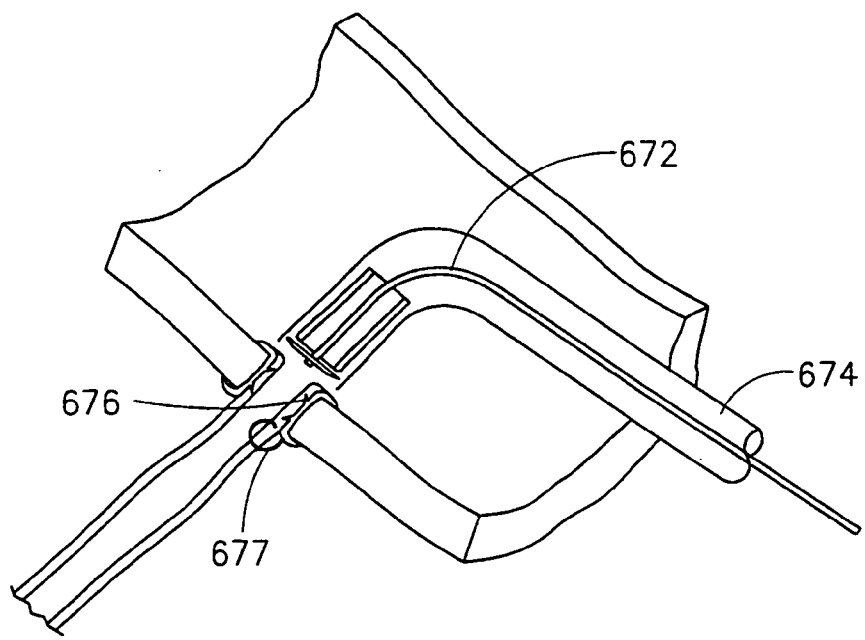

FIGS. 14A–D illustrate a method of cutting a graft to size, during an anastomosis process in accordance with a preferred embodiment of the invention. In FIG. 14A, an endoscope/guiding catheter 674 is used to form a hole in aorta 30 and place a connector 670 in the hole. In FIG. 14B, the attachment of connector 670 to the aorta is completed. Thereafter, various activities may be performed through the connector, preferably using catheter 674. In FIG. 14C, a graft 38 is provided through catheter 674, attached to a far anastomosis and then the catheter is retracted. In FIG. 14D, a plurality of spikes 676 in connector 670 extend and engage the graft. Preferably, this extension is a result of the release of a constraint of catheter 674. Alternatively, a balloon or other expandable element (not shown) is expanded in connector 670. The excess portion of graft 38 is then removed, for example using a cutting tool 672 which cuts the graft against the inside of catheter 674. Possibly, one or more of spikes 676 may fold from outside the connector in, for example as shown by reference number 677. Preferably, the graft is urged against the inner surface of catheter 674 by an inner element or a balloon, which balloon may also deflect such spikes.

It should be appreciated that imaging devices may be used to track the process of anastomosis, including, the location, the quality of the seal and the relative positions of the tools, grafts and/or connectors. Such imaging devices may be external to the body, internal to the body and/or provided at catheter 34, such as near tip 37. Possible imaging devices include: optical sensors, ultrasound sensors, fluoroscopy, open MRI and CT.

In many of the above described embodiments a balloon is suggested when describing an inflatable member. It should be appreciated that in many embodiments what is required is a framework which can controllably change its configuration, radially or axial, and/or possibly to apply force. In some cases, a continuous surface is required, in others, only the relative positions of certain points on the balloon are important. Other framework types besides balloons are known to provide one or more of these properties and may be used in the above described preferred embodiments of the invention. In some cases, these frameworks will be covered with a flexible covering, to reduce the danger of clotting and/or are removed after use.

The above description stresses CABG procedures and especially the aorta-to-graft anastomosis. However., it should be noted that many other types of blood vessels and/or grafts may be connected using the methods described herein. In one example, instead of connecting to the aorta, the anastomosis may originate from the descending aorta, from the LIMA or the RIMA or from other secondary blood vessels. In particular, in the LIMA, RIMA and other vessels which supply areas having a corollary blood supply, the vessel itself may serve as the graft which is navigated to the clogged artery. Preferably, the vessel is blocked, for example using suturing or an expanding balloon, prior to being severed and navigated. Alternatively, the graft is exited from the severed end of the vessel, rather than from its side. In addition, although many examples are described regarding the aorta, they are equally applicable to other blood vessel. Also, it is noted that some of the above described procedures can be applied to the backside of the heart, which is not directly accessible from the chest.

Alternatively or additionally, blood vessels in other parts of the body may be bypassed, for example in the brain. Typically, bypass operations in the brain are not performed for fear of damaging sensitive brain structures. In a preferred embodiment of the invention, a graft is navigated from a source vessel (such as the external or internal carotid), through cavities which exist in the brain, to a clogged vessel, past its occlusion. Possibly, a small part of this travel will be through brain tissue. However, only a minimum of brain tissue need to be damaged. Alternatively, the travel is through brain tissue which is known to be less important, for example, by performing the procedure while the patient is awake and exciting the tissue to determine responses from the patient. Preferably, this procedure is performed using real-time imaging. Alternatively or additionally, an image guided system, preferably incorporating a position sensor at the tip of the graft, is used. Typically, the connectors, grafts and/or insertion devices are smaller and/or more flexible when used for brain vascular surgery than for vessels in the trunk, such as coronary vessels.

It should be appreciated that many of the structures described herein may also be applied to other invasive and/or implantable devices, beyond those used for anastomosis, especially such devices which are inflatable, expandable and/or otherwise deployed. However, as will be appreciated, that some of the above described structures solve particular problems of anastomosis, for example the problems of coordination between several actions, controllability and operation across the vessel wall.

It will be appreciated that the above described methods of vascular surgery may be varied in many ways, including, changing the order of steps, which steps are performed inside the body and which outside, the order of making the anastomosis connections, the order of steps inside each anastomosis, the exact materials used for the anastomotic connectors and/or which vessel is a "side" side and which vessel (or graft) is an "end" side of an end-to-side anastomosis. In addition, a multiplicity of various features, both of method and of devices have been described. It should be appreciated that different features may be combined in different ways. In particular, not all the features shown above in a particular embodiment are necessary in every similar preferred embodiment of the invention. Further, combinations of the above features are also considered to be within the scope of some preferred embodiments of the invention. Also within the scope of the invention are surgical kits which include sets of medical devices suitable for making a single or a small number of anastomosis connections. When used in the following claims, the terms "comprises", "comprising", "includes", "including" or the like means "including but not limited to".

It will be appreciated by a person skilled in the art that the present invention is not limited by what has thus far been described. Rather, the scope of the present invention is limited only by the following claims.

What is claimed is:

1. A method of providing a connector to a blood vessel, comprising:
    providing a distal end of a hole puncher adjacent a blood vessel;
    punching a hole in the blood vessel, by the hole puncher;
    transporting a connector including at least one spike for attaching to the blood vessel through a lumen of the hole puncher, while the distal end of the hole puncher is adjacent the blood vessel; and
    engaging the blood vessel punched by the hole puncher, by the at least one spike,
    wherein transporting the connector through the lumen comprises transporting the connector from a proximal end of the hole puncher to the distal end of the hole puncher.

2. A method according to claim 1, wherein providing the distal end of the hole puncher adjacent the blood vessel comprises pressing the hole puncher against an outer wall of the blood vessel.

3. A method according to claim 1, comprising removing a sub-assembly of the hole puncher from a channel of the hole puncher, while the hole puncher is adjacent the blood vessel and transporting the connector through the channel from which the subassembly was removed.

4. A method according to claim 3, wherein removing the sub-assembly comprises removing a central cutter and a surrounding sheath.

5. A method according to claim 3, wherein removing the sub-assembly comprises removing a central cutter while a surrounding sheath, that participated in the punching of the hole, remains with an end adjacent the blood vessel.

6. A method according to claim 1, wherein transporting the connector through the lumen is performed while the hole puncher is in contact with the blood vessel.

7. A method of treating a blood vessel, comprising:
    providing a hole puncher, including a tissue engager and a surrounding sheath, adjacent a blood vessel;
    punching a hole in the blood vessel by the hole puncher, utilizing the surrounding sheath;
    removing the tissue engager from a channel of the hole puncher, while the surrounding sheath, utilized in the punching, remains in the vicinity of the blood vessel; and
    transporting a tool other than the tissue engager through the channel, to the vicinity of the blood vessel.

8. A method according to claim 7, wherein the tool other than the tissue engager comprises a connector.

9. A method according to claim 8, wherein the connector comprises at least one spike.

10. A method according to claim 7, wherein punching the hole is performed utilizing both the tissue engager and the surrounding sheath.

11. A method according to claim 7, wherein the tissue engager includes an indent adapted to engage a wall of the blood vessel.

12. A method according to claim 7, wherein the tissue engager has a sharp distal end adapted to penetrate a hole in the blood vessel.

13. A method according to claim 7, wherein the tissue engager is rotatable while being adjacent the blood vessel.

14. A method according to claim 13, wherein the tissue engager is rotatable relative to the outer sheath, while being adjacent the blood vessel.

15. A method according to claim 7, wherein the tissue engager is adapted to be vibrated while being adjacent the blood vessel.

16. A method according to claim 7, wherein punching a hole in the blood vessel comprises rotating the tissue engager adjacent the blood vessel.

17. A method according to claim 16, wherein punching a hole in the blood vessel comprises rotating the tissue engager, relative to the outer sheath, adjacent the blood vessel.

18. A method according to claim 7, wherein punching a hole in the blood vessel comprises vibrating the tissue engager adjacent the blood vessel.

19. A method according to claim 7, wherein transporting the tool through the channel comprises transporting the tool through the channel after removing the tissue engager from the channel.

* * * * *